US008349887B2

(12) United States Patent
Fraser et al.

(10) Patent No.: US 8,349,887 B2
(45) Date of Patent: *Jan. 8, 2013

(54) METHODS OF TREATING CACHEXIA WITH MACROCYCLIC MODULATORS OF THE GHRELIN RECEPTOR

(75) Inventors: Graeme L. Fraser, Québec (CA); Hamid R. Hoveyda, Québec (CA); Mark L. Peterson, Québec (CA)

(73) Assignee: Tranzyme Pharma Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,929

(22) Filed: Jun. 30, 2011

(65) Prior Publication Data

US 2011/0288163 A1 Nov. 24, 2011

Related U.S. Application Data

(60) Division of application No. 12/333,026, filed on Dec. 11, 2008, which is a continuation of application No. 11/149,512, filed on Jun. 10, 2005, now Pat. No. 7,491,695, which is a continuation-in-part of application No. 10/872,142, filed on Jun. 18, 2004, now Pat. No. 7,521,420.

(60) Provisional application No. 60/479,223, filed on Jun. 18, 2003, provisional application No. 60/621,642, filed on Oct. 26, 2004, provisional application No. 60/622,005, filed on Oct. 27, 2004, provisional application No. 60/642,271, filed on Jan. 7, 2005.

(51) Int. Cl.
*A01N 43/02* (2006.01)

(52) U.S. Cl. ........ 514/449; 514/450; 514/497; 514/510; 514/520

(58) Field of Classification Search ........................ None
See application file for complete search history.

(56) References Cited

U.S. PATENT DOCUMENTS

| 6,548,501 | B2 | 4/2003 | Hakkinen |
| 6,586,403 | B1 | 7/2003 | Mathison et al. |
| 6,852,722 | B2 | 2/2005 | Hakkinen |
| 7,169,899 | B1 | 1/2007 | Deslongchamps et al. |
| 7,452,862 | B2 | 11/2008 | Deslongchamps et al. |
| 7,476,653 | B2 | 1/2009 | Hoveyda et al. |
| 7,491,695 | B2 * | 2/2009 | Fraser et al. ............... 514/1.1 |
| 7,521,420 | B2 * | 4/2009 | Fraser et al. ............... 514/1.1 |
| 7,550,431 | B2 | 6/2009 | Deslongchamps et al. |
| RE42,013 | E | 12/2010 | Hoveyda et al. |
| RE42,624 | E | 8/2011 | Fraser et al. |
| 8,008,440 | B2 | 8/2011 | Deslongchamps et al. |
| 8,022,252 | B2 | 9/2011 | Deslongchamps et al. |
| 8,088,733 | B2 | 1/2012 | Fraser et al. |
| 2008/0194672 | A1 | 8/2008 | Hoveyda et al. |
| 2008/0287371 | A1 | 11/2008 | Fraser et al. |
| 2009/0137835 | A1 | 5/2009 | Marsault et al. |
| 2009/0170757 | A1 | 7/2009 | Fraser et al. |
| 2009/0198050 | A1 | 8/2009 | Marsault et al. |
| 2009/0221689 | A1 | 9/2009 | Marsault et al. |
| 2009/0240027 | A1 | 9/2009 | Marsault et al. |
| 2009/0275648 | A1 | 11/2009 | Fraser et al. |
| 2009/0312540 | A1 | 12/2009 | Deslongchamps et al. |
| 2010/0093720 | A1 | 4/2010 | Marsault et al. |
| 2011/0105389 | A1 | 5/2011 | Hoveyda et al. |
| 2011/0237785 | A1 | 9/2011 | Marsault et al. |
| 2011/0245159 | A1 * | 10/2011 | Hoveyda et al. ............... 514/4.9 |
| 2011/0245459 | A1 | 10/2011 | Marsault et al. |

FOREIGN PATENT DOCUMENTS

| EP | 1 159 964 | 12/2001 |
| JP | 2002-12556 A | 1/2002 |
| JP | 2003-511387 A | 3/2003 |
| WO | WO 01/25257 | 4/2001 |
| WO | WO 2004/111077 | 12/2004 |
| WO | WO 2005/012331 | 2/2005 |
| WO | WO 2005/012332 | 2/2005 |

OTHER PUBLICATIONS

Office Action corresponding to Japanese Application No. 2007-516589 dated May 6, 2011.
U.S. Appl. No. 13/218,784, filed Aug. 26, 2011.
U.S. Appl. No. 10/961,856, filed Oct. 7, 2004.
U.S. Appl. No. 13/305,349, filed Nov. 28, 2011.
Examination Report corresponding to Australian Application No. 2005264907 dated Oct. 20, 2011.
W.-C. Qui et al. J. Gastroenterol. (2008) 14(9), pp. 1419-1424.
J. Rudinger. In: Peptide Hormones, JA Parsons, Ed. (1976) 1-7.
D. Voet and J.G. Voet. Biochemistry, 2nd Edition. (1995), pp. 235-241.
D.E. Smilek, et al. Proc. Natl. Acad. Sci. USA (1991) 88, pp. 9633-9637.
W.S. Messer, "Vasopressin and Oxytocin", web document updated Apr. 3, 2000; <http://www.neurosci.pharm.utoledo.edu/MBC3320/vasopressin.htm>; 5 pages.
S. Rudikoff, et al. Proc. Natl. Acad. Sci. USA (1982) 79, pp. 1979-1983.
J.-M. Cao et al. Trends Endocrin. Metab. (2006) 17(1), pp. 14-18.
Arvat et al. "Ghrelin and synthetic GH secretagogues" *Best Practice and Research Clinical Endocrinology and Metabolism* 16(3): 505-517 (2002).
International Search Report and the Written Opinion of the International Searching Authority for International application PCT/US2005/020654 mailed on Dec. 16, 2005.
Trudel et al. "Ghrelin/motilin-related peptide is a potent prokinetic to reverse gastric postoperative ileus in rat" *American Journal of Physiology* 282(6): G948-G952 (2002).

(Continued)

*Primary Examiner* — Anish Gupta
*Assistant Examiner* — Li Lee
(74) *Attorney, Agent, or Firm* — Myers Bigel Sibley & Sajovec, PA

(57) ABSTRACT

The present invention provides novel conformationally-defined macrocyclic compounds that have been demonstrated to be selective modulators of the ghrelin receptor (growth hormone secretagogue receptor, GHS-R1a and subtypes, isoforms and variants thereof). Methods of synthesizing the novel compounds are also described herein. These compounds are useful as agonists of the ghrelin receptor and as medicaments for treatment and prevention of a range of medical conditions including, but not limited to, metabolic and/or endocrine disorders, gastrointestinal disorders, cardiovascular disorders, obesity and obesity-associated disorders, central nervous system disorders, genetic disorders, hyperproliferative disorders and inflammatory disorders.

6 Claims, 21 Drawing Sheets

OTHER PUBLICATIONS

Ahnfelt-Ronne et al. "Do Growth Hormone-Releasing Peptides Act as Ghrelin Secretagogues?" *Endocrine* 14(1): 133-135 (2001).

Arcadi et al. "Electrophilic Cyclization of *o*-Acetoxy- and *o*-Benzyloxyalkynylpyridines: An Easy Entry into 2, 3-Disubsituted Furopyridines" *Organic Letters* 4(14): 2409-2412 (2002).

Ariyasu et al. "Stomach is a Major Source of Circulating Ghrelin, and Feeding State Determines Plasma Ghrelin-Like Immunoreactivity Levels in Humans" *The Journal of Clinical Endocrinology & Metabolism* 86(10);: 4756-4758 (2001).

Arvat et al. "Growth Hormone-Releasing Hormone and Growth Hormone Secretagogue-Receptor Ligands" *Endocrine* 14(1): 35-43 (2001).

Backes et al. "Solid Support Linker Strategies" *Current Opinion in Chemical Biology* 1: 86-93 (1997).

Baig et al. "Postoperative Ileus: A Review" *Diseases of the Colon & Rectum* 47: 516-526 (2002).

Baldanzi et al. "Ghrelin and des-acyl Ghrelin Inhibit Cell Death in Cardiomyocytes and Endothelial Cells through ERK1/2 and Pi 3-kinase/AKT" *The Journal of Cell Biology* 159(6): 1029-1037 (2002).

Baldwin et al. "Symbiotic Approach to Drug Design: Antihypertensive β-Adrenergic Blocking Agents" *Journal of Medicinal Chemistry* 22(11): 1284-1290 (1979).

Banks et al. "Extent and Direction of Ghrelin Transport Across the Blood-Brain Barrier ls Determined by its Unique Primary Structure" *The Journal of Pharmacology and Experimental Therapeutics* 302: 822-827 (2002).

Barreiro et al, "Developmental, State-Specific, and Hormonally Regulated Expression of Growth Hormone Secretagogue Receptor Messenger RNA in Rat Testis" *Biology of Reproduction* 68: 1631-1640 (2002).

Barth et al, "Tailoring Ultraresins Based on the Cross-Linking of Polyethylene Imines. Comparative Investigation of the Chemical Composition, the Swelling, the Mobility, the Chemical Accessibility, and the Performance in Solid-Phase Synthesis of Very High Loaded Resins" *Journal of Combinatorial Chemistry* 6: 340-349 (2004).

Bedendi et al. "cardiac Effects of Ghrelin and its Endogenous derivatives des-octanoyl Ghrelin and des-Gln$^{14}$-ghrelin" *European Journal of Pharmacology* 476: 87-95 (2003).

Bednarek et al. "Structure-Function Studies on the New Growth Hormone-Releasing Peptide, Ghrelin: Minimal Sequence of Ghrelin Necessary for Activation of Growth Hormone Secretagogue Receptor 1a" *Journal of Medicinal Chemistry* 43: 4370-4376 (2000).

Birr et al. "Der α,α-Dimethyl-3.5-dimethoxybenzyloxycarbonyl (Ddz)-Rest, eine photo- und säurelabile Stickstoff-Schutzgruppe für die Peptidehemie" *Liebigs Ann Chem* 763: 162-172 (1972).

Bossharth et al. "Palladium-Mediated Three-Component Sythesis of Furo[2,3-*b*]pyridones by One=Pot Coupling of 3-Iodopyridones, Alkynes, and Organic Halides" *Organic Letters* 5(14): 2441-2444 (2003).

Bowers "Growth Hormone Releasing Peptides: Physiology and Clinical Applications" *Current Opinion in Endocrinology & Diabetes* 7: 168-174 (2000).

Bowers et al. "Structure-Activity Relationships of a Synthetic Pentapeptide that Specifically Releases Growth Hormone in Vitro" *Endocrinology* 106(3): 663-667 (1980).

Broglio et al. "Endocrine and Non-Edocrine Actions of Ghrelin" *Hormone Research* 59: 109-117 (2003).

Camanni et al. "Growth Hormone-Releasing Peptides and Their Analogs" *Frontiers in Neuroendocrinology* 19: 47-72 (1998).

Camilleri "Advances in Diabetic Gastroparesis" *Reviews in Gastroenterological Disorders* 2(2): 47-56 (2002).

Carlini et al. "Ghrelin Increases Anxiety-Like Behavior and Memory Retention in Rats" *Biochemical and Biophysical Research Communications* 299: 739-743 (2002).

Carpino et al, "recent Developments in Ghrelin Receptor (GHS-R1a) Agonists and Antagonists" *Expert Opinion in Ther. Patents* 12(11): 1599-1618 (2002).

Carreira et al, "Agonist-Specific Coupling of Growth Hormone Secretagogue Receptor Type 1a to Different Intracellular Signaling Systems" *Neuroendocrinology* 79: 13-25 (2004).

Casanueva et al. "Ghrelin: The Link Connection Growth with Metabolism and Energy Homeostatis" *Reviews in Endocrine & Metabolic Disorders* 3: 325-338 (2002).

Cassoni et al, "Expression of Ghrelin and Biological Activity of Specific Receptors for Ghrelin and des-acyl Ghrelin in Human Prostate Neoplasms and Related Cell Lines" *European Journal of Endocrinology* 150: 173-184 (2004).

Chan et al. "Identification and Functional Characterization of Two Alternatively Spliced Growth Hormone Secretagogue Receptor Transcripts from the Pituitary of Black Seabream *Acanthopagrus schlegeli*" *Molecular and Cellular Endocrinology* 241: 81-95 (2004).

Chang et al. "A Highly Efficient and practical Synthesis of Chromene Derivatives Using Ring-Closing Olefin Metathesis" *Journal of Organic Chemistry* 63: 864-866 (1998).

Chang et al. "Activity of a Novel Nonpeptidyl Growth Hormone Secretagogue, L-700, 653, in Swine" *Endocrinology* 136(3): 1065-1071 (1995).

Cheng et al. "The Synergisitc Effects of His-D-Trp-Ala-Trp-D-Phe-Lys-NH$_2$ on Growth Hormone (GH)-Releasing Factor-Stimulated GH Release and Intracellular Adenosine 3', 5'-Monophosphate Accumulation in Rat Primary Pituitary Cell Culture" *Endocrinology* 124(6): 2791-2798 (1989).

Comins et al. "*N*- vs. *O*- Alkylation in the Mitsunobu Reaction of 2-Pyridone" *Tetrahedron Letters* 35(18) 2819-2822 (1994).

Cummings et al, "Plasma Ghrelin Levels After Diet-Induced Weight Loss or Gastric Bypass Surgery" *New England Journal of Medicine* 346(21): 1623-1630 (2002).

Cunha et al. "Ghrelin and Growth Hormone (GH) Secretagogues Potentiate GH-Releasing Hormone (GHRH)-Induced Cyclic Adenosine 3', 3'-Monophosphate Production in Cells Expressing Transfected GHRH and GH Secretagogue Receptors" *Endocrinology* 143(12): 4570-4582 (2002).

Deghenghi et al. "GH-Releasing Activity of Hexarelin, A New Growth Hormone Releasing Peptide, in iNfant and Adult Rats" *Life Sciences* 54(18): 1324-1328 (1994).

Deghenghi et al. "Somatostatin Octapeptides (Lanreotide, Octreotide, Vapreotide, and their Analogs) Share the Growth Hormone-Releasing Peptide Receptor in the Human Pituitary Gland" *Endocrine* 14(1): 29-33 (2001).

Deghenghi et al. "Targeting the Ghrelin Receptor" *Endocrine* 22(1): 13-18 (2003).

Depoortere et al. "Interaction of the Growth Hormone-Releasing Peptides Ghrelin and Growth Hormone-Releasing Peptide-6 with the Motilin Receptor in the Rabbit Gastric Antrum" *The Journal of Pharmacology and Experimental Therapeutics* 305: 660-667 (2003).

Devi "Heterodimerization of G-Protein-Coupled Receptors: Pharmacology, Signaling and Trafficking" *Trends in Pharmacological Sciences* 22(10): 532-537 (2001).

Edholm et al. "Ghrelin Stimulates Motility in the Small Intestine of Rats Through Intrinsic Cholinergic Neurons" *Regulatory Peptides* 121: 25-30 (2004).

Eggenweiler "Linkers for Solid-Phase Synthesis of Small Molecules: Coupling and Cleavage Techniques" *DDT* 3(12): 552-560 (1998).

Elias et al. "In Vitro Characterization of Four Novel Classes of Growth Hormone-Releasing Peptide" *Endocrinology* 136(12): 5694-5699 (1995).

Fehrentz et al. "Growth Hormone Secretagogues: Past, Present and Future" *Drugs* 5(8): 804-814 (2002).

Feighner et al. "Receptor for Motilin Identified in the Human Gastrointestinal System" *Science* 284: 2184-2188 (1999).

Frechet et al. "Use of Polymers as Protecting Groups in Organic Synthesis. II. Protection of Primary Alcohol Functional Groups" *Tetrahedron Letters* 35: 3055-3056 (1975).

Fujino et al. "Ghrelin Induces Fasted Motor Activity of the Gastrointestinal Tract in Conscious Fed Rats" *Journal of Physiology* 550(1): 227-240 (2004).

Ghigo et al, "Orally Active Growth Hormone Secretagogues: State of the Art and Clinical Perspectives" *Trends in Clinical Practice*.

Gross "A Concise Sterospecific Synthesis of Repinotan (BAYx3702)" *Tetrahedron Letters* 44: 8563-8565 (2003).

Halem et al. "Novel Analogs of Ghrelin: Physiological and Clinical Implications" *European Journal of Endocrinology* 151: S71-S75 (2004).

Hansen, Jr. et al. "Chemoselective N-Ethylation of Boc Amino Acids without Racemization" *Journal of Organic Chemistry* 50: 945-950 (1985).

Harrity et al. "Chromenes through Metal-Catalyzed Reactions of Styrenyl Ethers. Mechanism and Utility in Synthesis" *Journal of the American Chemical Society* 120: 2343-2351 (1998).

Hickey et al. "Efficacy and Specificity of L-692, 429, A Novel Nonpeptidyl Growth Hormone Secretagogue, in Beagles" *Endocrinology* 134(2): 695-701 (1994).

Hickey et al. "Repeat Administration of the GH Secretagogue MK-0677 Increases and Maintains Elevated IGF-I Levels in Beagles" *Journal of Endocrinology* 152: 182-192 (1997).

Hirano et al. "Chronic Intestinal Pseudo-Obstruction" *Digestive Diseases* 18: 83-92 (2000).

Hofslokken et al. "Convenient Method for the *ortho*-Formylation of Phenols" *Acta Chemica Scandinavica* 53: 258-262 (1999).

Hojo et al. "Poly peptide Synthesis Using the S-Alkyl Thioester of a Partially Protected Peptide Segment. Synthesis of the DNA-Binding Domain of *c*-Myb Protein (142-193)-$NH_2$" *Bulletin of the Chemical Society of Japan* 64: 111-117 (1991).

Horvath et al, "Minireview: Ghrelin and the regulation of Energy Balance—A Hypothalamic Perspective" *Endocrinology* 142(10): 4163-4169 (2001).

Hosoda et al. "Purification and Characterization of Rat des-$Gln^{14}$— Ghrelin, a Second Endogenous Ligand for the Growth Hormone Secretagogue Receptor" *The Journal of Biological Chemistry* 275(29): 21995-22000 (2000).

Hosoda et al. "Structural Divergence of Human Ghrelin" *The Journal of Biological Chemistry* 278(1): 64-70 (2003).

Howard et al. "A Receptor in Pituitary and Hypothalamus that Functions in Growth Hormone Relase" *Science* 273: 974-977 (1996).

Iwaki et al. "Novel Synthetic Strategy of Carbolines Via Palladium-Catalyzed Amination and Arylation Reaction" *J Chem Soc, Perkin Trans* 1: 1505-1510 (1999).

Jacks et al. "Effects of Acute and Repeated Intravenous Administration of L-692,585, A Novel Non-Peptidyl Growth Hormone Secretagogue, on Plasma Growth Hormone, IGF-1, ACTH, Cortisol, Prolactin, Insulin, and Thyroxine Levels in Beagles" *Journal of Endocrinology* 143: 399-406 (1994).

James "Linkers for Solid Phase Organic Synthesis" *Tetrahedron* 55: 4855-4946 (1999).

Kalff et al. "Surgical Manipulation of the Gut Elicits and Intestinal Muscularis Inflammatory Response Resulting in Postsurgical Ileus" *Annals of Surgery* 228(5): 652-663 (1998).

Kojima et al. "Ghrelin is a Growth-Hormone-Releasing Acylated Peptide from Stomach" *Nature* 402: 656-660 (1999).

Kojima et al, "Ghrelin, an Orexigenic Signaling Molecule from the Gastrointestinal Tract" *Curent Opinion in Pharmacology* 2: 665-668 (2002).

Kojima et al. "Purification and Distribution of Ghrelin: The Natural Endogenous Ligand for the Growth Hormone Secretagogue Receptor" *Hormone Research* 56(supp 1): 93-97 (2001).

Krsek et al. "Plasma Ghrelin Levels in Patients with Short Bowel Syndrome" *Endocrine Research* 28(1&2): 27-33 (2002).

Kurz et al. "Opioid-Induced Bowel Dysfunction: Pathophysiology and Potential new Therapies" *Drugs* 63(7): 649-671 (2003).

LePoul et al, "Adaptation of Aequorin Functional Assay to High Throughput Screening" *Journal of Biomolecular Screening* 7(1): 57-65 (2002).

Lindstrom et al. "Sythesis of Two Conformationally Constrained Analogues of the Minor Tobacco Alkaloid Anabasine" *Organic Letters* 2(15): 2291-2293 (2000).

Liu et al. "Selective N-Functionalization of 6-Substituted-2-Pyridones" *Tetrahedron Letters* 36(49): 8917-8920 (1995).

Locatelli et al. "Growth Hormone Secretagogues: Focus on the Growth Hormone-Releasing Peptides" *Pharmacological Research* 36(6): 415-423 (1997).

Luckey et al. "Mechanisms and Treatment of Postoperative Ileus" *Archives of Surgery* 138: 206-214 (2003).

Maarseveen et al. "Solid Phase Synthesis of Heterocycles by Cyclization/Cleavage Methodologies" *Combinatorial Chemistry & High Throughput Screening* 1: 185-214(1998).

Malagon et al. "Intracellular Signaling Mechanism Mediating Ghrelin-Stimulated Growth Hormone Release in Somatotropes" *Endocrinology* 144(12): 5372-5380 (2003).

Manhas et al, "Steroids. Part X. A Convenient Synthesis of Alkyl Aryl Ethers" *Journal of the American Chemical Society* 94: 461-463 (1972).

Marguet et al. "New Synthesis of *sn*-1, 2- and *sn*-2,3-*O*-Diacylglycerols—Application to the Synthesis of Enantiopure Phosphonates Analogous to Triglycerides: A New Class of Inhibitors of Lipases" *European Journal of Organic Chemistry* pp. 1671-1678 (1999).

Meldal et al. "PEGA: A Flow Stable Polyethylene Glycol Dimethyl Acrylamide Copolymer for Solid Phase Synthesis" *Tetrahedron Letters* 33(21): 3077-3080 (1992).

Moreaux et al. "Activation of the GHS-Receptor Accelerates Gastric Emptying in Dogs" *Department of Gastrointestinal an Demerging Diseases*, Johnson & Johnson Pharmaceutical Research & Development 1 page, no date.

Murray et al. "Ghrelin for the Gastroenterologist: History and Potential" *Gastroenterology* 125: 1492-1502 (2003).

Nagaya et al. "Ghrelin Improves Left ventricular Dysfunction and Cardiac Cachexia in Heart Failure" *Current Opinion in Pharmacology* 3: 146-151 (2003).

Nagaya et al. "Ghrelin, a Novel Growth Hormone-Releasing Peptide, in the Treatment of Chronic Heart Failure" *Regulatory Peptides* 114: 71-77 (2003).

Nakano et al. "An Efficient Synthesis of (S)-(-)-Befunolol Hydrochloride, Involving the Regioselective Condensation of (R)-Glycidol and 2-Acetyl-7-Hydroxybenzofuran" *Heterocycles* 20(10): 1975-1978 (1983).

Nakazato et al. "A Role for Ghrelin in the Central Regulation of Feeding" *Nature* 409: 194-198 (2001).

Nargund et al. "Peptidomimetic Growth Hormone Secretagogues, Design Considerations and Therapeutic Potential" *Journal of Medicinal Chemistry* 41(17): 3103-3127 (1998).

Ong et al. "Identification of a Pituitary Growth Hormone-Releasing Peptide (GHRP) Receptor subtype by Photoaffinity Labeling" *Endocrinology* 139(1): 432-435 (1998).

Palucki et al. "Spiro(indoline-3,4'-piperidine) Growth Hormone Secretagogues as Ghrelin Mimetics" *Bioorganic & Medicinal Chemistry Letters* 11: 1955-1957 (2001).

Park et al. "Oligomerization of G Protein-Coupled Receptors: Past, Present, and Future" *Biochemistry* 43(50): 15643-15656 (2004).

Peeters "Central and Peripheral Mechanisms y which Ghrelin Regulates Gut Motility" *Journal of Physiology and Pharmacology* 54(suppl 4): 95-103 (2003).

Persico et al. "Use of Hydrogen Bonds to Control Molecular Aggregation. Behavior of a Self-Complementary Dipyridone Designed to Self-Replicate" *Journal of Organic Chemistry* 58: 95-99 (1993).

Peschke et al. "New Growth Hormone Secretagogues: C-Terminal Modified Sulfonamide-Analogues of NN703" *Bioorganic & Medicinal Chemistry Letters* 9: 1295-1298 (1999).

Rapp et al. "Continuous Flow Peptide Synthesis on Pspoe-Graft-Copolymers" in *Innovation and perspectives in solid-phase synthesis* (Epton, R., ed.) pp. 205-210, SPCC, Birmingham. (1990).

Rios et al. "G-Protein-Coupled Receptor Dimerization: Modulation of Receptor Function" *Pharmacology & Therapeutics* 92: 71-87 (2001).

Roussel Jr., et al. "Risk Factors Associated with Development of Postoperative Ileus in Horses" *JAVMA* 219(1): 72-78 (2001).

Samson et al. "Motilin: A Novel Growth Hormone Releasing Agent" *Brain Research Bulletin* 12: 57-62 (1984).

Sato et al. "CsF in Organic Synthesis. Tuning of *N*- or *O*- Alkylation of 2-Pyridone" *Synlett* pp. 845-846 (Aug. 1995).

Semple et al. "3-Aryl Pyridone Derivatives. Potent and Selective Kappa Opioid Receptor Agonists" *Bioorganic & Medicinal Chemistry Letters* 12: 197-200 (2002).

Shiao et al. "A Facile Synthesis of Bromo-2-Alkoxypyridines" *Heterocycles* 31(5): 819-824 (1990).

Sibilia et al. "Ghrelin Protects Against Ethanol-Induced Gastric Ulcers in Rats: Studies on the Mechanisms of Action" *Endocrinology* 144(1): 353-359 (2003).

Smith et al. "Current Concepts in Diabetic Gastroparesis" *Drugs* 63(13): 1339-1358 (2003).

Smith et al, "Growth Hormone Secretagogues: Prospects and Potential Pitfalls" *Best Practice & Research Clinical Endocrinology & Metabolism* 18(3): 333-347 (2004).

Smith et al. "Peptidomimetic Regulation of Growth Hormone Secretion" *Endocrine Reviews* 18(5): 621-645 (1997).

Solomon et al. "Chemical Synthesis and Characterization of Duplex DNA Containing a New Base Pair: A Nondisruptive, Benzofused Pyrimiine Analog" *Journal of Organic Chemistry* 58: 2232-2243 (1993).

Svensson et al, "Growth Hormone Secretagogues" *Expert Opinion on Therapeutic Patents* 10(7): 1071-1080 (2000).

Tack et al, "Influence of Ghrelin on Gastric Emptying and Meal-Related Symptoms in Idiopathic Gastroparesis" *Aliment Pharmacol Ther* 22: 847-853 (2005).

Tack et al. "Influence of Ghrelin on Interdigestive Gastrointestinal motility in Humans" *Gut* 55:327-333 (2006).

Tannenbaum et al. "Interrelationship Between the Novel Peptide Ghrelin and Somatostatin/Growth Hormone-Releasing Hormone in Regulation of Pulsatile Growth Hormone Secretion" *Endocrinology* 144(3): 967-974 (2003).

Tee et al, "Kinetics and Mechanism of Bromination of 2-Pyridone and Related Derivatives in Aqueous Solution" *Journal of the American Chemical Society* 104: 4142-4146 (1982).

Theodoridis "Nitrogen Protecting Gropus: Recent Developments and New Applications" *Tetrahedron Letters* 56: 2339-2358 (2000).

Thompson et al. "Ghrelin and Des-Octanoyl Ghrelin Promote Adipogenesis Directly in Vivo by a Mechanism Independent of the Type 1a Growth Hormone Secretagogue Receptor" *Endocrinology* 145(1): 234-242 (2004).

Tomasetto et al. "Identification oand Characterization of a Novel Gastric Peptide Hormone: The Motilin-Related Peptide" *Gastroenterology* 119: 395-405 (2000).

Torsello et al. "Differential Orexigenic Effects of Hexarelin and Its Analogs in the Rat Hypothalamus: Indication for Multiple Growth Hormone Secretagogue Receptor Subtypes" *Neuroendocrinology* 72: 327-332 (2000).

Trudel et al. "Ghrelin/Motilin-Related Peptide is a Potent Prokinetic to Reverse Gastric Postoperative Ileus in Rat" *American Journal of Gastrointestinal and Liver Physiology* 282: G948-G952 (2002).

Trudel et al, "Two New Peptides to Improve Post-Operative Gastric Ileus in Dog" *Peptides* 24: 531-534 (2003).

Van Hoogmoed et al. "Survey of Prokinetic use in Horses with Gastrointestinal Injury" *Veterinary Surgery* 33: 279-285 (2004).

Vedejs et al. "Heteroarene-2-sulfonyl Chlorides (BtsCl; ThsCl): Reagents for Nitrogen Protection and >99% Racemization-Free Phenylglycine Activation with $SoCl_2$" *Journal of the American Chemical Society* 118: 9796-9797 (1996).

Zdravkovic et al. "A Clinical Study Investigating the Pharmacokinetic Interaction Between NN703 (tabimorelin), a Potential Inhibitor of CYP3A4 Activity, and Midazolam, a CYP3A4 Substrate" *European Journal of Pharmacology* 58: 683-688 (2003).

Zhang et al. "Lactone and Lactam Library Synthesis by Silver Ion-Assisted Orthogonal Cyclization of Unprotected Peptides" *Journal of the American Chemical Society* 121: 3311-3320 (1999).

Lasseter et al. "Ghrelin Agonist (TZP-101): Safety, Pharmacokinetics and Pharmacodynamic Evaluation in Healthy Volunteers: A Phase 1, First-in-Human Study" *J. Clin. Pharmacol.* 48: 193-202 (2008).

\* cited by examiner

METHODS OF TREATING CACHEXIA WITH MACROCYCLIC MODULATORS OF THE GHRELIN RECEPTOR

RELATED APPLICATION INFORMATION

This application is a divisional application of U.S. patent application Ser. No. 12/333,026, filed Dec. 11, 2008, which is a continuation application of U.S. patent application Ser. No. 11/149,512, filed Jun. 10, 2005, now U.S. Pat. No. 7,491,695, issued Feb. 17, 2009 and reissue application U.S. patent application Ser. No. 12/635/872, now allowed, which is a continuation-in-part under 35 U.S.C. §120 of U.S. patent application Ser. No. 10/872,142, filed Jun. 18, 2004, now U.S. Pat. No. 7,521,420, issued Apr. 21, 2009, which claims the benefit under 35 U.S.C. §119(e) of U.S. Provisional Patent Application Ser. No. 60/479,223, filed Jun. 18, 2003. The continuation-in-part application also claims the benefit under 35 U.S.C. §119(e) of U.S. Provisional Patent Application Ser. No. 60/621,642, filed Oct. 26, 2004, U.S. Provisional Patent Application Ser. No. 60/622,005, filed Oct. 27, 2004, and U.S. Provisional Patent Application Ser. No. 60/642,271, filed Jan. 7, 2005. The disclosures of the above-referenced applications are incorporated herein by reference in their entireties.

FIELD OF THE INVENTION

The present invention relates to novel conformationally-defined macrocyclic compounds that bind to and/or are functional modulators of the ghrelin (growth hormone secretagogue) receptor including GHS-R1a and subtypes, isoforms and/or variants thereof. The present invention also relates to intermediates of these compounds, pharmaceutical compositions containing these compounds and methods of using the compounds. These novel macrocyclic compounds are useful as therapeutics for a range of disease indications. In particular, these compounds are useful for treatment and prevention of gastrointestinal disorders including, but not limited to, post-operative ileus, gastroparesis, including diabetic gastroparesis, opioid bowel dysfunction, chronic intestinal pseudo-obstruction, short bowel syndrome and functional gastrointestinal disorders.

BACKGROUND OF THE INVENTION

The improved understanding of various physiological regulatory pathways enabled through the research efforts in genomics and proteomics has begun to impact the discovery of novel pharmaceutical agents. In particular, the identification of key receptors and their endogenous ligands has created new opportunities for exploitation of these receptor/ligand pairs as therapeutic targets. For example, ghrelin is a recently characterized 28-amino acid peptide hormone isolated originally from the stomach of rats with the orthologue subsequently identified in humans. (Kojima, M.; Hosoda, H. et al. *Nature* 1999, 402, 656-660.) The existence of this peptide in a range of other species suggests a conserved and important role in normal body function. This peptide has been demonstrated to be the endogenous ligand for a previously orphan G protein-coupled receptor (GPCR), type 1 growth hormone secretatogue receptor (hGHS-R1a) (Howard, A. D.; Feighner, S. D.; et al. A receptor in pituitary and hypothalamus that functions in growth hormone release. *Science* 1996, 273, 974-977.) found predominantly in the brain (arcuate nucleus and ventromedial nucleus in the hypothalamus, hippocampus and substantia nigra) and pituitary. (U.S. Pat. No. 6,242,199; Intl. Pat. Appl. Nos. WO 97/21730 and WO 97/22004) The receptor has also been detected in other areas of the central nervous system (CNS) and in peripheral tissues, for instance adrenal and thyroid glands, heart, lung, kidney, and skeletal muscles. This receptor was identified and cloned prior to the isolation and characterization of the endogenous peptide ligand and is distinct from other receptors involved in the regulation of growth hormone (GH) secretion, in particular, the growth hormone-releasing hormone (GHRH) receptor.

A unique characteristic of both the rat and human peptides is the presence of the n-octanoyl (Oct) moiety on $Ser^3$. However, the des-acyl form predominates in circulation, with approximately 90% of the hormone in this form. This group is derived from a post-translational modification and appears relevant for bioactivity and possibly also for transport into the CNS. (Banks, W. A.; Tschöp, M.; Robinson, S. M.; Heiman, M. L. Extent and direction of ghrelin transport across the blood-brain barrier is determined by its unique primary structure. *J. Pharmacol. Exp. Ther.* 2002, 302, 822-827.) In a GH-releasing assay, the des-octanoyl form of the hormone was at least 100-fold less potent than the parent peptide, although it has been suggested that the des-acyl species may be responsible for some of the other biological effects associated with ghrelin. This des-acyl form has also been postulated to be primarily responsible for the cardiovascular and cell proliferation effects attributed to ghrelin, while the acylated form participates in maintenance of energy balance and growth hormone release. (Baldanzi, G.; Filighenddu, N.; Cutrupi, S.; et al. Ghrelin and des-acyl ghrelin inhibit cell death in cardiomyocytes and endothelial cells through ERK1/2 and PI-3 kinase/AKT. *J. Cell Biol.* 2002, 159, 1029-1037) Similarly, des-$Gln^{14}$-ghrelin and its octanoylated derivative have been isolated as endogenous forms of the hormone arising from alternative splicing of the ghrelin gene, but both are found to be inactive in stimulating GH release in vivo. (Hosoda, H.; Kojima, M.; Matsuo, H.; Kangawa, K. Purification and characterization of rat des-$Gln^{14}$-ghrelin, a second endogenous ligand for the growth hormone secretagogue receptor. *J. Biol. Chem.* 2000, 275, 21995-2120.). Other minor forms of ghrelin produced by post-translational processing have been observed in plasma, although no specific activity has been attributed to them. (Hosoda, H.; Kojima, M.; et al. Structural divergence of human ghrelin. Identification of multiple ghrelin-derived molecules produced by post-translational processing. *J. Biol. Chem.* 2003, 278, 64-70.)

Even prior to the isolation of this receptor and its endogenous peptide ligand, a significant amount of research was devoted to finding agents that can stimulate GH secretion. The proper regulation of human GH has significance not only for proper body growth, but also a range of other critical physiological effects. GH and other GH-stimulating peptides, such as GHRH and growth hormone releasing factor (GRF), as well as their derivatives and analogues, are administered via injection. Therefore, to better take advantage of these positive effects, attention was focused on the development of orally active therapeutic agents that would increase GH secretion, termed GH secretagogues (GHS). Additionally, use of these agents was expected to more closely mimic the pulsatile physiological release of GH.

Beginning with the identification of the growth hormone-releasing peptides (GHRP) in the late 1970's, (Bowers, C. Y. Growth hormone-releasing peptides: physiology and clinical applications. *Curr. Opin. Endocrinol. Diabetes* 2000, 7, 168-174; Camanni, F.; Ghigo, E.; Arvat, E. Growth hormone-releasing peptides and their analogs. *Front. Neurosci.* 1998, 19, 47-72; Locatelli, V.; Torsello, A. Growth hormone secretagogues: focus on the growth hormone-releasing peptides. *Pharmacol. Res.* 1997, 36, 415-423.) a host of agents have been studied for their potential to act as GHS. In addition to their stimulation of GH release and concomitant positive effects in that regard, GHS were projected to have utility in the treatment of a variety of other disorders, including wasting conditions (cachexia) as seen in HIV patients and cancer-induced anorexia, musculoskeletal frailty in the elderly, and growth hormone deficient diseases. Many efforts over the past 25 years have yielded a number of potent, orally available GHS. (Smith, R. G.; Sun, Y. X.; Beatancourt, L.; Asnicar, M. Growth hormone secretagogues: prospects and pitfalls. *Best Pract. Res. Clin. Endocrinol. Metab.* 2004, 18, 333-347; Fehrentz, J.-A.; Martinez, J.; Boeglin, D.; Guerlavais, V.; Deghenghi, R. Growth hormone secretagogues: Past, present and future. *IDrugs* 2002, 5, 804-814; Svensson, J. *Exp. Opin. Ther. Patents* 2000, 10, 1071-1080; Nargund, R. P.; Patchett, A. A.; et al. Peptidomimetic growth hormone secretagogues. Design considerations and therapeutic potential. *J. Med. Chem.* 1998, 41, 3103-3127; Ghigo, E; Arvat, E.; Camanni, F. Orally active growth hormone secretagogues: state of the art and clinical perspective. *Ann. Med.* 1998, 30, 159-168; Smith, R. G.; Van der Ploeg, L. H. T.; Howard, A. D.; Feighner, S. D.; et al. Peptidomimetic regulation of growth hormone secretion. *Endocr. Rev.* 1997, 18, 621-645.) These include small peptides, such as hexarelin (Zentaris) and ipamorelin (Novo Nordisk), and adenosine analogues, as well as small molecules such as carpomorelin (Pfizer), L-252,564 (Merck), MK-0677 (Merck), NN703 (Novo Nordisk), G-7203 (Genentech), S-37435 (Kaken) and SM-130868 (Sumitomo), designed to be orally active for the stimulation of growth hormone. However, clinical testing with such agents have rendered disappointing results due to, among other things, lack of efficacy over prolonged treatment or undesired side effects, including irreversible inhibition of cytochrome P450 enzymes (Zdravkovic M.; Olse, A. K.; Christiansen, T.; et al. *Eur. J. Clin. Pharmacol.* 2003, 58, 683-688.) Therefore, there remains a need for pharmacological agents that could effectively target the GHS-R1a receptor for therapeutic action.

Despite its involvement in GH modulation, ghrelin is primarily synthesized in the oxyntic gland of the stomach, although it is also produced in lesser amounts in other organs, including the kidney, pancreas and hypothalamus. (Kojima, M.; Hsoda, H.; Kangawa, K. Purification and distribution of ghrelin: the natural endogenous ligand for the growth hormone secretagogue receptor. *Horm. Res.* 2001, 56 (Suppl. 1), 93-97; Ariyasu, H.; Takaya, K.; Tagami, T.; et al. Stomach is a major source of circulating ghrelin, and feeding state determines plasma ghrelin-like immunoreactivity levels in humans. *J. Clin. Endocrinol. Metab.* 2001, 86, 4753-4758) In addition to its role in stimulating GH release, the hormone has a variety of other endocrine and non-endocrine functions (Broglio, F.; Gottero, C.; Arvat, E.; Ghigo, E. Endocrine and non-endocrine actions of ghrelin. *Horm. Res.* 2003, 59, 109-117) and has been shown to interact with a number of other systems in playing a role in maintaining proper energy balance. (Horvath, T. L.; Diano, S.; Sotonyi, P.; Heiman, M.; Tschöp, M. Ghrelin and the regulation of energy balance—a hypothalamic perspective. *Endocrinology* 2001, 142, 4163-4169; Casanueva, F. F.; Dieguez, C. Ghrelin: the link connecting growth with metabolism and energy homeostasis. *Rev. Endocrinol. Metab. Disord.* 2002, 3, 325-338). In particular, ghrelin plays a role as an orexigenic signal in the control of feeding, in which it acts to counteract the effects of leptin. Indeed, it was the first gut peptide proven to have such orexigenic properties. (Kojima, M.; Kangawa, K. Ghrelin, an orexigenic signaling molecule from the gastrointestinal tract. *Curr. Opin. Pharmacology* 2002, 2, 665-668.) The hormone also is implicated in the hypothalamic regulation of the synthesis and secretion of a number of other neuropeptides involved in appetite and feeding behavior. Levels of ghrelin are elevated in response to fasting or extended food restriction. (Nakazato, M.; Murakami, N.; Date, Y.; Kojima, M.; et al. A role for ghrelin in the central regulation of feeding. *Nature* 2001, 409, 194-198) For example, subjects suffering with anorexia or bulimia exhibit elevated ghrelin levels. Circulating levels of the hormone have been found to rise before meals and fall after meals. In addition, diet-induced weight loss leads to increased ghrelin levels, although obese subjects who have gastric bypass surgery do not likewise experience such an increase. (Cummings, D. E.; Weigle, D. S.; Frayo, R. S.; et al. Plasma ghrelin levels after diet-induced weight loss or gastric bypass surgery. *N. Engl. J. Med.* 2002, 346, 1623-1630)

This intimate involvement of ghrelin in control of food intake and appetite has made it an attractive target for obesity research. Indeed, few other natural substances have been demonstrated to be involved in the modulation of both GH secretion and food intake.

An additional effect of ghrelin that has not to date been exploited for therapeutic purposes is in modulating gastric motility and gastric acid secretion. The prokinetic activity appears to be independent of the GH-secretory action and is likely mediated by the vagal-cholinergic muscarinic pathway. The dose levels required are equivalent to those necessary for the hormone's GH and appetite stimulation actions. It is noteworthy that, in contrast to its inactivity for ghrelin's other actions, the des-Gln$^{14}$ peptide demonstrated promotion of motility as well. (Trudel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. *Peptides* 2003, 24, 531-534; Trudel, L.; Tomasetto, C.; Rio, M. C.; Bouin, M.; Plourde, V.; Eberling, P.; Poitras, P. Ghrelin/motilin-related peptide is a potent prokinetic to reverse gastric postoperative ileus in rats. *Am. J. Physiol.* 2002, 282, G948-G952; Peeters, T. L. Central and peripheral mechanisms by which ghrelin regulates gut motility. *J. Physiol. Pharmacol.* 2003, 54 (Supp. 4), 95-103.)

Ghrelin also has been implicated in various aspects of reproduction and neonatal development. (Arvat, E.; Gianotti, L.; Giordano, R.; et al. Growth hormone-releasing hormone and growth hormone secretagogue-receptor ligands. Focus on reproductive system. *Endocrine* 2001, 14, 35-43) Also of significance are the cardiovascular effects of ghrelin, since the peptide is a powerful vasodilator. As such, ghrelin agonists have potential for the treatment of chronic heart failure (Nagaya, N.; Kangawa, K. Ghrelin, a novel growth hormone-releasing peptide, in the treatment of chronic heart failure. *Regul. Pept.* 2003, 114, 71-77; Nagaya, N.; Kangawa, K. Ghrelin improves left ventricular dysfunction and cardiac cachexia in heart failure. *Curr. Opin. Pharmacol.* 2003, 3, 146-151; Bedendi, I.; Alloatti, G.; Marcantoni, A.; Malan, D.; Catapano, F.; Ghé, C.; et al. Cardiac effects of ghrelin and its endogenous derivatives des-octanoyl ghrelin and des-Gln$^{14}$-ghrelin. *Eur. J. Pharmacol.* 2003, 476, 87-95) Intl. Pat. Appl. Publ. WO 2004/014412 describes the use of ghrelin agonists for the protection of cell death in myocardial cells and as a cardioprotectant treatment for conditions leading to heart failure. Lastly, evidence has been obtained that ghrelin may have implications in anxiety and other CNS disorders as well as the improvement of memory. (Carlini, V. P., Monzon, M. E., Varas, M. M., Cragnolini, A. B., Schioth, H. B., Scimonelli, T. N., de Barioglio, S. R. Ghrelin increases anxiety-like behavior and memory retention in rats. *Biochem. Biophys. Res. Commun.* 2002, 299, 739-743)

The myriad effects of ghrelin in humans have suggested the existence of subtypes for its receptor, although none have as yet been identified. (Torsello, A.; Locatelli, Y.; Melis, M. R.; Succu, S.; Spano, M. S.; Deghenghi, R.; Muller, E. E.; Argiolas, A.; Torsello, A.; Locatelli, V.; et al. Differential orexigenic effects of hexarelin and its analogs in the rat hypothalamus: indication for multiple growth hormone secretagogue receptor subtypes. *Neuroendocrinology* 2000, 72, 327-332.) However, a truncated, inactive form of GHS-R1a, termed GHS-R1b, was isolated and identified during the original characterization studies. Evidence is mounting that additional receptor subtypes could be present in different tissues to explain the diverse effects displayed by the endogenous peptides and synthetic GHS. For instance, high affinity binding sites for ghrelin and des-acyl ghrelin have also been found in breast cancer cell lines, cardiomyocytes, and guinea pig heart that are involved in mediating the antiproliferative, cardioprotective and negative cardiac inotropic effects of these peptides. Similarly, specific GHS binding sites besides GHS-R1a and GHS-R1b have been found in prostate cancer cells. Further, ghrelin and des-acyl ghrelin exert different effects on cell proliferation in prostate carcinoma cell lines. (Cassoni, P.; Ghé, C.; Marrocco, T.; et al. Expression of ghrelin and biological activity of specific receptors for ghrelin and des-acyl ghrelin in human prostate neoplasms and related cell lines. *Eur. J. Endocrinol.* 2004, 150, 173-184) These various receptor subtypes may then be implicated independently in the wide array of biological activities displayed by the endogenous peptides and synthetic GHS. Indeed, recently, the existence of receptor subtypes was offered as an explanation for the promotion of fat accumulation by ghrelin, despite its potent stimulation of the lipolytic hormone, growth hormone. (Thompson, N. M.; Gill, D. A. S.; Davies, R.; Loveridge, N.; Houston, P. A.; Robinson, I. C. A. F.; Wells, T. Ghrelin and des-octanoyl ghrelin promote adipogenesis directly in vivo by a mechanism independent of the type 1a growth hormone secretagogue receptor. *Endocrinology* 2004, 145, 234-242.) Further, this work suggested that the ratio of ghrelin and des-acyl ghrelin production could help regulate the balance between adipogenesis and lipolysis in response to nutritional status.

The successful creation of peptidic ghrelin analogues that separate the GH-modulating effects of ghrelin from the effects on weight gain and appetite provides strong evidence for the existence and physiological relevance of other receptor subtypes. (Halem, H. A.; Taylor, J. E.; Dong, J. Z.; Shen, Y.; Datta, R.; Abizaid, A.; Diano, S.; Horvath, T.; Zizzari, P.; Bluet-Pajot, M.-T.; Epelbaum, J.; Culler, M. D. Novel analogs of ghrelin: physiological and clinical implications. *Eur. J. Endocrinol.* 2004, 151, S71-S75.) BIM-28163 functions as an antagonist at the GHS-R1a receptor and inhibits receptor activation by native ghrelin. However, this same molecule is a full agonist with respect to stimulating weight gain and food intake. Additionally, the existence of a still uncharacterized receptor subtype has been proposed based on binding studies in various tissues that showed differences between peptidic and non-peptidic GHS. (Ong, H.; Menicoll, N.; Escher, F.; Collu, R.; Deghenghi, R.; Locatelli, V.; Ghigo, E.; Muccioli, G.; Boghen, M.; Nilsson, M. *Endocrinology* 1998, 139, 432-435.) Differences between overall GHS-R expression and that of the GHS-R1a subtype in rat testis have been reported. (Barreiro, M. L.; Suominen, J. S.; Gaytan, F.; Pinilla, L.; Chopin, L. K.; Casanueva, F. F.; Dieguez, C.; Aguilar, E.; Toppari, J.; Tena-Sempere, M. Developmental, stage-specific, and hormonally regulated expression of growth hormone secretagogue receptor messenger RNA in rat testis. *Biol. Reproduction* 2003, 68, 1631-1640) A GHS-R subtype on cholinergic nerves is postulated as an explanation for the differential actions of ghrelin and a peptidic GHS on neural contractile response observed during binding studies at the motilin receptor. (Depoortere, I.; Thijs, T.; Thielemans, L.; Robberecht, P.; Peeters, T. L. Interaction of the growth hormone-releasing peptides ghrelin and growth hormone-releasing peptide-6 with the motilin receptor in the rabbit gastric antrum. *J. Pharmacol. Exp. Ther.* 2003, 305, 660-667.)

The variety of activities associated with the ghrelin receptor could also be due to different agonists activating different signaling pathways as has been shown for ghrelin and adenosine, both of which interact as agonists at GHS-R1a (Carreira, M. C.; Camina, J. P.; Smith, R. G.; Casanueva, F. F. Agonist-specific coupling of growth hormone secretagogue receptor type 1a to different intracellular signaling systems. Role of adenosine. *Neuroendocrinology* 2004, 79, 13-25.)

The functional activity of a GPCR has been shown to often require the formation of dimers or other multimeric complexes with itself or other proteins. (Park, P. S.; Filipek, S.; Wells, J. W.; Palczewski, K. Oligomerization of G protein-coupled receptors: past, present, and future. *Biochemistry* 2004, 43, 15643-15656; Rios, C. D.; Jordan, B. A.; Gomes, I.; Devi, L. A. G-protein-coupled receptor dimerization: modulation of receptor function. *Pharmacol. Ther.* 2001, 92, 71-87; Devi, L. A. Heterodimerization of G-protein-coupled receptors: pharmacology, signaling and trafficking. *Trends Pharmacol. Sci.* 2001, 22, 532-537.) Likewise, the activity of the ghrelin receptor might also be at least partially governed by such complexes. For example, certain reports indicate that interaction of GHS-R1a with GHRH (Cunha, S. R.; Mayo, K. E. Ghrelin and growth hormone (GH) secretagogues potentiate GH-releasing hormone (GHRH)-induced cyclic adenosine 3',5'-monophosphate production in cells expressing transfected GHRH and GH secretagogue receptors. *Endocrinology* 2002, 143, 4570-4582; Malagón, M. M.; Luque, R. M.; Ruiz-Guerrero, E.; Rodríguez-Pacheco, F.; García-Navarro, S.; Casanueva, F. F.; Gracia-Navarro, F.; Castaño, J. P. Intracellular signaling mechanisms mediating ghrelin-stimulated growth hormone release in somatotropes *Endocrinology* 2003, 144, 5372-5380) or between receptor subtypes (Chan, C. B.; Cheng, C. H. K. Identification and functional characterization of two alternatively spliced growth hormone secretagogue receptor transcripts from the pituitary of black seabream *Acanthopagrus schlegeli*. *Mol. Cell. Endocrinol.* 2004, 214, 81-95) may be involved in modulating the function of the receptor.

The vast majority of reported approaches to exploiting the ghrelin receptor for therapeutic purposes have focused on modulating metabolic functions. Similarly, the vast majority of literature on GHS focuses on conditions that can be treated via its GH promoting actions. Some embodiments of the invention described herein, in particular, take advantage of selective activation of the ghrelin receptor to provide an avenue for the treatment of diseases characterized by GI dysmotility. The improved GI motility observed with ghrelin demonstrates that ghrelin agonists may be useful in correcting conditions associated with reduced or restricted motility (Murray, C. D. R.; Kamm, M. A.; Bloom, S. R.; Emmanuel, A. V. Ghrelin for the gastroenterologist: history and potential. *Gastroenterology* 2003, 125, 1492-1502; Fujino, K.; Inui, A.; Asakawa, A.; Kihara, N.; Fujimura, M.; Fujimiya, M. Ghrelin induces fasting motor activity of the gastrointestinal tract in conscious fed rats. *J. Physiol.* 2003, 550, 227-240; Edholm, T.; Levin, F.; Hellström, P. M.; Schmidt, P. T. Ghrelin stimulates motility in the small intestine of rats through intrinsic cholinergic neurons. *Regul. Pept.* 2004, 121, 25-30.)

Included among these conditions is post-operative ileus (POI, Luckey, A.; Livingston, E.; Taché, Y. Mechanisms and treatment of postoperative ileus. *Arch. Surg.* 2003, 138, 206-214; Baig, M. K.; Wexner, S. D. Postoperative ileus: a review. *Dis. Colon Rectum* 2004, 47, 516-526). POI is defined as the impairment of GI motility that routinely occurs following abdominal, intestinal, gynecological and pelvic surgeries. In the U.S. alone, 4.3 million surgeries annually induce POI, accounting for an economic impact of over $1 billion. POI is considered a deleterious response to surgical manipulation with a variable duration that generally persists for 72 hours. It is characterized by pain, abdominal distention or bloating, nausea and vomiting, accumulation of gas and fluids in the bowel, and delayed passage of stool. Patients are neither able to tolerate oral feeding nor to have bowel movements until gut function returns. POI leads to numerous undesirable consequences, including increased patient morbidity, the costly prolongation of hospital stays and, further, is a major cause of hospital readmission. In addition, opiate drugs given as analgesics after surgery exacerbate this condition due to their well-recognized side effect of inhibiting bowel function.

Surgical manipulation of the stomach or intestine causes a disorganization of the gut-brain signaling pathways, impairing GI activity and triggering POI. Ghrelin acts locally in the stomach to stimulate and coordinate the firing of vagal afferent neurons and thereby modulate gut motility. Thus, ghrelin accelerates gastric emptying in humans (Inui, A.; Asakawa, A.; Bowers, C. Y.; Mantovani, G.; Laviano, A.; Meguid, M. M.; Fujimiya, M. Ghrelin, appetite, and gastric motility: the emerging role of the stomach as an endocrine organ. *FASEB J.* 2004, 18, 439-456; Peeters, T. L. Central and peripheral mechanisms by which ghrelin regulates gut motility. *J. Physiol. Pharmacol.* 2003, 54(Supp. 4), 95-103.) and is a potent agent proven to treat POI in animal models (Trudel, L.; Tomasetto, C.; Rio, M. C.; Bouin, M.; Plourde, V.; Eberling, P.; Poitras, P. Ghrelin/motilin-related peptide is a potent prokinetic to reverse gastric postoperative ileus in rats. *Am. J. Physiol.* 2002, 282, G948-G952; Trudel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. *Peptides* 2003, 24, 531-534). Ghrelin agonists duplicate the effects of ghrelin, thus targeting directly the underlying cause of POI to accelerate normalization of gut function and enable more rapid discharge from the hospital. Intravenous administration is often the preferred route of treatment for POI due to the impaired GI motility in these patients that impedes oral therapy. No agent is currently approved by the U.S. FDA specifically for the treatment of POI.

Another major motility disorder is gastroparesis, a particular problem for both type I and type II diabetics. (Camilleri, M. Advances in diabetic gastroparesis. *Rev. Gastroenterol. Disord.* 2002, 2, 47-56; Tack et al. *Gastroenterology* 2004; 126: A485; Moreaux, B.; VandenBerg, J.; Thielmans, L.; Meulemans, A.; Coulie, B. Activation of the GHS receptor accelerates gastric emptying in the dog. *Digestive Disease Week*, 15-20 May 2004, New Orleans, La., USA Abstract M1009; Tack et al. *Gastroenterology* 2004, 126: A74) Gastroparesis ("stomach paralysis") is a syndrome characterized by delayed gastric emptying in the absence of any mechanical obstruction. It is variably characterized by abdominal pain, nausea, vomiting, weight loss, anorexia, early satiety, malnutrition, dehydration, gastroesophageal reflux, cramping and bloating. This chronic condition can lead to frequent hospitalization, increased disability and decreased quality of life. Severe, symptomatic gastroparesis is common in individuals suffering from diabetes, affecting from 5-10% of diabetics for a total patient population of 1 million in the U.S. alone. Neuropathy is a frequent, debilitating complication of diabetes. Visceral neuropathy results in GI dysfunction, especially involving the stomach, leading to impaired gastric motility. Ghrelin promotes gastric emptying both by stimulating the vagus nerve and via direct prokinetic action at the gastric mucosa. Moreover, a recent clinical study indicates that intravenous administration of the natural ghrelin peptide is an effective acute therapy in diabetic gastroparesis patients. A ghrelin agonist would therefore be highly effective in overcoming the fundamental motility barrier faced by gastroparesis patients and correcting this condition. As with POI, no accepted or efficacious therapy for diabetic gastroparesis is available and most current therapies aim to provide only symptomatic relief. Further, many of the therapeutics in development have a mechanism of action similar to earlier products that have failed in this indication. Surgical procedures may ameliorate the disease process, but offer no possibility of cure.

Opioid-induced bowel dysfunction (OBD, Kurz, A.; Sessler, D. J. Opioid-Induced Bowel Dysfunction. *Drugs* 2003, 63, 649-671.) is the term applied to the confluence of symptoms involving the reduced GI motility that results from treatment with opioid analgesics. Approximately 40-50% of patients taking opioids for pain control experience OBD. It is characterized by hard, dry stools, straining, incomplete evacuation, bloating, abdominal distension and increased gastric reflux. In addition to the obvious short-term distress, this condition leads to physical and psychological deterioration in patients undergoing long term opioid treatment. Further, the dysfunction can be so severe as to become a dose-limiting adverse effect that actually prevents adequate pain control. As with POI, a ghrelin agonist can be expected to counteract the dysmotility resulting from opioid use.

Two less common conditions may also be helped through the GI motility stimulation effects of ghrelin and ghrelin agonists. Short bowel syndrome is a condition that occurs after resection of a substantial portion of small intestine and is characterized by malnutrition. Patients are observed to have decreased ghrelin levels resulting from loss of the ghrelin-producing neuroendocrine cells of the intestine. It is possible the short bowel feeds back on the release of the hormone. (Krsek, M.; Rosicka, M.; Haluzik, M.; et al. Plasma ghrelin levels in patients with short bowel syndrome. *Endocr. Res.* 2002, 28, 27-33.) Chronic intestinal pseudo-obstruction is a syndrome defined by the presence of chronic intestinal dilation and dysmotility in the absence of mechanical obstruction or inflammation. Both genetic and acquired causes are known to result in this disorder, which affects high numbers of individuals worldwide annually. (Hirano, I.; Pandolfino, J. Chronic intestinal pseudo-obstruction. *Dig. Dis.* 2000, 18, 83-92.)

Other conditions and disorders that could be addressed through stimulation of the ghrelin receptor are: emesis such as caused by cancer chemotherapy, constipation such as associated with the hypomotility phase of irritable bowel syndrome (IBS), delayed gastric emptying associated with wasting conditions, gastroesophageal reflux disease (GERD), gastric ulcers (Sibilia, V.; Rindi, G.; Pagani, F.; Rapetti, D.; Locatelli, V.; Torsello, A.; Campanini, N.; Degenghi, R.; Netti, C. Ghrelin protects against ethanol-induced gastric ulcers in rats: studies on the mechanism of action. *Endocrinology* 2003, 144, 353-359.) and Crohn's disease.

Additionally, GI dysmotility is a significant problem in other mammals as well. For example, the motility dysfunction termed ileus or colic is the number one cause of mortality among horses. Further, ileus is one of the most common complications of equine intestinal surgery, in other words, post-operative ileus. This condition may also have a non-surgical etiology. Some horses may be predisposed to ileus based upon the anatomy and functioning of their digestive tract. Virtually any horse is susceptible to colic with only minor differences based upon age, sex and breed. Additionally, ileus may affect other animals, for example canines. (Roussel, A. J., Jr.; Cohen, N. D.; Hooper, R. N.; Rakestraw, P. C. Risk factors associated with development of postoperative ileus in horses. *J. Am. Vet. Med. Assoc.* 2001, 219, 72-78; Van Hoogmoed, L. M.; Nieto, J. E.; Snyder, J. R.; Harmon, F. A. Survey of prokinetic use in horses with gastrointestinal injury. *Vet. Surg.* 2004, 33, 279-285.)

Importantly, for most of the above conditions, no specific, approved therapeutics exist and most therapies simply address symptomatic relief. However, specific modulation of the ghrelin receptor provides an opportunity to directly target the site of pathophysiological disturbance to better treat the underlying condition and improve clinical outcome. Further, unlike other agents that interact at the GHS-R1a receptor, the compounds of the invention are believed not to stimulate concurrent GH secretion. This separation of the gastrointestinal and GH effects has not previously been reported for any modulators of this receptor. However, as already mentioned, the existence of analogues that separate the appetite control and GH modulatory effects associated with ghrelin has been recently reported.

WO 01/00830 reports on short gastrointestinal peptides (SGIP) that secrete growth hormone and also promote GI motility, but these were not shown to be due to action at the ghrelin receptor. U.S. Pat. No. 6,548,501 discloses specific compounds, but as GHS, useful for stimulation of GI motility. Moreover, other endogenous factors are known to stimulate secretion of GH, but do not promote GI motility. Indeed, many actually inhibit this physiological function. Specific receptor agonists such as the compounds of the present invention have much better potential to be selective and effective therapeutic agents.

Work has continued at the development of potent and selective GHS with a number of small molecule derivatives now being known as has been recently summarized. (Carpino, P. *Exp. Opin. Ther. Patents* 2002, 12, 1599-1618.) Specific GHS are described in the following U.S. Pat. Nos. and Intl. Pat. Appl. Publs. WO 89/07110; WO 89/07111; WO 92/07578; WO 93/04081; WO 94/11012; WO 94/13696; WO 94/19367; WO 95/11029; WO 95/13069; WO 95/14666; WO 95/17422; WO 95/17423; WO 95/34311; WO 96/02530; WO 96/15148; WO 96/22996; WO 96/22997; WO 96/24580; WO 96/24587; WO 96/32943; WO 96/33189; WO 96/35713; WO 96/38471; WO 97/00894; WO 97/06803; WO 97/07117; WO 97/09060; WO 97/11697; WO 97/15191; WO 97/15573; WO 97/21730; WO 97/22004; WO 97/22367; WO 97/22620; WO 97/23508; WO 97/24369; WO 97/34604; WO 97/36873; WO 97/38709; WO 97/40023; WO 97/40071; WO 97/41878; WO 97/41879; WO 97/43278; WO 97/44042; WO 97/46252; WO 98/03473; WO 98/10653; WO 98/18815; WO 98/22124; WO 98/46569; WO 98/51687; WO 98/58947; WO 98/58948; WO 98/58949; WO 98/58950; WO 99/08697; WO 99/09991; WO 99/36431; WO 99/39730; WO 99/45029; WO 99/58501; WO 99/64456; WO 99/65486, WO 99/65488; WO 00/01726; WO 00/10975; WO 01/47558; WO 01/92292; WO 01/96300; WO 01/97831; U.S. Pat. No. 3,239,345; U.S. Pat. No. 4,036,979; U.S. Pat. No. 4,411,890; U.S. Pat. No. 5,492,916; U.S. Pat. No. 5,494,919; U.S. Pat. No. 5,559,128; U.S. Pat. No. 5,663,171; U.S. Pat. No. 5,721,250; U.S. Pat. No. 5,721,251; U.S. Pat. No. 5,723,616; U.S. Pat. No. 5,726,319; U.S. Pat. No. 5,767,124; U.S. Pat. No. 5,798,337; U.S. Pat. No. 5,830,433; U.S. Pat. No. 5,919,777; U.S. Pat. No. 6,034,216; U.S. Pat. No. 6,548,501; U.S. Pat. No. 6,559,150; U.S. Pat. No. 6,576,686; U.S. Pat. No. 6,686,359; and U.S. Pat. Appl. Nos. 2002/0168343; 2003/100494; 2003/130284; 2003/186844.

Despite this immense body of work, cyclic compounds have rarely been found to act at the receptor. When they have, antagonist activity has been more prevalent. For example, the 14-amino acid compound, vapreotide, an SRIH-14 agonist and somatostatin mimetic, was demonstrated to be a ghrelin antagonist. (Deghenghi R, Papotti M, Ghigo E, et al. Somatostatin octapeptides (lanreotide, octreotide, vapreotide, and their analogs) share the growth hormone-releasing peptide receptor in the human pituitary gland. *Endocrine* 2001, 14, 29-33.) The binding and antagonist activities of analogues of cortistatin, a cyclic neuropeptide known to bind nonselectively to somatostatin receptors, to the growth hormone secretagogue receptor have been reported (Intl. Pat. Appl. WO 03/004518). (Deghenghi R, Broglio F, Papotti M, et al. Targeting the ghrelin receptor—Orally active GHS and cortistatin analogs. *Endocrine* 2003, 22, 13-18) In particular, one of these analogues, EP-01492 (cortistatin-8) has been advanced into preclinical studies for the treatment of obesity as a ghrelin antagonist. These compounds exhibit an $IC_{50}$ of 24-33 nM. In addition, these cyclic compounds and their derivatives, plus their use with metal binding agents have been described for their ability to be useful for radiodiagnostic or radiotherapeutic use in the treatment of tumors and acromegaly.

Cyclic and linear analogues of growth hormone 177-191 have been studied as treatments for obesity (WO 99/12969), with one particular compound, AOD9604, having entered the clinic for this indication. A compound already studied that is most similar to the molecules of the present invention is the GHS, G-7203 ($EC_{50}$=0.43 nM), the cyclic peptide analogue of the growth hormone releasing peptide, GHRP-2 (Elias, K. A.; Ingle, G. S.; Burnier, J. P.; Hammonds, G.; McDowell, R. S.; Rawson, T. E.; Somers, T. C.; Stanley, M. S.; Cronin, M. J. In vitro characterization of four novel classes of growth hormone-releasing peptide. *Endocrinol.* 1995, 136, 5694-5699). However, simplification of this cyclic derivative led to still potent, linear compounds, whereas, for compounds of the invention, linear analogues have been found to be devoid of ghrelin receptor activity.

The macrocyclic compounds of the invention possess agonist activity. As previously mentioned, however, unlike other agonists of the hGHS-R1a receptor, the compounds of the invention unexpectedly have an insignificant stimulatory effect on the release of growth hormone. Accordingly, the compounds of the present invention can exhibit selective action in the GI tract or for metabolic disorders without side effects due to GH release.

SUMMARY OF THE INVENTION

The present invention provides novel conformationally-defined macrocyclic compounds. These compounds can function as modulators, in particular agonists, of the ghrelin (growth hormone secretagogue) receptor (GHS-R1a).

According to aspects of the present invention, the present invention relates to compounds according to formula I, II and/or III:

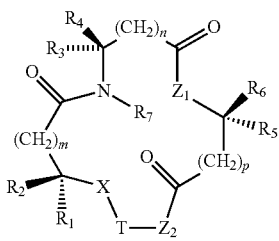

or an optical isomer, enantiomer, diastereomer, racemate or stereochemical mixture thereof, wherein:

$R_1$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below, or alternatively $R_1$ and $R_9$ together form a 3-, 4-, 5-, 6- or 7-membered ring, optionally comprising an O, S or additional N atom in the ring, wherein the ring is optionally substituted with $R_8$ as defined below;

$R_2$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below; or alternatively $R_2$ and $R_9$ together form a 3-, 4-, 5-, 6- or 7-membered ring, optionally comprising an O, S or additional N atom in the ring, wherein the ring is optionally substituted with $R_8$ as defined below;

$R_3$ is hydrogen or the side chain of an amino acid, or alternatively $R_3$ and $R_4$ together form a 3-, 4-, 5-, 6- or 7-membered ring, optionally comprising an O or S atom in the ring, wherein the ring is optionally substituted with $R_8$ as defined below, or alternatively, $R_3$ and $R_7$ or $R_3$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_4$ is hydrogen or the side chain of an amino acid, or alternatively $R_4$ and $R_3$ together form a 3-, 4-, 5-, 6- or 7-membered ring, optionally comprising an O or S atom in the ring, wherein the ring is optionally substituted with $R_8$ as defined below, or alternatively $R_4$ and $R_7$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_5$ and $R_6$ are each independently hydrogen or the side chain of an amino acid or alternatively $R_5$ and $R_6$ together form a 3-, 4-, 5-, 6- or 7-membered ring, optionally comprising an O, S or N atom in the ring, wherein the ring is optionally substituted with $R_8$ as defined below;

$R_7$ is hydrogen, lower alkyl, substituted lower alkyl, cycloalkyl, substituted cycloalkyl, a heterocyclic group, or a substituted heterocyclic group, or alternatively $R_3$ and $R_7$ or $R_4$ and $R_7$ together form a 4-, 5-, 6-, 7- or 8-membered heterocyclic ring optionally comprising an O, S or additional N atom in the ring, wherein the ring is optionally substituted with $R_8$ as described below;

$R_8$ is substituted for one or more hydrogen atoms on the 3-, 4-, 5-, 6-, 7- or 8-membered ring structure and is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfonyl, sulfonyl and sulfonamido, or, alternatively, $R_8$ is a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

X is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl, or alternatively $R_9$ and $R_1$ together form a 3-, 4-, 5-, 6- or 7-membered ring, optionally comprising an O, S or additional N atom in the ring, wherein the ring is optionally substituted with $R_8$ as defined above;

$Z_1$ is O or $NR_{11}$, wherein $R_{11}$ is hydrogen, lower alkyl, or substituted lower alkyl, or alternatively $R_3$ and $R_{11}$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined above;

$Z_2$ is O or $NR_{12}$, wherein $R_{12}$ is hydrogen, lower alkyl, or substituted lower alkyl;

m, n and p are each independently 0, 1 or 2;

T is a bivalent radical of formula IV:

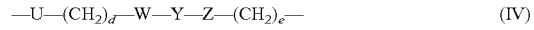

wherein d and e are each independently 0, 1, 2, 3, 4 or 5; Y and Z are each optionally present; U is $—CR_{21}R_{22}—$ or $—C(=O)—$ and is bonded to X of formula I; W, Y and Z are each independently selected from the group consisting of $—O—$, $—NR_{23}—$, $—S—$, $—SO—$, $—SO_2—$, $—C(=O)—O—$, $—O—C(=O)—$, $—C(=O)—NH—$, $—NH—C(=O)—$, $—SO_2—NH—$, $—NH—SO_2—$, $—CR_{24}R_{25}—$, $—CH=CH—$ with the configuration Z or E, $—C\equiv C—$ and the ring structures below:

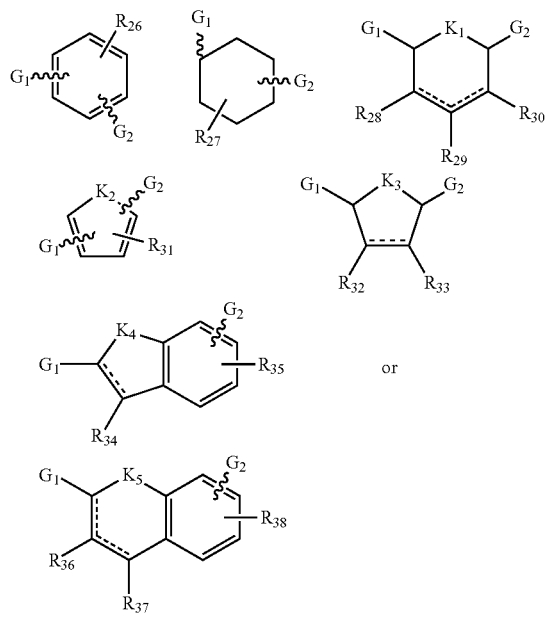

wherein $G_1$ and $G_2$ are each independently a covalent bond or a bivalent radical selected from the group consisting of $—O—$, $—NR_{39}—$, $—S—$, $—SO—$, $—SO_2—$, $—C(=O)—$, $—C(=O)—O—$, $—O—C$ (=O)—, —C(=O)NH—, —NH—C(=O)—, —SO$_2$—NH—, —NH—SO$_2$—, —CR$_{40}$R$_{41}$—, —CH=CH— with the configuration Z or E, and —C≡C—; with G$_1$ being bonded closest to the group U; wherein any carbon atom in the rings not otherwise defined, is optionally replaced by N, with the proviso that the ring cannot contain more than four N atoms; K$_1$, K$_2$, K$_3$, K$_4$ and K$_5$ are each independently O, NR$_{42}$ or S, wherein R$_{42}$ is as defined below;

R$_{21}$ and R$_{22}$ are each independently hydrogen, lower alkyl, or substituted lower alkyl, or alternatively R$_{21}$ and R$_{22}$ together form a 3- to 12-membered cyclic ring optionally comprising one or more heteroatoms selected from the group consisting of O, S and N, wherein the ring is optionally substituted with R$_8$ as defined above;

R$_{23}$, R$_{39}$ and R$_{42}$ are each independently hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl or sulfonamido;

R$_{24}$ and R$_{25}$ are each independently hydrogen, lower alkyl, substituted lower alkyl, R$_{AA}$, wherein R$_{AA}$ is a side chain of an amino acid such as a standard or unusual amino acid, or alternatively R$_{24}$ and R$_{25}$ together form a 3- to 12-membered cyclic ring optionally comprising one or more heteroatoms selected from the group consisting of O, S and N; or alternatively one of R$_{24}$ or R$_{25}$ is hydroxy, alkoxy, aryloxy, amino, mercapto, carbamoyl, amidino, ureido or guanidino while the other is hydrogen, lower alkyl or substituted lower alkyl, except when the carbon to which R$_{24}$ and R$_{25}$ are bonded is also bonded to another heteroatom;

R$_{26}$, R$_{31}$, R$_{35}$ and R$_{38}$ are each optionally present and, when present, are substituted for one or more hydrogen atoms on the indicated ring and each is independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl and sulfonamido;

R$_{27}$ is optionally present and is substituted for one or more hydrogen atoms on the indicated ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl and sulfonamido;

R$_{28}$, R$_{29}$, R$_{30}$, R$_{32}$, R$_{33}$, R$_{34}$, R$_{36}$ and R$_{37}$ are each optionally present and, when no double bond is present to the carbon atom to which it is bonded in the ring, two groups are optionally present, and when present, is substituted for one hydrogen present in the ring, or when no double bond is present to the carbon atom to which it is bonded in the ring, is substituted for one or both of the two hydrogen atoms present on the ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen; and R$_{40}$ and R$_{41}$ are each independently hydrogen, lower alkyl, substituted lower alkyl, R$_{AA}$ as defined above, or alternatively R$_{40}$ and R$_{41}$ together form a 3- to 12-membered cyclic ring optionally comprising one or more heteroatoms selected from the group consisting of O, S and N wherein the ring is optionally substituted with R$_8$ as defined above, or alternatively one of R$_{40}$ and R$_{41}$ is hydroxy, alkoxy, aryloxy, amino, mercapto, carbamoyl, amidino, ureido or guanidino, while the other is hydrogen, lower alkyl or substituted lower alkyl, except when the carbon to which R$_{40}$ and R$_{41}$ are bonded is also bonded to another heteroatom;

with the proviso that T is not an amino acid residue, dipeptide fragment, tripeptide fragment or higher order peptide fragment comprising standard amino acids;

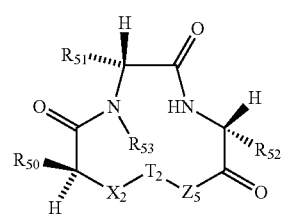

(II)

or an optical isomer, enantiomer, diastereomer, racemate or stereochemical mixture thereof, wherein:

R$_{50}$ is —(CH$_2$)$_{ss}$CH$_3$, —CH(CH$_3$)(CH$_2$)$_{tt}$CH$_3$, —(CH$_2$)$_{uu}$CH(CH$_3$)$_2$, —C(CH$_3$)$_3$, —(CHR$_{55}$)$_{vv}$—R$_{56}$, or —CH(OR$_{57}$)CH$_3$, wherein ss is 1, 2 or 3; tt is 1 or 2; uu is 0, 1 or 2; and vv is 0, 1, 2, 3 or 4; R$_{55}$ is hydrogen or C$_1$-C$_4$ alkyl; R$_{56}$ is amino, hydroxy, alkoxy, cycloalkyl or substituted cycloalkyl; and R$_{57}$ is hydrogen, alkyl, acyl, amino acyl, sulfonyl, carboxyalkyl or carboxyaryl;

R$_{51}$ is hydrogen, C$_1$-C$_4$ alkyl or C$_1$-C$_4$ alkyl substituted with hydroxy or alkoxy;

R$_{52}$ is —(CHR$_{58}$)$_{ww}$R$_{59}$, wherein ww is 0, 1, 2 or 3; R$_{58}$ is hydrogen, C$_1$-C$_4$ alkyl, amino, hydroxy or alkoxy; R$_{59}$ is aryl, substituted aryl, heteroaryl, substituted heteroaryl, cycloalkyl or substituted cycloalkyl;

R$_{53}$ is hydrogen or C$_1$-C$_4$ alkyl;

X$_2$ is O, NR$_9$ or N(R$_{10}$)$_2^+$;

wherein R$_9$ is hydrogen, lower alkyl, substituted lower alkyl, sulfonyl, sulfonamido or amidino and R$_{10}$ is hydrogen, lower alkyl, or substituted lower alkyl;

Z$_5$ is O or NR$_{12}$, wherein R$_{12}$ is hydrogen, lower alkyl, or substituted lower alkyl; and T$_2$ is a bivalent radical of formula V:

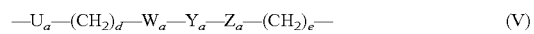

—U$_a$—(CH$_2$)$_d$—W$_a$—Y$_a$—Z$_a$—(CH$_2$)$_e$—  (V)

wherein d and e are independently 0, 1, 2, 3, 4 or 5; Y$_a$ and Z$_a$ are each optionally present; U$_a$ is —CR$_{60}$R$_{61}$— or —C(=O)— and is bonded to X$_2$ of formula II, wherein R$_{60}$ and R$_{61}$ are each independently hydrogen, lower alkyl, or substituted lower alkyl, or alternatively R$_{21}$ and R$_{22}$ together form a 3- to 12-membered cyclic ring optionally comprising one or more heteroatoms selected from the group consisting of O, S and N, wherein the ring is optionally substituted with $R_8$ as defined above; $W_a$, $Y_a$ and $Z_a$ are each independently selected from the group consisting of: —O—, —$NR_{62}$—, —S—, —SO—, —$SO_2$—, —C(=O)—O—, —O—C(=O)—, —C(=O)—NH—, —NH—C(=O)—, —$SO_2$—NH—, —NH—$SO_2$—, —$CR_{63}R_{64}$—, —CH=CH— with the configuration Z or E, —C≡C—, and the ring structures depicted below:

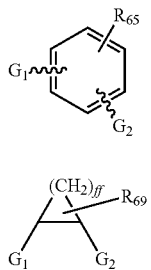 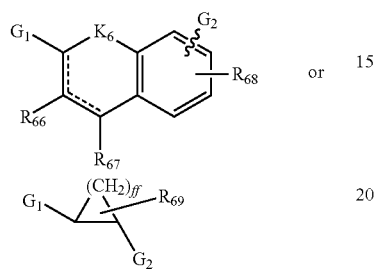 or wherein $G_1$ and $G_2$ are as defined above, and wherein any carbon atom in the ring is optionally replaced by N, with the proviso that the aromatic ring cannot contain more than four N atoms and the cycloalkyl ring cannot contain more than two N atoms;

$R_{62}$ is hydrogen, alkyl, substituted alkyl, cycloalkyl, substituted cycloalkyl, a heterocyclic group, a substituted heterocyclic group, aryl, substituted aryl, heteroaryl, substituted heteroaryl, formyl, acyl, carboxyalkyl, carboxyaryl, amido, amidino, sulfonyl or sulfonamido;

$R_{63}$ and $R_{64}$ are each independently hydrogen, lower alkyl, substituted lower alkyl or $R_{AA}$; or alternatively $R_{63}$ and $R_{64}$ together form a 3- to 12-membered cyclic ring optionally comprising one or more heteroatoms selected from the group consisting of O, S and N; or alternatively one of $R_{63}$ and $R_{64}$ is hydroxy, alkoxy, aryloxy, amino, mercapto, carbamoyl, amidino, ureido or guanidino, while the other is hydrogen, lower alkyl or substituted lower alkyl, except when the carbon to which $R_{63}$ and $R_{64}$ are bonded is also bonded to another heteroatom; and $R_{AA}$ indicates the side chain of an amino acid such as a standard or unusual amino acid;

$R_{65}$ and $R_{68}$ are each optionally present, and, when present are substituted for one or more hydrogen atoms on the ring and each is independently halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl or sulfonamido;

$R_{66}$ and $R_{67}$ are each optionally present, and when no double bond is present to the carbon atom to which it is bonded in the ring, two groups are optionally present, and, when present, each is substituted for one hydrogen present in the ring, or when no double bond is present to the carbon atom to which it is bonded in the ring, is substituted for one or both of the two hydrogen atoms present on the ring and each is independently alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen;

$R_{69}$ is optionally present, and when present is substituted for one or more hydrogen atoms on the ring and each is independently alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl or sulfonamido;

$K_6$ is O or S; and ff is 1, 2, 3, 4 or 5;

with the proviso that $T_2$ is not an amino acid residue, dipeptide fragment, tripeptide fragment or higher order peptide fragment comprising standard amino acids;

or

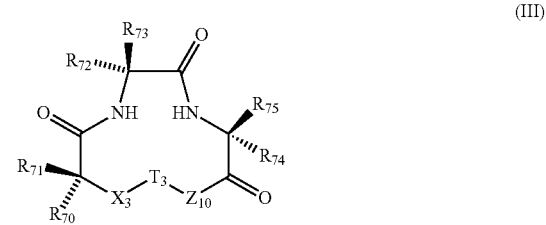

(III)

or an optical isomer, enantiomer, diastereomer, racemate or stereochemical mixture thereof, wherein:

$R_{70}$ is hydrogen, $C_1$-$C_4$ alkyl or alternatively $R_{70}$ and $R_{71}$ together form a 4-, 5-, 6-, 7- or 8-membered ring, optionally comprising an O, N or S atom in the ring, wherein the ring is optionally substituted with $R_{8a}$ as defined below;

$R_{71}$ is hydrogen, —$(CH_2)_{aa}CH_3$, —$CH(CH_3)(CH_2)_{bb}CH_3$, —$(CH_2)_{cc}CH(CH_3)_2$, —$(CH_2)_{dd}$—$R_{76}$ or —$CH(OR_{77})CH_3$ or, alternatively $R_{71}$ and $R_{70}$ together form a 4-, 5-, 6-, 7- or 8-membered ring, optionally comprising an O, N or S atom in the ring, wherein the ring is optionally substituted with $R_{8a}$ as defined below; wherein aa is 0, 1, 2, 3, 4 or 5; bb is 1, 2 or 3; cc is 0, 1, 2 or 3; and dd is 0, 1, 2, 3 or 4; $R_{76}$ is aryl, substituted aryl, heteroaryl, substituted heteroaryl, cycloalkyl or substituted cycloalkyl; $R_{77}$ is hydrogen, alkyl, acyl, amino acyl, sulfonyl, carboxyalkyl or carboxyaryl;

$R_{72}$ is $C_1$-$C_4$ alkyl; or alternatively $R_{72}$ and $R_{73}$ together form a 3-, 4-, 5-, 6- or 7-membered ring, optionally comprising an O or S atom in the ring, wherein the ring is optionally substituted with $R_{8b}$ as defined below;

$R_{73}$ is hydrogen, or alternatively $R_{73}$ and $R_{72}$ together form a 3-, 4-, 5-, 6- or 7-membered ring, optionally comprising an O, S or N atom in the ring, wherein the ring is optionally substituted with $R_{8b}$ as defined below;

$R_{74}$ is hydrogen or $C_1$-$C_4$ alkyl or alternatively $R_{74}$ and $R_{75}$ together form a 3-, 4-, 5-, 6- or 7-membered ring, optionally comprising an O, N or S atom in the ring, wherein the ring is optionally substituted with $R_{8c}$ as defined below;

$R_{75}$ is —(CHR$_{78}$)R$_{79}$ or alternatively $R_{75}$ and $R_{74}$ together form a 3-, 4-, 5-, 6- or 7-membered ring, optionally comprising an O, N or S atom in the ring, wherein the ring is optionally substituted with $R_{8c}$ as defined below; wherein $R_{78}$ is hydrogen, $C_1$-$C_4$ alkyl, amino, hydroxy or alkoxy, and $R_{79}$ is selected from the group consisting of the following structures:

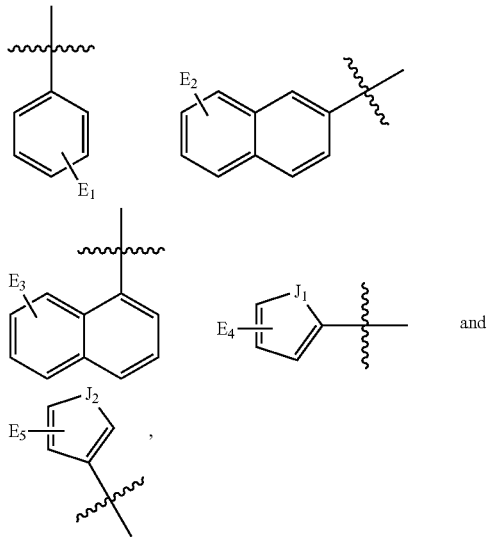

wherein $E_1$, $E_2$, $E_3$, $E_4$ and $E_5$ are each optionally present and when present are each independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, cyano, sulfinyl, sulfonyl and sulfonamido, and represent substitution at one or more available positions on the monocyclic or bicyclic aromatic ring, wherein said substitution is made with the same or different selected group member, and $J_1$ and $J_2$ are each independently O or S;

$R_{8a}$, $R_{8b}$ and $R_{8c}$ are each independently substituted for one or more hydrogen atoms on the 3-, 4-, 5-, 6-, 7- or 8-membered ring structure and are independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_{8a}$, $R_{8b}$ and $R_{8c}$ are each independently a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

$X_3$ is O, NR$_9$ or N(R$_{10}$)$_2^+$;
wherein $R_9$ is hydrogen, lower alkyl, substituted lower alkyl, sulfonyl, sulfonamido or amidino and $R_{10}$ is hydrogen, lower alkyl, or substituted lower alkyl;
$Z_{10}$ is O or NR$_{12}$, wherein $R_{12}$ is hydrogen, lower alkyl, or substituted lower alkyl; and
$T_3$ is the same as defined for $T_2$ with the exception that $U_a$ is bonded to $X_3$ of formula III.

According to further aspects of the present invention, the compound is a ghrelin receptor agonist or a GHS-R1a receptor agonist.

Further aspects of the present invention provide pharmaceutical compositions comprising: (a) a compound of the present invention; and (b) a pharmaceutically acceptable carrier, excipient or diluent.

Additional aspects of the present invention provide kits comprising one or more containers containing pharmaceutical dosage units comprising an effective amount of one or more compounds of the present invention packaged with optional instructions for the use thereof.

Aspects of the present invention further provide methods of stimulating gastrointestinal motility, modulating GHS-R1a receptor activity in a mammal and/or treating a gastrointestinal disorder comprising administering to a subject in need thereof an effective amount of a modulator that modulates a mammalian GHS-R1a receptor. In particular embodiments, interaction of the modulator and the GHS-R1a receptor does not result in a significant amount of growth hormone release. In still other embodiments, the modulator is a compound of formula I, II and/or III.

Additional aspects of the present invention provide methods of diagnosing tumors and/or acromegaly, comprising administering compounds of the present invention and a radiolabeled metal binding agent and detecting the binding of the composition to a biological target, and treating tumors and/or acromegaly comprising administering a therapeutically effective amount of a composition comprising a compound of the present invention.

Further aspects of the present invention relate to methods of making the compounds of formula I, II and/or III.

Aspects of the present invention further relate to methods of preventing and/or treating disorders described herein, in particular, gastrointestinal disorders, including post-operative ileus, gastroparesis, such as diabetic and post-surgical gastroparesis, opioid-induced bowel dysfunction, chronic intestinal pseudo-obstruction, short bowel syndrome, emesis such as caused by cancer chemotherapy, constipation such as associated with the hypomotility phase of irritable bowel syndrome (IBS), delayed gastric emptying associated with wasting conditions, gastroesophageal reflux disease (GERD), gastric ulcers, Crohn's disease, gastrointestinal disorders characterized by dysmotility and other diseases and disorders of the gastrointestinal tract.

The present invention also relates to compounds of formula I, II and/or III used for the preparation of a medicament for prevention and/or treatment of the disorders described herein.

The foregoing and other aspects of the present invention are explained in greater detail in the specification set forth below.

DETAILED DESCRIPTION

Figure 1:
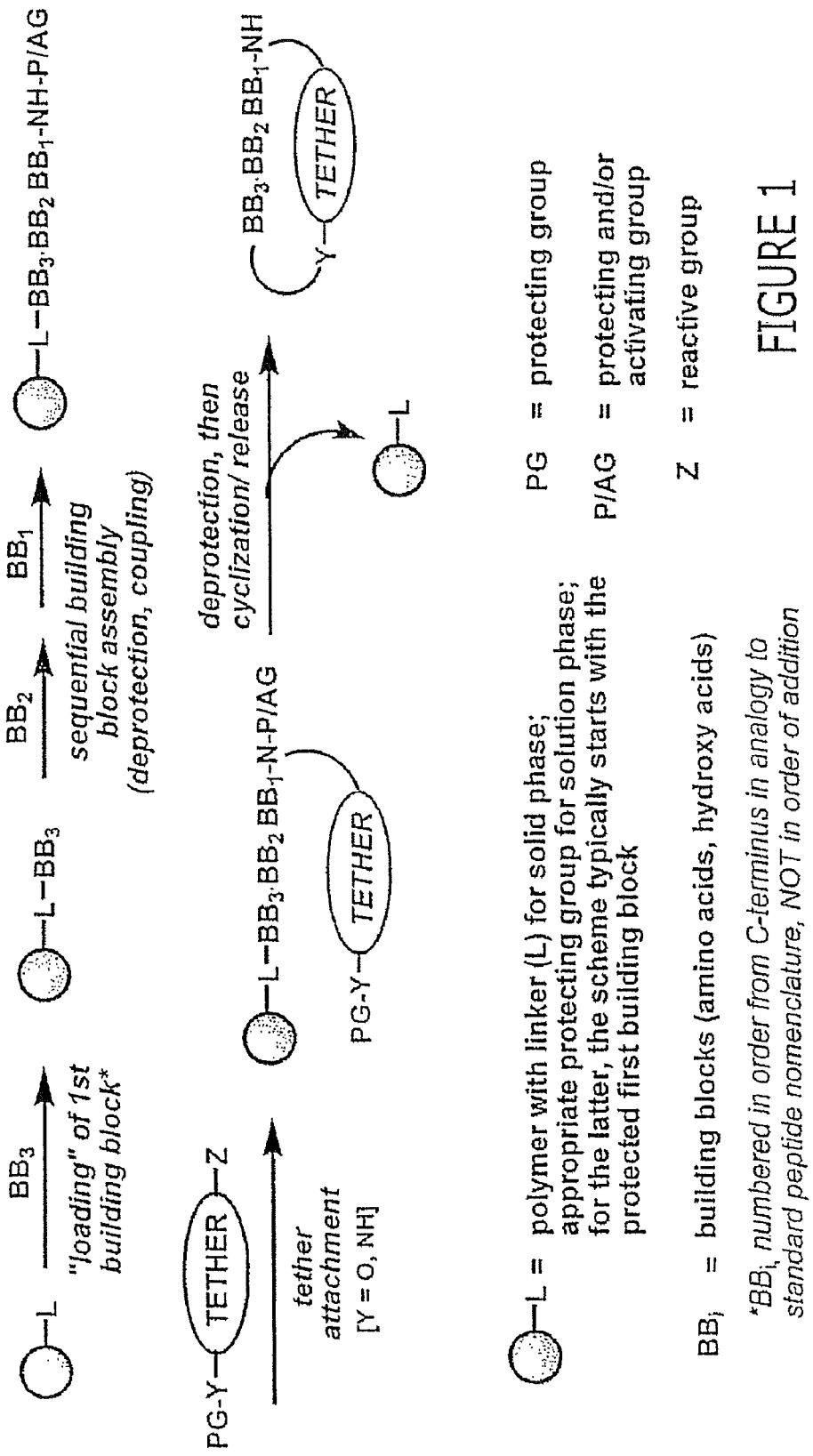
FIG. 1 shows a scheme presenting a general synthetic strategy to provide conformationally-defined macrocycles of the present invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

The term "alkyl" refers to straight or branched chain saturated or partially unsaturated hydrocarbon groups having from 1 to 20 carbon atoms, in some instances 1 to 8 carbon atoms. The term "lower alkyl" refers to alkyl groups containing 1 to 6 carbon atoms. Examples of alkyl groups include, but are not limited to, methyl, ethyl, isopropyl, tert-butyl, 3-hexenyl, and 2-butynyl. By "unsaturated" is meant the presence of 1, 2 or 3 double or triple bonds, or a combination of the two. Such alkyl groups may also be optionally substituted as described below.

When a subscript is used with reference to an alkyl or other hydrocarbon group defined herein, the subscript refers to the number of carbon atoms that the group may contain. For example, $C_2$-$C_4$ alkyl indicates an alkyl group with 2, 3 or 4 carbon atoms.

The term "cycloalkyl" refers to saturated or partially unsaturated cyclic hydrocarbon groups having from 3 to 15 carbon atoms in the ring, in some instances 3 to 7, and to alkyl groups containing said cyclic hydrocarbon groups. Examples of cycloalkyl groups include, but are not limited to, cyclopropyl, cyclopropylmethyl, cyclopentyl, 2-(cyclohexyl)ethyl, cycloheptyl, and cyclohexenyl. Cycloalkyl as defined herein also includes groups with multiple carbon rings, each of which may be saturated or partially unsaturated, for example decalinyl, [2.2.1]-bicycloheptanyl or adamantanyl. All such cycloalkyl groups may also be optionally substituted as described below.

The term "aromatic" refers to an unsaturated cyclic hydrocarbon group having a conjugated pi electron system that contains 4n+2 electrons where n is an integer greater than or equal to 1. Aromatic molecules are typically stable and are depicted as a planar ring of atoms with resonance structures that consist of alternating double and single bonds, for example benzene or naphthalene.

The term "aryl" refers to an aromatic group in a single or fused carbocyclic ring system having from 6 to 15 ring atoms, in some instances 6 to 10, and to alkyl groups containing said aromatic groups. Examples of aryl groups include, but are not limited to, phenyl, 1-naphthyl, 2-naphthyl and benzyl. Aryl as defined herein also includes groups with multiple aryl rings which may be fused, as in naphthyl and anthracenyl, or unfused, as in biphenyl and terphenyl. Aryl also refers to bicyclic or tricyclic carbon rings, where one of the rings is aromatic and the others of which may be saturated, partially unsaturated or aromatic, for example, indanyl or tetrahydronaphthyl (tetralinyl). All such aryl groups may also be optionally substituted as described below.

The term "heterocycle" or "heterocyclic" refers to saturated or partially unsaturated monocyclic, bicyclic or tricyclic groups having from 3 to 15 atoms, in some instances 3 to 7, with at least one heteroatom in at least one of the rings, said heteroatom being selected from O, S or N. Each ring of the heterocyclic group can contain one or two O atoms, one or two S atoms, one to four N atoms, provided that the total number of heteroatoms in each ring is four or less and each ring contains at least one carbon atom. The fused rings completing the bicyclic or tricyclic heterocyclic groups may contain only carbon atoms and may be saturated or partially unsaturated. The N and S atoms may optionally be oxidized and the N atoms may optionally be quaternized. Heterocyclic also refers to alkyl groups containing said monocyclic, bicyclic or tricyclic heterocyclic groups. Examples of heterocyclic rings include, but are not limited to, 2- or 3-piperidinyl, 2- or 3-piperazinyl, 2- or 3-morpholinyl. All such heterocyclic groups may also be optionally substituted as described below The term "heteroaryl" refers to an aromatic group in a single or fused ring system having from 5 to 15 ring atoms, in some instances 5 to 10, which have at least one heteroatom in at least one of the rings, said heteroatom being selected from O, S or N. Each ring of the heteroaryl group can contain one or two O atoms, one or two S atoms, one to four N atoms, provided that the total number of heteroatoms in each ring is four or less and each ring contains at least one carbon atom. The fused rings completing the bicyclic or tricyclic groups may contain only carbon atoms and may be saturated, partially unsaturated or aromatic. In structures where the lone pair of electrons of a nitrogen atom is not involved in completing the aromatic pi electron system, the N atoms may optionally be quaternized or oxidized to the N-oxide. Heteroaryl also refers to alkyl groups containing said cyclic groups. Examples of monocyclic heteroaryl groups include, but are not limited to pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to indolyl, benzothiazolyl, benzoxazolyl, benzothienyl, quinolinyl, tetrahydroisoquinolinyl, isoquinolinyl, benzimidazolyl, benzopyranyl, indolizinyl, benzopyranyl, isobenzofuranyl, chromonyl, coumarinyl, benzopyranyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrolinyl, acridinyl, phenanthridinyl, and xanthenyl. All such heteroaryl groups may also be optionally substituted as described below.

The term "hydroxy" refers to the group —OH.

The term "alkoxy" refers to the group —OR$_a$, wherein R$_a$ is alkyl, cycloalkyl or heterocyclic. Examples include, but are not limited to methoxy, ethoxy, tert-butoxy, cyclohexyloxy and tetrahydropyranyloxy.

The term "aryloxy" refers to the group —OR$_b$ wherein R$_b$ is aryl or heteroaryl. Examples include, but are not limited to phenoxy, benzyloxy and 2-naphthyloxy.

The term "acyl" refers to the group —C(=O)—R$_c$ wherein R$_c$ is alkyl, cycloalkyl, heterocyclic, aryl or heteroaryl. Examples include, but are not limited to, acetyl, benzoyl and furoyl.

The term "amino acyl" indicates an acyl group that is derived from an amino acid.

The term "amino" refers to an —NR$_d$R$_e$ group wherein R$_d$ and R$_e$ are independently selected from the group consisting of hydrogen, alkyl, cycloalkyl, heterocyclic, aryl and heteroaryl. Alternatively, R$_d$ and R$_e$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amido" refers to the group —C(=O)—NR$_f$R$_g$ wherein R$_f$ and R$_g$ are independently selected from the group consisting of hydrogen, alkyl, cycloalkyl, heterocyclic, aryl and heteroaryl. Alternatively, R$_f$ and R$_g$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amidino" refers to the group —C(=NR$_h$)NR$_i$R$_j$ wherein R$_h$ is selected from the group consisting of hydrogen, alkyl, cycloalkyl, heterocyclic, aryl and heteroaryl; and R$_i$ and R$_j$ are independently selected from the group consisting of hydrogen, alkyl, cycloalkyl, heterocyclic, aryl and heteroaryl. Alternatively, R$_i$ and R$_j$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carboxy" refers to the group —CO$_2$H.

The term "carboxyalkyl" refers to the group —CO$_2$R$_k$, wherein R$_k$ is alkyl, cycloalkyl or heterocyclic.

The term "carboxyaryl" refers to the group —CO$_2$R$_m$, wherein R$_m$ is aryl or heteroaryl.

The term "cyano" refers to the group —CN.

The term "formyl" refers to the group —C(=O)H, also denoted —CHO.

The term "halo," "halogen" or "halide" refers to fluoro, fluorine or fluoride, chloro, chlorine or chloride, bromo, bromine or bromide, and iodo, iodine or iodide, respectively.

The term "oxo" refers to the bivalent group =O, which is substituted in place of two hydrogen atoms on the same carbon to form a carbonyl group.

The term "mercapto" refers to the group —SR$_n$ wherein R$_n$ is hydrogen, alkyl, cycloalkyl, heterocyclic, aryl or heteroaryl.

The term "nitro" refers to the group —NO$_2$.

The term "trifluoromethyl" refers to the group —CF$_3$.

The term "sulfinyl" refers to the group —S(=O)R$_p$ wherein R$_p$ is alkyl, cycloalkyl, heterocyclic, aryl or heteroaryl.

The term "sulfonyl" refers to the group —S(=O)$_2$—R$_{q1}$ wherein R$_{q1}$ is alkyl, cycloalkyl, heterocyclic, aryl or heteroaryl.

The term "aminosulfonyl" refers to the group —NR$_{q2}$—S(=O)$_2$—R$_{q3}$ wherein R$_{q2}$ is hydrogen, alkyl, cycloalkyl, heterocyclic, aryl or heteroaryl; and R$_{q3}$ is alkyl, cycloalkyl, heterocyclic, aryl or heteroaryl.

The term "sulfonamido" refers to the group —S(=O)$_2$—NR$_r$R$_s$ wherein R$_r$ and R$_s$ are independently selected from the group consisting of hydrogen, alkyl, cycloalkyl, heterocyclic, aryl or heteroaryl. Alternatively, R$_r$ and R$_s$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carbamoyl" refers to a group of the formula —N(R$_t$)—C(=O)—OR$_u$ wherein R$_t$ is selected from hydrogen, alkyl, cycloalkyl, heterocyclic, aryl or heteroaryl; and R$_u$ is selected from alkyl, cycloalkyl, heterocyclic, aryl or heteroaryl.

The term "guanidino" refers to a group of the formula —N(R$_v$)—C(=NR$_w$)—NR$_x$R$_y$, wherein R$_v$, R$_w$, R$_x$ and R$_y$ are independently selected from hydrogen, alkyl, cycloalkyl, heterocyclic, aryl or heteroaryl. Alternatively, R$_x$ and R$_y$ together form a heterocyclic ring or 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "ureido" refers to a group of the formula —N($R_z$)—C(=O)—N$R_{aa}R_{bb}$ wherein $R_z$, $R_{aa}$ and $R_{bb}$ are independently selected from hydrogen, alkyl, cycloalkyl, heterocyclic, aryl or heteroaryl. Alternatively, $R_{aa}$ and $R_{bb}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by substituents independently selected from unsubstituted alkyl, unsubstituted cycloalkyl, unsubstituted heterocyclic, unsubstituted awl, unsubstituted heteroaryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, guanidino, ureido and groups of the formulas —N$R_{cc}$C(=O)$R_{dd}$, —N$R_{ee}$C(=N$R_{ff}$)$R_{gg}$, —OC(=O)N$R_{hh}R_{ii}$, —OC(=O)$R_{jj}$, —OC(=O)O$R_{kk}$, —N$R_{mm}$SO$_2R_{nn}$, or —N$R_{pp}$SO$_2$N$R_{qq}$N$_{rr}$ wherein $R_{cc}$, $R_{dd}$, $R_{ee}$, $R_{ff}$, $R_{gg}$, $R_{hh}$, $R_{ii}$, $R_{jj}$, $R_{mm}$, $R_{pp}$, $R_{qq}$ and $R_{rr}$ are independently selected from hydrogen, unsubstituted alkyl, unsubstituted cycloalkyl, unsubstituted heterocyclic, unsubstituted aryl or unsubstituted heteroaryl; and wherein $R_{kk}$ and $R_{nn}$ are independently selected from unsubstituted alkyl, unsubstituted cycloalkyl, unsubstituted heterocyclic, unsubstituted aryl or unsubstituted heteroaryl. Alternatively, $R_{gg}$ and $R_{hh}$, $R_{jj}$ and $R_{kk}$ or $R_{pp}$ and $R_{qq}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N. In addition, the term "substituted" for awl and heteroaryl groups includes as an option having one of the hydrogen atoms of the group replaced by cyano, nitro or trifluoromethyl.

A substitution is made provided that any atom's normal valency is not exceeded and that the substitution results in a stable compound. Generally, when a substituted form of a group is present, such substituted group is preferably not further substituted or, if substituted, the substituent comprises only a limited number of substituted groups, in some instances 1, 2, 3 or 4 such substituents.

When any variable occurs more than one time in any constituent or in any formula herein, its definition on each occurrence is independent of its definition at every other occurrence. Also, combinations of substituents and/or variables are permissible only if such combinations result in stable compounds.

A "stable compound" or "stable structure" refers to a compound that is sufficiently robust to survive isolation to a useful degree of purity and formulation into an efficacious therapeutic agent.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "unnatural" or "unusual" refers to the wide selection of non-natural, rare or synthetic amino acids such as those described by Hunt, S. in *Chemistry and Biochemistry of the Amino Acids*, Barrett, G. C., Ed., Chapman and Hall: New York, 1985.

The term "residue" with reference to an amino acid or amino acid derivative refers to a group of the formula:

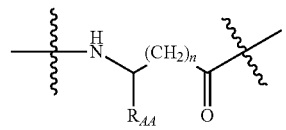

wherein $R_{AA}$ is an amino acid side chain, and n=0, 1 or 2 in this instance.

The term "fragment" with respect to a dipeptide, tripeptide or higher order peptide derivative indicates a group that contains two, three or more, respectively, amino acid residues.

The term "amino acid side chain" refers to any side chain from a standard or unnatural amino acid, and is denoted $R_{AA}$. For example, the side chain of alanine is methyl, the side chain of valine is isopropyl and the side chain of tryptophan is 3-indolylmethyl.

The term "agonist" refers to a compound that duplicates at least some of the effect of the endogenous ligand of a protein, receptor, enzyme or the like.

The term "antagonist" refers to a compound that inhibits at least some of the effect of the endogenous ligand of a protein, receptor, enzyme or the like.

The term "growth hormone secretagogue" (GHS) refers to any exogenously administered compound or agent that directly or indirectly stimulates or increases the endogenous release of growth hormone, growth hormone-releasing hormone, or somatostatin in an animal, in particular, a human. A GHS may be peptidic or non-peptidic in nature, in some instances, with an agent that can be administered orally. In some instances, the agent can induce a pulsatile response.

The term "modulator" refers to a compound that imparts an effect on a biological or chemical process or mechanism. For example, a modulator may increase, facilitate, upregulate, activate, inhibit, decrease, block, prevent, delay, desensitize, deactivate, down regulate, or the like, a biological or chemical process or mechanism. Accordingly, a modulator can be an "agonist" or an "antagonist." Exemplary biological processes or mechanisms affected by a modulator include, but are not limited to, receptor binding and hormone release or secretion. Exemplary chemical processes or mechanisms affected by a modulator include, but are not limited to, catalysis and hydrolysis.

The term "variant" when applied to a receptor is meant to include dimers, trimers, tetramers, pentamers and other biological complexes containing multiple components. These components can be the same or different.

The term "peptide" refers to a chemical compound comprised of two or more amino acids covalently bonded together.

The term "peptidomimetic" refers to a chemical compound designed to mimic a peptide, but which contains structural differences through the addition or replacement of one of more functional groups of the peptide in order to modulate its activity or other properties, such as solubility, metabolic stability, oral bioavailability, lipophilicity, permeability, etc. This can include replacement of the peptide bond, side chain modifications, truncations, additions of functional groups, etc. When the chemical structure is not derived from the peptide, but mimics its activity, it is often referred to as a "non-peptide peptidomimetic."

The term "peptide bond" refers to the amide [—C(=O)—NH—] functionality with which individual amino acids are typically covalently bonded to each other in a peptide.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in "Protective Groups in Organic Synthesis," Theodora W. Greene and Peter G. Wuts, editors, John Wiley & Sons, New York, 3$^{rd}$ edition, 1999 [ISBN 0471160199]. Examples of amino protecting groups include, but are not limited to, phthalimido, trichloroacetyl, benzyloxycarbonyl, tert-butoxycarbonyl, and adamantyloxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9-fluorenylmethoxycarbonyl (Fmoc), tert-butoxycarbonyl (Boc) and $\alpha,\alpha$-dimethyl-3,5-dimethoxybenzyloxycarbonyl (Ddz). For a recent discussion of newer nitrogen protecting groups: Theodoridis, G. *Tetrahedron* 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to methyl ester, tert-butyl ester, benzyl ester, trimethylsilylethyl ester, and 2,2,2-trichloroethyl ester.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry.

The term "solid support," "solid phase" or "resin" refers to a mechanically and chemically stable polymeric matrix utilized to conduct solid phase chemistry. This is denoted by "Resin," "P—" or the following symbol:

Examples of appropriate polymer materials include, but are not limited to, polystyrene, polyethylene, polyethylene glycol, polyethylene glycol grafted or covalently bonded to polystyrene (also termed PEG-polystyrene, TentaGel™, Rapp, W.; Zhang, L.; Bayer, E. In *Innovations and Perspectives in Solid Phase Synthesis. Peptides, Polypeptides and Oligonucleotides*; Epton, R., Ed.; SPCC Ltd.: Birmingham, UK; p 205), polyacrylate (CLEAR™), polyacrylamide, polyurethane, PEGA [polyethyleneglycol poly(N,N-dimethylacrylamide) co-polymer, Meldal, M. *Tetrahedron Lett.* 1992, 33, 3077-3080], cellulose, etc. These materials can optionally contain additional chemical agents to form cross-linked bonds to mechanically stabilize the structure, for example polystyrene cross-linked with divinylbenzene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, —$NH_2$ or —OH, for further derivatization or reaction. The term is also meant to include "Ultraresins" with a high proportion ("loading") of these functional groups such as those prepared from polyethyleneimines and cross-linking molecules (Barth, M.; Rademann, J. *J. Comb. Chem.* 2004, 6, 340-349). At the conclusion of the synthesis, resins are typically discarded, although they have been shown to be able to be reused such as in Frechet, J. M. J.; Haque, K. E. *Tetrahedron Lett.* 1975, 16, 3055.

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed "liquid-phase" chemistry.

The term "linker" when used in reference to solid phase chemistry refers to a chemical group that is bonded covalently to a solid support and is attached between the support and the substrate typically in order to permit the release (cleavage) of the substrate from the solid support. However, it can also be used to impart stability to the bond to the solid support or merely as a spacer element. Many solid supports are available commercially with linkers already attached.

Abbreviations used for amino acids and designation of peptides follow the rules of the IUPAC-IUB Commission of Biochemical Nomenclature in *J. Biol. Chem.* 1972, 247, 977-983. This document has been updated: *Biochem. J.,* 1984, 219, 345-373; *Eur. J. Biochem.,* 1984, 138, 9-37; 1985, 152, 1; *Internat. J. Pept. Prot. Res.,* 1984, 24, following p 84; *J. Biol. Chem.,* 1985, 260, 14-42; *Pure Appl. Chem.,* 1984, 56, 595-624; *Amino Acids and Peptides,* 1985, 16, 387-410; and in *Biochemical Nomenclature and Related Documents,* 2nd edition, Portland Press, 1992, pp 39-67. Extensions to the rules were published in the JCBN/NC-IUB Newsletter 1985, 1986, 1989; see *Biochemical Nomenclature and Related Documents,* 2nd edition, Portland Press, 1992, pp 68-69.

The term "effective amount" or "effective" is intended to designate a dose that causes a relief of symptoms of a disease or disorder as noted through clinical testing and evaluation, patient observation, and/or the like, and/or a dose that causes a detectable change in biological or chemical activity. The detectable changes may be detected and/or further quantified by one skilled in the art for the relevant mechanism or process. As is generally understood in the art, the dosage will vary depending on the administration routes, symptoms and body weight of the patient but also depending upon the compound being administered.

Administration of two or more compounds "in combination" means that the two compounds are administered closely enough in time that the presence of one alters the biological effects of the other. The two compounds can be administered simultaneously (concurrently) or sequentially. Simultaneous administration can be carried out by mixing the compounds prior to administration, or by administering the compounds at the same point in time but at different anatomic sites or using different routes of administration. The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The term "pharmaceutically active metabolite" is intended to mean a pharmacologically active product produced through metabolism in the body of a specified compound.

The term "solvate" is intended to mean a pharmaceutically acceptable solvate form of a specified compound that retains the biological effectiveness of such compound. Examples of solvates, without limitation, include compounds of the invention in combination with water, isopropanol, ethanol, methanol, DMSO, ethyl acetate, acetic acid, or ethanolamine.

1. Compounds

Novel macrocyclic compounds of the present invention include macrocyclic compounds comprising a building block structure including a tether component that undergoes cyclization to form the macrocyclic compound. The building block structure can comprise amino acids (standard and unnatural), hydroxy acids, hydrazino acids, aza-amino acids, specialized moieties such as those that play a role in the introduction of peptide surrogates and isosteres, and a tether component as described herein. The tether component can be selected from the following:

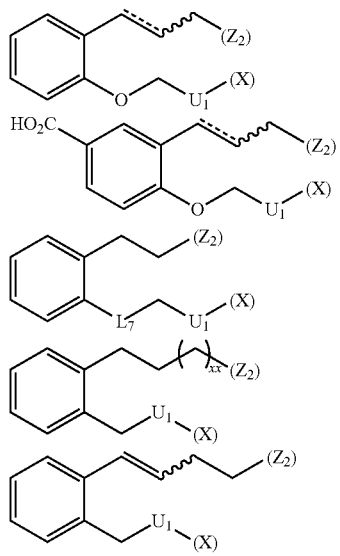

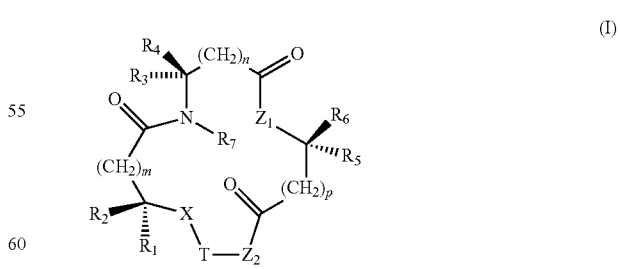

wherein $(Z_2)$ is the site of a covalent bond of T to $Z_2$, and $Z_2$ is as defined below for formula I, and wherein (X) is the site of a covalent bond of T to X, and X is as defined below for formula I; $L_7$ is —$CH_2$— or —O—; $U_1$ is —$CR_{101}R_{102}$— or —C(=O)—; $R_{100}$ is lower alkyl; $R_{101}$ and $R_{102}$ are each independently hydrogen, lower alkyl or substituted lower alkyl; xx is 2 or 3; yy is 1 or 2; zz is 1 or 2; and aaa is 0 or 1.

Macrocyclic compounds of the present invention further include those of formula I, formula II and/or formula III:

(I)

or an optical isomer, enantiomer, diastereomer, racemate or stereochemical mixture thereof, wherein:

$R_1$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below, or alternatively $R_1$ and $R_9$ together form a 3-, 4-, 5-, 6- or 7-membered ring, optionally comprising an O, S or additional N atom in the ring, wherein the ring is optionally substituted with $R_8$ as defined below;

$R_2$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below; or alternatively $R_2$ and $R_9$ together form a 3-, 4-, 5-, 6- or 7-membered ring, optionally comprising an O, S or additional N atom in the ring, wherein the ring is optionally substituted with $R_8$ as defined below;

$R_3$ is hydrogen or the side chain of an amino acid, or alternatively $R_3$ and $R_4$ together form a 3-, 4-, 5-, 6- or 7-membered ring, optionally comprising an O or S atom in the ring, wherein the ring is optionally substituted with $R_8$ as defined below, or alternatively, $R_3$ and $R_7$ or $R_3$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_4$ is hydrogen or the side chain of an amino acid, or alternatively $R_4$ and $R_3$ together form a 3-, 4-, 5-, 6- or 7-membered ring, optionally comprising an O or S atom in the ring, wherein the ring is optionally substituted with $R_8$ as defined below, or alternatively $R_4$ and $R_7$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_5$ and $R_6$ are each independently hydrogen or the side chain of an amino acid or alternatively $R_5$ and $R_6$ together form a 3-, 4-, 5-, 6- or 7-membered ring, optionally comprising an O, S or N atom in the ring, wherein the ring is optionally substituted with $R_8$ as defined below;

$R_7$ is hydrogen, lower alkyl, substituted lower alkyl, cycloalkyl, substituted cycloalkyl, a heterocyclic group, or a substituted heterocyclic group, or alternatively $R_3$ and $R_7$ or $R_4$ and $R_7$ together form a 4-, 5-, 6-, 7- or 8-membered heterocyclic ring optionally comprising an O, S or additional N atom in the ring, wherein the ring is optionally substituted with $R_8$ as described below;

$R_8$ is substituted for one or more hydrogen atoms on the 3-, 4-, 5-, 6-, 7- or 8-membered ring structure and is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_8$ is a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

X is O, $NR_9$ or $N(R_{10})_2^+$;
wherein $R_9$ is hydrogen, lower alkyl, substituted lower alkyl, sulfonyl, sulfonamido or amidino and $R_{10}$ is hydrogen, lower alkyl, or substituted lower alkyl, or alternatively $R_9$ and $R_1$ together form a 3-, 4-, 5-, 6- or 7-membered ring, optionally comprising an O, S or additional N atom in the ring, wherein the ring is optionally substituted with $R_8$ as defined above;

$Z_1$ is O or $NR_{11}$,
wherein $R_{11}$ is hydrogen, lower alkyl, or substituted lower alkyl, or alternatively $R_3$ and $R_{11}$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined above;

$Z_2$ is O or $NR_{12}$, wherein $R_{12}$ is hydrogen, lower alkyl, or substituted lower alkyl;

m, n and p are each independently 0, 1 or 2;

T is a bivalent radical of formula IV:

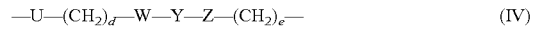

$$—U—(CH_2)_d—W—Y—Z—(CH_2)_e— \qquad (IV)$$

wherein d and e are each independently 0, 1, 2, 3, 4 or 5; Y and Z are each optionally present; U is —$CR_{21}R_{22}$— or —C(=O)— and is bonded to X of formula I; W, Y and Z are each independently selected from the group consisting of —O—, —$NR_{23}$—, —S—, —SO—, —$SO_2$—, —C(=O)—O—, —O—C(=O)—, —C(=O)—NH—, —NH—C(=O)—, —$SO_2$—NH—, —NH—$SO_2$—, —$CR_{24}R_{25}$—, —CH=CH— with the configuration Z or E, —C≡C— and the ring structures below:

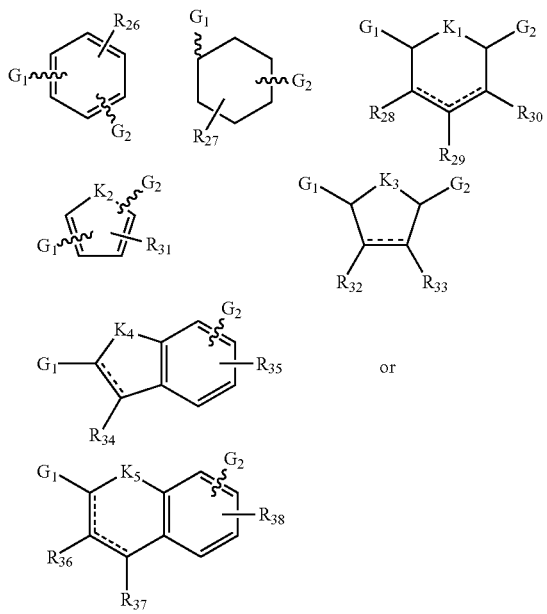

wherein $G_1$ and $G_2$ are each independently a covalent bond or a bivalent radical selected from the group consisting of —O—, —$NR_{39}$—, —S—, —SO—, —$SO_2$—, —C(=O)—, —C(=)—O—, —O—C(=O)—, —C(=O)NH—, —NH—C(=O)—, —$SO_2$—NH—, —NH—$SO_2$—, —$CR_{40}R_{41}$—, —CH=CH— with the configuration Z or E, and —C≡C—; with $G_1$ being bonded closest to the group U; wherein any carbon atom in the rings not otherwise defined, is optionally replaced by N, with the proviso that the ring cannot contain more than four N atoms; $K_1$, $K_2$, $K_3$, $K_4$ and $K_5$ are each independently O, $NR_{42}$ or S, wherein $R_{42}$ is as defined below;

$R_{21}$ and $R_{22}$ are each independently hydrogen, lower alkyl, or substituted lower alkyl, or alternatively $R_{21}$ and $R_{22}$ together form a 3- to 12-membered cyclic ring optionally comprising one or more heteroatoms selected from the group consisting of O, S and N, wherein the ring is optionally substituted with $R_8$ as defined above;

$R_{23}$, $R_{39}$ and $R_{42}$ are each independently hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl or sulfonamido;

$R_{24}$ and $R_{25}$ are each independently hydrogen, lower alkyl, substituted lower alkyl, $R_{AA}$, wherein $R_{AA}$ is a side chain of an amino acid such as a standard or unusual amino acid, or alternatively $R_{24}$ and $R_{25}$ together form a 3- to 12-membered cyclic ring optionally comprising one or more heteroatoms selected from the group consisting of O, S and N; or alternatively one of $R_{24}$ or $R_{25}$ is hydroxy, alkoxy, aryloxy, amino, mercapto, carbamoyl, amidino, ureido or guanidino while the other is hydrogen, lower alkyl or substituted lower alkyl, except when the carbon to which $R_{24}$ and $R_{25}$ are bonded is also bonded to another heteroatom;

$R_{26}$, $R_{31}$, $R_{35}$ and $R_{38}$ are each optionally present and, when present, are substituted for one or more hydrogen atoms on the indicated ring and each is independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl and sulfonamido;

$R_{27}$ is optionally present and is substituted for one or more hydrogen atoms on the indicated ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl and sulfonamido;

$R_{28}$, $R_{29}$, $R_{30}$, $R_{32}$, $R_{33}$, $R_{34}$, $R_{36}$ and $R_{37}$ are each optionally present and, when no double bond is present to the carbon atom to which it is bonded in the ring, two groups are optionally present, and when present, is substituted for one hydrogen present in the ring, or when no double bond is present to the carbon atom to which it is bonded in the ring, is substituted for one or both of the two hydrogen atoms present on the ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen; and $R_{40}$ and $R_{41}$ are each independently hydrogen, lower alkyl, substituted lower alkyl, $R_{AA}$ as defined above, or alternatively $R_{40}$ and $R_{41}$ together form a 3- to 12-membered cyclic ring optionally comprising one or more heteroatoms selected from the group consisting of O, S and N wherein the ring is optionally substituted with $R_8$ as defined above, or alternatively one of $R_{40}$ and $R_{41}$ is hydroxy, alkoxy, aryloxy, amino, mercapto, carbamoyl, amidino, ureido or guanidino, while the other is hydrogen, lower alkyl or substituted lower alkyl, except when the carbon to which $R_{40}$ and $R_{41}$ are bonded is also bonded to another heteroatom;

with the proviso that T is not an amino acid residue, dipeptide fragment, tripeptide fragment or higher order peptide fragment comprising standard amino acids;

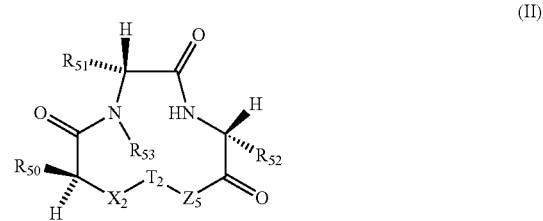

(II)

or an optical isomer, enantiomer, diastereomer, racemate or stereochemical mixture thereof, wherein:

$R_{50}$ is $-(CH_2)_{ss}CH_3$, $-CH(CH_3)(CH_2)_{tt}CH_3$, $-(CH_2)_{uu}CH(CH_3)_2$, $-C(CH_3)_3$, $-(CHR_{55})_{vv}-R_{56}$, or $-CH(OR_{57})CH_3$, wherein ss is 1, 2 or 3; tt is 1 or 2; uu is 0, 1 or 2; and vv is 0, 1, 2, 3 or 4; $R_{55}$ is hydrogen or $C_1$-$C_4$ alkyl; $R_{56}$ is amino, hydroxy, alkoxy, cycloalkyl or substituted cycloalkyl; and $R_{57}$ is hydrogen, alkyl, acyl, amino acyl, sulfonyl, carboxyalkyl or carboxyaryl;

$R_{51}$ is hydrogen, $C_1$-$C_4$ alkyl or $C_1$-$C_4$ alkyl substituted with hydroxy or alkoxy;

$R_{52}$ is $-(CHR_{58})_{ww}R_{59}$, wherein ww is 0, 1, 2 or 3; $R_{58}$ is hydrogen, $C_1$-$C_4$ alkyl, amino, hydroxy or alkoxy; $R_{59}$ is aryl, substituted aryl, heteroaryl, substituted heteroaryl, cycloalkyl or substituted cycloalkyl;

$R_{53}$ is hydrogen or $C_1$-$C_4$ alkyl;

$X_2$ is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl;

$Z_5$ is O or $NR_{12}$, wherein $R_{12}$ is hydrogen, lower alkyl, or substituted lower alkyl; and $T_2$ is a bivalent radical of formula V:

$$-U_a-(CH_2)_d-W_a-Y_a-Z_a-(CH_2)_e- \quad (V)$$

wherein d and e are independently 0, 1, 2, 3, 4 or 5; $Y_a$ and $Z_a$ are each optionally present; $U_a$ is $-CR_{60}R_{61}-$ or $-C(=O)-$ and is bonded to $X_2$ of formula II, wherein $R_{60}$ and $R_{61}$ are each independently hydrogen, lower alkyl, or substituted lower alkyl, or alternatively $R_{21}$ and $R_{22}$ together form a 3- to 12-membered cyclic ring optionally comprising one or more heteroatoms selected from the group consisting of O, S and N, wherein the ring is optionally substituted with $R_8$ as defined above; $W_a$, $Y_a$ and $Z_a$ are each independently selected from the group consisting of: $-O-$, $-NR_{62}-$, $-S-$, $-SO-$, $-SO_2-$, $-C(=O)-O-$, $-O-C(=O)-$, $-C(=O)-NH-$, $-NH-C(=O)-$, $-SO_2-NH-$, $-NH-SO_2-$, $-CR_{63}R_{64}-$, $-CH=CH-$ with the configuration Z or E, $-C\equiv C-$, and the ring structures depicted below:

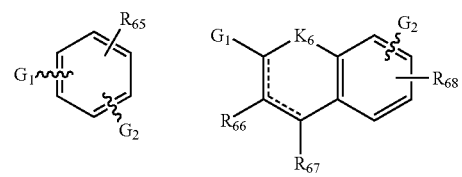

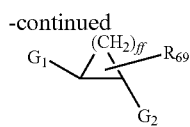

wherein $G_1$ and $G_2$ are as defined above, and wherein any carbon atom in the ring is optionally replaced by N, with the proviso that the aromatic ring cannot contain more than four N atoms and the cycloalkyl ring cannot contain more than two N atoms;

$R_{62}$ is hydrogen, alkyl, substituted alkyl, cycloalkyl, substituted cycloalkyl, a heterocyclic group, a substituted heterocyclic group, aryl, substituted aryl, heteroaryl, substituted heteroaryl, formyl, acyl, carboxyalkyl, carboxyaryl, amido, amidino, sulfonyl or sulfonamido;

$R_{63}$ and $R_{64}$ are each independently hydrogen, lower alkyl, substituted lower alkyl or $R_{AA}$; or alternatively $R_{63}$ and $R_{64}$ together form a 3- to 12-membered cyclic ring optionally comprising one or more heteroatoms selected from the group consisting of O, S and N; or alternatively one of $R_{63}$ and $R_{64}$ is hydroxy, alkoxy, aryloxy, amino, mercapto, carbamoyl, amidino, ureido or guanidino, while the other is hydrogen, lower alkyl or substituted lower alkyl, except when the carbon to which $R_{63}$ and $R_{64}$ are bonded is also bonded to another heteroatom; and $R_{AA}$ indicates the side chain of a standard or unusual amino acid;

$R_{65}$ and $R_{68}$ are each optionally present, and, when present are substituted for one or more hydrogen atoms on the ring and each is independently halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl or sulfonamido;

$R_{66}$ and $R_{67}$ are each optionally present, and when no double bond is present to the carbon atom to which it is bonded in the ring, two groups are optionally present, and, when present, each is substituted for one hydrogen present in the ring, or when no double bond is present to the carbon atom to which it is bonded in the ring, is substituted for one or both of the two hydrogen atoms present on the ring and each is independently alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen;

$R_{69}$ is optionally present, and when present is substituted for one or more hydrogen atoms on the ring and each is independently alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl or sulfonamido;

$K_6$ is O or S; and ff is 1, 2, 3, 4 or 5;

with the proviso that $T_2$ is not an amino acid residue, dipeptide fragment, tripeptide fragment or higher order peptide fragment comprising standard amino acids; or

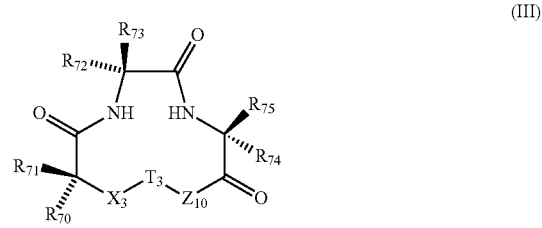

(III)

or an optical isomer, enantiomer, diastereomer, racemate or stereochemical mixture thereof, wherein:

$R_{70}$ is hydrogen, $C_1$-$C_4$ alkyl or alternatively $R_{70}$ and $R_{71}$ together form a 4-, 5-, 6-, 7- or 8-membered ring, optionally comprising an O, N or S atom in the ring, wherein the ring is optionally substituted with $R_{8a}$ as defined below;

$R_{71}$ is hydrogen, —$(CH_2)_{aa}CH_3$, —$CH(CH_3)(CH_2)_{bb}CH_3$, —$(CH_2)_{cc}CH(CH_3)_2$, —$(CH_2)_{dd}$—$R_{76}$ or —$CH(OR_{77})CH_3$ or, alternatively $R_{71}$ and $R_{70}$ together form a 4-, 5-, 6-, 7- or 8-membered ring, optionally comprising an O, N or S atom in the ring, wherein the ring is optionally substituted with $R_{8a}$ as defined below; wherein aa is 0, 1, 2, 3, 4 or 5; bb is 1, 2 or 3; cc is 0, 1, 2 or 3; and dd is 0, 1, 2, 3 or 4; $R_{76}$ is aryl, substituted aryl, heteroaryl, substituted heteroaryl, cycloalkyl or substituted cycloalkyl; $R_{77}$ is hydrogen, alkyl, acyl, amino acyl, sulfonyl, carboxyalkyl or carboxyaryl;

$R_{72}$ is $C_1$-$C_4$ alkyl; or alternatively $R_{72}$ and $R_{73}$ together form a 3-, 4-, 5-, 6- or 7-membered ring, optionally comprising an O or S atom in the ring, wherein the ring is optionally substituted with $R_{8b}$ as defined below;

$R_{73}$ is hydrogen, or alternatively $R_{73}$ and $R_{72}$ together form a 3-, 4-, 5-, 6- or 7-membered ring, optionally comprising an O, S or N atom in the ring, wherein the ring is optionally substituted with $R_{8b}$ as defined below;

$R_{74}$ is hydrogen or $C_1$-$C_4$ alkyl or alternatively $R_{74}$ and $R_{75}$ together form a 3-, 4-, 5-, 6- or 7-membered ring, optionally comprising an O, N or S atom in the ring, wherein the ring is optionally substituted with $R_{8c}$ as defined below;

$R_{75}$ is —$(CHR_{78})R_{79}$ or alternatively $R_{75}$ and $R_{74}$ together form a 3-, 4-, 5-, 6- or 7-membered ring, optionally comprising an O, N or S atom in the ring, wherein the ring is optionally substituted with $R_{8c}$ as defined below; wherein $R_{78}$ is hydrogen, $C_1$-$C_4$ alkyl, amino, hydroxy or alkoxy, and $R_{79}$ is selected from the group consisting of the following structures:

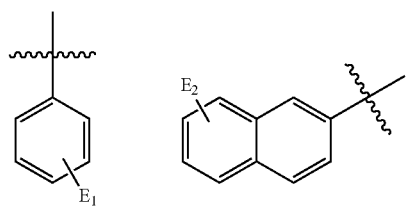

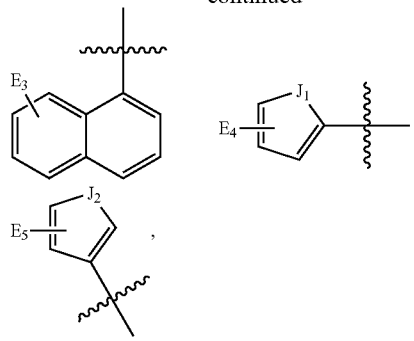

and

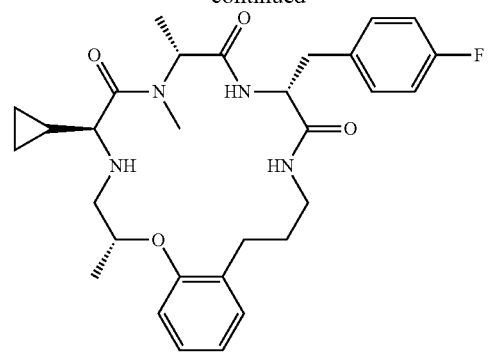

wherein $E_1$, $E_2$, $E_3$, $E_4$ and $E_5$ are each optionally present and when present are each independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, cyano, sulfinyl, sulfonyl and sulfonamido, and represent substitution at one or more available positions on the monocyclic or bicyclic aromatic ring, wherein said substitution is made with the same or different selected group member, and $J_1$ and $J_2$ are each independently O or S;

$R_{8a}$, $R_{8b}$ and $R_{8c}$ are each independently substituted for one or more hydrogen atoms on the 3-, 4-, 5-, 6-, 7- or 8-membered ring structure and are independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_{8a}$, $R_{8b}$ and $R_{8c}$ are each independently a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

$X_3$ is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl;

$Z_{10}$ is O or $NR_{12}$, wherein $R_{12}$ is hydrogen, lower alkyl, or substituted lower alkyl; and $T_3$ is the same as defined for $T_2$ with the exception that $U_a$ is bonded to $X_3$ of formula III.

In some embodiments of the present invention, the compound can have one of the following structures:

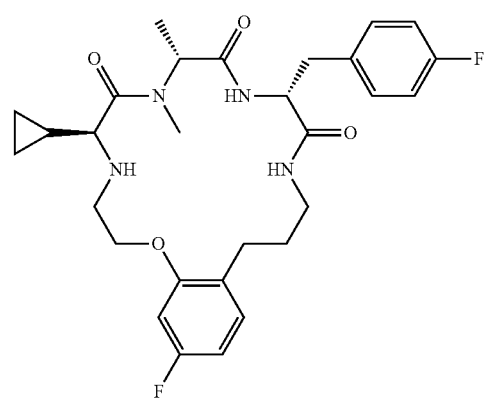

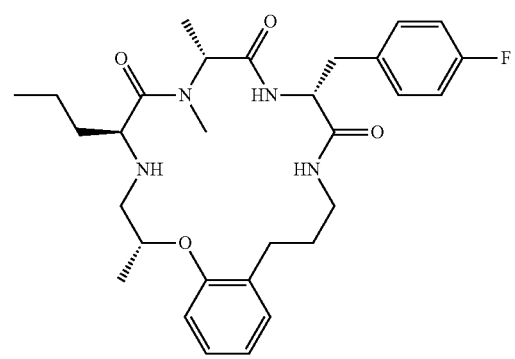

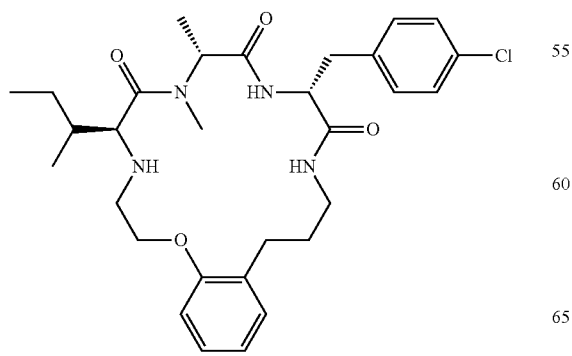

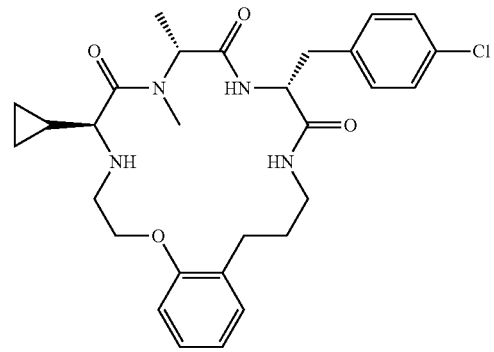

37
-continued
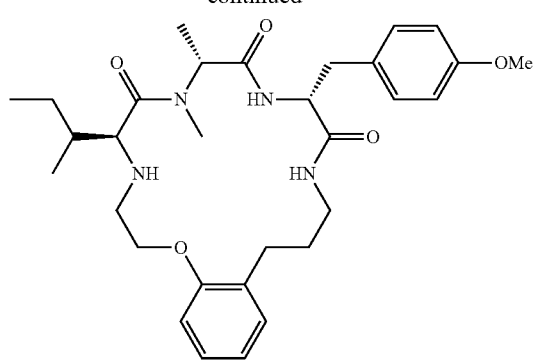
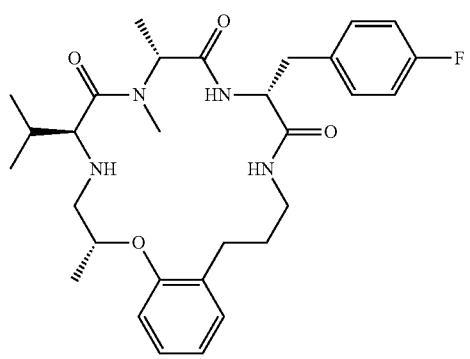
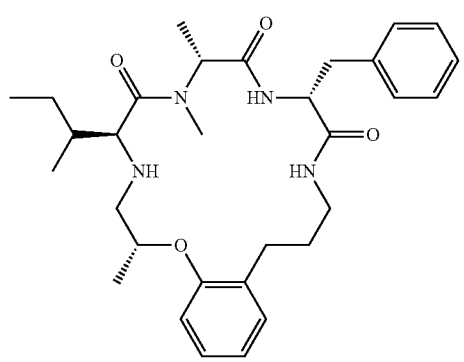
38
-continued
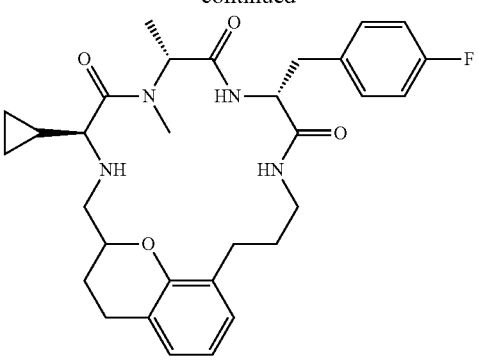
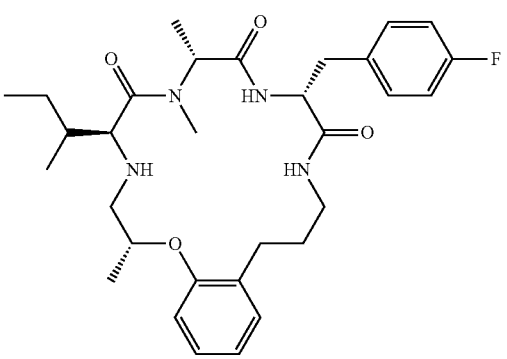
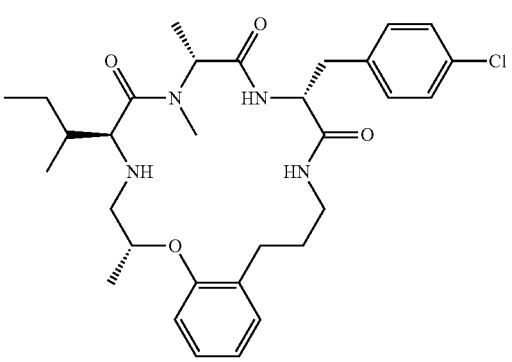

39
-continued
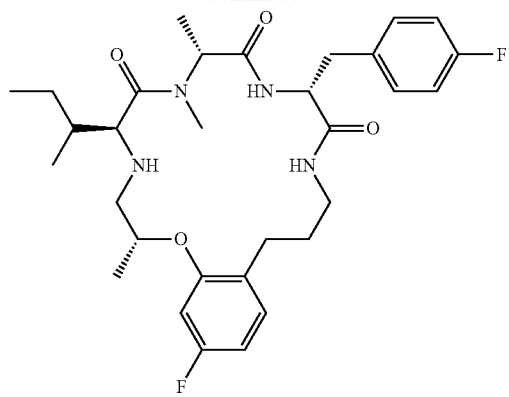
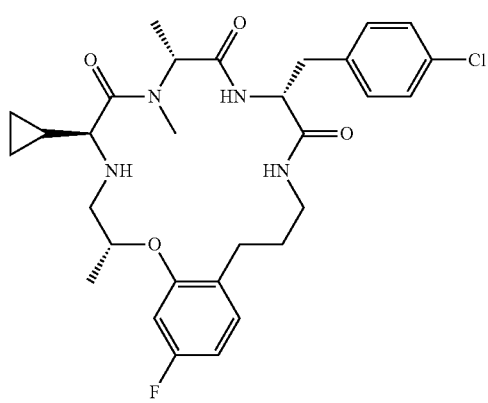
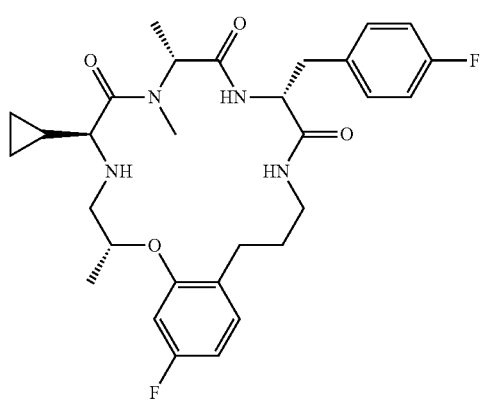
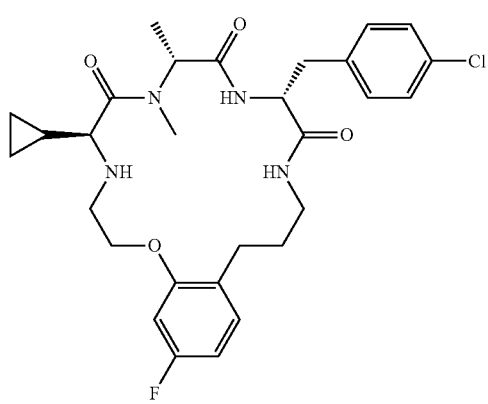
40
-continued
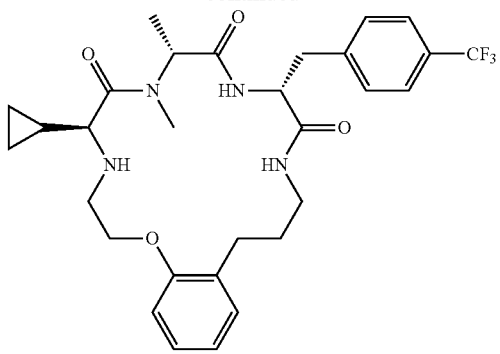
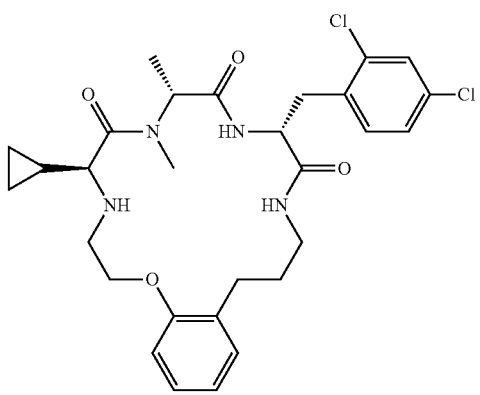
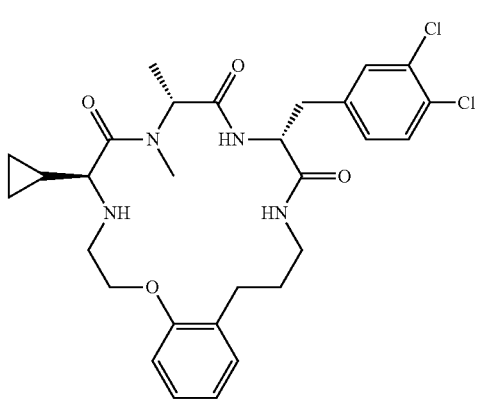
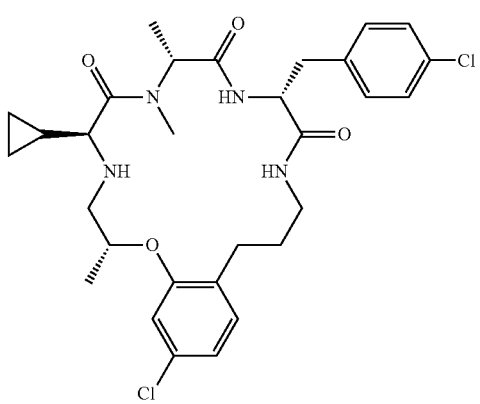

-continued

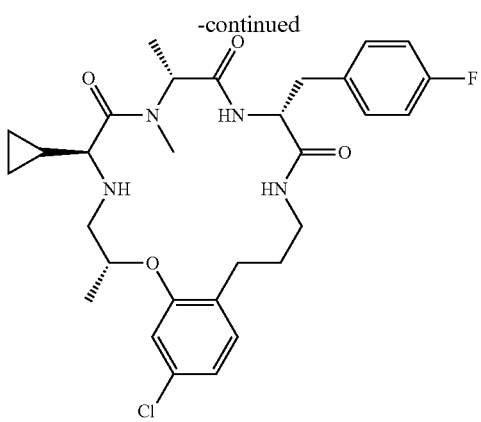

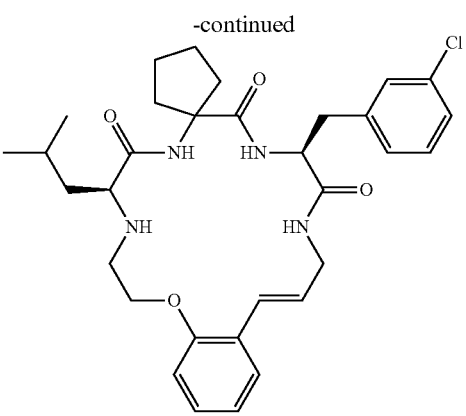

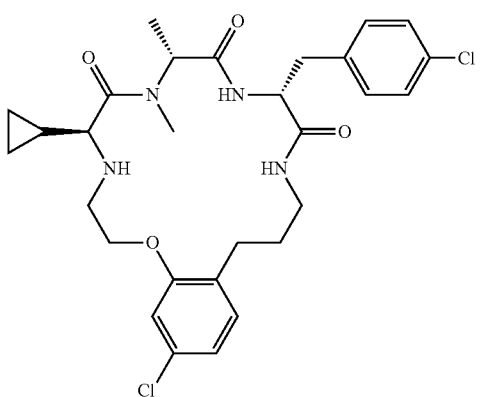

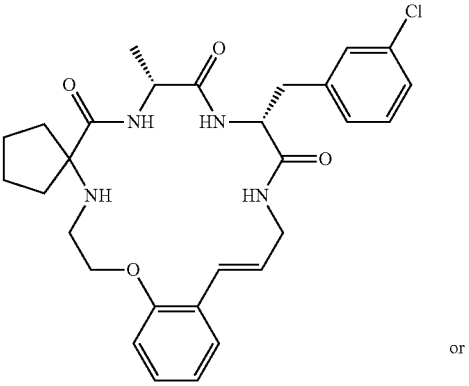

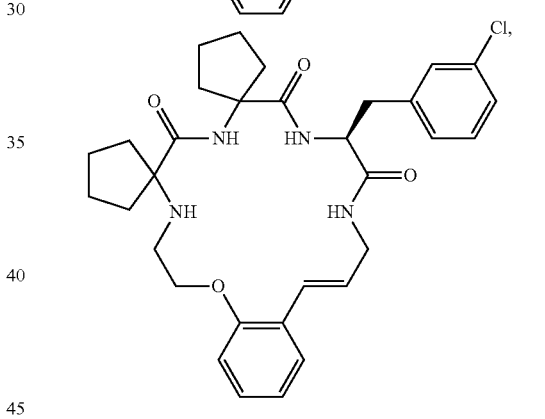

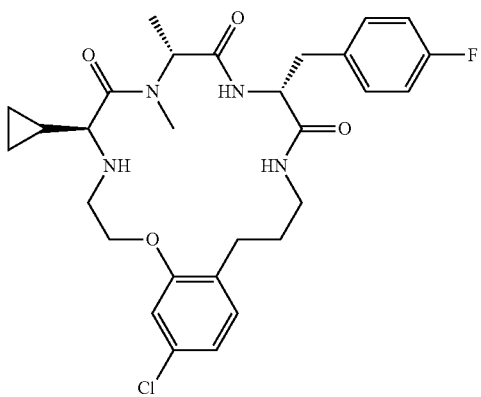

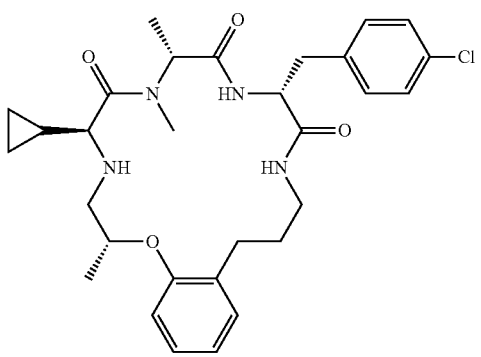

or an optical isomer, enantiomer, diastereomer, racemate or stereochemical mixture thereof.

The present invention includes isolated compounds. An isolated compound refers to a compound that, in some embodiments, comprises at least 10%, at least 25%, at least 50% or at least 70% of the compounds of a mixture. In some embodiments, the compound, pharmaceutically acceptable salt thereof or pharmaceutical composition containing the compound exhibits a statistically significant binding and/or antagonist activity when tested in biological assays at the human ghrelin receptor.

In the case of compounds, salts, or solvates that are solids, it is understood by those skilled in the art that the inventive compounds, salts, and solvates may exist in different crystal or polymorphic forms, all of which are intended to be within the scope of the present invention and specified formulas.

The compounds of formula I, II and/or III disclosed herein have asymmetric centers. The inventive compounds may exist as single stereoisomers, racemates, and/or mixtures of enantiomers and/or diastereomers. All such single stereoisomers, racemates, and mixtures thereof are intended to be within the scope of the present invention. In particular embodiments, however, the inventive compounds are used in optically pure form. The terms "S" and "R" configuration as used herein are as defined by the IUPAC 1974 Recommendations for Section E, Fundamentals of Stereochemistry (*Pure Appl. Chem.* 1976, 45, 13-30.)

Unless otherwise depicted to be a specific orientation, the present invention accounts for all stereoisomeric forms. The compounds may be prepared as a single stereoisomer or a mixture of stereoisomers. The non-racemic forms may be obtained by either synthesis or resolution. The compounds may, for example, be resolved into the component enantiomers by standard techniques, for example formation of diastereomeric pairs via salt formation. The compounds also may be resolved by covalently bonding to a chiral moiety. The diastereomers can then be resolved by chromatographic separation and/or crystallographic separation. In the case of a chiral auxiliary moiety, it can then be removed. As an alternative, the compounds can be resolved through the use of chiral chromatography. Enzymatic methods of resolution could also be used in certain cases.

As generally understood by those skilled in the art, an "optically pure" compound is one that contains only a single enantiomer. As used herein, the term "optically active" is intended to mean a compound comprising at least a sufficient excess of one enantiomer over the other such that the mixture rotates plane polarized light. Optically active compounds have the ability to rotate the plane of polarized light. The excess of one enantiomer over another is typically expressed as enantiomeric excess (e.e.). In describing an optically active compound, the prefixes D and L or R and S are used to denote the absolute configuration of the molecule about its chiral center(s). The prefixes "d" and "l" or (+) and (−) are used to denote the optical rotation of the compound (i.e., the direction in which a plane of polarized light is rotated by the optically active compound). The "l" or (−) prefix indicates that the compound is levorotatory (i.e., rotates the plane of polarized light to the left or counterclockwise) while the "d" or (+) prefix means that the compound is dextrorotatory (i.e., rotates the plane of polarized light to the right or clockwise). The sign of optical rotation, (−) and (+), is not related to the absolute configuration of the molecule, R and S.

A compound of the invention having the desired pharmacological properties will be optically active and, can be comprised of at least 90% (80% e.e.), at least 95% (90% e.e.), at least 97.5% (95% e.e.) or at least 99% (98% e.e.) of a single isomer.

Likewise, many geometric isomers of double bonds and the like can also be present in the compounds disclosed herein, and all such stable isomers are included within the present invention unless otherwise specified. Also included in the invention are tautomers and rotamers of formula I, II and/or III.

The use of the following symbols at the right refers to substitution of one or more hydrogen atoms of the indicated ring with the defined substituent R.

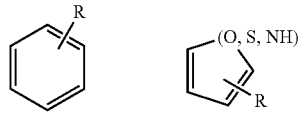

The use of the following symbol indicates a single bond or an optional double bond: -----

Embodiments of the present invention further provide intermediate compounds formed through the synthetic methods described herein to provide the compounds of formula I, II and/or III. The intermediate compounds may possess utility as a therapeutic agent for the range of indications described herein and/or a reagent for further synthesis methods and reactions.

2. Synthetic Methods

The compounds of formula I, II and/or II can be synthesized using traditional solution synthesis techniques or solid phase chemistry methods. In either, the construction involves four phases: first, synthesis of the building blocks comprising recognition elements for the biological target receptor, plus one tether moiety, primarily for control and definition of conformation. These building blocks are assembled together, typically in a sequential fashion, in a second phase employing standard chemical transformations. The precursors from the assembly are then cyclized in the third stage to provide the macrocyclic structures. Finally, the post-cyclization processing fourth stage involving removal of protecting groups and optional purification provides the desired final compounds. Synthetic methods for this general type of macrocyclic structure are described in Intl. Pat. Appls. WO 01/25257, WO 2004/111077, WO 2005/012331 and WO 2005/012332, including purification procedures described in WO 2004/111077 and WO 2005/012331.

In some embodiments of the present invention, the macrocyclic compounds of formula I, II and/or III may be synthesized using solid phase chemistry on a soluble or insoluble polymer matrix as previously defined. For solid phase chemistry, a preliminary stage involving the attachment of the first building block, also termed "loading," to the resin must be performed. The resin utilized for the present invention preferentially has attached to it a linker moiety, L. These linkers are attached to an appropriate free chemical functionality, usually an alcohol or amine, although others are also possible, on the base resin through standard reaction methods known in the art, such as any of the large number of reaction conditions developed for the formation of ester or amide bonds. Some linker moieties for the present invention are designed to allow for simultaneous cleavage from the resin with formation of the macrocycle in a process generally termed "cyclization-release." (van Maarseveen, J. H. Solid phase synthesis of heterocycles by cyclization/cleavage methodologies. *Comb. Chem. High Throughput Screen.* 1998, 1, 185-214; Ian W. James, Linkers for solid phase organic synthesis. *Tetrahedron* 1999, 55, 4855-4946; Eggenweiler, H.-M. Linkers for solid-phase synthesis of small molecules: coupling and cleavage techniques. *Drug Discovery Today* 1998, 3, 552-560; Backes, B. J.; Ellman, J. A. Solid support linker strategies. *Curr. Opin. Chem. Biol.* 1997, 1, 86-93. Of particular utility in this regard for compounds of the invention is the 3-thiopropionic acid linker. (Hojo, H.; Aimoto, S. *Bull. Chem. Soc. Jpn.* 1991, 64, 111-117; Zhang, L.; Tam, J. *J. Am. Chem. Soc.* 1999, 121, 3311-3320.)

Such a process provides material of higher purity as only cyclic products are released from the solid support and minimal contamination with the linear precursor occurs as would happen in solution phase. After sequential assembly of all the building blocks and tether into the linear precursor using known or standard reaction chemistry, base-mediated intramolecular attack on the carbonyl attached to this linker by an appropriate nucleophilic functionality that is part of the tether building block results in formation of the amide or ester bond that completes the cyclic structure as shown (Scheme 1). An analogous methodology adapted to solution phase can also be applied as would likely be preferable for larger scale applications.

Scheme 1. Cyclization-release Stratyegy

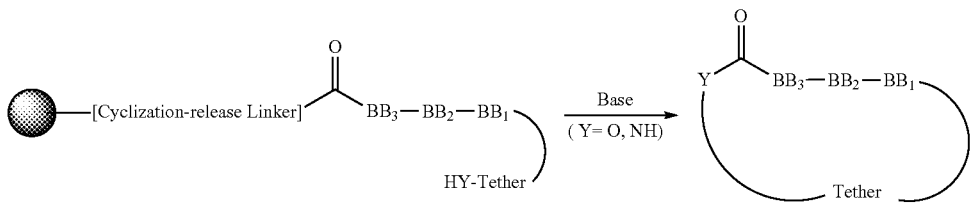

Although this description accurately represents the pathway for one of the methods of the present invention, the thioester strategy, another method of the present invention, that of ring-closing metathesis (RCM), proceeds through a modified route where the tether component is actually assembled during the cyclization step. However, in the RCM methodology as well, assembly of the building blocks proceeds sequentially, followed by cyclization (and release from the resin if solid phase). An additional post-cyclization processing step is required to remove particular byproducts of the RCM reaction, but the remaining subsequent processing is done in the same manner as for the thioester or analogous base-mediated cyclization strategy.

Moreover, it will be understood that steps including the methods provided herein may be performed independently or at least two steps may be combined. Additionally, steps including the methods provided herein, when performed independently or combined, may be performed at the same temperature or at different temperatures without departing from the teachings of the present invention.

Novel macrocyclic compounds of the present invention include those formed by a novel process including cyclization of a building block structure to form a macrocyclic compound comprising a tether component described herein. Accordingly, the present invention provides methods of manufacturing the compounds of the present invention comprising (a) assembling building block structures, (b) chemically transforming the building block structures, (c) cyclizing the building block structures including a tether component, (d) removing protecting groups from the building block structures, and (e) optionally purifying the product obtained from step (d). In some embodiments, assembly of the building block structures may be sequential. In further embodiments, the synthesis methods are carried out using traditional solution synthesis techniques or solid phase chemistry techniques.

A. Amino Acids

Amino acids, Boc- and Fmoc-protected amino acids and side chain protected derivatives, including those of N-methyl and unnatural amino acids, were obtained from commercial suppliers [for example Advanced ChemTech (Louisville, Ky., USA), Bachem (Bubendorf, Switzerland), ChemImpex (Wood Dale, Ill., USA), Novabiochem (subsidiary of Merck KGaA, Darmstadt, Germany), PepTech (Burlington, Mass., USA), Synthetech (Albany, Oreg., USA)] or synthesized through standard methodologies known to those in the art. Ddz-amino acids were either obtained commercially from Orpegen (Heidelberg, Germany) or Advanced ChemTech (Louisville, Ky., USA) or synthesized using standard methods utilizing Ddz-OPh or Ddz-$N_3$. (Birr, C.; Lochinger, W.; Stahnke, G.; Lang, P. The α,α-dimethyl-3,5-dimethoxybenzyloxycarbonyl (Ddz) residue, an N-protecting group labile toward weak acids and irradiation. *Justus Liebigs Ann. Chem.* 1972, 763, 162-172.) Bts-amino acids were synthesized by known methods. (Vedejs, E.; Lin, S.; Klapara, A.; Wang, J. "Heteroarene-2-sulfonyl Chlorides (BtsCl, ThsCl): Reagents for Nitrogen Protection and >99% Racemization-Free Phenylglycine Activation with $SOCl_2$." *J. Am. Chem. Soc.* 1996, 118, 9796-9797. Also WO 01/25257, WO 2004/111077) N-Alkyl amino acids, in particular N-methyl amino acids, are commercially available from multiple vendors (Bachem, Novabiochem, Advanced ChemTech, ChemImpex). In addition, N-alkyl amino acid derivatives were accessed via literature methods. (Hansen, D. W., Jr.; Pilipauskas, D. *J. Org. Chem.* 1985, 50, 945-950.)

B. Tethers

Tethers were obtained from the methods previously described in Intl. Pat. Appl. WO 01/25257, WO 2004/111077, WO 2005/012331 and U.S. Provisional Patent Application Ser. No. 60/622,055. Procedures for synthesis of tethers as described herein are presented in the Examples below. Exemplary tethers (T) include, but are not limited to, the following:

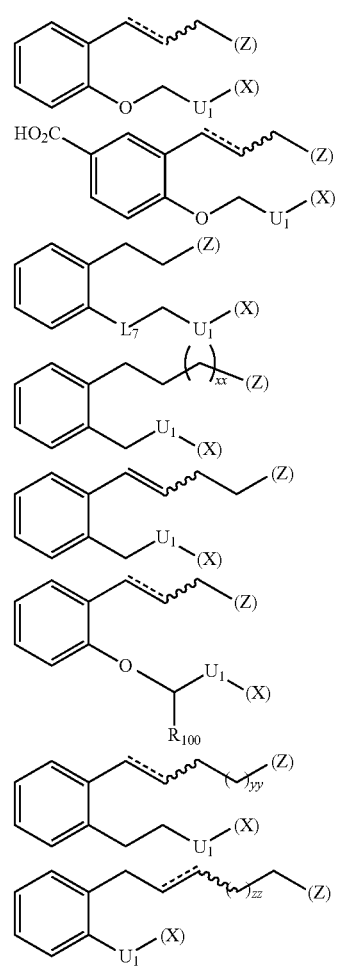

-continued

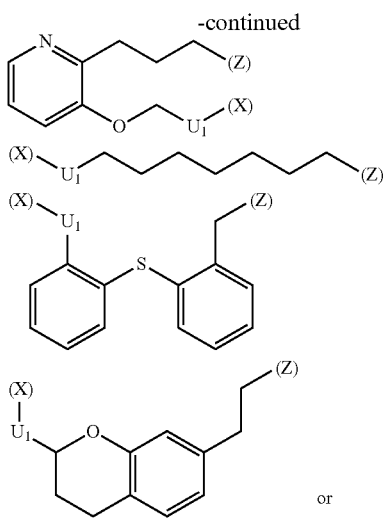

or

and intermediates in the manufacture thereof, wherein (Z) is the site of a covalent bond of T to $Z_2$, $Z_5$ or $Z_{10}$ and $Z_2$, $Z_5$ and $Z_{10}$ are defined above for formulae I, II and III, respectively, and wherein (X) is the site of a covalent bond of T to X, $X_2$ or $X_3$ and X, $X_2$ and $X_3$ are defined above for formula I, II and III, respectively, $L_7$ is —$CH_2$— or —O—; $U_1$ is —$CR_{101}R_{102}$— or —C(=O)—; $R_{100}$ is lower alkyl; $R_{101}$ and $R_{102}$ are each independently hydrogen, lower alkyl or substituted lower alkyl; xx is 2 or 3; yy is 1 or 2; zz is 1 or 2; and aaa is 0 or 1.

C. Solid Phase Techniques

Specific solid phase techniques for the synthesis of the macrocyclic compounds of the invention have been described in WO 01/25257, WO 2004/111077, WO 2005/012331 and WO 2005/012332. Solution phase synthesis routes, including methods amenable to larger scale manufacture, were described in U.S. Provisional Patent Application Ser. Nos. 60/622,055 and 60/642,271.

In certain cases, however, the lability of protecting groups precluded the use of the standard basic medium for cyclization in the thioester strategy discussed above. In these cases, either of two acidic methods was employed to provide macrocyclization under acid conditions. One method utilized HOAc, while the other method employed HOAt (Scheme 2). For example, the acetic acid cyclization was used for compound 219.

After executing the deprotection of the Ddz or Boc group on the tether, the resin was washed sequentially with DCM (2×), DCM-MeOH (1:1, 2×), DCM (2×), and DIPEA-DCM (3:7, 1×). The resin was dried under vacuum for 10 min, then added immediately to a solution of HOAc in degassed DMF (5% v/v). The reaction mixture was agitated at 50-70° C., O/N. The resin was filtered, washed with THF, and the combined filtrate and washes evaporated under reduced pressure (water aspirator, then oil pump) to afford the macrocycle.

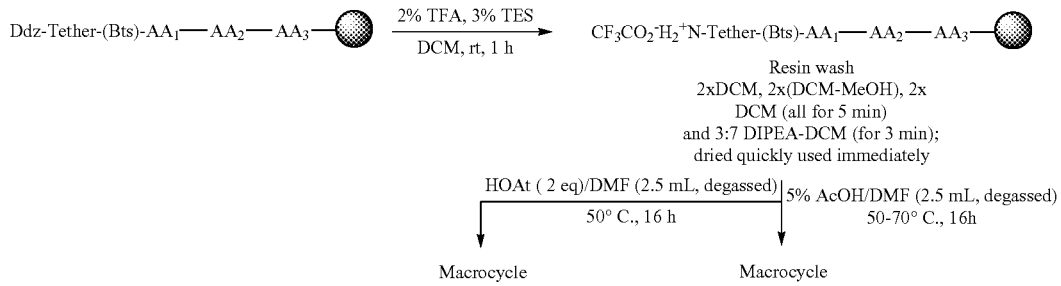

Scheme 2: Alternative Cyclization Methodologies

For a representative macrocycle with tether $T_1$, $AA_3$=Leu, $AA_2$=Leu, $AA_1$=Phe, the application of the HOAt method shown in Scheme 2 provided the cyclic peptidomimetic in 10% yield, while the acetic acid method was more effective, and gave 24% overall yield of the same macrocycle. This latter methodology was particularly effective for compounds containing His(Mts) residues. For example, with tether T8, $AA_3$=Phe, $AA_2$=Acp, $AA_1$=His(Mts), the macrocycle was obtained in 20% overall yield, although the majority of the product no longer had the Mts group on histidine (15:1 versus still protected).

Figure 2:
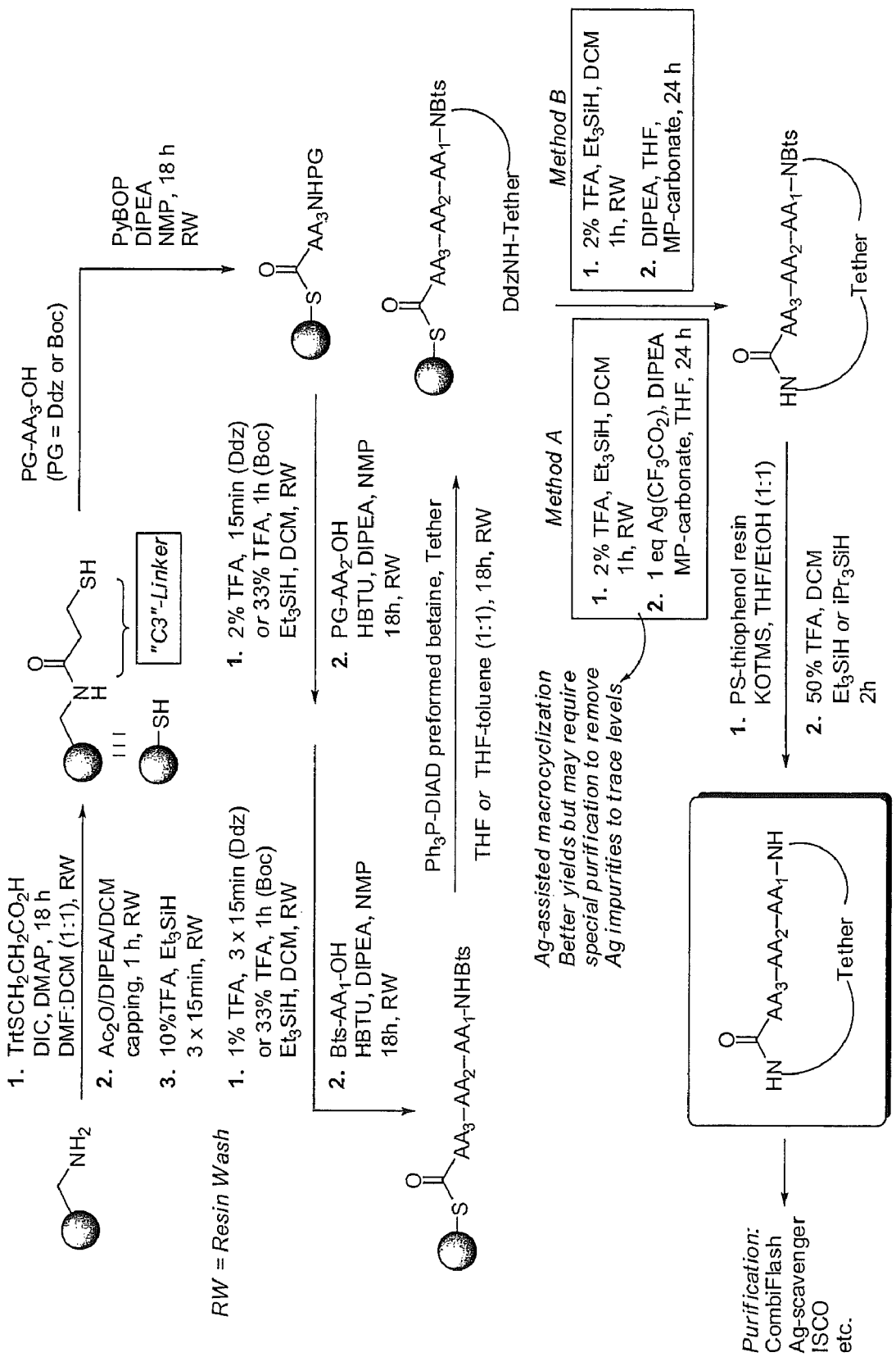
FIG. 2 shows a general thioester strategy for making macrocyclic compounds of the present invention.
Figure 3:
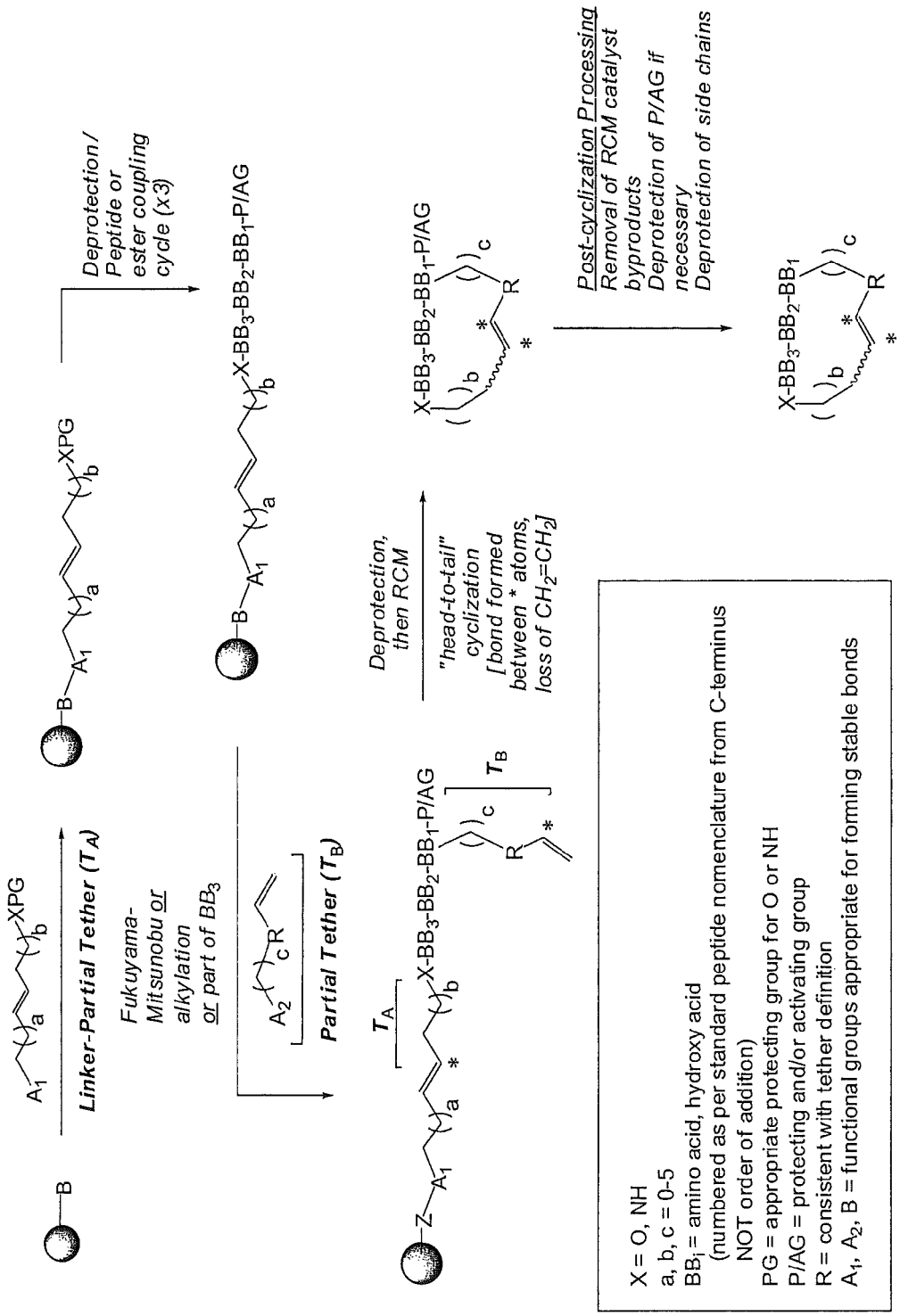
FIG. 3 shows a general ring-closing metathesis (RCM) strategy for macrocyclic compounds of the present invention.
Figure 4A:
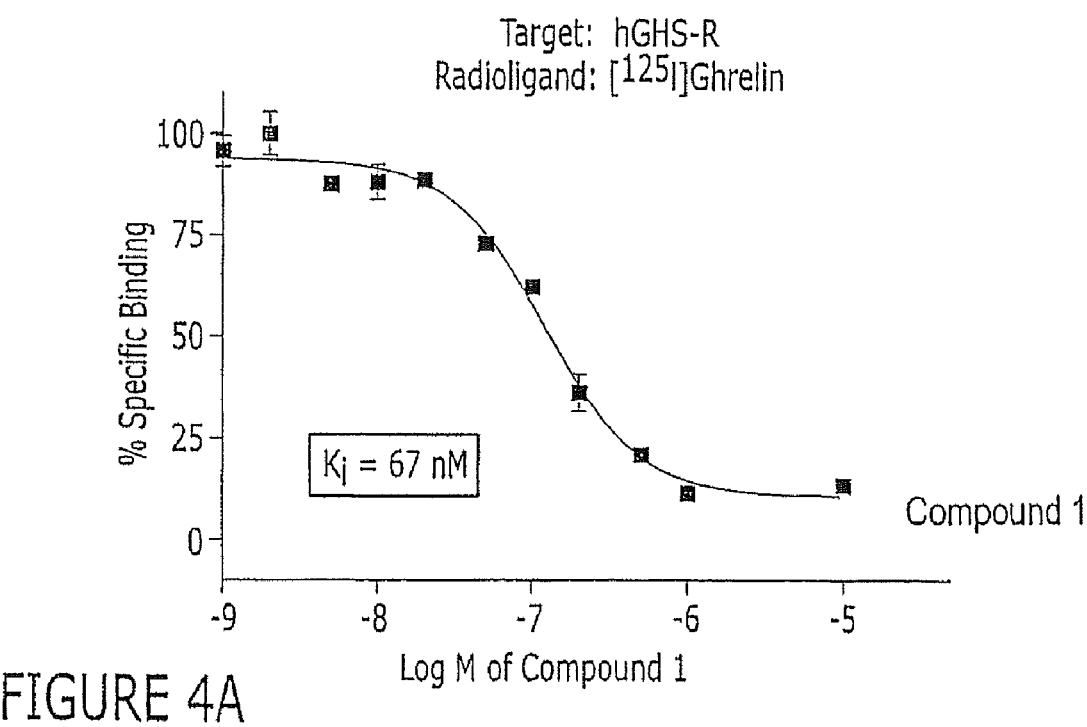
FIG. 4 (panels A through E) shows competitive binding curves for binding of exemplary compounds of the present invention to the hGHS-R1a receptor.
Figure 4B:
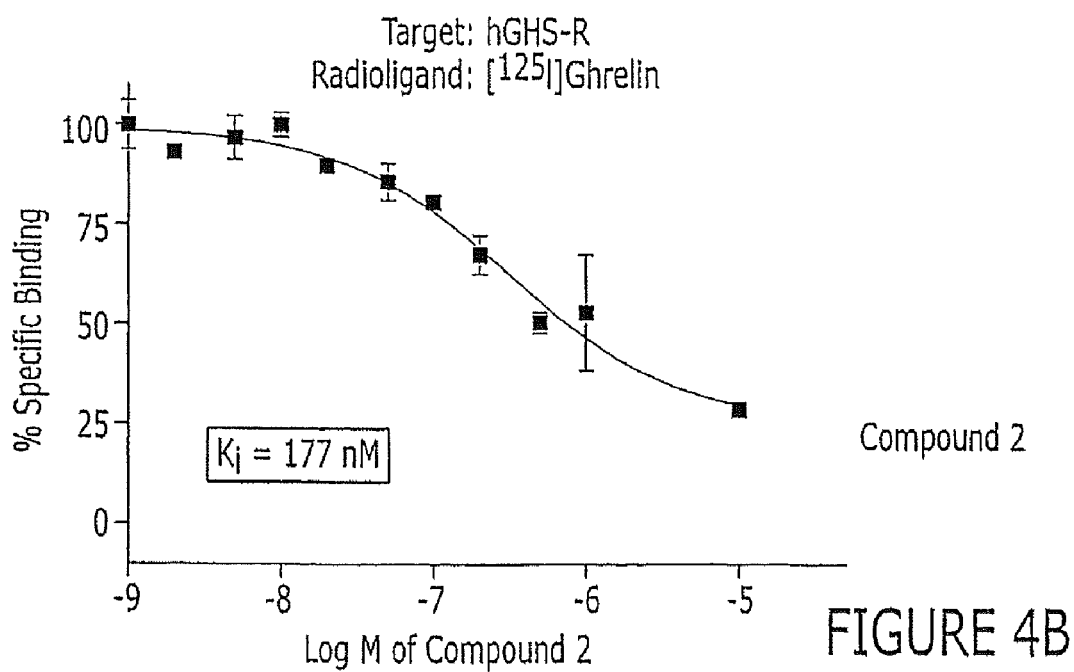
Figure 4C:
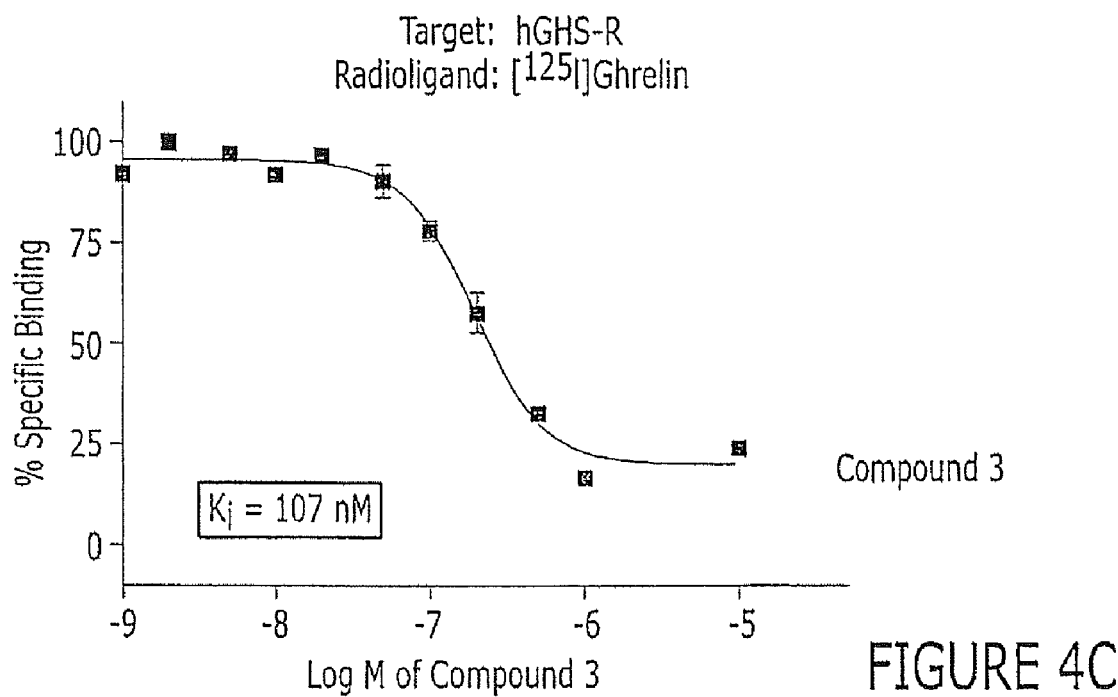
Figure 4D:
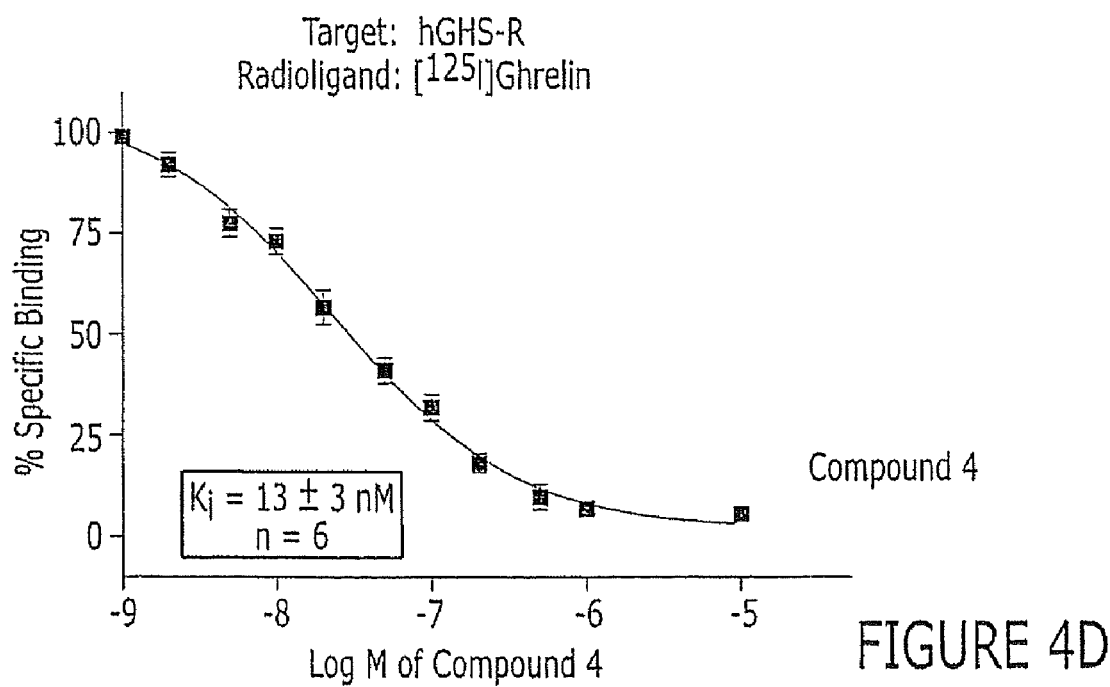
Figure 4E:
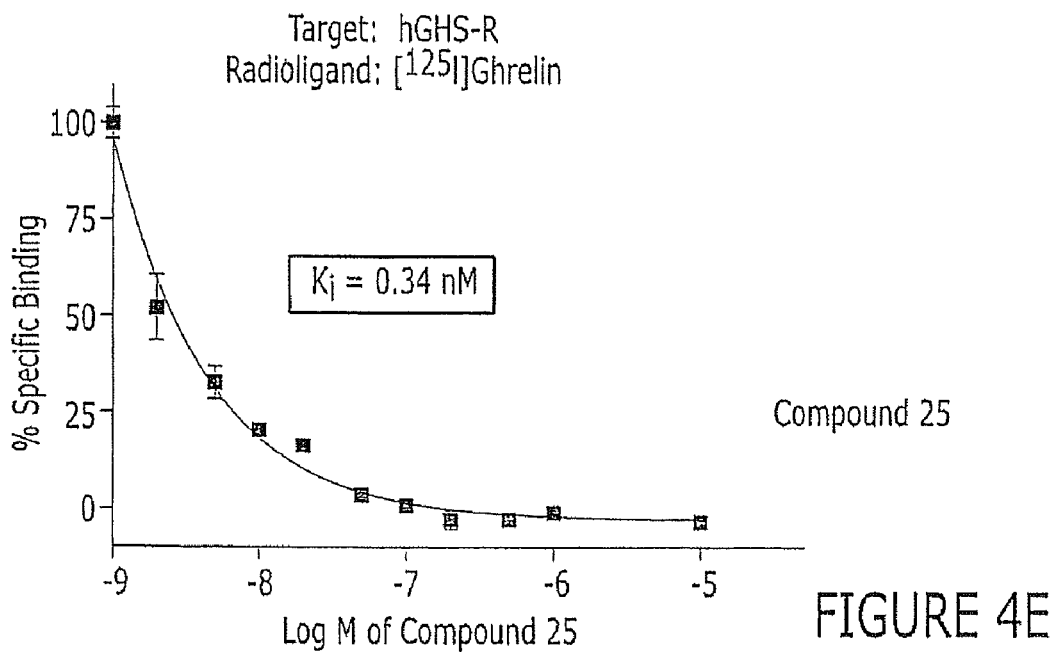
Figure 5A:
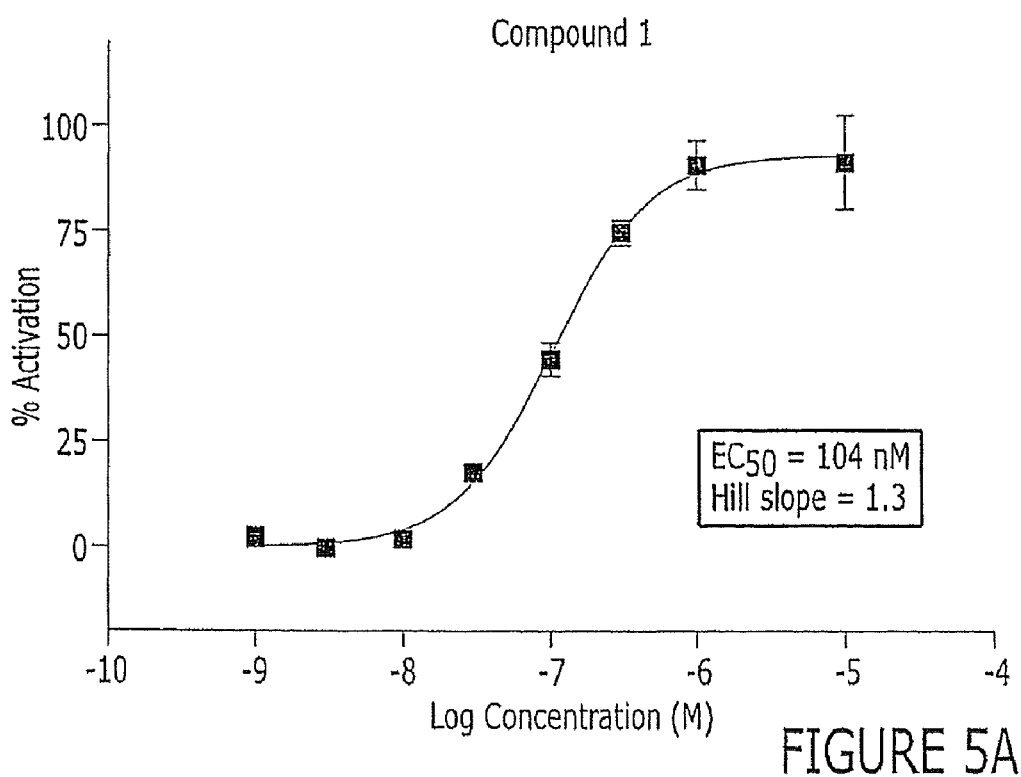
FIG. 5 (panels A through E) shows concentration-response curves for activation of the hGHS-R1a receptor by exemplary compounds of the present invention.
Figure 5B:
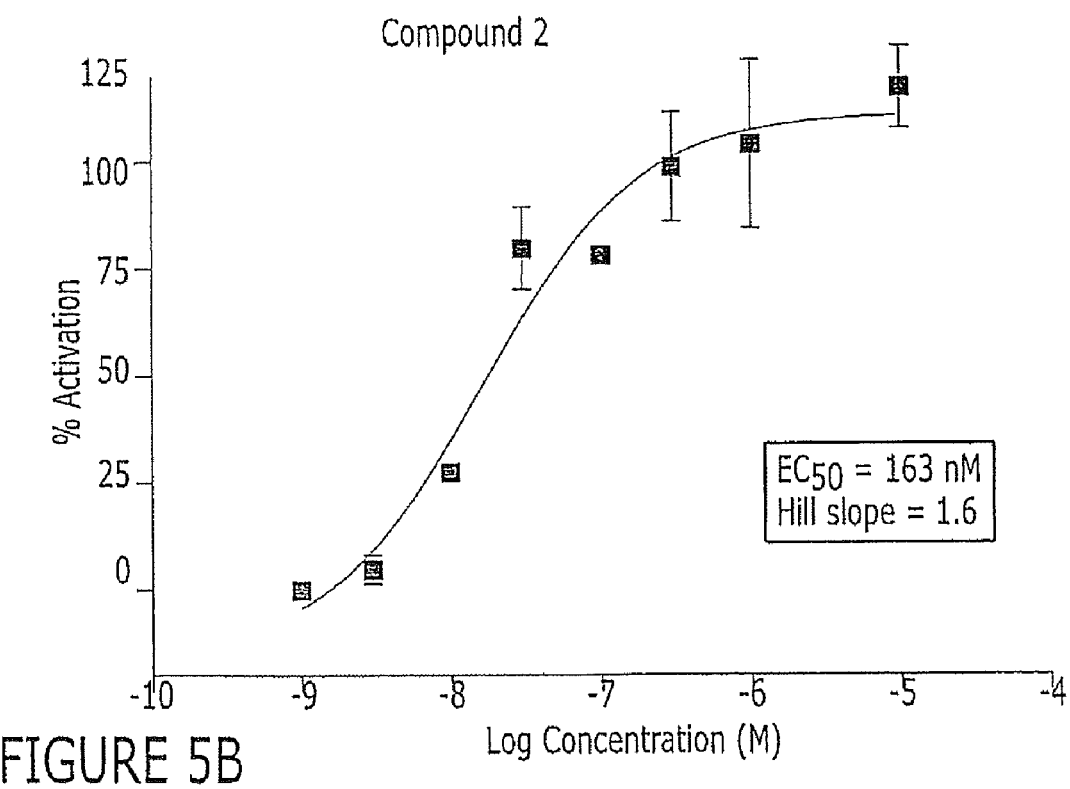
Figure 5C:
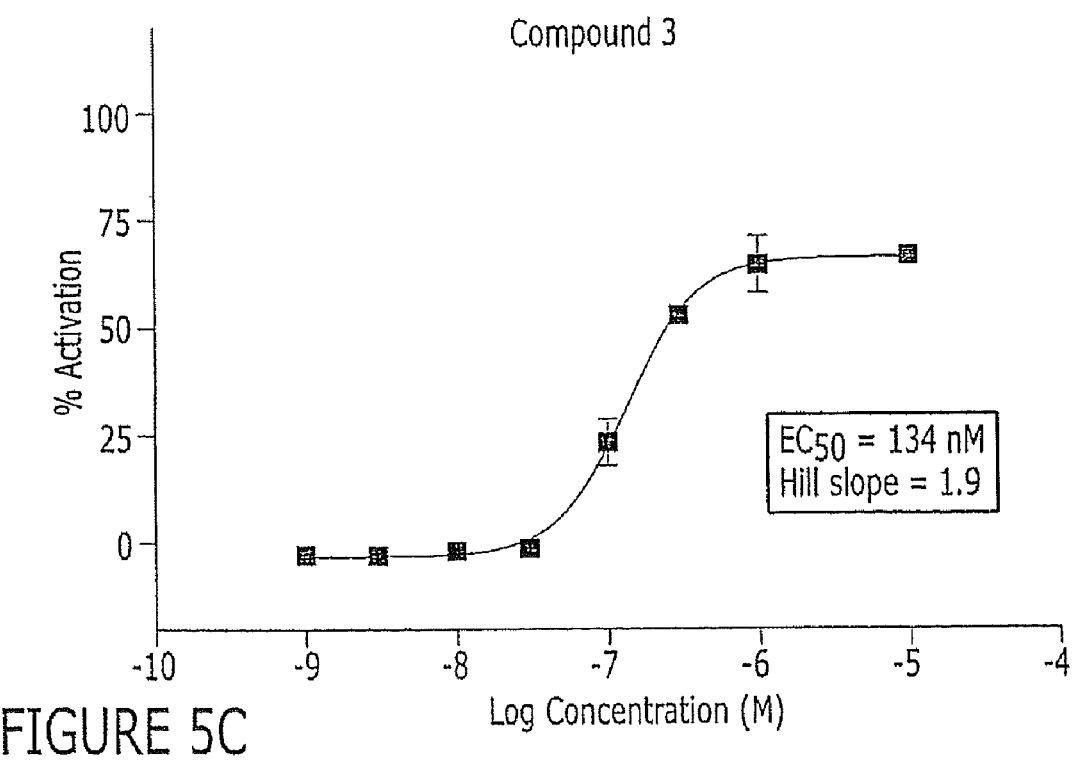
Figure 5D:
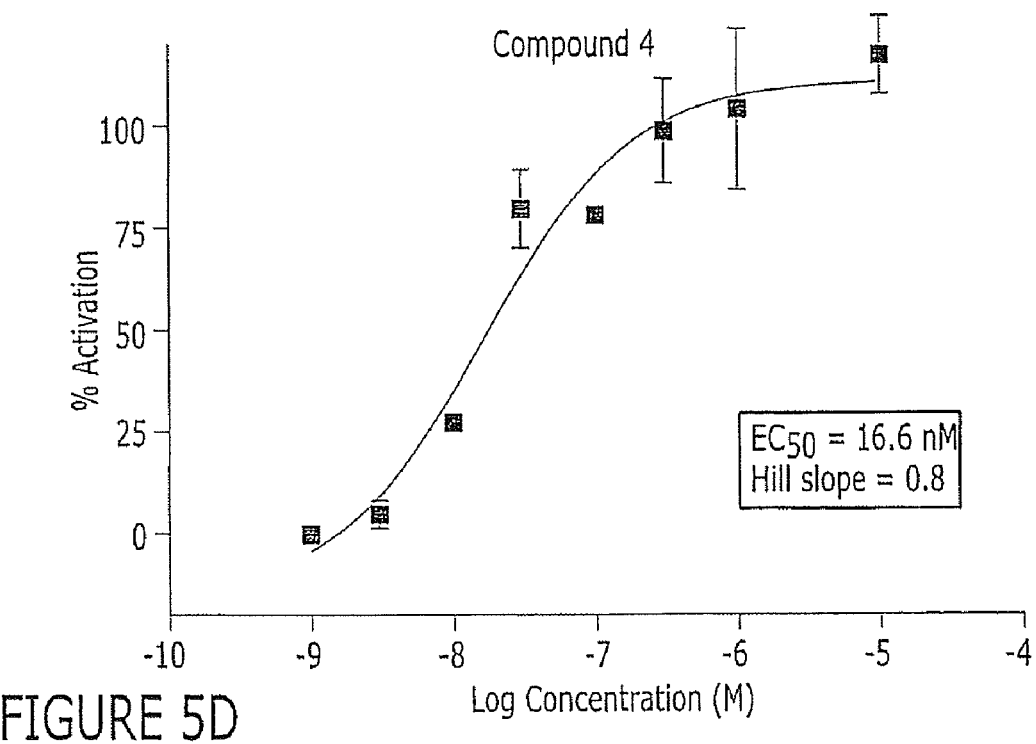
Figure 5E:
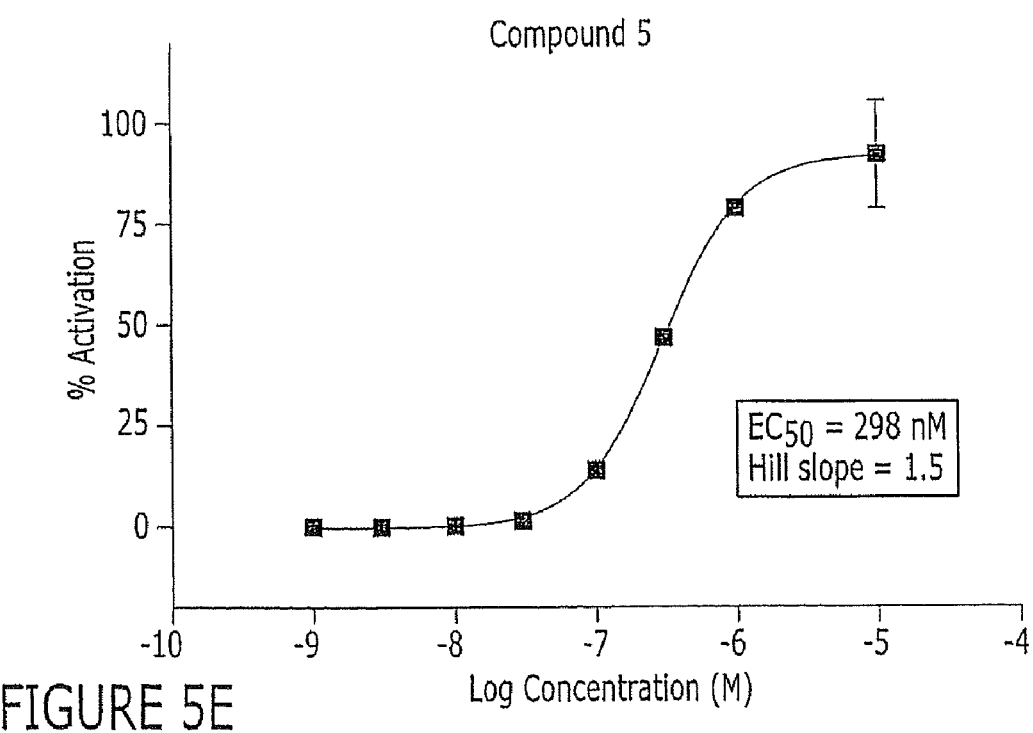
Figure 6A:
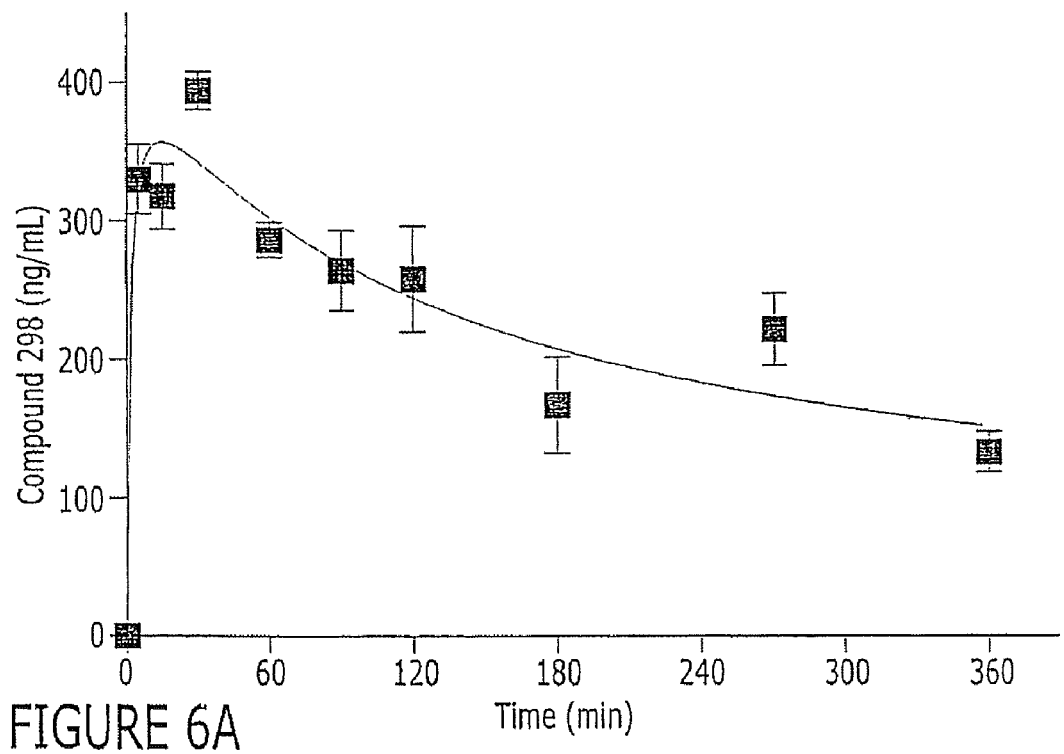
FIG. 6 shows graphs depicting pharmacokinetic parameters for exemplary compounds of the present invention, specifically after oral administration of 8 mg/kg compound 298 (panel A), after subcutaneous injection of 2 mg/kg compound 298 with cyclodextrin (panel B), after intravenous administration of 2 mg/kg compound 25 with cyclodextrin (panel C) and after intravenous administration of 2 mg/kg compound 298 with cyclodextrin (panel D).
Figure 6B:
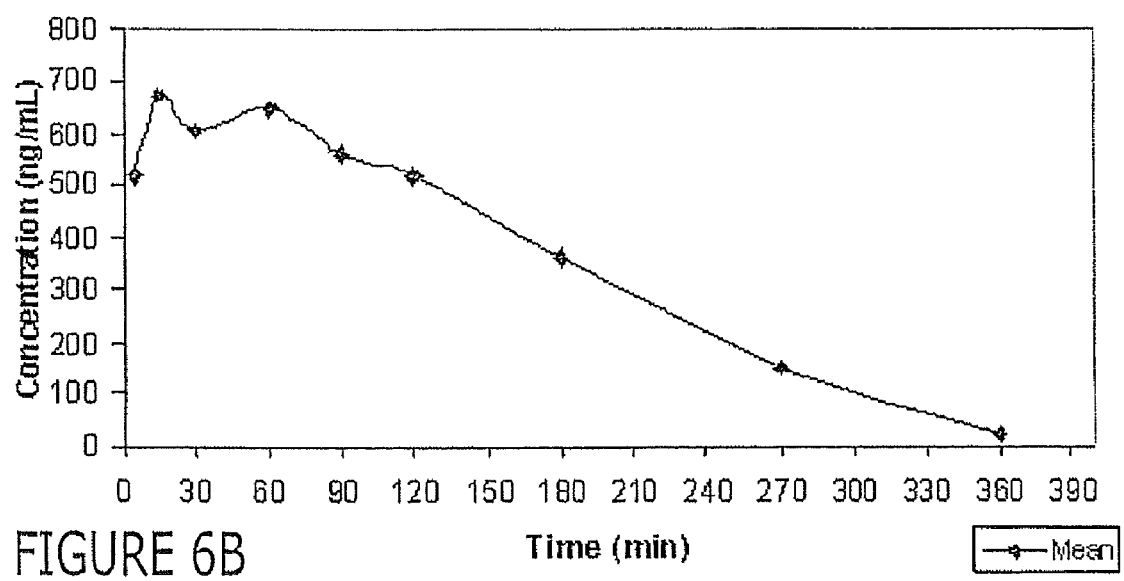
Figure 6C:
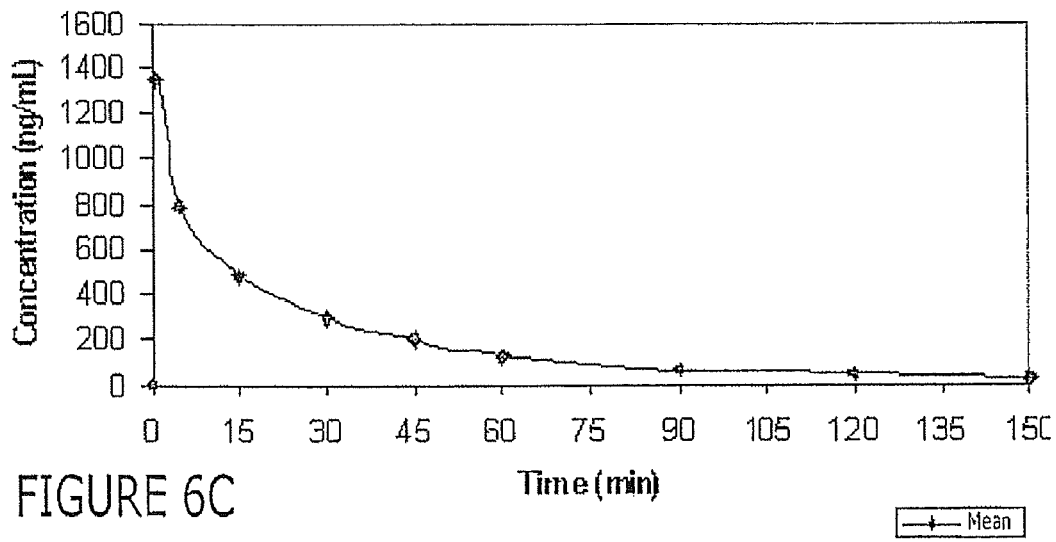
Figure 6D:
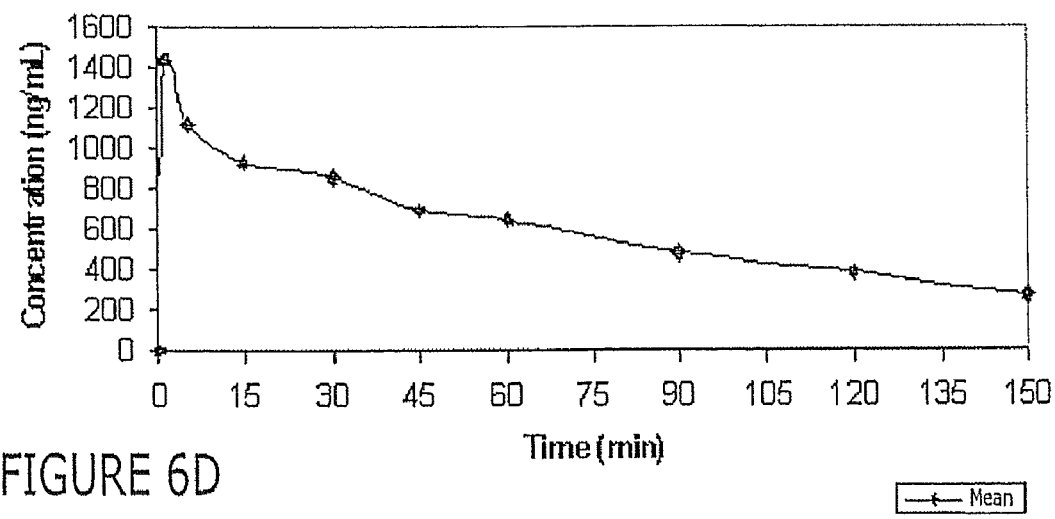

Synthesis of representative macrocyclic compounds of the present invention are shown in the Examples below. Table 1A below presents a summary of the synthesis of 224 representative compounds of the present invention. The reaction methodology employed for the construction of the macrocyclic molecule is indicated in Column 2 and relates to the particular scheme of the synthetic strategy, for example, use of the thioester strategy as shown in FIG. 2 or the RCM approach as shown in FIG. 3. Column 3 indicates if any substituents are present on $N_{BB1}$. Columns 4-6 and 8 indicate the individual building blocks employed for each compound, amino acids, hydroxy acids or tether utilizing either standard nomenclature or referring to the building block designations presented elsewhere in this application. Column 7 indicates the method used for attachment of the tether, either a Mitsunobu reaction (previously described in WO 01/25257) or reductive amination (previously described in WO 2004/111077). The relevant deprotection and coupling protocols as appropriate for the nature of the building block are performed utilizing standard procedures and those described in WO 2004/111077 for the assembly of the cyclization precursors. The building blocks are listed in the opposite order from which they are added in order to correlate the building block number with standard peptide nomenclature. Hence $BB_3$ is added first, followed by $BB_2$, then $BB_1$, finally the tether (T). In the case of the RCM, the tether is not formed completely until the cyclization step, but the portion of the tether attached to $BB_1$ is still added at this stage of the sequence, unless it is already part of that building block. The final macrocycles are obtained after application of the appropriate deprotection sequences. If any reaction was required to be carried out post-cyclization, it is listed in Column 9. All of the macrocycles presented in Table 1A were purified and met internal acceptance criteria. Yields (Column 10) are either isolated or as calculated based upon CLND analysis. It should be noted that compounds 58 and 99 were not cyclized and represent the linear analogues of compounds 10 and 133, respectively. The lack of binding potency observed with these linear analogues illustrates the importance of the macrocyclic structural feature for the desired activity.

TABLE 1A

Synthesis of Representative Compounds of the Present Invention

| Compound | Macrocyclic Assembly Method | $N_{BB1}$-$\underline{R}$ | $BB_1$ | $BB_2$ | $BB_3$ | Tether Attachment Method | Tether | Additional Reaction** | Yield (%)* |
|---|---|---|---|---|---|---|---|---|---|
| 1 | Thioester Strategy | H | Bts-Nle | Boc-Sar | Boc-(D)Phe | Mitsunobu Reaction | Boc-T9 | None | 10.1 |
| 2 | Thioester Strategy | H | Bts-Ile | Boc-(D)Ala | Boc-(D)Phe | Mitsunobu Reaction | Boc-T9 | None | 13.8 |
| 3 | Thioester Strategy | H | Bts-Val | Boc-Sar | Boc-(D)Phe | Mitsunobu Reaction | Boc-T9 | None | 10.3 |
| 4 | Thioester Strategy | H | Bts-Nva | Boc-(D)NMeAla | Boc-(D)Phe | Mitsunobu Reaction | Boc-T9 | None | 4.6 |
| 5 | Thioester Strategy | H | Bts-Nva | Boc-NEtGly | Boc-(D)Phe | Mitsunobu Reaction | Boc-T9 | None | 8.6 |
| 6 | Thioester Strategy | H | Bts-Nva | Ddz-Sar | Ddz-(D)Trp(Boc) | Mitsunobu Reaction | Ddz-T9 | None | 8.1 |
| 7 | Thioester Strategy | H | Bts-Nva | Ddz-Sar | Ddz-(D)Tyr(But) | Mitsunobu Reaction | Ddz-T9 | None | 8.8 |
| 8 | Thioester Strategy | H | Bts-Leu | Boc-Acp | Boc-Phe | Mitsunobu Reaction | Boc-T8 | None | 20.9 |
| 9 | Thioester Strategy | H | Bts-Val | Boc-Acp | Boc-Phe | Mitsunobu Reaction | Boc-T9 | None | 9.7 |
| 10 | Thioester Strategy | H | Bts-Nva | Boc-Sar | Boc-(D)Phe | Mitsunobu Reaction | Boc-T9 | None | 9.9 |
| 11 | Thioester Strategy | H | Bts-Nva | Boc-Sar | Boc-(D)Phe | Mitsunobu Reaction | Boc-T8 | None | 9.9 |
| 12 | Thioester Strategy | H | Bts-(D)Val | Boc-Nle | Boc-Nle | Mitsunobu Reaction | Boc-T8 | None | 2.9 |
| 13 | Thioester Strategy | H | Bts-(D)Val | Boc-Nva | Boc-Phe | Mitsunobu Reaction | Boc-T8 | None | 5.8 |
| 14 | Thioester Strategy | H | Bts-Ile | Boc-(D)Ala | Boc-Phe | Mitsunobu Reaction | Boc-T8 | None | 27.5 |
| 15 | Thioester Strategy | H | Bts-Ile | Boc-(D)NMeAla | Boc-(D)Phe | Mitsinobu Reaction | Boc-T9 | None | 19.5 |
| 16 | Thioester Strategy | H | Bts-allo-Ile | Boc-(D)NMeAla | Boc-(D)Phe | Mitsunobu Reaction | Boc-T9 | None | 23.9 |
| 17 | Thioester Strategy | H | Bts-Cpg | Boc-(D)NMeAla | Boc-(D)Phe | Reductive Amination Reaction | Boc-T9 | None | 24.8 |
| 18 | Thioester Strategy | H | Bts-Acp | Boc-Acp | Boc-Phe | Mitsunobu Reaction | Boc-T8 | None | 6.8 |
| 19 | Thioester Strategy | H | Bts-Val | Boc-(D)NMeAla | Boc-Phe | Mitsunobu Reaction | Boc-T8 | None | 12.7 |
| 20 | Thioester Strategy | H | Bts-Leu | Boc-Acp | Boc-Phe(2-Cl) | Mitsunobu Reaction | Boc-T8 | None | 22.0 |
| 21 | Thioester Strategy | H | Bts-Leu | Boc-Acp | Boc-Phe(3-Cl) | Mitsunobu Reaction | Boc-T8 | None | 24.7 |
| 22 | Thioester Strategy | H | Bts-Leu | Boc-Acp | Boc-1Nal | Mitsunobu Reaction | Boc-T8 | None | 10.3 |
| 23 | Thioester Strategy | H | Bts-Ile | Boc-(D)NMeAla | Boc-(D)Phe(2-Cl) | Mitsunobu Reaction | Boc-T9 | None | 32.6 |
| 24 | Thioester Strategy | H | Bts-Ile | Boc-(D)NMeAla | Boc-(D)Phe(3-Cl) | Mitsunobu Reaction | Boc-T9 | None | 22.4 |
| 25 | Thioester Strategy | H | Bts-Ile | Boc-(D)NMeAla | Boc-(D)Phe(4-Cl) | Mitsunobu Reaction | Boc-T9 | None | 21.0 |
| 26 | Thioester Strategy | H | Bts-Ile | Boc-(D)NMeAla | Boc-(D)Phe(4-F) | Mitsunobu Reaction | Boc-T9 | None | 15.5 |
| 27 | Thioester Strategy | H | Bts-Ile | Boc-(D)NMeAla | Boc-(D)Tyr(OMe) | Mitsunobu Reaction | Boc-T9 | None | 20.2 |
| 28 | Thioester Strategy | H | Bts-Ile | Boc-(D)NMeAla | Boc-(D)Bip | Mitsunobu Reaction | Boc-T9 | None | 31.6 |
| 29 | Thioester Strategy | H | Bts-Ile | Boc-(D)NMeAla | Boc-(D)Dip | Mitsunobu Reaction | Boc-T9 | None | 26.1 |
| 30 | Thioester Strategy | H | Bts-Ile | Boc-(D)NMeAla | Boc-(D)1Nal | Mitsunobu Reaction | Boc-T9 | None | 31.9 |

TABLE 1A-continued

Synthesis of Representative Compounds of the Present Invention

| Compound | Macrocyclic Assembly Method | $N_{BB1}$-R | $BB_1$ | $BB_2$ | $BB_3$ | Tether Attachment Method | Tether | Additional Reaction** | Yield (%)* |
|---|---|---|---|---|---|---|---|---|---|
| 31 | Thioester Strategy | H | Bts-Ile | Boc-(D)NMeAla | Boc-(D)2Nal | Mitsunobu Reaction | Boc-T9 | None | 21.9 |
| 32 | Thioester Strategy | H | Bts-Ile | Boc-(D)NMeAla | Boc-(D)2Pal | Reductive Amination Reaction | Boc-T9 | None | 6.7 |
| 33 | Thioester Strategy | H | Bts-Ile | Boc-(D)NMeAla | Boc-(D)4-ThzAla | Mitsunobu Reaction | Boc-T9 | None | 7.5 |
| 34 | Thioester Strategy | H | Bts-Ile | Boc-(D)NMeAla | Boc-(D)2-Thi | Mitsunobu Reaction | Boc-T9 | None | 14.2 |
| 35 | Thioester Strategy | H | Bts-Ile | Boc-(D)NMeAla | Boc-(D)Phe | Mitsunobu Reaction | Boc-T33a | None | 9.4 |
| 36 | Thioester Strategy | H | Bts-Ile | Boc-(D)NMeAla | Boc-(D)Phe | Mitsunobu Reaction | Boc-T33b | None | 13.0 |
| 37 | RCM Strategy | H | Fmoc-Ile | Fmoc-(D)NMeAla | Fmoc-(D)Phe | Mitsunobu Reaction | $T_{A1} + T_{B4}$ | None | 24.6 |
| 38 | RCM Strategy | H | Fmoc-Ile | Fmoc-(D)NMeAla | Fmoc-(D)Phe | Mitsunobu Reaction | $T_{A2} + T_{B1}$ | Hydrogenation | 44.2 |
| 39 | Thioester Strategy | H | Bts-Nva | Boc-(D)NMeAla | Boc-(D)Phe | Mitsunobu Reaction | Boc-T8 | None | 21.4 |
| 40 | Thioester Strategy | H | Bts-Ile | Boc-(D)NMeAla | Boc-(D)Phe | Mitsunobu Reaction | Boc-T8 | None | 18.6 |
| 41 | Thioester Strategy | H | Bts-Ile | Boc-(D)NMeAbu | Boc-(D)Phe | Mitsunobu Reaction | Boc-T9 | None | 10.6 |
| 42 | Thioester Strategy | H | Bts-Tle | Boc-(D)NMeAla | Boc-(D)Phe | Mitsunobu Reaction | Boc-T9 | None | 1.7 |
| 43 | Thioester Strategy | H | Bts-Ile | Boc-(D)NEtAla | Boc-(D)Phe | Mitsunobu Reaction | Boc-T9 | None | 0.4 |
| 44 | Thioester Strategy | H | Bts-Leu | Boc-Acp | Boc-Phe | Mitsunobu Reaction | Boc-T1 | None | 7.8 |
| 45 | Thioester Strategy | H | Bts-Leu | Ddz-Acp | Ddz-Glu(OBut) | Mitsunobu Reaction | Ddz-T8 | None | 11.6 |
| 46 | Thioester Strategy | H | Bts-Leu | Boc-Acp | Boc-Val | Mitsunobu Reaction | Boc-T8 | None | 13.6 |
| 47 | Thioester Strategy | H | Bts-Leu | Boc-Acp | Boc-Leu | Mitsunobu Reaction | Boc-T8 | None | 9.2 |
| 48 | Thioester Strategy | H | Bts-Leu | Boc-Acp | Boc-Nva | Mitsunobu Reaction | Boc-T8 | None | 17.5 |
| 49 | Thioester Strategy | H | Bts-Nva | Boc-Sar | Boc-(D)Ala | Reductive Amination Reaction | Boc-T9 | None | 7.5 |
| 50 | Thioester Strategy | H | Bts-Nva | Ddz-Sar | Ddz-(D)Glu(OBut) | Mitsunobu Reaction | Ddz-T9 | None | 10.1 |
| 51 | Thioester Strategy | H | Bts-Nva | Boc-Sar | Boc-Gly | Mitsunobu Reaction | Boc-T9 | None | 6.6 |
| 52 | Thioester Strategy | H | Bts-Nva | Boc-Sar | Boc-(D)Nle | Mitsunobu Reaction | Boc-T9 | None | 8.7 |
| 53 | Thioester Strategy | H | Bts-Nva | Ddz-Sar | Ddz-(D)Orn(Boc) | Mitsunobu Reaction | Ddz-T9 | None | 8.3 |
| 54 | Thioester Strategy | H | Bts-Nva | Ddz-Sar | Ddz-(D)Ser(But) | Mitsunobu Reaction | Ddz-T9 | None | 6.2 |
| 55 | Thioester Strategy | H | Bts-(D)Nva | Boc-Sar | Boc-(D)Phe | Mitsunobu Reaction | Boc-T9 | None | 8.0 |
| 56 | Thioester Strategy | H | Bts-(D)Nva | Boc-Sar | Boc-Phe | Mitsunobu Reaction | Boc-T9 | None | 9.3 |
| 57 | Thioester Strategy | H | Bts-Nva | Boc-Sar | Boc-Phe | Mitsunobu Reaction | Boc-T9 | None | 8.9 |
| 58 | Thioester Strategy, linear | Ac | Bts-Nva | Boc-Sar | Boc-(D)Phe | Mitsunobu Reaction | Boc-T9 | No cyclization | 5.9 |
| 59 | Thioester Strategy | H | Bts-Nva | Boc-Ala | Boc-(D)Phe | Mitsunobu Reaction | Boc-T9 | None | 8.0 |
| 60 | Thioester Strategy | H | Bts-Nva | Boc-(D)Ala | Boc-(D)Phe | Mitsunobu Reaction | Boc-T9 | None | 13.1 |
| 61 | Thioester Strategy | H | Bts-Nva | Boc-Gly | Boc-(D)Phe | Mitsunobu Reaction | Boc-T9 | None | 8.4 |
| 62 | Thioester Strategy | H | Bts-Nva | Boc-Leu | Boc-(D)Phe | Mitsunobu Reaction | Boc-T9 | None | 7.0 |
| 63 | Thioester Strategy | H | Bts-Nva | Boc-(D)Leu | Boc-(D)Phe | Mitsunobu Reaction | Boc-T9 | None | 11.7 |
| 64 | Thioester Strategy | H | Bts-Nva | Boc-Phe | Boc-(D)Phe | Mitsunobu Reaction | Boc-T9 | None | 8.5 |
| 65 | Thioester Strategy | H | Bts-Nva | Boc-(D)Phe | Boc-(D)Phe | Mitsunobu Reaction | Boc-T9 | None | 8.6 |

TABLE 1A-continued

Synthesis of Representative Compounds of the Present Invention

| Compound | Macrocyclic Assembly Method | N$_{BB1}$-R | BB$_1$ | BB$_2$ | BB$_3$ | Tether Attachment Method | Tether | Additional Reaction** | Yield (%)* |
|---|---|---|---|---|---|---|---|---|---|
| 66 | Thioester Strategy | H | Bts-Nva | Boc-Aib | Boc-(D)Phe | Mitsunobu Reaction | Boc-T9 | None | 15.8 |
| 67 | Thioester Strategy | H | Bts-Nva | Boc-Acp | Boc-(D)Phe | Mitsunobu Reaction | Boc-T9 | None | 11.7 |
| 68 | Thioester Strategy | H | Bts-Nva | Ddz-Lys | Boc-(D)Phe | Mitsunobu Reaction | Ddz-T9 | None | 7.9 |
| 69 | Thioester Strategy | H | Bts-Nva | Ddz-(D)Lys(Boc) | Boc-(D)Phe | Mitsunobu Reaction | Ddz-T9 | None | 11.2 |
| 70 | Thioester Strategy | H | Bts-Nva | Ddz-Glu(OBut) | Boc-(D)Phe | Mitsunobu Reaction | Ddz-T9 | None | 10.0 |
| 71 | Thioester Strategy | H | Bts-Nva | Ddz-(D)Glu(OBut) | Boc-(D)Phe | Mitsunobu Reaction | Ddz-T9 | None | 9.9 |
| 72 | Thioester Strategy | H | Bts-Ala | Boc-Sar | Boc-(D)Phe | Mitsunobu Reaction | Boc-T9 | None | 5.2 |
| 73 | Thioester Strategy | H | Bts-Glu | Boc-Sar | Boc-(D)Phe | Mitsunobu Reaction | Boc-T9 | None | 6.8 |
| 74 | Thioester Strategy | H | Bts-Lys | Boc-Sar | Boc-(D)Phe | Mitsunobu Reaction | Boc-T9 | None | 6.0 |
| 75 | Thioester Strategy | H | Bts-Phe | Boc-Sar | Boc-(D)Phe | Mitsunobu Reaction | Boc-T9 | None | 9.5 |
| 76 | Thioester Strategy | H | Bts-Ser | Boc-Sar | Boc-(D)Phe | Mitsunobu Reaction | Boc-T9 | None | 15.1 |
| 77 | Thioester Strategy | H | Bts-Nva | Boc-Sar | Boc-(D)Phe | Mitsunobu Reaction | Boc-T12 | None | 12.6 |
| 78 | Thioester Strategy | H | Bts-Nva | Boc-Sar | Boc-(D)Phe | Mitsunobu Reaction | Boc-T27 | None | 6.8 |
| 79 | Thioester Strategy | H | Bts-Nva | Boc-NMeAla | Boc-(D)Phe | Mitsunobu Reaction | Boc-T9 | None | 1.9 |
| 80 | Thioester Strategy | H | Bts-Gly | Boc-Sar | Boc-(D)Phe | Mitsunobu Reaction | Boc-T9 | None | 1.3 |
| 81 | Thioester Strategy | H | Bts-Nva | Boc-Sar | Boc-(D)Phe | Mitsunobu Reaction | Boc-T1 | None | 5.3 |
| 82 | Thioester Strategy | H | Bts-Nva | Boc-Sar | Boc-(D)Phe | Mitsunobu Reaction | Boc-T3 | None | 3.9 |
| 83 | Thioester Strategy | H | Bts-Nva | Boc-Sar | Boc-(D)Phe | Mitsunobu Reaction | Boc-T16 | None | 1.8 |
| 84 | Thioester Strategy | H | Bts-Nva | Boc-Sar | Boc-(D)Phe | Mitsunobu Reaction | Boc-T4 | None | 2.6 |
| 85 | Thioester Strategy | H | Bts-Nva | Boc-Sar | Boc-(D)Phe | Mitsunobu Reaction | Boc-T5 | None | 4.7 |
| 86 | Thioester Strategy | H | Bts-Nva | Boc-Sar | Boc-(D)Phe | Mitsunobu Reaction | Boc-T14 | None | 0.4 |
| 87 | Thioester Strategy | H | Bts-Leu | Boc-Acp | Boc-Ala | Mitsunobu Reaction | Boc-T9 | None | 4.8 |
| 88 | Thioester Strategy | H | Bts-Leu | Ddz-Acp | Ddz-Tyr(But) | Mitsunobu Reaction | Ddz-T9 | None | 18.8 |
| 89 | Thioester Strategy | H | Bts-Leu | Ddz-Acp | Ddz-Trp(Boc) | Mitsunobu Reaction | Ddz-T9 | None | 16.5 |
| 90 | Thioester Strategy | H | Bts-Leu | Boc-Acp | Boc-Hfe | Mitsunobu Reaction | Boc-T9 | None | 8.5 |
| 91 | Thioester Strategy | H | Bts-Leu | Ddz-Acp | Ddz-Lys(Boc) | Mitsunobu Reaction | Ddz-T9 | None | 6.8 |
| 92 | Thioester Strategy | H | Bts-Leu | Ddz-Acp | Ddz-Glu(OBut) | Mitsunobu Reaction | Ddz-T9 | None | 9.1 |
| 93 | Thioester Strategy | H | Bts-Leu | Boc-Ala | Boc-Phe | Mitsunobu Reaction | Boc-T9 | None | 9.2 |
| 94 | Thioester Strategy | H | Bts-Leu | Boc-(D)Ala | Boc-Phe | Mitsunobu Reaction | Boc-T9 | None | 21.8 |
| 95 | Thioester Strategy | H | Bts-Leu | Boc-Aib | Boc-Phe | Mitsunobu Reaction | Boc-T9 | None | 19.3 |
| 96 | Thioester Strategy | H | Bts-(D)Leu | Boc-Acp | Boc-Phe | Mitsunobu Reaction | Boc-T9 | None | 7.0 |
| 97 | Thioester Strategy | H | Bts-Leu | Boc-Acp | Boc-(D)Phe | Mitsunobu Reaction | Boc-T9 | None | 9.2 |
| 98 | Thioester Strategy | H | Bts-(D)Leu | Boc-Acp | Boc-(D)Phe | Mitsunobu Reaction | Boc-T9 | None | 15.3 |
| 99 | Thioester Strategy, linear | Ac | Bts-Leu | Boc-Acp | Boc-Phe | Mitsunobu Reaction | Boc-T9 | No cyclization | 10.4 |
| 100 | Thioester Strategy | H | Bts-Ala | Boc-Acp | Boc-Phe | Mitsunobu Reaction | Boc-T9 | None | 10.4 |
| 101 | Thioester Strategy | H | Bts-Nle | Boc-Acp | Boc-Phe | Mitsunobu Reaction | Boc-T9 | None | 19.0 |

TABLE 1A-continued

Synthesis of Representative Compounds of the Present Invention

| Compound | Macrocyclic Assembly Method | $N_{BB1}$-R | BB$_1$ | BB$_2$ | BB$_3$ | Tether Attachment Method | Tether | Additional Reaction** | Yield (%)* |
|---|---|---|---|---|---|---|---|---|---|
| 102 | Thioester Strategy | H | Bts-Phe | Boc-Acp | Boc-Phe | Mitsunobu Reaction | Boc-T9 | None | 15.8 |
| 103 | Thioester Strategy | H | Bts-Lys | Boc-Acp | Boc-Phe | Mitsunobu Reaction | Boc-T9 | None | 12.9 |
| 104 | Thioester Strategy | H | Bts-Glu | Boc-Acp | Boc-Phe | Mitsunobu Reaction | Boc-T9 | None | 9.3 |
| 105 | Thioester Strategy | H | Bts-Ser | Boc-Acp | Boc-Phe | Mitsunobu Reaction | Boc-T9 | None | 11.9 |
| 106 | Thioester Strategy | H | Bts-Leu | Boc-Acp | Boc-Phe | Mitsunobu Reaction | Boc-T3 | None | 6.3 |
| 107 | Thioester Strategy | H | Bts-Leu | Boc-Acp | Boc-Phe | Mitsunobu Reaction | Boc-T5 | None | 4.2 |
| 108 | Thioester Strategy | H | Bts-Leu | Boc-Acp | Boc-Phe | Mitsunobu Reaction | Boc-T12 | None | 18.3 |
| 109 | Thioester Strategy | H | Bts-Leu | Boc-Acp | Boc-Phe | Mitsunobu Reaction | Boc-T11 | None | 10.1 |
| 110 | Thioester Strategy | H | Bts-Leu | Boc-Acp | Boc-Gly | Mitsunobu Reaction | Boc-T9 | None | 2.9 |
| 111 | Thioester Strategy | H | Bts-Leu | Boc-Acc | Boc-Phe | Mitsunobu Reaction | Boc-T9 | None | 3.0 |
| 112 | Thioester Strategy | H | Bts-Gly | Boc-Acp | Boc-Phe | Mitsunobu Reaction | Boc-T9 | None | 3.2 |
| 113 | Thioester Strategy | H | Bts-Leu | Boc-Acp | Boc-Phe | Mitsunobu Reaction | Boc-T9 | None | 16.9 |
| 114 | Thioester Strategy | H | Bts-Leu | Boc-Acp | Boc-Phe | Mitsunobu Reaction | Boc-T16 | None | 2.9 |
| 115 | Thioester Strategy | H | Bts-Leu | Boc-Acp | Boc-Phe | Mitsunobu Reaction | Boc-T6 | None | 0.5 |
| 116 | Thioester Strategy | H | Bts-Leu | Ddz-Acp | Ddz-Glu(Et) | Mitsunobu Reaction | Ddz-T8 | None | 11.8 |
| 117 | Thioester Strategy | H | Bts-Abu | Boc-(D)NMeAla | Boc-(D)Phe | Mitsunobu Reaction | Boc-T9 | None | 19.7 |
| 118 | Thioester Strategy | H | Bts-Leu | Boc-(D)NMeAla | Boc-(D)Phe | Mitsunobu Reaction | Boc-T9 | None | 21.0 |
| 119 | Thioester Strategy | H | Bts-Thr | Boc-(D)NMeAla | Boc-(D)Phe | Mitsunobu Reaction | Boc-T9 | None | 12.2 |
| 120 | Thioester Strategy | H | Bts-Thr(OMe) | Boc-(D)NMeAla | Boc-(D)Phe | Reductive Amination Reaction | Boc-T9 | None | 17.5 |
| 121 | Thioester Strategy | H | Bts-Acc | Boc-(D)NMeAla | Boc-(D)Phe | Mitsunobu Reaction | Boc-T9 | None | 5.8 |
| 122 | Thioester Strategy | H | Bts-Phe(2-Cl) | Boc-Acp | Boc-Phe | Mitsunobu Reaction | Boc-T8 | None | 22.1 |
| 123 | Thioester Strategy | H | Bts-Phe(3-Cl) | Boc-Acp | Boc-Phe | Mitsunobu Reaction | Boc-T8 | None | 13.6 |
| 124 | Thioester Strategy | H | Bts-Phe(4-Cl) | Boc-Acp | Boc-Phe | Mitsunobu Reaction | Boc-T8 | None | 9.8 |
| 125 | Thioester Strategy | H | Bts-Phe(4-F) | Boc-Acp | Boc-Phe | Mitsunobu Reaction | Boc-T8 | None | 15.8 |
| 126 | Thioester Strategy | H | Bts-Hfe | Boc-Acp | Boc-Phe | Mitsunobu Reaction | Boc-T8 | None | 9.8 |
| 127 | Thioester Strategy | H | Bts-Tyr(OMe) | Boc-Acp | Boc-Phe | Mitsunobu Reaction | Boc-T8 | None | 14.5 |
| 128 | Thioester Strategy | H | Bts-Bip | Boc-Acp | Boc-Phe | Mitsunobu Reaction | Boc-T8 | None | 17.8 |
| 129 | Thioester Strategy | H | Bts-Dip | Boc-Acp | Boc-Phe | Mitsunobu Reaction | Boc-T8 | None | 11.0 |
| 130 | Thioester Strategy | H | Bts-1Nal | Boc-Acp | Boc-Phe | Mitsunobu Reaction | Boc-T8 | None | 18.8 |
| 131 | Thioester Strategy | H | Bts-2Nal | Boc-Acp | Boc-Phe | Mitsunobu Reaction | Boc-T8 | None | 15.0 |
| 132 | Thioester Strategy | H | Bts-3Pal | Boc-Acp | Boc-Phe | Reductive Amination Reaction | Boc-T8 | None | 17.0 |
| 133 | Thioester Strategy | H | Bts-4Pal | Boc-Acp | Boc-Phe | Reductive Amination Reaction | Boc-T8 | None | 9.5 |
| 134 | Thioester Strategy | H | Bts-4-ThzAla | Boc-Acp | Boc-Phe | Mitsunobu Reaction | Boc-T8 | None | 12.0 |
| 135 | Thioester Strategy | H | Bts-2-Thi | Boc-Acp | Boc-Phe | Mitsunobu Reaction | Boc-T8 | None | 4.0 |
| 136 | Thioester Strategy | H | Bts-Abu | Boc-Acp | Boc-Phe | Mitsunobu Reaction | Boc-T8 | None | 13.3 |

TABLE 1A-continued

Synthesis of Representative Compounds of the Present Invention

| Compound | Macrocyclic Assembly Method | $N_{BB1}$-R | $BB_1$ | $BB_2$ | $BB_3$ | Tether Attachment Method | Tether | Additional Reaction** | Yield (%)* |
|---|---|---|---|---|---|---|---|---|---|
| 137 | Thioester Strategy | H | Bts-Nva | Boc-Acp | Boc-Phe | Mitsunobu Reaction | Boc-T8 | None | 19.0 |
| 138 | Thioester Strategy | H | Bts-Ile | Boc-Acp | Boc-Phe | Mitsunobu Reaction | Boc-T8 | None | 13.8 |
| 139 | Thioester Strategy | H | Bts-Val | Boc-hcLeu | Boc-Phe | Reductive Amination Reaction | Boc-T8 | None | 18.4 |
| 140 | Thioester Strategy | H | Bts-Val | Boc-hc(4O)Leu | Boc-Phe | Reductive Amination Reaction | Boc-T8 | None | 16.7 |
| 141 | Thioester Strategy | H | Bts-Val | Boc-(4O)Acp | Boc-Phe | Reductive Amination Reaction | Boc-T8 | None | 15.7 |
| 142 | Thioester Strategy | H | Bts-Val | Boc-(3-4)InAcp | Boc-Phe | Reductive Amination Reaction | Boc-T8 | None | 17.0 |
| 143 | Thioester Strategy | H | Bts-Val | Boc-hc(4S)Leu | Boc-Phe | Reductive Amination Reaction | Boc-T8 | None | 16.1 |
| 144 | Thioester Strategy | H | Bts-Ile | Boc-(D)NMeVal | Boc-(D)Phe | Reductive Amination Reaction | Boc-T9 | None | 5.7 |
| 145 | Thioester Strategy | H | Bts-Ile | Boc-NMeVal | Boc-(D)Phe | Reductive Amination Reaction | Boc-T9 | None | 4.9 |
| 146 | Thioester Strategy | H | Bts-Ile | Boc-NMeNva | Boc-(D)Phe | Reductive Amination Reaction | Boc-T9 | None | 23.3 |
| 147 | Thioester Strategy | H | Bts-Ile | Boc-(D)NMeLeu | Boc-(D)Phe | Reductive Amination Reaction | Boc-T9 | None | 14.4 |
| 148 | Thioester Strategy | H | Bts-Ile | Boc-NMeLeu | Boc-(D)Phe | Reductive Amination Reaction | Boc-T9 | None | 25.4 |
| 149 | Thioester Strategy | H | Bts-Ile | Boc-(D)NMeIle | Boc-(D)Phe | Reductive Amination Reaction | Boc-T9 | None | 11.4 |
| 150 | Thioester Strategy | H | Bts-Ile | Boc-NMeIle | Boc-(D)Phe | Reductive Amination Reaction | Boc-T9 | None | 7.0 |
| 151 | Thioester Strategy | H | Bts-Ile | Ddz-(D)Ser(But) | Boc-(D)Phe | Mitsunobu Reaction | Ddz-T9 | None | 8.2 |
| 152 | Thioester Strategy | H | Bts-Ile | Ddz-NMeSer(But) | Boc-(D)Phe | Reductive Amination Reaction | Ddz-T9 | None | 22.1 |
| 153 | Thioester Strategy | H | Bts-Leu | Boc-Acp | Boc-Phe(4-Cl) | Mitsunobu Reaction | Boc-T8 | None | 13.5 |
| 154 | Thioester Strategy | H | Bts-Leu | Boc-Acp | Boc-Phe(4-F) | Mitsunobu Reaction | Boc-T8 | None | 14.4 |
| 155 | Thioester Strategy | H | Bts-Leu | Boc-Acp | Boc-Hfe | Mitsunobu Reaction | Boc-T8 | None | 13.5 |
| 156 | Thioester Strategy | H | Bts-Leu | Boc-Acp | Boc-Tyr(OMe) | Mitsunobu Reaction | Boc-T8 | None | 13.2 |
| 157 | Thioester Strategy | H | Bts-Leu | Boc-Acp | Boc-Bip | Mitsunobu Reaction | Boc-T8 | None | 20.2 |
| 158 | Thioester Strategy | H | Bts-Leu | Boc-Acp | Boc-Dip | Mitsunobu Reaction | Boc-T8 | None | 11.3 |
| 159 | Thioester Strategy | H | Bts-Leu | Boc-Acp | Boc-2Nal | Mitsunobu Reaction | Boc-T8 | None | 20.5 |
| 160 | Thioester Strategy | H | Bts-Leu | Boc-Acp | Boc-2Pal | Reductive Amination Reaction | Boc-T8 | None | 2.8 |
| 161 | Thioester Strategy | H | Bts-Leu | Boc-Acp | Boc-3Pal | Reductive Amination Reaction | Boc-T8 | None | 16.5 |
| 162 | Thioester Strategy | H | Bts-Leu | Boc-Acp | Boc-4Pal | Reductive Amination Reaction | Boc-T8 | None | 16.7 |
| 163 | Thioester Strategy | H | Bts-Leu | Boc-Acp | Boc-4-ThzAla | Mitsunobu Reaction | Boc-T8 | None | 10.0 |
| 164 | Thioester Strategy | H | Bts-Leu | Boc-Acp | Boc-2-Thi | Mitsunobu Reaction | Boc-T8 | None | 12.5 |
| 165 | Thioester Strategy | H | Bts-Leu | Boc-Acp | Boc-Abu | Mitsunobu Reaction | Boc-T8 | None | 13.0 |

TABLE 1A-continued

Synthesis of Representative Compounds of the Present Invention

| Compound | Macrocyclic Assembly Method | $N_{BB1}$-R | $BB_1$ | $BB_2$ | $BB_3$ | Tether Attachment Method | Tether | Additional Reaction** | Yield (%)* |
|---|---|---|---|---|---|---|---|---|---|
| 166 | Thioester Strategy | H | Bts-Leu | Boc-Acp | Boc-Ile | Mitsunobu Reaction | Boc-T8 | None | 11.1 |
| 167 | Thioester Strategy | H | Bts-Leu | Boc-Acp | Boc-allo-Ile | Mitsunobu Reaction | Boc-T8 | None | 15.3 |
| 168 | Thioester Strategy | H | Bts-Leu | Boc-Acp | Boc-Acp | Mitsunobu Reaction | Boc-T8 | None | 4.2 |
| 169 | Thioester Strategy | H | Bts-Ile | Boc-(D)NMeAla | Boc-(D)Hfe | Mitsunobu Reaction | Boc-T9 | None | 17.0 |
| 170 | Thioester Strategy | H | Bts-Ile | Boc-(D)NMeAla | Boc-(D)3Pal | Reductive Amination Reaction | Boc-T9 | None | 14.5 |
| 171 | Thioester Strategy | H | Bts-Ile | Boc-(D)NMeAla | Boc-(D)4Pal | Reductive Amination Reaction | Boc-T9 | None | 16.4 |
| 172 | Thioester Strategy | H | Bts-Ile | Boc-(D)NMeAla | Boc-Abu | Mitsunobu Reaction | Boc-T9 | None | 12.0 |
| 173 | Thioester Strategy | H | Bts-Ile | Boc-(D)NMeAla | Boc-(D)Nva | Mitsunobu Reaction | Boc-T9 | None | 16.8 |
| 174 | Thioester Strategy | H | Bts-Ile | Boc-(D)NMeAla | Boc-(D)Val | Mitsunobu Reaction | Boc-T9 | None | 13.9 |
| 175 | Thioester Strategy | H | Bts-Ile | Boc-(D)NMeAla | Boc-(D)Ile | Mitsunobu Reaction | Boc-T9 | None | 15.1 |
| 176 | Thioester Strategy | H | Bts-Ile | Boc-(D)NMeAla | Boc-(D)Leu | Mitsunobu Reaction | Boc-T9 | None | 9.4 |
| 177 | Thioester Strategy | H | Bts-Ile | Boc-(D)NMeAla | Boc-(D)Phe | Mitsunobu Reaction | Boc-T11 | None | 9.3 |
| 178 | Thioester Strategy | H | Bts-Ile | Boc-(D)NMeAla | Boc-(D)Phe | Mitsunobu Reaction | Boc-T28 | None | 11.2 |
| 179 | Thioester Strategy | H | Bts-Ile | Boc-(D)NMeAla | Boc-(D)Phe | Mitsunobu Reaction | Boc-T29 | None | 8.6 |
| 180 | Thioester Strategy | H | Bts-Ile | Boc-(D)NMeAla | Boc-(D)Phe | Mitsunobu Reaction | Boc-T30 | None | 10.0 |
| 181 | RCM Strategy | H | Fmoc-Ile | Fmoc-(D)NMeAla | Fmoc-(D)Phe | Mitsunobu Reaction | $T_{A1} + T_{B7}$ | None | 49.5 |
| 182 | RCM Strategy | H | Fmoc-Ile | Fmoc-(D)NMeAla | Fmoc-(D)Phe | Mitsunobu Reaction | $T_{A1} + T_{B7}$ | Hydrogenation | 47.7 |
| 183 | RCM Strategy | H | Fmoc-Ile | Fmoc-(D)NMeAla | Fmoc-(D)Phe | Mitsunobu Reaction | $T_{A2} + T_{B7}$ | None | 59.0 |
| 184 | RCM Strategy | H | Fmoc-Ile | Fmoc-(D)NMeAla | Fmoc-(D)Phe | Mitsunobu Reaction | $T_{A2} + T_{B7}$ | Hydrogenation | 50.6 |
| 185 | RCM Strategy | H | Fmoc-Ile | Fmoc-(D)NMeAla | Fmoc-(D)Phe | Mitsunobu Reaction | $T_{A1} + T_{B6}$ | None | 12.4 |
| 186 | RCM Strategy | H | Fmoc-Ile | Fmoc-(D)NMeAla | Fmoc-(D)Phe | Mitsunobu Reaction | $T_{A2} + T_{B6}$ | None | 3.0 |
| 187 | RCM Strategy | H | Fmoc-Ile | Fmoc-(D)NMeAla | Fmoc-(D)Phe | Mitsunobu Reaction | $T_{A1} + T_{B3}$ | None | 30.9 |
| 188 | RCM Strategy | H | Fmoc-Ile | Fmoc-(D)NMeAla | Fmoc-(D)Phe | Mitsunobu Reaction | $T_{A2} + T_{B3}$ | None | 34.9 |
| 189 | RCM Strategy | H | Fmoc-Ile | Fmoc-(D)NMeAla | Fmoc-(D)Phe | Mitsunobu Reaction | $T_{A2} + T_{B3}$ | Hydrogenation | 24.0 |
| 190 | RCM Strategy | H | Fmoc-Ile | Fmoc-(D)NMeAla | Fmoc-(D)Phe | Mitsunobu Reaction | $T_{A1} + T_{B4}$ | Hydrogenation | 32.5 |
| 191 | RCM Strategy | H | Fmoc-Ile | Fmoc-(D)NMeAla | Fmoc-(D)Phe | Mitsunobu Reaction | $T_{A2} + T_{B4}$ | None | 32.2 |
| 192 | RCM Strategy | H | Fmoc-Ile | Fmoc-(D)NMeAla | Fmoc-(D)Phe | Mitsunobu Reaction | $T_{A2} + T_{B4}$ | Hydrogenation | 22.2 |
| 193 | RCM Strategy | H | Fmoc-Ile | Fmoc-(D)NMeAla | Fmoc-(D)Phe | Mitsunobu Reaction | $T_{A1} + T_{B1}$ | None | 47.7 |
| 194 | RCM Strategy | H | Fmoc-Ile | Fmoc-(D)NMeAla | Fmoc-(D)Phe | Mitsunobu Reaction | $T_{A1} + T_{B1}$ | Hydrogenation | 23.7 |
| 195 | RCM Strategy | H | Fmoc-Ile | Fmoc-(D)NMeAla | Fmoc-(D)Phe | Mitsunobu Reaction | $T_{A2} + T_{B1}$ | None | 66.8 |
| 196 | Thioester Strategy | H | Bts-Ile | Boc-(D)NMeAla | Boc-(D)Phe | Mitsunobu Reaction | Ddz-T32(Boc) | None | 13.0 |
| 197 | Thioester Strategy | H | Bts-Ile | Boc-(D)NMeAla | Boc-(D)Phe | Mitsunobu Reaction | Ddz-TB1(But) | None | 10.6 |
| 199 | Thioester Strategy | H | Bts-Val | Boc-Acc | Boc-Phe | Reductive Amination Reaction | Boc-T8 | None | 16.0 |
| 200 | Thioester Strategy | H | Bts-Val | Boc-Acp | Boc-Phe | Mitsunobu Reaction | Boc-T8 | None | 14.7 |

TABLE 1A-continued

Synthesis of Representative Compounds of the Present Invention

| Compound | Macrocyclic Assembly Method | $N_{BB1}$-R | $BB_1$ | $BB_2$ | $BB_3$ | Tether Attachment Method | Tether | Additional Reaction** | Yield (%)* |
|---|---|---|---|---|---|---|---|---|---|
| 201 | Thioester Strategy | Me | Bts-Nva | Boc-(D)NMeAla | Boc-(D)Phe | Reductive Amination Reaction | Boc-T9 | Reductive animation reaction with formaldehyde | 32.4 |
| 202 | Thioester Strategy | Ac | Bts-Nva | Boc-(D)NMeAla | Boc-(D)Phe | Reductive Amination Reaction | Boc-T9 | Acetylation | 14.2 |
| 203 | Thioester Strategy | Me | Bts-Leu | Boc-Acp | Boc-Phe | Reductive Amination Reaction | Boc-T8 | Reductive animation reaction with formaldehyde | 7.7 |
| 204 | Thioester Strategy | Ac | Bts-Leu | Boc-Acp | Boc-Phe | Reductive Amination Reaction | Boc-T8 | Acetylation | 11.5 |
| 205 | Thioester Strategy | H | Bts-Ile | Boc-(D)NMeAla | Boc-(D)Abu | Mitsunobu Reaction | Boc-T9 | None | 19.9 |
| 206 | Thioester Strategy | H | Bts-Ile | Boc-(D)NMeAla | Boc-(D)Phe | Mitsunobu Reaction | Boc-T34 | None | 26.2 |
| 207 | Thioester Strategy | H | Bts-Val | Boc-hc(4N)Leu | Boc-Phe | Mitsunobu Reaction | Boc-T9 | None | <1 |
| 208 | Thioester Strategy | H | Bts-allo-Ile | Boc-Acp | Boc-Phe | Mitsunobu Reaction | Boc-T8 | None | 16.7 |
| 209 | Thioester Strategy | H | Bts-Ile | Boc-(D)NMeAla | Boc-(D)allo-Ile | Mitsunobu Reaction | Boc-T9 | None | 8.6 |
| 210 | Thioester Strategy | H | Bts-2Pal | Boc-Acp | Boc-Phe | Reductive Amination Reaction | Boc-T8 | None | 1.1 |
| 211 | Thioester Strategy | H | Bts-Val | Boc-hc(4N)Leu | Boc-Phe | Reductive Amination Reaction | Boc-T8 | None | <1 |
| 212 | Thioester Strategy | H | Bts-Ile | Boc-NMcAbu | Boc-(D)Phe | Mitsunobu Reaction | Boc-T9 | None | 1.2 |
| 213 | Thioester Strategy | H | Bts-Ile | Boc-(D)4-Thz | Boc-(D)Phe | Reductive Amination Reaction | Boc-T9 | None | 1.0 |
| 214 | RCM Strategy | H | Fmoc-Ile | Fmoc-(D)NMeAla | Fmoc-(D)Phe | Mitsunobu Reaction | $T_{A1} + T_{B3}$ | Hydrogenation | 14.9 |
| 215 | isolated from synthesis of compound 151 | | | | | | | | |
| 216 | Thioester Strategy | H | Bts-Val | Boc-Acc | Boc-Phe | Reductive Amination Reaction | Boc-T9 | None | 11.6 |
| 218 | Thioester Strategy | H | Bts-hcLeu | Boc-Acp | Boc-Phe | Mitsunobu Reaction | Boc-T8 | None | 0.1 |
| 219 | Acetic Acid Cyclization | H | Bts-His(Mts) | Boc-Acp | Boc-Phe | Reductive Amination Reaction | Boc-T8 | None | 19.0 |
| 220 | Thioester Strategy | H | Bts-Nva | Boc-Pro | Boc-(D)Phe | Mitsunobu Reaction | Boc-T9 | None | 15.0 |
| 221 | Thioester Strategy | H | Bts-Nva | Boc-(D)Pro | Boc-(D)Phe | Mitsunobu Reaction | Boc-T9 | None | 14.9 |
| 222 | Thioester Strategy | H | Bts-Leu | Boc-Pro | Boc-Phe | Mitsunobu Reaction | Boc-T9 | None | 11.7 |
| 223 | Thioester Strategy | H | Bts-Leu | Boc-(D)Pro | Boc-Phe | Mitsunobu Reaction | Boc-T9 | None | 20.4 |
| 224 | RCM Strategy | H | Fmoc-Ile | Fmoc-(D)Hyp(But) | Fmoc-(D)Phe | Mitsunobu Reaction | $T_{A1} + T_{B2}$ | Hydrogenation | 8.2 |
| 225 | Thioester Strategy | H | Bts-Pro | Boc-(D)NMeAla | Boc-(D)Phe | Reductive Amination Reaction | Boc-T9 | None | 10.0 |
| 226 | Thioester Strategy | H | Bts-Pip | Boc-(D)NMeAla | Boc-(D)Phe | Reductive Amination Reaction | Boc-T9 | None | 13.5 |

*Overall Yield: based on theoretical resin loading, starting from ~500 mg resin
**Additional reactions conducted post-cyclization, except where otherwise noted, to reach the desired product Table 1B below presents a summary of the synthesis of 122 representative compounds of the present invention, and Table 1C presents the synthesis of an additional 15 representative compounds. For Table 1B, the reaction methodology employed for the construction of the macrocyclic molecule is indicated in Column 2 and relates to the particular scheme of the synthetic strategy. Columns 3-6 indicate the individual building blocks employed for each compound, amino acids or tether utilizing either standard nomenclature or referring to the building block designations presented elsewhere in this application. Column 7 indicates the method used for attachment of the tether. The building blocks are listed in the opposite order from which they are added in order to correlate the building block number with standard peptide nomenclature. Column 8 indicates if any additional reaction chemistry was applied, such as to remove auxiliary protection or to reduce a double bond (as was performed with many RCM intermediate products). All of the macrocycles in Tables 1B and 1C were purified and met the acceptance criteria. Yields (Column 9-10) are either isolated or as calculated based upon CLND analysis.

TABLE 1B

Synthesis of Representative Compounds of the Present Invention

| Compound | Macrocyclic Assembly Method | $BB_1$ | $BB_2$ | $BB_3$ | Tether | Tether Attachment | Additional Reaction** | Amount (mg)* | Yield (%)* |
|---|---|---|---|---|---|---|---|---|---|
| 298 | Thioester Strategy | Bts-Cpg | Boc-(D)NMeAla | Boc-(D)Phe(4-F) | Boc-T33a | Mitsunobu Reaction | None | 29.7 | 12 |
| 299 | Thioester Strategy | Bts-Cpg | Boc-(D)NMeAla | Boc-(D)Phe(4-Cl) | Boc-T9 | Mitsunobu Reaction | None | 54.1 | 17 |
| 301 | Thioester Strategy | Bts-Tyr(But) | Boc-Acp | Boc-Phe(3-Cl) | Ddz-T8 | Mitsunobu Reaction | None | 36.5 | 10 |
| 303 | Thioester Strategy | Bts-Val | Boc-(4O)Acp | Boc-Phe | Boc-T8 | Mitsunobu Reaction | None | 60 | 16 |
| 305 | Thioester Strategy | Bts-Ile | Boc-(D)NMeAla | Boc-(D)His(Mts) | Boc-T9 | Reductive Amination Reaction | None | 110 | 31 |
| 306 | Thioester Strategy | Bts-Cpg | Boc-(D)NMeAla | Boc-(D)Phe(4-F) | Boc-T11 | Mitsunobu Reaction | None | 51 | 8 |
| 307 | RCM Strategy | Fmoc-Cpg | Fmoc-(D)NMeAla | Fmoc-(D)Phe(4-F) | $T_{A2} + T_{B6}$ | Mitsunobu Reaction | None | 13.6 | 10 |
| 308 | Thioester Strategy | Bts-Cpg | Boc-(D)NMeAla | Boc-(D)Phe(4-Cl) | Boc-T8 | Mitsunobu Reaction | None | 43.8 | 14 |
| 309 | Thioester Strategy | Bts-Cpg | Boc-(D)NMeAla | Boc-(D)Phe(4-F) | Boc-T9 | Mitsunobu Reaction | None | 38.2 | 13 |
| 310 | Thioester Strategy | Bts-Cpg | Boc-(D)NMeAla | Boc-(D)3-Thi | Boc-T9 | Mitsunobu Reaction | None | 33.3 | 11 |
| 311 | Thioester Strategy | Boc-Cpg | Boc-(D)NMeAla | Boc-(D)Tyr(3-tBu) | Boc-T9 | Reductive Amination Reaction | None | 18.6 | 5.1 |
| 312 | Thioester Strategy | Bts-Cpg | Boc-(D)NMeAla | Boc-(D)Phe(2-F) | Boc-T9 | Mitsunobu Reaction | None | 42.9 | 14 |
| 313 | Thioester Strategy | Bts-Cpg | Boc-(D)NMeAla | Boc-(D)Phe(3-F) | Boc-T9 | Mitsunobu Reaction | None | 38.2 | 13 |
| 314 | Thioester Strategy | Bts-Cpg | Boc-(D)NMeAla | Boc-(D)Phe(2,4-diCl) | Boc-T9 | Mitsunobu Reaction | None | 39.7 | 12 |
| 315 | Thioester Strategy | Bts-Cpg | Boc-(D)NMeAla | Boc-(D)Phe(3,4-diCl) | Boc-T9 | Mitsunobu Reaction | None | 35.3 | 11 |
| 316 | Thioester Strategy | Bts-Cpg | Boc-(D)NMeAla | Boc-(D)Phe(3,4-diF) | Boc-T9 | Mitsunobu Reaction | None | 40.7 | 13 |
| 317 | Thioester Strategy | Bts-Cpg | Boc-(D)NMeAla | Boc-(D)Phe(3,5-diF) | Boc-T9 | Mitsunobu Reaction | None | 37.6 | 12 |
| 318 | Thioester Strategy | Bts-Cpg | Boc-(D)NMeAla | Boc-(D)Phe(pentaF) | Boc-T9 | Mitsunobu Reaction | None | 36.1 | 11 |
| 319 | Thioester Strategy | Bts-Cpg | Boc-(D)NMeAla | Boc-(D)Phe(4-Br) | Boc-T9 | Mitsunobu Reaction | None | 37.5 | 11 |
| 320 | Thioester Strategy | Bts-Cpg | Boc-(D)NMeAla | Boc-(D)Phe(4-I) | Boc-T9 | Mitsunobu Reaction | None | 43.4 | 12 |
| 321 | Thioester Strategy | Bts-Cpg | Boc-(D)NMeAla | Boc-(D)Phe(4-CN) | Boc-T9 | Mitsunobu Reaction | None | 34.5 | 11 |
| 322 | Thioester Strategy | Bts-Cpg | Boc-(D)NMeAla | Boc-(D)Phe(4-CF3) | Boc-T9 | Mitsunobu Reaction | None | 40.8 | 12 |
| 323 | Thioester Strategy | Bts-Cpg | Boc-(D)NMeAla | Boc-(D)Phe(3,4-diOMe) | Boc-T9 | Mitsunobu Reaction | None | 27.3 | 8 |
| 324 | Thioester Strategy | Bts-Cpg | Boc-(D)NMcAla | Boc-(D)Trp | Boc-T9 | Mitsunobu Reaction | None | 38.6 | 12 |
| 325 | Thioester Strategy | Bts-Ile | Boc-Acp | Boc-Phe(3-F) | Boc-T8 | Mitsunobu Reaction | None | 33.7 | 10 |
| 326 | Thioester Strategy | Bts-Ile | Boc-Acp | Boc-Phe(3-Br) | Boc-T8 | Mitsunobu Reaction | None | 37.5 | 10 |
| 327 | Thioester Strategy | Bts-Ile | Boc-Acp | Boc-Phe(3,S-diF) | Boc-T8 | Mitsunobu Reaction | None | 35.2 | 11 |
| 328 | Thioester Strategy | Bts-Ile | Boc-Acp | Boc-Phe(3-OMe) | Boc-T8 | Mitsunobu Reaction | None | 31.5 | 10 |
| 329 | Thioester Strategy | Bts-Ile | Boc-Acp | Boc-Phe(3-CN) | Boc-T8 | Mitsunobu Reaction | None | 26.9 | 8 |

TABLE 1B-continued

Synthesis of Representative Compounds of the Present Invention

| Compound | Macrocyclic Assembly Method | BB$_1$ | BB$_2$ | BB$_3$ | Tether | Tether Attachment | Additional Reaction** | Amount (mg)* | Yield (%)* |
|---|---|---|---|---|---|---|---|---|---|
| 330 | Thioester Strategy | Bts-Ile | Boc-Acp | Boc-Phe(3,4-diCl) | Boc-T8 | Mitsunobu Reaction | None | 38.4 | 11 |
| 331 | Thioester Strategy | Bts-Ile | Boc-Acp | Boc-Phe(3,4-diF) | Boc-T8 | Mitsunobu Reaction | None | 37 | 11 |
| 332 | Thioester Strategy | Bts-Ile | Boc-Acp | Boc-Phe(3-CF$_3$) | Boc-T8 | Mitsunobu Reaction | None | 30.6 | 9 |
| 333 | Thioester Strategy | Bts-Ile | Boc-Acp | Boc-3-Thi | Boc-T8 | Mitsunobu Reaction | None | 49.6 | 18 |
| 334 | Thioester Strategy | Bts-Acp | Boc-Aib | Boc-Phe(3-Cl) | Boc-T8 | Mitsunobu Reaction | None | 32 | 11 |
| 335 | Thioester Strategy | Boc-Thr(OMe) | Boc-(D)NMeAla | Boc-(D)Phe(4-F) | Boc-T9 | Reductive Amination Reaction | None | 62.2 | 18 |
| 336 | Thioester Strategy | Bts-Ser(OMe) | Boc-(D)NMeAla | Boc-(D)Phe(4-F) | Boc-T9 | Mitsunobu Reaction | None | 37.7 | 12 |
| 337 | Thioester Strategy | Boc-Dap(Cbz) | Boc-(D)NMeAla | Boc-(D)Phe(4-F) | Boc-T9 | Reductive Amination Reaction | Hydrogenolysis | 67.5 | 7 |
| 338 | Thioester Strategy | Bts-Dab(Boc) | Boc-(D)NMeAla | Boc-(D)Phe(4-F) | Boc-T9 | Mitsunobu Reaction | None | 60 | 20 |
| 339 | Thioester Strategy | Bts-Orn(Boc) | Boc-(D)NMeAla | Boc-(D)Phe(4-F) | Boc-T9 | Mitsunobu Reaction | None | 63 | 20 |
| 340 | Thioester Strategy | Boc-Met | Boc-(D)NMeAla | Boc-(D)Phe(4-F) | Boc-T9 | Reductive Amination Reaction | None | 14.4 | 4 |
| 341 | Thioester Strategy | Bts-3-Thi | Boc-Acp | Boc-Phe(3-Cl) | Boc-T8 | Mitsunobu Reaction | None | 48 | 14 |
| 342 | Thioester Strategy | Bts-Phe(2-CN) | Boc-Acp | Boc-Phe(3-Cl) | Boc-T8 | Mitsunobu Reaction | None | 37.7 | 10 |
| 343 | Thioester Strategy | Bts-Phe(2-OMe) | Boc-Acp | Boc-Phe(3-Cl) | Boc-T8 | Mitsunobu Reaction | None | 91.3 | 25 |
| 344 | Thioester Strategy | Bts-Ser(OMe) | Boc-Acp | Boc-Phe(3-Cl) | Boc-T8 | Mitsunobu Reaction | None | 22.1 | 7 |
| 345 | Thioester Strategy | Bts-Ile | Boc-(40)Acp | Boc-Phe(3-Cl) | Boc-T8 | Mitsunobu Reaction | None | 48 | 13 |
| 346 | Thioester Strategy | Bts-Cpg | Boc-Acp | Boc-Phe(3-Cl) | Boc-T8 | Mitsunobu Reaction | None | 52.1 | 16 |
| 347 | Thioester Strategy | Bts-Ile | Boc-Acp | Boc-Ser(OBzl) | Boc-T8 | Mitsunobu Reaction | None | 17.1 | 6 |
| 348 | Thioester Strategy | Bts-Ile | Boc-Acp | Boc-Ser(OBzl) | Boc-T8 | Mitsunobu Reaction | None | 104.4 | 33 |
| 349 | Thioester Strategy | Bts-Aib | Boc-Acp | Boc-Phe(3-Cl) | Boc-T8 | Mitsunobu Reaction | None | 23.6 | 7 |
| 350 | Thioester Strategy | Bts-Aib | Boc-Aib | Boc-Phe(3-Cl) | Boc-T8 | Mitsunobu Reaction | None | 44 | 15 |
| 351 | Thioester Strategy | Bts-Acp | Boc-(D)Ala | Boc-Phe(3-Cl) | Boc-T8 | Mitsunobu Reaction | None | 39.1 | 13 |
| 352 | Thioester Strategy | Bts-Acp | Boc-Ala | Boc-Phe(3-Cl) | Boc-T8 | Mitsunobu Reaction | None | 15.7 | 5 |
| 353 | RCM Strategy | Fmoc-Ile | Fmoc-(D)NMeAla | Fmoc-(D)Phe(4-F) | $T_{A1} + T_{B4}$ | Mitsunobu Reaction | None | 47.8 | 25 |
| 354 | Thioester Strategy | Bts-Cpg | Boc-(D)NMeAla | Boc-(D)Phe(4-F) | Boc-T65 | Mitsunobu Reaction | None | 26.8 | 9 |
| 355 | Thioester Strategy | Bts-Cpg | Boc-(D)NMeAla | Boc-(D)Phe(4-F) | Boc-T70 | Mitsunobu Reaction | None | 36.8 | 12 |
| 356 | Thioester Strategy | Bts-Cpg | Boc-(D)NMeAla | Boc-(D)Phe(4-F) | Boc-T72 | Mitsunobu Reaction | None | 10 | 3 |
| 357 | Thioester Strategy | Bts-Cpg | Boc-(D)NMeAla | Boc-(D)Phe(4-F) | Ddz-T74(Boc) | Mitsunobu Reaction | None | 41.8 | 11 |
| 358 | RCM Strategy | Fmoc-Ile | Fmoc-Acp | Fmoc-Phe(3-Cl) | $T_{A1} + T_{B4}$ | Mitsunobu Reaction | None | 26.1 | 26 |
| 359 | Thioester Strategy | Bts-Ile | Boc-Acp | Boc-Phe(3-Cl) | Boc-T58 | Mitsunobu Reaction | None | 43.6 | 12 |
| 360 | RCM Strategy | Fmoc-Ile | Fmoc-Acp | Fmoc-Phe(3-Cl) | $T_{A2} + T_{B6}$ | Mitsunobu Reaction | None | 36.3 | 18 |
| 361 | RCM Strategy | Fmoc-Ile | Fmoc-Acp | Fmoc-Phe(3-Cl) | $T_{A2} + T_{B4}$ | Mitsunobu Reaction | None | 36.3 | 32 |
| 362 | RCM Strategy | Fmoc-Ile | Fmoc-Acp | Fmoc-Phe(3-Cl) | $T_{A2} + T_{B1}$ | Mitsunobu Reaction | Hydrogenation | 59.4 | 57 |
| 363 | RCM Strategy | Fmoc-Ile | Fmoc-Acp | Fmoc-Phe(3-Cl) | $T_{A2} + T_{B7}$ | Mitsunobu Reaction | Hydrogenation | 41.8 | 44 |
| 364 | RCM Strategy | Fmoc-Ile | Fmoc-Acp | Fmoc-Phe(3-Cl) | $T_{A2} + T_{B7}$ | Mitsunobu Reaction | Hydrogenation | 49.1 | 51 |

TABLE 1B-continued

Synthesis of Representative Compounds of the Present Invention

| Compound | Macrocyclic Assembly Method | BB$_1$ | BB$_2$ | BB$_3$ | Tether | Tether Attachment | Additional Reaction** | Amount (mg)* | Yield (%)* |
|---|---|---|---|---|---|---|---|---|---|
| 365 | RCM Strategy | Fmoc-Ile | Fmoc-Acp | Fmoc-Phe(3-Cl) | T$_{A1}$ + T$_{B10}$ | Mitsunobu Reaction | Hydrogenation | 31.2 | 35 |
| 366 | RCM Strategy | Fmoc-Ile | Fmoc-Acp | Fmoc-Phe(3-Cl) | T$_{A1}$ + T$_{B7}$ | Mitsunobu Reaction | Hydrogenation | 33.3 | 37 |
| 367 | Thioester Strategy | Bts-Cpg | Boc-(D)NMeAla | Boc-(D)Phe(4-F) | Boc-T33b | Mitsunobu Reaction | None | 21.1 | 6 |
| 368 | Thioester Strategy | Bts-Ile | Boc-Acp | Boc-Phe(3-Cl) | Boc-T33a | Mitsunobu Reaction | None | 21.8 | 10 |
| 369 | Thioester Strategy | Bts-Ile | Boc-Acp | Boc-Phe(3-Cl) | Boc-T9 | Mitsunobu Reaction | None | 21.1 | 4 |
| 370 | RCM Strategy | Fmoc-Ile | Fmoc-Acp | Fmoc-Phe(3-Cl) | T$_{A2}$ + T$_{B6}$ | Mitsunobu Reaction | Hydrogenation | 8.9 | NA |
| 371 | RCM Strategy | Fmoc-Ile | Fmoc-Acp | Fmoc-Phe(3-Cl) | T$_{A2}$ + T$_{B4}$ | Mitsunobu Reaction | Hydrogenation | 9.9 | NA |
| 372 | Thioester Strategy | Bts-Cpg | Boc-(D)NMeAla | Boc-(D)Phe(4-F) | BOC-T69 | Mitsunobu Reaction | None | 30.9 | 10 |
| 373 | Thioester Strategy | Bts-Cpg | Boc-(D)NMeAla | Boc-(D)Phe(4-F) | Boc-T71 | Mitsunobu Reaction | None | 34.9 | 11 |
| 374 | Thioester Strategy | Bts-Cpg | Boc-(D)NMeAla | Boc-(D)Phe(4-F) | Ddz-T73(Boc) | Mitsunobu Reaction | None | 42.7 | 12 |
| 375 | Thioester Strategy | Bts-Cpg | Boc-(D)NMeAla | Boc-(D)Phe(4-F) | Boc-T39 | Mitsunobu Reaction | None | 22.3 | 7 |
| 376 | Thioester Strategy | Bts-Cpg | Boc-(D)NMeAla | Boc-(D)Phe(4-F) | Boc-T40 | Mitsunobu Reaction | None | 7.5 | 2 |
| 377 | Thioester Strategy | Bts-Cpg | Boc-(D)NMeAla | Boc-(D)Phe(4-F) | Boc-T10 | Mitsunobu Reaction | None | 14.6 | 5 |
| 378 | Thioester Strategy | Bts-Cpg | Boc-(D)NMeAla | Boc-(D)Phe(4-F) | Boc-T58 | Mitsunobu Reaction | None | 65.3 | 21 |
| 379 | Thioester Strategy | Bts-Cpg | Boc-(D)NMeAla | Boc-(D)Phe(4-F) | Boc-T67 | Mitsunobu Reaction | None | 36.3 | 12 |
| 380 | Thioester Strategy | Bts-Ile | Boc-Acp | Boc-Phe(3-Cl) | Boc-T66 | Mitsunobu Reaction | None | 16.5 | 5 |
| 381 | Thioester Strategy | Bts-Ile | Boc-Acp | Boc-Phe(3-Cl) | Boc-T65 | Mitsunobu Reaction | None | 22.5 | 7 |
| 382 | Thioester Strategy | Bts-Ile | Boc-Acp | Boc-Phe(3-Cl) | Boc-T70 | Mitsunobu Reaction | None | 24.5 | 7 |
| 383 | Thioester Strategy | Bts-Ile | Boc-Acp | Boc-Phe(3-Cl) | Boc-T69 | Mitsunobu Reaction | None | 25.2 | 7 |
| 384 | Thioester Strategy | Bts-Ile | Boc-Acp | Boc-Phe(3-Cl) | Boc-T71 | Mitsunobu Reaction | None | 21.9 | 6 |
| 385 | Thioester Strategy | Bts-Ile | Boc-Acp | Boc-Phe(3-Cl) | Boc-T11 | Mitsunobu Reaction | None | 23.3 | 7 |
| 386 | Thioester Strategy | Bts-Ile | Boc-Acp | Boc-Phe(3-Cl) | Boc-T39 | Mitsunobu Reaction | None | 12 | 4 |
| 387 | Thioester Strategy | Bts-tle | Boc-Acp | Boc-Phe(3-Cl) | Boc-T68 | Mitsunobu Reaction | None | 17.1 | 5 |
| 388 | Thioester Strategy | Bts-Ile | Boc-Acp | Boc-Phe(3-Cl) | Boc-T67 | Mitsunobu Reaction | None | 30 | 9 |
| 389 | Thioester Strategy | Bts-Cpg | Boc-(D)NMeAla | Boc-(D)Phe(4-F) | Boc-T68 | Mitsunobu Reaction | None | 16.1 | 5 |
| 390 | Thioester Strategy | Bts-Ile | Boc-Acp | Boc-Phe(3-Cl) | Boc-T18 | Mitsunobu Reaction | None | 28.7 | 10 |
| 391 | Thioester Strategy | Bts-Cpg | Boc-(D)NMeAla | Boc-(D)Phe(3,4,5-triF) | Boc-T9 | Mitsunobu Reaction | None | 45.4 | 14 |
| 392 | Thioester Strategy | Bts-Ile | Boc-Acp | Boc-Phe(3-Cl) | Boc-T40 | Mitsunobu Reaction | None | 4.3 | 1 |
| 393 | Thioester Strategy | Bts-Ile | Boc-Acp | Boc-Phe(3-Cl) | Boc-T45 | Mitsunobu Reaction | None | 2.1 | 1 |
| 394 | Thioester Strategy | Bts-Cpg | Boc-(D)NMeAla | Boc-(D)Phe(4-F) | Boc-T38 | Mitsunobu Reaction | None | 3.7 | 1 |
| 395 | RCM Strategy | Fmoc-Ile | Fmoc-(4N)Acp | Fmoc-Phe(3-Cl) | T$_{A1}$ + T$_{B2}$ | Mitsunobu Reaction | Hydrogenation | 0.2 | 0.2 |
| 396 | Thioester Strategy | Bts-Acp | Boc-(D)NMeAla | Boc-Phe(3-Cl) | Boc-T8 | Mitsunobu Reaction | None | 2.3 | 1 |
| 397 | Thioester Strategy | Bts-Acp | NMeAla | Boc-Phe(3-Cl) | Boc-T8 | Mitsunobu Reaction | None | 1.4 | 0.4 |
| 398 | RCM Strategy | Bts-Cpg | Boc-(D)NMeAla | Boc-(D)Phe(4-F) | T$_{A2}$ + T$_{B6}$ | Mitsunobu Reaction | Hydrogenation | 3.8 | 1 |
| 399 | Thioester Strategy | Bts-Ile | Boc-Acp | Boc-Phe(3-Cl) | Boc-T33b | Mitsunobu Reaction | None | 5.7 | 4 |
| 400 | Thioester Strategy | Bts-Cpg | Boc-(D)NMeAla | Boc-(D)Phe(4-F) | Boc-T66 | Mitsunobu Reaction | None | 28.3 | 9 |
| 401 | Thioester Strategy | Bts-Cpg | Boc-(D)NMeAla | Boc-(D)Phe(4-F) | Boc-T8 | Mitsunobu Reaction | None | 31.5 | 11 |

TABLE 1B-continued

Synthesis of Representative Compounds of the Present Invention

| Compound | Macrocyclic Assembly Method | BB$_1$ | BB$_2$ | BB$_3$ | Tether | Tether Attachment | Additional Reaction** | Amount (mg)* | Yield (%)* |
|---|---|---|---|---|---|---|---|---|---|
| 402 | Thioester Strategy | Bts-Ile | Boc-Acp | Boc-Phe(3-Cl) | Boc-T8 | Mitsunobu Reaction | None | 29.1 | 9 |
| 403 | Thioester Strategy | Bts-Cpg | Boc-(D)NMeAla | Boc-(D)Phe | Boc-T33a | Mitsunobu Reaction | None | 103 | 11 |
| 405 | Thioester Strategy | Bts-Nva | Boc-(D)NMeAla | Boc-(D)Phe(4-F) | Boc-T33a | Mitsunobu Reaction | None | 38.8 | 12 |
| 406 | Thioester Strategy | Bts-Cpg | Boc-(D)NMeAla | Boc-(D)Phe(4-F) | Boc-T75a | Mitsunobu Reaction | None | 45 | 13 |
| 407 | Thioester Strategy | Bts-Ile | Boc-(D)NMeAla | Boc-(D)Phe(4-F) | Boc-T33a | Mitsunobu Reaction | None | 138.5 | 16 |
| 408 | Thioester Strategy | Bts-Ile | Boc-(D)NMeAla | Boc-(D)Phe(4-F) | Boc-T75a | Mitsunobu Reaction | None | 146.2 | 21 |
| 409 | Thioester Strategy | Bts-Val | Boc-(D)NMeAla | Boc-(D)Phe(4-F) | Boc-T33a | Mitsunobu Reaction | None | 125.7 | 19 |
| 410 | RCM Strategy | Bts-Nva | Boc-(D)NMeAla | Boc-(D)Phe | Boc-T75a | Mitsunobu Reaction | None | 36 | 11 |
| 415 | Thioester Strategy | Bts-Cpg | Boc-(D)NMeAla | Boc-(D)Phe(4-Cl) | Boc-T33a | Mitsunobu Reaction | None | 127.5 | 12 |
| 417 | Thioester Strategy | Bts-Cpg | Boc-(D)NMeAla | Boc-(D)Phe(4-Cl) | Boc-T69 | Mitsunobu Reaction | None | 45.6 | 13 |
| 430 | Thioester Strategy | Bts-Cpg | Boc-(D)NMeAla | Boc-(D)Phe(4-Cl) | Boc-T75a | Mitsunobu Reaction | None | 50.7 | 14 |
| 431 | Thioester Strategy | Bts-Ile | Boc-(D)NMeAla | Boc-(D)Phe | Boc-T33a | Mitsunobu Reaction | None | 57.9 | 17 |
| 432 | Thioester Strategy | Bts-Ile | Boc-(D)NMeAla | Boc-(D)Phe(4-Cl) | Boc-T33a | Mitsunobu Reaction | None | 141 | 13 |

*Overall Yield: based on theoretical resin loading, starting from ~500 mg resin
**Additional reactions conducted post-cyclization to reach the desired product

TABLE 1C

Synthesis of Representative Compounds of the Present Invention

| Compound | Macrocyclic Assembly Method | BB$_1$ | BB$_2$ | BB$_3$ | Tether | Tether Attachment | Additional Reaction** | Amount (mg) | Yield (%) |
|---|---|---|---|---|---|---|---|---|---|
| 435 | Thioester Strategy | Bts-Cpg | Boc-(D)NMeAla | Boc-(D)Phe | Boc-T75a | Mitsunobu Reaction | None | 29.7 | 9 |
| 436 | Thioester Strategy | Bts-Cpg | Boc-(D)NMeAla | Boc-(D)Phe | Boc-T76 | Mitsunobu Reaction | None | 37.8 | 11 |
| 437 | Thioester Strategy | Bts-Acp | Boc-Acp | Boc-Phe(3-Cl) | Boc-T8 | Mitsunobu Reaction | None | 8.3 | 2 |
| 438 | Thioester Strategy | Bts-Leu | Boc-Acp | Boc-Phe(3-Cl) | Boc-T33a | Mitsunobu Reaction | None | 51.2 | 5 |
| 439 | Thioester Strategy | Bts-Ile | Boc-(3/4O)Acp | Boc-Phe(3-Cl) | Boc-T8 | Mitsunobu Reaction | None | 5.9 | 2 |
| 440 | RCM Strategy | Bts-Ile | Fmoc-(D)NMeSer(OBzl) | Fmoc-(D)Phe(4-F) | T$_{A1}$ + T$_{B2}$ | Mitsunobu Reaction | Hydrogenation | 2.7 | 2 |
| 441 | Thioester Strategy | Bts-Ile | Ddz-Acp | Ddz-Phe(4-CO$_2$tBu) | Ddz-T8 | Mitsunobu Reaction | None | 9.8 | 3 |
| 442 | Thioester Strategy | Bts-Ile | Ddz-Acp | Ddz-Ser(But) | Ddz-T8 | Mitsunobu Reaction | None | 17.1 | 6 |
| 443 | Thioester Strategy | Bts-Ile | Boc-Acp | Boc-Ser(OMe) | Boc-T8 | Mitsunobu Reaction | None | 19 | 7 |
| 444 | Thioester Strategy | Boc-Leu | Boc-Acp | Boc-His(Mts) | Boc-T8 | Reductive Animation Reaction | None | 21 | 7 |
| 445 | Thioester Strategy | Bts-Ile | Ddz-(D)NMeAla | Ddz-(D)Tyr(But) | Boc-T9 | Mitsunobu Reaction | None | 15.5 | 5 |
| 446 | Thioester Strategy | Bts-Cpg | Boc-(D)NMeAla | Boc-(D)Phe(4-F) | Boc-T45 | Mitsunobu Reaction | None | 3.2 | 1 |
| 447 | RCM Strategy | Bts-Ile | Fmoc-Acp | Fmoc-Phe(3-Cl) | T$_{A1}$ + T$_{B9}$ | Mitsunobu Reaction | Hydrogenation | 18.2 | 21 |
| 448 | RCM Strategy | Bts-Nva | Fmoc-Sar | Fmoc-(DL)αMePhe | T$_{A1}$ + T$_{B2}$ | Mitsunobu Reaction | Hydrogenation | 4.8 | 2 |
| 449 | Thioester Strategy | Bts-Ile | Boc-Acp | Boc-Phe(3-Cl) | Boc-T77 | Mitsunobu Reaction | None | 2.6 | 1 |

*Overall Yield: based on theoretical resin loading, starting from ~500 mg resin
**Additional reactions conducted post-cyclization to obtain the desired product The tables directly below present analytical data obtained for compounds 1-197, 199-216, 218-230 (Table 2A), compounds 298, 299, 301, 303, 304-403, 405-410, 415, 417 and 430-432 (Table 2B) and compounds 435-449 (Table 2C), as determined by LC-MS analysis of the purified products. These compounds were further examined for their ability to interact at the human ghrelin receptor utilizing the biological test methods described below.

TABLE 2A

Analytical Characterization for Representative Compounds of the Present Invention

| Compound | Molecular Formula | MW Calc (g/mol) | MS [(M + H)+] Found |
|---|---|---|---|
| 1 | C29H40N4O4 | 508.7 | 509 |
| 2 | C29H40N4O4 | 508.7 | 509 |
| 3 | C28H38N4O4 | 494.6 | 495 |
| 4 | C29H40N4O4 | 508.7 | 509 |
| 5 | C29H40N4O4 | 508.7 | 509 |
| 6 | C30H39N5O4 | 533.7 | 534 |
| 7 | C28H38N4O5 | 510.6 | 511 |
| 8 | C32H42N4O4 | 546.7 | 547 |
| 9 | C31H42N4O4 | 534.7 | 535 |
| 10 | C28H38N4O4 | 494.6 | 495 |
| 11 | C28H36N4O4 | 492.6 | 493 |
| 12 | C28H45N4O4 | 501.7 | 502 |
| 13 | C30H40N4O4 | 520.7 | 521 |
| 14 | C29H38N4O4 | 506.6 | 507 |
| 15 | C30H42N4O4 | 522.7 | 523 |
| 16 | C30H42N4O4 | 522.7 | 523 |
| 17 | C29H38N4O4 | 506.6 | 507 |
| 18 | C32H40N4O4 | 544.7 | 545 |
| 19 | C29H38N4O4 | 506.6 | 507 |
| 20 | C32H41N4O4Cl | 581.1 | 581 |
| 21 | C32H41N4O4Cl | 581.1 | 581 |
| 22 | C36H44N4O4 | 596.8 | 597 |
| 23 | C30H41N4O4Cl | 557.1 | 557 |
| 24 | C30H41N4O4Cl | 557.1 | 557 |
| 25 | C30H41N4O4Cl | 557.1 | 557 |
| 26 | C30H41N4O4F | 540.7 | 541 |
| 27 | C31H44N4O5 | 552.7 | 553 |
| 28 | C36H46N4O4 | 598.8 | 599 |
| 29 | C36H46N4O4 | 598.8 | 599 |
| 30 | C34H44N4O4 | 572.7 | 573 |
| 31 | C34H44N4O4 | 572.7 | 573 |
| 32 | C29H41N5O4 | 523.7 | 524 |
| 33 | C27H39N5O4S | 529.7 | 530 |
| 34 | C28H40N4O4S | 528.7 | 529 |
| 35 | C31H44N4O4 | 536.7 | 537 |
| 36 | C31H44N4O4 | 536.7 | 537 |
| 37 | C31H42N4O3 | 518.7 | 519 |
| 38 | C31H44N4O3 | 520.7 | 521 |
| 39 | C29H38N4O4 | 506.6 | 507 |
| 40 | C30H40N4O4 | 520.7 | 521 |
| 41 | C31H44N4O4 | 536.7 | 537 |
| 42 | C30H42N4O4 | 522.7 | 523 |
| 43 | C31H44N4O4 | 536.7 | 537 |
| 44 | C25H38N4O4 | 458.6 | 459 |
| 45 | C28H40N4O6 | 528.6 | 529 |
| 46 | C28H42N4O4 | 498.7 | 499 |
| 47 | C29H44N4O4 | 512.7 | 513 |
| 48 | C28H42N4O4 | 498.7 | 499 |
| 49 | C22H34N4O4 | 418.5 | 419 |
| 50 | C24H36N4O6 | 476.6 | 477 |
| 51 | C21H32N4O4 | 404.5 | 405 |
| 52 | C25H40N4O4 | 460.6 | 461 |
| 53 | C24H39N5O4 | 461.6 | 462 |
| 54 | C22H34N4O5 | 434.5 | 435 |
| 55 | C28H38N4O4 | 494.6 | 495 |
| 56 | C28H38N4O4 | 494.6 | 495 |
| 57 | C28H38N4O4 | 494.6 | 495 |
| 58 | C30H43N5O5 | 553.7 | 554 |
| 59 | C28H38N4O4 | 494.6 | 495 |
| 60 | C28H38N4O4 | 494.6 | 495 |
| 61 | C27H36N4O4 | 480.6 | 481 |
| 62 | C31H44N4O4 | 536.7 | 537 |
| 63 | C31H44N4O4 | 536.7 | 537 |
| 64 | C34H42N4O4 | 570.7 | 571 |
| 65 | C34H42N4O4 | 570.7 | 571 |
| 66 | C29H40N4O4 | 508.7 | 509 |
| 67 | C31H42N4O4 | 534.7 | 535 |
| 68 | C31H45N5O4 | 551.7 | 552 |
| 69 | C31H45N5O4 | 551.7 | 552 |
| 70 | C30H40N4O6 | 552.7 | 553 |
| 71 | C30H40N4O6 | 552.7 | 553 |
| 72 | C26H34N4O4 | 466.6 | 467 |
| 73 | C28H36N4O6 | 524.6 | 525 |
| 74 | C29H41N5O4 | 523.7 | 524 |
| 75 | C32H38N4O4 | 542.7 | 543 |
| 76 | C26H34N4O5 | 482.6 | 483 |
| 77 | C31H36N4O3S | 544.7 | 545 |
| 78 | C23H34N4O4 | 430.5 | 431 |
| 79 | C29H41N4O4 | 509.7 | 510 |
| 80 | C25H33N4O4 | 453.6 | 454 |
| 81 | C21H33N4O4 | 405.5 | 406 |
| 82 | C23H33N4O3 | 413.5 | 414 |
| 83 | C23H35N4O3 | 415.5 | 416 |
| 84 | C25H33N4O3 | 437.6 | 438 |
| 85 | C26H35N4O3 | 451.6 | 452 |
| 86 | C22H30N5O3S | 444.6 | 445 |
| 87 | C26H40N4O4 | 472.6 | 473 |
| 88 | C32H44N4O5 | 564.7 | 565 |
| 89 | C34H45N5O4 | 587.8 | 588 |
| 90 | C33H46N4O4 | 562.7 | 563 |
| 91 | C29H47N5O4 | 529.7 | 530 |
| 92 | C28H42N4O6 | 530.7 | 531 |
| 93 | C29H40N4O4 | 508.7 | 509 |
| 94 | C29H40N4O4 | 508.7 | 509 |
| 95 | C30H42N4O4 | 522.7 | 523 |
| 96 | C32H44N4O4 | 548.7 | 549 |
| 97 | C32H44N4O4 | 548.7 | 549 |
| 98 | C32H44N4O4 | 548.7 | 549 |
| 99 | C34H49N5O5 | 607.8 | 608 |
| 100 | C29H38N4O4 | 506.6 | 507 |
| 101 | C32H44N4O4 | 548.7 | 549 |
| 102 | C35H42N4O4 | 582.7 | 583 |
| 103 | C32H45N5O4 | 563.7 | 564 |
| 104 | C31H40N4O6 | 564.7 | 565 |
| 105 | C29H38N4O5 | 522.6 | 523 |
| 106 | C27H38N4O3 | 466.6 | 467 |
| 107 | C30H40N4O3 | 504.7 | 505 |
| 108 | C35H42N4O3S | 598.8 | 599 |
| 109 | C31H43N5O4 | 549.7 | 550 |
| 110 | C25H39N4O4 | 459.6 | 460 |
| 111 | C30H40N4O4 | 520.7 | 521 |
| 112 | C28H37N4O4 | 493.6 | 494 |
| 113 | C32H45N4O4 | 549.7 | 550 |
| 114 | C27H41N4O3 | 469.6 | 470 |
| 115 | C30H41N4O3 | 505.7 | 506 |
| 116 | C30H44N4O6 | 556.7 | 557 |
| 117 | C28H38N4O4 | 494.6 | 495 |
| 118 | C30H42N4O4 | 522.7 | 523 |
| 119 | C28H38N4O5 | 510.6 | 511 |
| 120 | C29H40N4O5 | 524.7 | 525 |
| 121 | C28H36N4O4 | 492.6 | 493 |
| 122 | C35H39N4O4Cl | 615.2 | 615 |
| 123 | C35H39N4O4Cl | 615.2 | 615 |
| 124 | C35H39N4O4Cl | 615.2 | 615 |
| 125 | C35H39N4O4F | 598.7 | 599 |
| 126 | C36H42N4O4 | 594.7 | 595 |
| 127 | C36H42N4O5 | 610.7 | 611 |
| 128 | C41H44N4O4 | 656.8 | 657 |
| 129 | C41H44N4O4 | 656.8 | 657 |
| 130 | C39H42N4O4 | 630.8 | 631 |
| 131 | C39H42N4O4 | 630.8 | 631 |
| 132 | C34H39N5O4 | 581.7 | 582 |
| 133 | C34H39N5O4 | 581.7 | 582 |
| 134 | C32H37N5O4S | 587.7 | 588 |
| 135 | C33H38N4O4S | 586.7 | 587 |
| 136 | C30H38N4O4 | 518.6 | 519 |
| 137 | C31H40N4O4 | 532.7 | 533 |

TABLE 2A-continued

Analytical Characterization for Representative Compounds of the Present Invention

| Compound | Molecular Formula | MW Calc (g/mol) | MS [(M + H)+] Found |
|---|---|---|---|
| 138 | C32H42N4O4 | 546.7 | 547 |
| 139 | C32H42N4O4 | 546.7 | 547 |
| 140 | C31H40N4O5 | 548.7 | 549 |
| 141 | C30H38N4O5 | 534.6 | 535 |
| 142 | C35H40N4O4 | 580.7 | 581 |
| 143 | C31H40N4O4S | 564.7 | 565 |
| 144 | C32H46N4O4 | 550.7 | 551 |
| 145 | C32H46N4O4 | 550.7 | 551 |
| 146 | C32H46N4O4 | 550.7 | 551 |
| 147 | C33H48N4O4 | 564.8 | 565 |
| 148 | C33H48N4O4 | 564.8 | 565 |
| 149 | C33H48N4O4 | 564.8 | 565 |
| 150 | C33H48N4O4 | 564.8 | 565 |
| 151 | C29H40N4O5 | 524.7 | 525 |
| 152 | C30H42N4O5 | 538.7 | 539 |
| 153 | C32H41N4O4Cl | 581.1 | 581 |
| 154 | C32H41N4O4F | 564.7 | 565 |
| 155 | C33H44N4O4 | 560.7 | 561 |
| 156 | C33H44N4O5 | 576.7 | 577 |
| 157 | C38H46N4O4 | 622.8 | 623 |
| 158 | C38H46N4O4 | 622.8 | 623 |
| 159 | C36H44N4O4 | 596.8 | 597 |
| 160 | C31H41N5O4 | 547.7 | 548 |
| 161 | C31H41N5O4 | 547.7 | 548 |
| 162 | C31H41N5O4 | 547.7 | 548 |
| 163 | C29H39N5O4S | 553.7 | 554 |
| 164 | C30H40N4O4S | 552.7 | 553 |
| 165 | C27H40N4O4 | 484.6 | 485 |
| 166 | C29H44N4O4 | 512.7 | 513 |
| 167 | C29H44N4O4 | 1.0 | 2 |
| 168 | C29H42N4O4 | 510.7 | 511 |
| 169 | C31H44N4O4 | 536.7 | 537 |
| 170 | C29H41N5O4 | 523.7 | 524 |
| 171 | C29H41N5O4 | 523.7 | 524 |
| 172 | C25H40N4O4 | 460.6 | 461 |
| 173 | C26H42N4O4 | 474.6 | 475 |
| 174 | C26H42N4O4 | 474.6 | 475 |
| 175 | C27H44N4O4 | 488.7 | 489 |
| 176 | C27H44N4O4 | 488.7 | 489 |
| 177 | C29H41N5O4 | 523.7 | 524 |
| 178 | C29H40N4O4 | 508.7 | 509 |
| 179 | C30H42N4O3 | 506.7 | 507 |
| 180 | C31H44N4O3 | 520.7 | 521 |
| 181 | C26H40N4O3 | 456.6 | 457 |
| 182 | C26H42N4O3 | 458.6 | 459 |
| 183 | C27H42N4O3 | 470.6 | 471 |
| 184 | C27H44N4O3 | 472.7 | 473 |
| 185 | C25H38N4O4 | 458.6 | 459 |
| 186 | C26H40N4O4 | 472.6 | 473 |
| 187 | C30H40N4O3 | 504.7 | 505 |
| 188 | C31H42N4O3 | 518.7 | 519 |
| 189 | C31H44N4O3 | 520.7 | 521 |
| 190 | C31H44N4O3 | 520.7 | 521 |
| 191 | C32H44N4O3 | 532.7 | 533 |
| 192 | C32H46N4O3 | 534.7 | 535 |
| 193 | C30H40N4O3 | 504.7 | 505 |
| 194 | C30H42N4O3 | 506.7 | 507 |
| 195 | C31H42N4O3 | 518.7 | 519 |
| 196 | C31H44N6O4 | 564.7 | 565 |
| 197 | C31H42N4O6 | 566.7 | 567 |
| 199 | C29H36N4O4 | 504.6 | 505 |
| 200 | C31H40N4O4 | 532.7 | 533 |
| 201 | C30H42N4O4 | 522.7 | 523 |
| 202 | C31H42N4O5 | 550.7 | 551 |
| 203 | C33H44N4O4 | 560.7 | 561 |
| 204 | C34H44N4O5 | 588.7 | 589 |
| 205 | C25H40N4O4 | 460.6 | 461 |
| 206 | C31H46N6O5 | 582.7 | 583 |
| 207 | C31H43N5O4 | 549.7 | 550 |
| 208 | C32H42N4O4 | 546.7 | 547 |
| 209 | C27H44N4O4 | 488.7 | 489 |
| 210 | C34H39N5O4 | 581.7 | 582 |
| 211 | C31H41N5O4 | 547.7 | 548 |
| 212 | C31H44N4O4 | 536.7 | 537 |
| 213 | C30H40N4O4S | 552.7 | 553 |
| 214 | C30H42N4O3 | 506.7 | 507 |
| 215 | C33H48N4O5 | 580.8 | 581 |
| 216 | C29H38N4O4 | 506.6 | 507 |
| 218 | C33H42N4O4 | 558.7 | 559 |
| 219 | C32H38N6O4 | 570.7 | 571 |
| 220 | C30H40N4O4 | 520.7 | 521 |
| 221 | C30H40N4O4 | 520.7 | 521 |
| 222 | C31H42N4O4 | 534.7 | 535 |
| 223 | C31H42N4O4 | 534.7 | 535 |
| 224 | C31H42N4O5 | 550.7 | 551 |
| 225 | C29H38N4O4 | 506.6 | 507 |
| 226 | C30H40N4O4 | 520.7 | 521 |
| 227 | C30H40N4O4 | 520.7 | 521 |
| 228 | C30H40N4O4 | 520.7 | 521 |
| 229 | C31H42N4O4 | 534.7 | 535 |
| 230 | C31H42N4O4 | 534.7 | 535 |

Notes
1. Molecular formulas and molecular weights are calculated automatically from the structure via ActivityBase software (IDBS, Guildford, Surrey, UK).
2. M + H obtained from LC-MS analysis using standard methods.
3. All analyses conducted on material after preparative purification by the methods described above.

TABLE 2B

Analytical Characterization for Representative Compounds of the Present Invention

| Compound | Molecular Formula | MW Calc (g/mol) | MS [(M + H)+] Found |
|---|---|---|---|
| 298 | C30H39N4O4F | 538.7 | 539 |
| 299 | C29H37N4O4Cl | 541.1 | 541 |
| 301 | C35H39N4O5Cl | 631.2 | 631 |
| 303 | C30H38N4O5 | 534.6 | 535 |
| 305 | C27H40N6O4 | 512.6 | 513 |
| 306 | C28H36N5O4 | 525.6 | 526 |
| 307 | C25H35N4O4F | 474.6 | 475 |
| 308 | C29H35N4O4Cl | 539.1 | 539 |
| 309 | C29H37N4O4F | 524.6 | 525 |
| 310 | C27H36N4O4S | 512.7 | 513 |
| 311 | C33H46N4O5 | 578.7 | 579 |
| 312 | C29H37N4O4F | 524.6 | 525 |
| 313 | C29H37N4O4F | 524.6 | 525 |
| 314 | C29H36N4O4Cl2 | 575.5 | 575 |
| 315 | C29H36N4O4Cl2 | 575.5 | 575 |
| 316 | C29H36N4O4F2 | 542.6 | 543 |
| 317 | C29H36N4O4F2 | 542.6 | 543 |
| 318 | C29H33N4O4F5 | 596.6 | 597 |
| 319 | C29H37N4O4Br | 585.5 | 585 |
| 320 | C29H37N4O4I | 632.5 | 633 |
| 321 | C30H37N5O4 | 531.6 | 532 |
| 322 | C30H37N4O4F3 | 574.6 | 575 |
| 323 | C31H42N4O6 | 566.7 | 567 |
| 324 | C31H39N5O4 | 545.7 | 546 |
| 325 | C32H41N4O4F | 564.7 | 565 |
| 326 | C32H41N4O4Br | 625.6 | 625 |
| 327 | C32H40N4O4F2 | 582.7 | 583 |
| 328 | C33H44N4O5 | 576.7 | 577 |
| 329 | C33H41N5O4 | 571.7 | 572 |
| 330 | C32H40N4O4Cl2 | 615.6 | 616 |
| 331 | C32H40N4O4F2 | 582.7 | 583 |
| 332 | C33H41N4O4F3 | 614.7 | 615 |
| 333 | C30H40N4O4S | 552.7 | 553 |
| 334 | C30H37N4O4Cl | 553.1 | 553 |
| 335 | C29H39N4O5F | 542.6 | 543 |
| 336 | C28H37N4O5F | 528.6 | 529 |
| 337 | C27H36N5O4F | 513.6 | 514 |
| 338 | C28H38N5O4F | 527.6 | 528 |
| 339 | C29H40N5O4F | 541.7 | 542 |
| 340 | C29H39N4O4FS | 558.7 | 559 |

TABLE 2B-continued

Analytical Characterization for Representative Compounds of the Present Invention

| Compound | Molecular Formula | MW Calc (g/mol) | MS [(M + H)+] Found |
|---|---|---|---|
| 341 | C33H37N4O4SCl | 621.2 | 621 |
| 342 | C36H38N5O4Cl | 640.2 | 640 |
| 343 | C36H41N4O5Cl | 645.2 | 645 |
| 344 | C30H37N4O5Cl | 569.1 | 569 |
| 345 | C31H39N4O5Cl | 583.1 | 583 |
| 346 | C31H37N4O4Cl | 565.1 | 565 |
| 347 | C33H44N4O5 | 576.7 | 577 |
| 348 | C31H42N4O5 | 550.7 | 551 |
| 349 | C30H37N4O4Cl | 553.1 | 553 |
| 350 | C28H35N4O4Cl | 527.1 | 527 |
| 351 | C29H35N4O4Cl | 539.1 | 539 |
| 352 | C29H35N4O4Cl | 539.1 | 539 |
| 353 | C31H41N4O3F | 536.7 | 537 |
| 354 | C29H33N4O4F | 520.6 | 521 |
| 355 | C29H36N4O4F2 | 542.6 | 543 |
| 356 | C30H36N4O4F4 | 592.6 | 593 |
| 357 | C30H40N5O6FS | 617.7 | 618 |
| 358 | C33H43N4O3Cl | 579.2 | 579 |
| 359 | C34H47N4O4Cl | 611.2 | 611 |
| 360 | C28H41N4O4Cl | 533.1 | 533 |
| 361 | C34H45N4O3Cl | 593.2 | 593 |
| 362 | C33H45N4O3Cl | 581.2 | 581 |
| 363 | C29H45N4O3Cl | 533.1 | 533 |
| 364 | C29H43N4O3Cl | 531.1 | 531 |
| 365 | C27H41N4O3Cl | 505.1 | 505 |
| 366 | C28H43N4O3Cl | 519.1 | 519 |
| 367 | C30H39N4O4F | 538.7 | 539 |
| 368 | C33H45N4O4Cl | 597.2 | 597 |
| 369 | C32H43N4O4Cl | 583.2 | 583 |
| 370 | C28H43N4O4Cl | 535.1 | 535 |
| 371 | C34H47N4O3Cl | 595.2 | 595 |
| 372 | C29H36N4O4F2 | 542.6 | 543 |
| 373 | C29H36N4O4FCl | 559.1 | 559 |
| 374 | C30H40N5O6FS | 617.7 | 618 |
| 375 | C30H39N4O4F | 538.7 | 539 |
| 376 | C30H39N4O4F | 538.7 | 539 |
| 377 | C28H35N4O5F | 526.6 | 527 |
| 378 | C31H41N4O4F | 552.7 | 553 |
| 379 | C30H37N4O4F | 536.6 | 537 |
| 380 | C32H41N4O4Cl | 581.1 | 581 |
| 381 | C32H39N4O4Cl | 579.1 | 579 |
| 382 | C32H42N4O4FCl | 601.2 | 601 |
| 383 | C32H42N4O4FCl | 601.2 | 601 |
| 384 | C32H42N4O4Cl2 | 617.6 | 617 |
| 385 | C31H42N5O4Cl | 584.1 | 584 |
| 386 | C33H45N4O4Cl | 597.2 | 597 |
| 387 | C33H43N4O4Cl | 595.2 | 595 |
| 388 | C33H43N4O4Cl | 595.2 | 595 |
| 389 | C30H37N4O4F | 536.6 | 537 |
| 390 | C26H40N5O3Cl | 506.1 | 506 |
| 391 | C29H35N4O4F3 | 560.6 | 561 |
| 392 | C33H45N4O4Cl | 597.2 | 597 |
| 393 | C27H41N4O5Cl | 537.1 | 537 |
| 394 | C30H39N4O4F | 538.7 | 539 |
| 395 | C31H42N5O4Cl | 584.1 | 584 |
| 396 | C30H37N4O4Cl | 553.1 | 553 |
| 397 | C30H37N4O4Cl | 553.1 | 553 |
| 398 | C25H37N4O4F | 476.6 | 477 |
| 399 | C33H45N4O4Cl | 597.2 | 597 |
| 400 | C29H35N4O4F | 522.6 | 523 |
| 401 | C29H35N4O4F | 522.6 | 523 |
| 402 | C32H41N4O4Cl | 581.1 | 581 |
| 403 | C30H40N4O4 | 520.7 | 521 |
| 405 | C30H41N4O4F | 540.7 | 541 |
| 406 | C30H38N4O4F2 | 556.6 | 557 |
| 407 | C31H43N4O4F | 554.7 | 555 |
| 408 | C31H42N4O4F2 | 572.7 | 573 |
| 409 | C30H41N4O4F | 540.7 | 541 |
| 410 | C30H42N4O4 | 522.7 | 523 |
| 415 | C30H39N4O4Cl | 555.1 | 555 |
| 417 | C29H36N4O4FCl | 559.1 | 559 |
| 430 | C30H38N4O4FCl | 573.1 | 573 |
| 431 | C31H44N4O4 | 536.7 | 537 |
| 432 | C31H43N4O4Cl | 571.2 | 571 |

Notes
1. Molecular formulas and molecular weights are calculated automatically from the structure via ActivityBase software (IDBS, Guildford, Surrey, UK).
2. M + H obtained from LC-MS analysis using standard methods.
3. All analyses conducted on material after preparative purification by the methods described above.

TABLE C

Analytical Characterization for Representative Compounds of the Present Invention

| Compound | Molecular Formula | MW Calc (g/mol) | MS [(M + H)+] Found |
|---|---|---|---|
| 435 | C30H39N4O4F | 538.7 | 539 |
| 436 | C31H40N4O4 | 532.7 | 533 |
| 437 | C32H39N4O4Cl | 579.1 | 579 |
| 438 | C33H45N4O4Cl | 597.2 | 597 |
| 439 | C32H39N4O5Cl | 595.1 | 595 |
| 440 | C37H47N4O5F | 646.8 | 647 |
| 441 | C33H42N4O6 | 590.7 | 591 |
| 442 | C26H38N4O5 | 486.6 | 487 |
| 443 | C27H40N4O5 | 500.6 | 501 |
| 444 | C29H40N6O4 | 536.7 | 537 |
| 445 | C30H42N4O5 | 538.7 | 539 |
| 446 | C24H35N4O5F | 478.6 | 479 |
| 447 | C26H39N4O3Cl | 491.1 | 492 |
| 448 | C29H40N4O4 | 508.7 | 509 |
| 449 | C31H42N5O4Cl | 584.1 | 584 |

Notes
1. Molecular formulas and molecular weights are calculated automatically from the structure via ActivityBase software (IDBS, Guildford, Surrey, UK).
2. M + H obtained from LC-MS analysis using standard methods.
3. All analyses conducted on material after preparative purification by the methods described above.

D. Chiral Purity Determination

General methods for the HPLC determination of stereoisomeric purity were employed according to techniques known to those skilled in the art and further optimized for the compounds of the present invention.

Method Chiral A: Grad35A-05 (Column: Chiralcel AS-RH, 0.46 cm×15 cm):

1. Isocratic plateau of 40 min at 35% ACN, 65% of a 50 mM solution of $CH_3COONH_4$ in $H_2O$.
2. 5 min gradient to 70% ACN, 30% of a 50 mM solution of $CH_3COONH_4$ in $H_2O$.
3. Isocratic plateau of 10 min at 70% ACN, 30% of a 50 mM solution of CH3COONH$_4$ in $H_2O$.
4. 5 min gradient to 35% ACN, 65% of a 50 mM solution of $CH_3COONH_4$ in $H_2O$.
5. Isocratic plateau of 10 min at 35% ACN, 65% of a 50 mM solution of $CH_3COONH_4$ in $H_2O$.
6. Flow: 0.5 mL/min
7. Column temperature: room temperature
8. Sample temperature: room temperature Method Chiral B: Grad40A-05 (Column: Chiralcel OD-RH, 0.46 cm×15 cm):

1. Isocratic plateau of 40 min at 40% ACN, 60% of a solution 50 mM of $CH_3COONH_4$ in $H_2O$.
2. 5 min gradient to 70% ACN, 30% of a solution 50 mM of $CH_3COONH_4$ in $H_2O$.

3. Isocratic plateau of 10 min at 70% ACN, 30% of a solution 50 mM of $CH_3COONH_4$ in $H_2O$.
4. 5 min gradient to 40% ACN, 60% of a solution 50 mM of $CH_3COONH_4$ in $H_2O$.
5. Isocratic plateau of 10 min at 40% ACN, 60% of a solution 50 mM of $CH_3COONH_4$ in $H_2O$.
6. Flow: 0.5 mL/min
7. Column temperature: room temperature
8. Sample temperature: room temperature Method Chiral C: Grad 55A-05 (Column: Chiralcel OD-RH, 0.46 cm×15 cm):
1. 40 min isocratic 55%/45% of ACN/50 mM $CH_3COONH_4$ in $H_2O$
2. 5 min gradient to 70%/30% of ACN/50 mM $CH_3COONH_4$ in $H_2O$
3. 10 min isocratic 70%/30% of ACN/50 mM $CH_3COONH_4$ in $H_2O$
4. 5 min gradient to 55%/44% of ACN/50 mM $CH_3COONH_4$ in $H_2O$
5. 10 min isocratic 55%/45% of ACN/50 mM $CH_3COONH_4$ in $H_2O$
6. Flow: 0.5 mL/min
7. Column temperature: room temperature
8. Sample temperature: room temperature Method Chiral D: Grad Iso100B_05 (Column: Chiralcel OD-RH, 0.46 cm×15 cm):
1. 40 min isocratic 27%/73% of ACN/50 mM $CH_3COONH_4$ in $H_2O$
2. 5 min gradient to 70%/30% of ACN/50 mM $CH_3COONH_4$ in $H_2O$
3. 10 min isocratic 70%/30% of ACN/50 mM $CH_3COONH_4$ in $H_2O$
4. 5 min gradient to 27%/73% of ACN/50 mM $CH_3COONH_4$ in $H_2O$
5. 10 min isocratic 27%/73% of ACN/50 mM $CH_3COONH_4$ in $H_2O$
6. Flow: 0.5 mL/min
7. Column temperature: room temperature
8. Sample temperature: room temperature 3. Biological Methods The compounds of the present invention were evaluated for their ability to interact at the human ghrelin receptor utilizing a competitive radioligand binding assay, fluorescence assay or Aequorin functional assay as described below. Such methods can be conducted in a high throughput manner to permit the simultaneous evaluation of many compounds.

Specific assay methods for the human (GHS-R1a), swine and rat GHS-receptors (U.S. Pat. No. 6,242,199, Intl. Pat. Appl. Nos. WO 97/21730 and 97/22004), as well as the canine GHS-receptor (U.S. Pat. No. 6,645,726), and their use in generally identifying agonists and antagonists thereof are known.

Appropriate methods for determining the functional activity of compounds of the present invention that interact at the human ghrelin receptor are also described below.

A. Competitive Radioligand Binding Assay (Ghrelin Receptor)

The competitive binding assay at the human growth hormone secretagogue receptor (hGHS-R1a) was carried out analogously to assays described in the literature. (Bednarek M A et al. Structure-function studies on the new growth hormone-releasing peptide ghrelin: minimal sequence of ghrelin necessary for activation of growth hormone secretagogue receptor 1a; *J. Med. Chem.* 2000, 43, 4370-4376; Palucki, B. L. et al. Spiro(indoline-3,4'-piperidine) growth hormone secretagogues as ghrelin mimetics; *Bioorg. Med. Chem. Lett.* 2002, 11, 1955-1957.)

Materials

Membranes (GHS-R/HEK 293) were prepared from HEK-293 cells stably transfected with the human ghrelin receptor (hGHS-R1a). These membranes were provided by PerkinElmer BioSignal (#RBHGHSM, lot#1887) and utilized at a quantity of 0.71 µg/assay point.
1. [$^{125}$I]-Ghrelin (PerkinElmer, #NEX-388); final concentration: 0.0070-0.0085 nM
2. Ghrelin (Bachem, #H-4864); final concentration: 1 µM
3. Multiscreen Harvest plates-GF/C (Millipore, #MAHFC1H60)
4. Deep-well polypropylene titer plate (Beckman Coulter, #267006)
5. TopSeal-A (PerkinElmer, #6005185)
6. Bottom seal (Millipore, #MATAH0P00)
7. MicroScint-0 (PerkinElmer, #6013611)
8. Binding Buffer: 25 mM Hepes (pH 7.4), 1 mM $CaCl_2$, 5 mM $MgCl_2$, 2.5 mM EDTA, 0.4% BSA Assay Volumes Competition experiments were performed in a 300 µl filtration assay format.
1. 220 µL of membranes diluted in binding buffer
2. 40 µL of compound diluted in binding buffer
3. 40 µL of radioligand ([$^{125}$I]-Ghrelin) diluted in binding buffer Final test concentrations (N=1) for compounds of the present invention:
10, 1, 0.5, 0.2, 0.1, 0.05, 0.02, 0.01, 0.005, 0.002, 0.001 µM.

Compound Handling

Compounds were provided frozen on dry ice at a stock concentration of 10 mM diluted in 100% DMSO and stored at −80° C. until the day of testing. On the test day, compounds were allowed to thaw at rt O/N and then diluted in assay buffer according to the desired test concentrations. Under these conditions, the maximal final DMSO concentration in the assay was 0.1%.

Assay Protocol

In deep-well plates, 220 µL of diluted cell membranes (final concentration: 0.71 µg/well) were combined with 40 µL of either binding buffer (total binding, N=5), 1 µM ghrelin (non-specific binding, N=3) or the appropriate concentration of test compound (N=2 for each test concentration). The reaction was initiated by addition of 40 µL of [$^{125}$I]-ghrelin (final conc. 0.0070-0.0085 nM) to each well. Plates were sealed with TopSeal-A, vortexed gently and incubated at rt for 30 min. The reaction was arrested by filtering samples through Multiscreen Harvest plates (pre-soaked in 0.5% polyethyleneimine) using a Tomtec Harvester, washed 9 times with 500 µL of cold 50 mM Tris-HCl (pH 7.4, 4° C.), and then plates were air-dried in a fumehood for 30 min A bottom seal was applied to the plates prior to the addition of 25 µL of MicroScint-0 to each well. Plates were than sealed with TopSeal-A and counted for 30 sec per well on a Top-Count Microplate Scintillation and Luminescence Counter (PerkinElmer) using a count delay of 60 sec. Results were expressed as counts per minute (cpm).

Data were analyzed by GraphPad Prism (GraphPad Software, San Diego, Calif.) using a variable slope non-linear regression analysis. $K_i$ values were calculated using a $K_d$ value of 0.01 nM for [$^{125}$I]-ghrelin (previously determined during membrane characterization).

$D_{max}$ values were calculated using the following formula:

$$D_{max}=1-\text{test concentration with maximal displacement}-\text{non-specific binding} \times 100 \text{ total binding}-\text{non-specific binding}$$

where total and non-specific binding represent the cpm obtained in the absence or presence of 1 μM ghrelin, respectively.

Binding activity at the gherlin receptor for representative compounds of the present invention is shown below in Table 3A through 3E. Compound structures for Tables 3A, 3B and 3D are presented with the various groups as defined for the general structure of formula I. For Tables 3B and 3D, in all entries, m, n and p are 0; X, $Z_1$ and $Z_2$ are each NH. For Table 3B, $R_1$ is H for all entries. The tethers (T) are illustrated with the bonding to X and $Z_2$ as indicated. The compounds themselves are shown for Tables 3C and 3E. Competitive binding curves for representative compounds 1, 2, 3, 4 and 25 are shown in FIG. 4.

| | | | Binding Activity at the Human Ghrelin Receptor for Compounds of the Invention | | |
|---|---|---|---|---|---|
| Compound | X | $R_1$ | $R_2$ | m | $R_7$ |
| 1 | N—H | H | 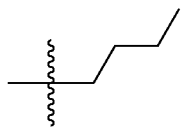 | 0 | $CH_3$ |
| 2 | N—H | H | 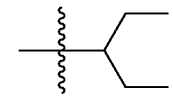 | 0 | H |
| 3 | N—H | H | 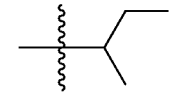 | 0 | $CH_3$ |
| 4 | N—H | H | 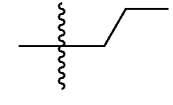 | 0 | $CH_3$ |
| 5 | N—H | H | 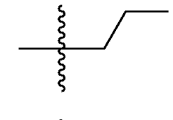 | 0 | $CH_2CH_3$ |
| 6 | N—H | H | 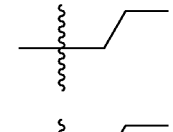 | 0 | Me |
| 7 | N—H | H |  | 0 | Me |
| 8 | N—H | H | 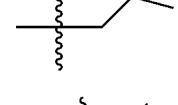 | 0 | H |
| 9 | N—H | H | 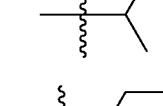 | 0 | H |
| 10 | N—H | H |  | 0 | $CH_3$ |
| 11 | N—H | H | 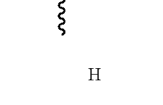 | 0 | $CH_3$ |
| 12 | N—H | 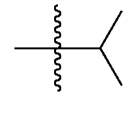 [SMILES: *C(C)C] | H | 0 | H |

-continued

| | | | | | |
|---|---|---|---|---|---|
| 13 | N—H | *isopropyl* | H | 0 | H |
| 14 | N—H | H | *sec-butyl* | 0 | H |
| 15 | N—H | H | *sec-butyl* | 0 | CH₃ |
| 16 | N—H | H | *sec-butyl* | 0 | CH₃ |
| 17 | N—H | H | *1-cyclopropylethyl* | 0 | CH₃ |
| 18 | N—H | *cyclohexyl (fused)* | | 0 | H |
| 19a | N—H | H | *isopropyl* | 0 | CH₃ |
| 19b | | diastereomer | | | |
| 20 | N—H | H | *isobutyl* | 0 | H |
| 21 | N—H | H | *isobutyl* | 0 | H |
| 22 | N—H | H | *isobutyl* | 0 | H |
| 23 | N—H | H | *sec-butyl* | 0 | CH₃ |
| 24 | N—H | H | *sec-butyl* | 0 | CH₃ |
| 25 | N—H | H | *sec-butyl* | 0 | CH₃ |

-continued

| | | | | | |
|---|---|---|---|---|---|
| 26 | N—H | H | sec-butyl | 0 | CH₃ |
| 27 | N—H | H | sec-butyl | 0 | CH₃ |
| 28 | N—H | H | sec-butyl | 0 | CH₃ |
| 29 | N—H | H | sec-butyl | 0 | CH₃ |
| 30 | N—H | H | sec-butyl | 0 | CH₃ |
| 31 | N—H | H | sec-butyl | 0 | CH₃ |
| 32 | N—H | H | sec-butyl | 0 | CH₃ |
| 33 | N—H | H | sec-butyl | 0 | CH₃ |
| 34 | N—H | H | sec-butyl | 0 | CH₃ |
| 35 | N—H | H | sec-butyl | 0 | CH₃ |
| 36 | N—H | H | sec-butyl | 0 | CH₃ |
| 37a | N—H | H | sec-butyl | 0 | CH₃ |
| 37b | | diastereomer | | | |
| 38 | N—H | H | sec-butyl | 0 | CH₃ |
| 39 | N—H | H | isopropyl-ethyl | 0 | CH₃ |

-continued
| | | | | | |
|---|---|---|---|---|---|
| 40 | N—H | H | 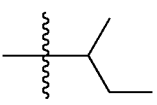 | 0 | CH₃ |
| 41 | N—H | H | 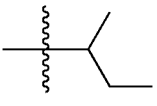 | 0 | CH₃ |
| 42 | N—H | H | 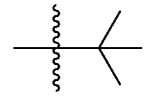 [SMILES: *C(C)(C)C] | 0 | CH₃ |
| 43 | N—H | H | 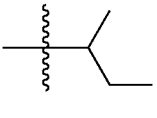 | 0 | CH₂CH₃ |
| 44 | N—H | H | 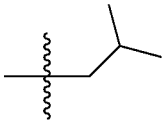 [SMILES: *CC(C)C] | 0 | H |
| 45 | N—H | H | 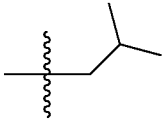 [SMILES: *CC(C)C] | 0 | H |
| 46 | N—H | H | 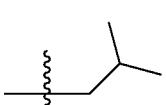 | 0 | H |
| 47 | N—H | H | 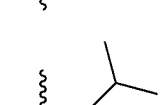 | 0 | H |
| 48 | N—H | H |  | 0 | H |
| 49 | N—H | H |  | 0 | Me |
| 50 | N—H | H |  | 0 | Me |
| 51 | N—H | H |  | 0 | Me |
| 52 | N—H | H | 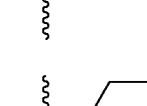 | 0 | Me |

-continued
| | | | | | |
|---|---|---|---|---|---|
| 53 | N—H | H | 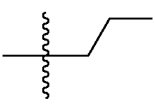 [SMILES: *CCC] | 0 | Me |
| 54 | N—H | H | 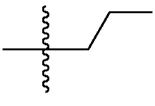 [SMILES: *CCC] | 0 | Me |
| 55 | N—H | 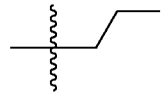 [SMILES: *CCC] | H | 0 | Me |
| 56 | N—H | 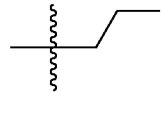 | H | 0 | Me |
| 57 | N—H | H | 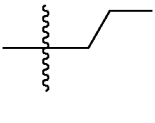 | 0 | Me |
| 58 | N—Ae | H | 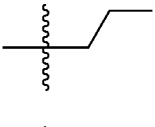 | 0 | Me |
| 59 | N—H | H | 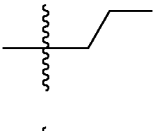 | 0 | Me |
| 60 | N—H | H |  | 0 | H |
| 61 | N—H | H |  | 0 | H |
| 62 | N—H | H |  | 0 | H |
| 63 | N—H | H | 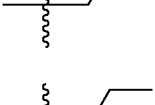 | 0 | H |
| 64 | N—H | H |  | 0 | H |
| 65 | N—H | H | 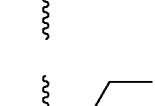 | 0 | H |
| 66 | N—H | H |  | 0 | H |

-continued
| | | | | | |
|---|---|---|---|---|---|
| 67 | N—H | H | 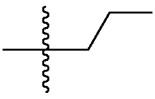 [SMILES: *CCC] | 0 | H |
| 68 | N—H | H | 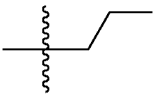 [SMILES: *CCC] | 0 | H |
| 69 | N—H | H | 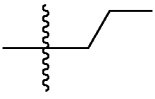 [SMILES: *CCC] | 0 | H |
| 70 | N—H | H | 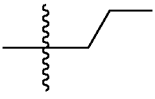 [SMILES: *CCC] | 0 | H |
| 71 | N—H | H | 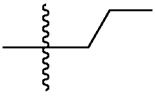 [SMILES: *CCC] | 0 | H |
| 72 | N—H | H | $CH_3$ | 0 | $CH_3$ |
| 73 | N—H | H | 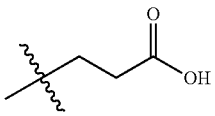 | 0 | $CH_3$ |
| 74 | N—H | H | 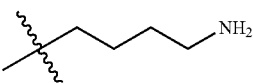 | 0 | $CH_3$ |
| 75 | N—H | H | 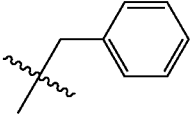 | 0 | $CH_3$ |
| 76 | N—H | H | 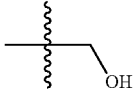 | 0 | $CH_3$ |
| 77 | N—H | H | 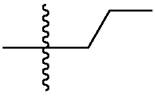 [SMILES: *CCC] | 0 | $CH_3$ |
| 78 | N—H | H | 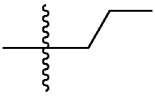 [SMILES: *CCC] | 0 | $CH_3$ |
| 79 | N—H | H | 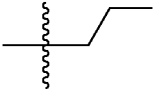 [SMILES: *CCC] | 0 | $CH_3$ |
| 80 | N—H | H | H | 0 | $CH_3$ |
| 81 | N—H | H | 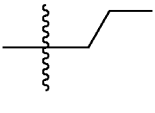 | 0 | $CH_3$ |

-continued
| | | | | | |
|---|---|---|---|---|---|
| 82 | N—H | H | 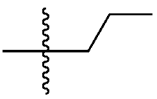 [SMILES: *CCC] | 0 | CH₃ |
| 83 | N—H | H | 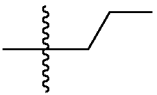 [SMILES: *CCC] | 0 | CH₃ |
| 84 | N—H | H | 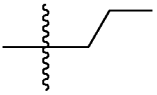 | 0 | CH₃ |
| 85 | N—H | H | 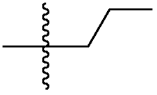 [SMILES: *CCC] | 0 | CH₃ |
| 86 | N—H | H | 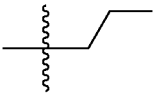 [SMILES: *CCC] | 0 | CH₃ |
| 87 | N—H | H | 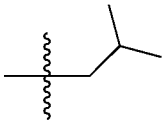 [SMILES: *CC(C)C] | 0 | H |
| 88 | N—H | H | 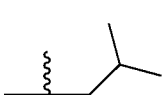 | 0 | H |
| 89 | N—H | H | 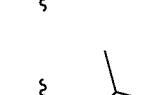 | 0 | H |
| 90 | N—H | H |  | 0 | H |
| 91 | N—H | H | 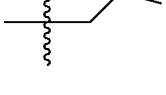 | 0 | H |
| 92 | N—H | H | 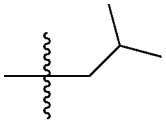 [SMILES: *CC(C)C] | 0 | H |
| 93 | N—H | H | 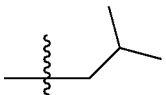 | 0 | H |

-continued
| | | | | | | |
|---|---|---|---|---|---|---|
| 94 | N—H | H | 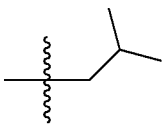 [SMILES: *CC(C)C] | | 0 | H |
| 95 | N—H | H | 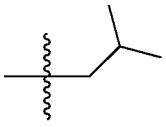 [SMILES: *CC(C)C] | | 0 | H |
| 96 | N—H | 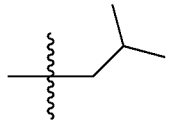 [SMILES: *CC(C)C] | H | | 0 | H |
| 97 | N—H | H | 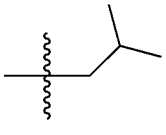 | | 0 | H |
| 98 | N—H | 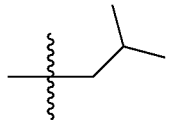 [SMILES: *CC(C)C] | H | | 0 | H |
| 99 | N-Ac | H | 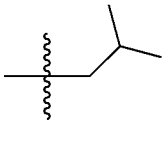 [SMILES: *CC(C)C] | | 0 | H |
| 100 | N—H | H | $CH_3$ | | 0 | H |
| 101 | N—H | H | 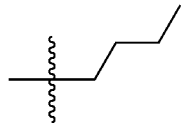 | | 0 | H |
| 102 | N—H | H | 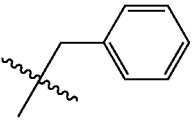 [SMILES: *Cc1ccccc1] | | 0 | H |
| 103 | N—H | H | 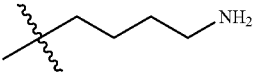 [SMILES: *CCCCN] | | 0 | H |
| 104 | N—H | H | 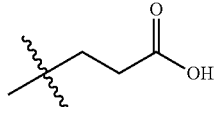 [SMILES: *CCC(=O)O] | | 0 | H |
| 105 | N—H | H | 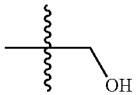 | | 0 | H |
| 106 | N—H | H | 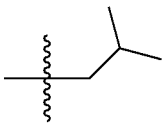 | | 0 | H |

-continued

| | | | | | |
|---|---|---|---|---|---|
| 107 | N—H | H | *sec*-butyl | 0 | H |
| 108 | N—H | H | *sec*-butyl | 0 | H |
| 109 | N—H | H | *sec*-butyl | 0 | H |
| 110 | N—H | H | *sec*-butyl | 0 | H |
| 111 | N—H | H | *sec*-butyl | 0 | H |
| 112 | N—H | H | H | 0 | H |
| 113 | N—H | H | *sec*-butyl | 0 | H |
| 114 | N—H | H | *sec*-butyl | 0 | H |
| 115 | N—H | H | *sec*-butyl | 0 | H |
| 116 | N—H | H | *sec*-butyl | 0 | H |
| 117 | N—H | H | *sec*-butyl | 0 | $CH_3$ |
| 118 | N—H | H | *sec*-butyl | 0 | $CH_3$ |
| 119 | N—H | H | CH(CH₃)CH(OH) | 0 | $CH_3$ |

-continued
| | | | | | |
|---|---|---|---|---|---|
| 120 | N—H | H | 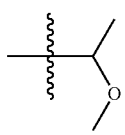 | 0 | CH₃ |
| 121 | N—H | | 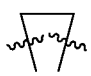 | 0 | CH₃ |
| 122 | N—H | H | 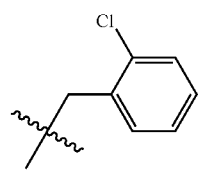 [SMILES: *Cc1ccccc1Cl] | 0 | H |
| 123 | N—H | H | 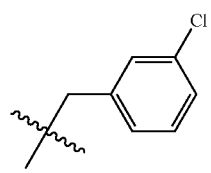 [SMILES: *Cc1cccc(Cl)c1] | 0 | H |
| 124 | N—H | H | 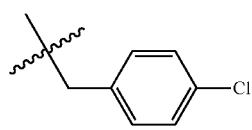 [SMILES: *Cc1ccc(Cl)cc1] | 0 | H |
| 125 | N—H | H | 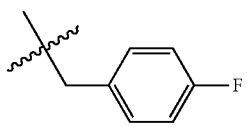 [SMILES: *Cc1ccc(F)cc1] | 0 | H |
| 126 | N—H | H | 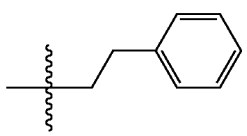 [SMILES: *CCc1ccccc1] | 0 | H |
| 127 | N—H | H | 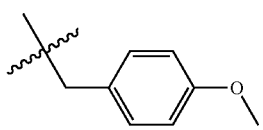 [SMILES: *Cc1ccc(OC)cc1] | 0 | H |
| 128 | N—H | H | 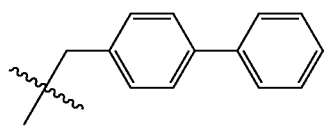 [SMILES: *Cc1ccc(-c2ccccc2)cc1] | 0 | H |
| 129 | N—H | H | 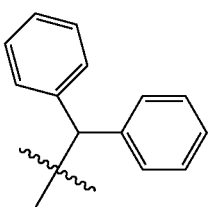 [SMILES: *C(c1ccccc1)c1ccccc1] | 0 | H |

| | | | | | |
|---|---|---|---|---|---|
| 130 | N—H | H | 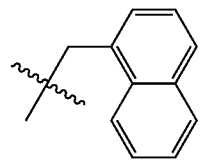 [SMILES: *Cc1cccc2ccccc12] | 0 | H |
| 131 | N—H | H | 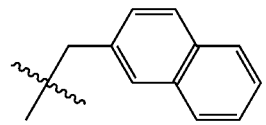 [SMILES: *Cc1ccc2ccccc2c1] | 0 | H |
| 132 | N—H | H | 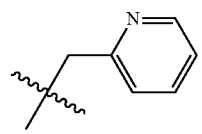 [SMILES: *Cc1ccccn1] | 0 | H |
| 133 | N—H | H | 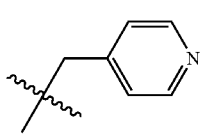 | 0 | H |
| 134 | N—H | H | 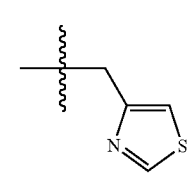 [SMILES: *Cc1cscn1] | 0 | H |
| 135 | N—H | H | 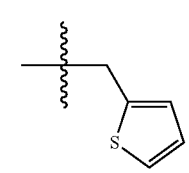 [SMILES: *Cc1cccs1] | 0 | H |
| 136a | N—H | H | 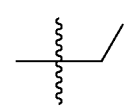 | 0 | H |
| 136b | | diastereomer | | | |
| 137 | N—H | H | 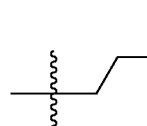 | 0 | H |
| 138 | N—H | H | 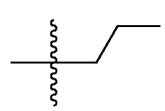 | 0 | H |
| 139 | N—H | H | 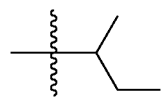 | 0 | H |
| 140 | N—H | H | 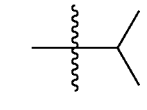 | 0 | H |
| 141 | N—H | H | 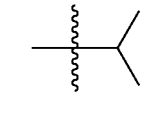 | 0 | H |

-continued

| | | | | | |
|---|---|---|---|---|---|
| 142 | N—H | H | (isopropyl) | 0 | H |
| 143 | N—H | H | (isopropyl) | 0 | H |
| 144 | N—H | H | (sec-butyl) | 0 | CH₃ |
| 145a | N—H | H | (sec-butyl) | 0 | CH₃ |
| 145b | | diastereomer | | | |
| 146a | N—H | H | (sec-butyl) | 0 | CH₃ |
| 146b | | diastereomer | | | |
| 147 | N—H | H | (sec-butyl) | 0 | CH₃ |
| 148 | N—H | H | (sec-butyl) | 0 | CH₃ |
| 149 | N—H | H | (sec-butyl) | 0 | CH₃ |
| 150a | N—H | H | (sec-butyl) | 0 | CH₃ |
| 150b | | diastereomer | | | |
| 151 | N—H | H | (sec-butyl) | 0 | H |
| 152a | N—H | H | (sec-butyl) | 0 | CH₃ |
| 152b | | diastereomer | | | |
| 153 | N—H | H | (isobutyl) | 0 | H |

-continued
| | | | | | |
|---|---|---|---|---|---|
| 154 | N—H | H | 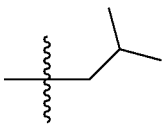 | 0 | H |
| 155 | N—H | H | 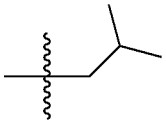 [SMILES: *CC(C)C] | 0 | H |
| 156 | N—H | H | 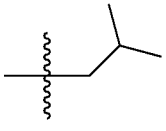 | 0 | H |
| 157 | N—H | H | 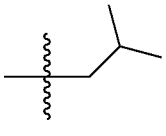 [SMILES: *CC(C)C] | 0 | H |
| 158 | N—H | H | 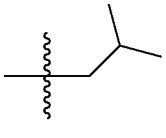 [SMILES: *CC(C)C] | 0 | H |
| 159 | N—H | H | 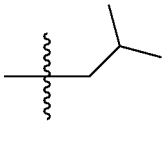 [SMILES: *CC(C)C] | 0 | H |
| 160a | N—H | H | 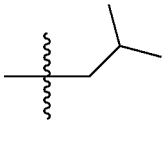 [SMILES: *CC(C)C] | 0 | H |
| 160b | | diastereomer | | | |
| 161a | N—H | H | 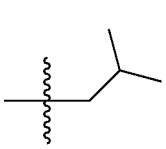 [SMILES: *CC(C)C] | 0 | H |
| 161b | | diastereomer | | | |
| 162a | N—H | H | 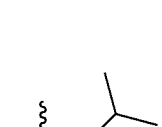 | 0 | H |
| 162b | | diastereomer | | | |
| 163 | N—H | H | 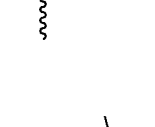 | 0 | H |
| 164 | N—H | H | 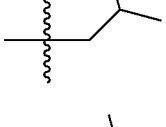 | 0 | H |

-continued
| | | | | | |
|---|---|---|---|---|---|
| 165 | N—H | H | 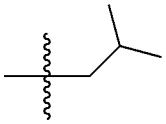 [SMILES: *CC(C)C] | 0 | H |
| 166 | N—H | H | 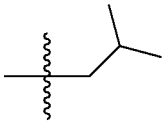 [SMILES: *CC(C)C] | 0 | H |
| 167 | N—H | H | 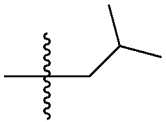 [SMILES: *CC(C)C] | 0 | H |
| 168 | N—H | H | 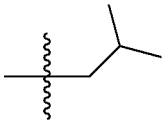 [SMILES: *CC(C)C] | 0 | H |
| 169 | N—H | H | 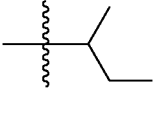 | 0 | $CH_3$ |
| 170 | N—H | H | 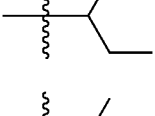 | 0 | $CH_3$ |
| 171 | N—H | H | 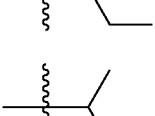 | 0 | $CH_3$ |
| 172 | N—H | H | 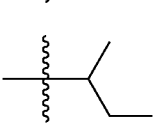 | 0 | $CH_3$ |
| 173 | N—H | H | 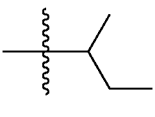 | 0 | $CH_3$ |
| 174 | N—H | H | 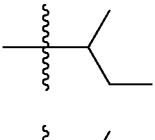 | 0 | $CH_3$ |
| 175 | N—H | H | 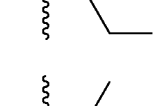 | 0 | $CH_3$ |
| 176 | N—H | H | 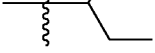 | 0 | $CH_3$ |
| 177 | N—H | H |  | 0 | $CH_3$ |

-continued

| | | | | | |
|---|---|---|---|---|---|
| 178 | N—H | H | isobutyl | 0 | CH₃ |
| 179 | N—H | H | isobutyl | 0 | CH₃ |
| 180 | N—H | H | isobutyl | 0 | CH₃ |
| 181 | N—H | H | isobutyl | 0 | CH₃ |
| 182a | N—H | H | isobutyl | 0 | CH₃ |
| 182b | | diastereomer | | | |
| 183 | N—H | H | isobutyl | 0 | CH₃ |
| 184 | N—H | H | isobutyl | 0 | CH₃ |
| 184 | | diastereomer | | | |
| 185 | N—H | H | isobutyl | 0 | CH₃ |
| 186 | N—H | H | isobutyl | 0 | CH₃ |
| 187 | N—H | H | isobutyl | 0 | CH₃ |
| 188 | N—H | H | isobutyl | 0 | CH₃ |
| 189a | N—H | H | isobutyl | 0 | CH₃ |
| 189b | | diastereomer | | | |
| 190 | N—H | H | isobutyl | 0 | CH₃ |

-continued

| | | | | | |
|---|---|---|---|---|---|
| 191 | N—H | H | *sec-butyl* | 0 | CH₃ |
| 192 | N—H | H | *sec-butyl* | 0 | CH₃ |
| 193 | N—H | H | *sec-butyl* | 0 | CH₃ |
| 194a | N—H | H | *sec-butyl* | 0 | CH₃ |
| 194b | | diastereomer | | | |
| 195 | N—H | H | *sec-butyl* | 0 | CH₃ |
| 196 | N—H | H | *sec-butyl* | 0 | CH₃ |
| 197 | N—H | H | *sec-butyl* | 0 | CH₃ |
| 199 | N—H | H | *iso-propyl* | 0 | H |
| 200 | N—H | H | *iso-propyl* | 0 | H |
| 201 | N—Me | H | *n-butyl* | 0 | CH₃ |
| 202 | N—Ac | H | *n-butyl* | 0 | CH₃ |
| 203 | N—Me | H | *iso-butyl* | 0 | H |
| 204 | N—Ac | H | *iso-butyl* | 0 | H |
| 205 | N—H | H | *sec-butyl* | 0 | CH₃ |

-continued

Figure 7A:
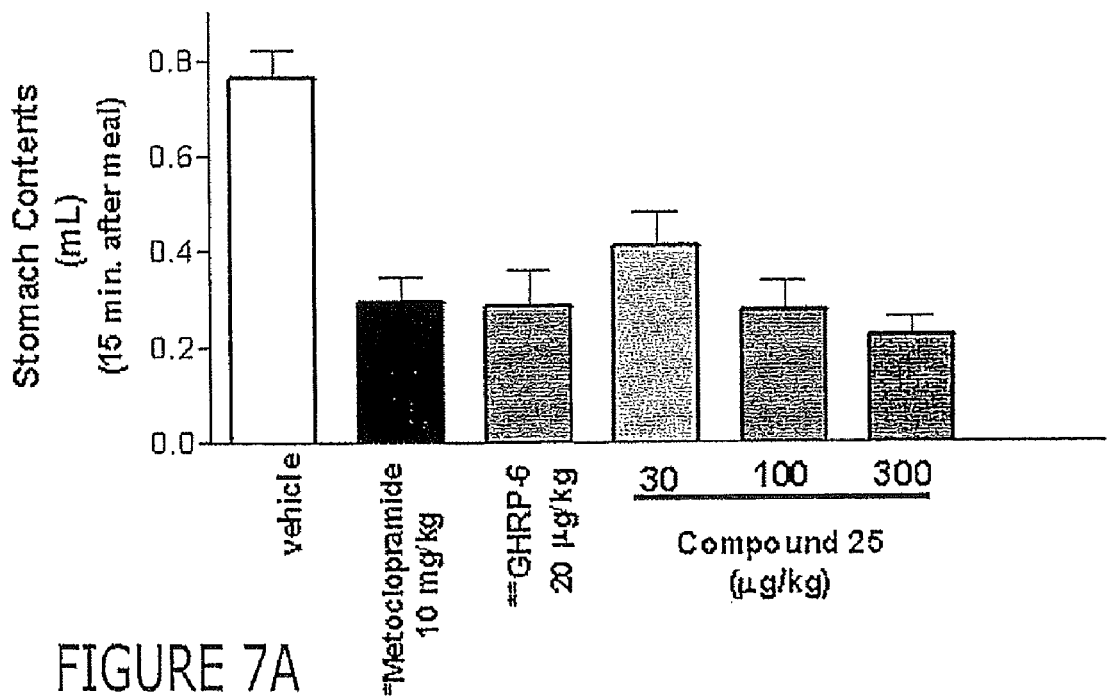
FIG. 7 (panels A and B) shows graphs presenting effects on gastric emptying for exemplary compounds of the present invention.

| | | | | | |
|---|---|---|---|---|---|
| 206 | N—H | H | (sec-butyl) | 0 | CH₃ |
| 207 | N—H | H | (isopropyl) | 0 | H |
| 208a | N—H | H | (sec-butyl) | 0 | H |
| 208b | | diastereomer | | | |
| 209 | N—H | H | (sec-butyl) | 0 | CH₃ |
| 210 | N—H | H | (2-pyridylmethyl, gem-dimethyl) | 0 | H |
| 211 | N—H | H | (isopropyl) | 0 | H |
| 212 | N—H | H | (sec-butyl) | 0 | CH₃ |
| 213 | N—H | H | (sec-butyl) | 0 | H |
| 214 | N—H | H | (sec-butyl) | 0 | CH₃ |
| 215 | N—H | H | (sec-butyl) | 0 | H |
| 216 | N—H | H | (isopropyl) | 0 | H |
| 218 | N—H | | (cycloheptyl) | 0 | H |
| 219 | N—H | H | (imidazolylmethyl) | 0 | H |
| 220 | | See Figure 7A | | | |
| 221 | | See Figure 7A | | | |

-continued

Figure 7B:
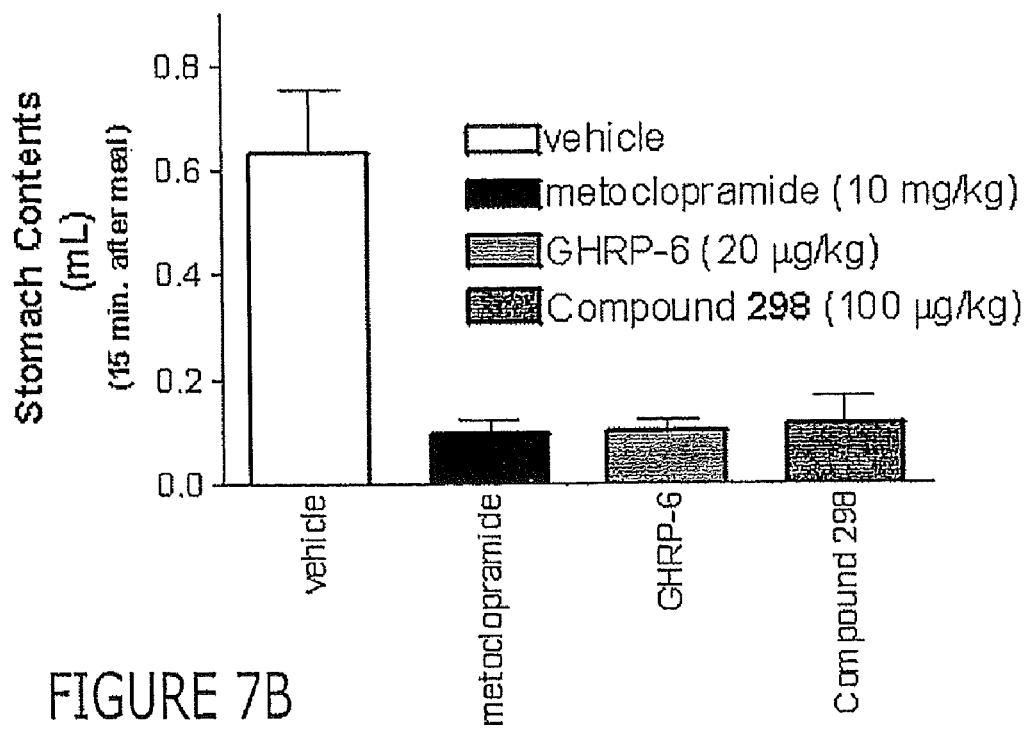

| | |
|---|---|
| 222 | See Figure 7A |
| 223 | See Figure 7A |
| 224 | See Figure 7A |
| 225 | See Figure 7B |
| 226 | See Figure 7B |
| 227 | See Figure 7B |
| 228 | See Figure 7B |
| 229 | See Figure 7B |
| 230a | See Figure 7B |
| 230b | diastereomer |

| Compound | $R_3$ | $R_4$ | n | $Z_1$ |
|---|---|---|---|---|
| 1 | H | H | 0 | N—H |
| 2 | $CH_3$ | H | 0 | N—H |
| 3 | H | H | 0 | N—H |
| 4 | H | $CH_3$ | 0 | N—H |
| 5 | H | H | 0 | N—H |
| 6 | H | H | 0 | N—H |
| 7 | H | H | 0 | N—H |
| 8 | | (cyclic) | 0 | N—H |
| 9 | | (cyclic) | 0 | N—H |
| 10 | H | H | 0 | N—H |
| 11 | H | H | 0 | N—H |
| 12 | H | (alkyl chain) | 0 | N—H |
| 13 | H | (alkyl chain) | 0 | N—H |
| 14 | $CH_3$ | H | 0 | N—H |
| 15 | $CH_3$ | H | 0 | N—H |
| 16 | $CH_3$ | H | 0 | N—H |
| 17 | $CH_3$ | H | 0 | N—H |
| 18 | | (cyclic) | 0 | N—H |
| 19a | $CH_3$ | H | 0 | N—H |
| 19b | | | | |
| 20 | | (cyclic) | 0 | N—H |
| 21 | | (cyclic) | 0 | N—H |
| 22 | | (cyclic) | 0 | N—H |

-continued

| | | | | |
|---|---|---|---|---|
| 23 | CH₃ | H | 0 | N—H |
| 24 | CH₃ | H | 0 | N—H |
| 25 | CH₃ | H | 0 | N—H |
| 26 | CH₃ | H | 0 | N—H |
| 27 | CH₃ | H | 0 | N—H |
| 28 | CH₃ | H | 0 | N—H |
| 29 | CH₃ | H | 0 | N—H |
| 30 | CH₃ | H | 0 | N—H |
| 31 | CH₃ | H | 0 | N—H |
| 32 | CH₃ | H | 0 | N—H |
| 33 | CH₃ | H | 0 | N—H |
| 34 | CH₃ | H | 0 | N—H |
| 35 | CH₃ | H | 0 | N—H |
| 36 | CH₃ | H | 0 | N—H |
| 37a | CH₃ | H | 0 | N—H |
| 37b | | | | |
| 38 | CH₃ | H | 0 | N—H |
| 39 | H | H | 0 | N—H |
| 40 | CH₃ | H | 0 | N—H |
| 41 | ![benzyl] | H | 0 | N—H |
| 42 | CH₃ | H | 0 | N—H |
| 43 | CH₃ | H | 0 | N—H |
| 44 | ![cyclohexyl] | | 0 | N—H |
| 45 | ![cyclohexyl] | | 0 | N—H |
| 46 | ![cyclohexyl] | | 0 | N—H |
| 47 | ![cyclohexyl] | | 0 | N—H |
| 48 | ![cyclohexyl] | | 0 | N—H |
| 49 | H | H | 0 | N—H |
| 50 | H | H | 0 | N—H |
| 51 | H | H | 0 | N—H |
| 52 | H | H | 0 | N—H |
| 53 | H | H | 0 | N—H |
| 54 | H | H | 0 | N—H |
| 55 | H | H | 0 | N—H |
| 56 | H | H | 0 | N—H |
| 57 | H | H | 0 | N—H |
| 58 | H | H | 0 | N—H |
| 59 | H | CH₃ | 0 | N—H |
| 60 | CH₃ | H | 0 | N—H |
| 61 | H | H | 0 | N—H |
| 62 | H | ![isobutyl] | 0 | N—H |

-continued
| | | | | | |
|---|---|---|---|---|---|
| 63 | 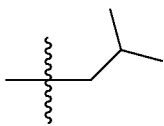 [SMILES: *CC(C)C] | H | 0 | N—H | |
| 64 | H | 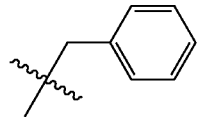 [SMILES: *Cc1ccccc1] | 0 | N—H | |
| 65 | 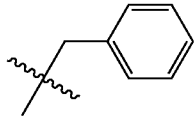 [SMILES: *Cc1ccccc1] | H | 0 | N—H | |
| 66 | CH₃ | CH₃ | 0 | N—H | |
| 67 | 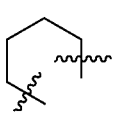 | | 0 | N—H | |
| 68 | H | 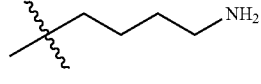 [SMILES: *CCCCN] | 0 | N—H | |
| 69 | 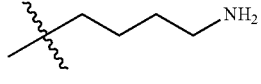 | H | 0 | N—H | |
| 70 | H | 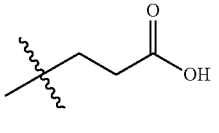 [SMILES: *CCC(=O)O] | 0 | N—H | |
| 71 | 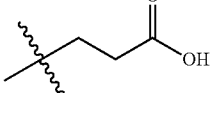 | H | 0 | N—H | |
| 72 | H | H | 0 | N—H | |
| 73 | H | H | 0 | N—H | |
| 74 | H | H | 0 | N—H | |
| 75 | H | H | 0 | N—H | |
| 76 | H | H | 0 | N—H | |
| 77 | H | H | 0 | N—H | |
| 78 | H | H | 0 | N—H | |
| 79 | H | CH₃ | 0 | N—H | |
| 80 | H | H | 0 | N—H | |
| 81 | H | H | 0 | N—H | |
| 82 | H | H | 0 | N—H | |
| 83 | H | H | 0 | N—H | |
| 84 | H | H | 0 | N—H | |
| 85 | H | H | 0 | N—H | |
| 86 | H | H | 0 | N—H | |
| 87 | 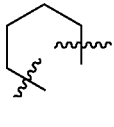 | | 0 | N—H | |
| 88 | 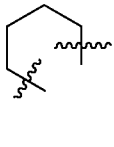 [SMILES: *CCCC*] | | 0 | N—H | |

-continued

| | | | | |
|---|---|---|---|---|
| 89 | | | 0 | N—H |
| 90 | | | 0 | N—H |
| 91 | | | 0 | N—H |
| 92 | | | 0 | N—H |
| 93 | H | CH$_3$ | 0 | N—H |
| 94 | CH$_3$ | H | 0 | N—H |
| 95 | CH$_3$ | CH$_3$ | 0 | N—H |
| 96 | | | 0 | N—H |
| 97 | | | 0 | N—H |
| 98 | | | 0 | N—H |
| 99 | | | 0 | N—H |
| 100 | | | 0 | N—H |
| 101 | | | 0 | N—H |
| 102 | | | 0 | N—H |
| 103 | | | 0 | N—H |
| 104 | | | 0 | N—H |

-continued
| 105 | 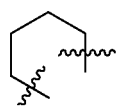 [SMILES: *CCCC*] | 0 | N—H |
| 106 | 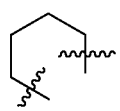 [SMILES: *CCCC*] | 0 | N—H |
| 107 | 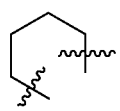 [SMILES: *CCCC*] | 0 | N—H |
| 108 | 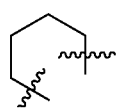 | 0 | N—H |
| 109 | 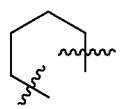 [SMILES: *CCCC*] | 0 | N—H |
| 110 | 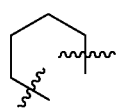 [SMILES: *CCCC*] | 0 | N—H |
| 111 |  | 0 | N—H |
| 112 | 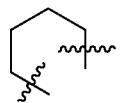 | 0 | N—H |
| 113 | 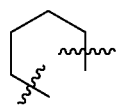 [SMILES: *CCCC*] | 0 | N—H |
| 114 | 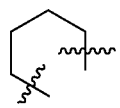 | 0 | N—H |
| 115 | 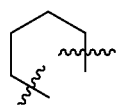 [SMILES: *CCCC*] | 0 | N—H |
| 116 | 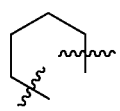 [SMILES: *CCCC*] | 0 | N—H |
| 117 | $CH_3$ | H | 0 | N—H |
| 118 | $CH_3$ | H | 0 | N—H |
| 119 | $CH_3$ | H | 0 | N—H |
| 120 | $CH_3$ | H | 0 | N—H |
| 121 | $CH_3$ | H | 0 | N—H |

-continued
| | | | |
|---|---|---|---|
| 122 | 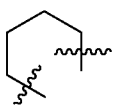 | 0 | N—H |
| 123 | 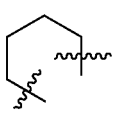 | 0 | N—H |
| 124 | 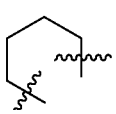 [SMILES: *CCCC*] | 0 | N—H |
| 125 | 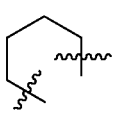 | 0 | N—H |
| 126 | 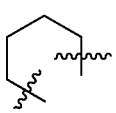 [SMILES: *CCCC*] | 0 | N—H |
| 127 | 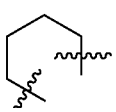 [SMILES: *CCCC*] | 0 | N—H |
| 128 | 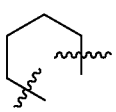 | 0 | N—H |
| 129 | 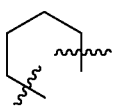 [SMILES: *CCCC*] | 0 | N—H |
| 130 | 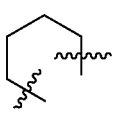 | 0 | N—H |
| 131 | 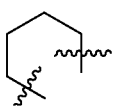 | 0 | N—H |
| 132 | 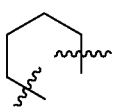 | 0 | N—H |
| 133 | 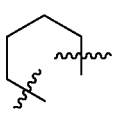 | 0 | N—H |
| 134 | 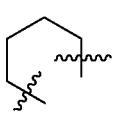 | 0 | N—H |

-continued
| 135 | 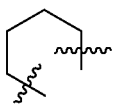 [SMILES: *CCCC*] | 0 | N—H |
| 136a | 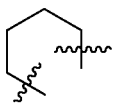 [SMILES: *CCCC*] | 0 | N—H |
| 136b | | | |
| 137 | 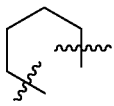 [SMILES: *CCCC*] | 0 | N—H |
| 138 | 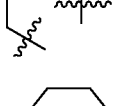 | 0 | N—H |
| 139 | 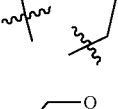 | 0 | N—H |
| 140 |  | 0 | N—H |
| 141 |  | 0 | N—H |
| 142 | 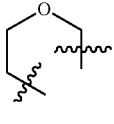 | 0 | N—H |
| 143 | 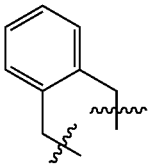 [SMILES: *Cc1ccccc1C*] | 0 | N—H |
| 144 |  | 0 | N—H |
| 145a | H | 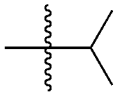 | 0 | N—H |
| 145b | | | | |
| 146a | H | 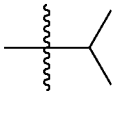 | 0 | N—H |
| 146b | | | | |

-continued
| | | | | |
|---|---|---|---|---|
| 147 | 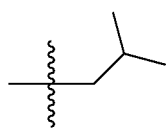 [SMILES: *CC(C)C] | H | 0 | N—H |
| 148 | H | 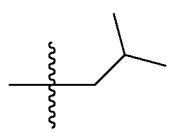 [SMILES: *CC(C)C] | 0 | N—H |
| 149 | 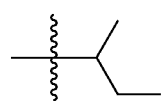 | H | 0 | N—H |
| 150a | H | 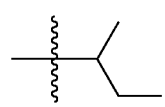 | 0 | N—H |
| 150b | | | | |
| 151 | 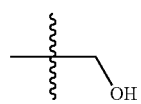 | H | 0 | N—H |
| 152a | H | 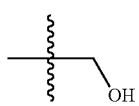 | 0 | N—H |
| 152b | | | | |
| 153 | 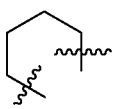 | | 0 | N—H |
| 154 | 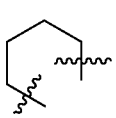 | | 0 | N—H |
| 155 | 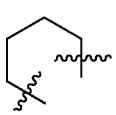 | | 0 | N—H |
| 156 | 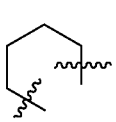 | | 0 | N—H |
| 157 | 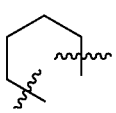 | | 0 | N—H |
| 158 | 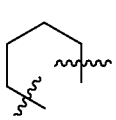 [SMILES: *CCCC*] | | 0 | N—H |

-continued

| | | | | |
|---|---|---|---|---|
| 159 | (structure) | | 0 | N—H |
| 160a | (structure) | | 0 | N—H |
| 160b | | | | |
| 161a | (structure) | | 0 | N—H |
| 161b | | | | |
| 162a | (structure) | | 0 | N—H |
| 162b | | | | |
| 163 | (structure) | | 0 | N—H |
| 164 | (structure) | | 0 | N—H |
| 165 | (structure) | | 0 | N—H |
| 166 | (structure) | | 0 | N—H |
| 167 | (structure) | | 0 | N—H |
| 168 | (structure) | | 0 | N—H |
| 169 | $CH_3$ | H | 0 | N—H |
| 170 | $CH_3$ | H | 0 | N—H |
| 171 | $CH_3$ | H | 0 | N—H |
| 172 | $CH_3$ | H | 0 | N—H |
| 173 | $CH_3$ | H | 0 | N—H |
| 174 | $CH_3$ | H | 0 | N—H |
| 175 | $CH_3$ | H | 0 | N—H |
| 176 | $CH_3$ | H | 0 | N—H |
| 177 | $CH_3$ | H | 0 | N—H |
| 178 | $CH_3$ | H | 0 | N—H |
| 179 | $CH_3$ | H | 0 | N—H |
| 180 | $CH_3$ | H | 0 | N—H |
| 181 | $CH_3$ | H | 0 | N—H |
| 182a | $CH_3$ | H | 0 | N—H |
| 182b | | | | |
| 183 | $CH_3$ | H | 0 | N—H |

-continued

| | | | | |
|---|---|---|---|---|
| 184 | CH₃ | H | 0 | N—H |
| 184 | CH₃ | H | 0 | N—H |
| 185 | CH₃ | H | 0 | N—H |
| 186 | CH₃ | H | 0 | N—H |
| 187 | CH₃ | H | 0 | N—H |
| 188 | CH₃ | H | 0 | N—H |
| 189a | CH₃ | H | 0 | N—H |
| 189b | | | | |
| 190 | CH₃ | H | 0 | N—H |
| 191 | CH₃ | H | 0 | N—H |
| 192 | CH₃ | H | 0 | N—H |
| 193 | CH₃ | H | 0 | N—H |
| 194a | CH₃ | H | 0 | N—H |
| 194b | | | | |
| 195 | CH₃ | H | 0 | N—H |
| 196 | CH₃ | H | 0 | N—H |
| 197 | | | 0 | N—H |
| 199 | | | 0 | N—H |
| 200 | CH₃ | H | 0 | N—H |
| 201 | CH₃ | H | 0 | N—H |
| 202 | CH₃ | H | 0 | N—H |
| 203 | | | 0 | N—H |
| 204 | | | 0 | N—H |
| 205 | CH₃ | H | 0 | N—H |
| 206 | CH₃ | H | 0 | N—H |
| 207 | | | 0 | N—H |
| 208a | | | 0 | N—H |
| 208b | | | | |
| 209 | CH₃ | H | 0 | N—H |
| 210 | | | 0 | N—H |
| 211 | | | 0 | N—H |
| 212 | H | | 0 | N—H |

-continued
| Compound | | R6 | p | Z2 |
|---|---|---|---|---|
| 213 | 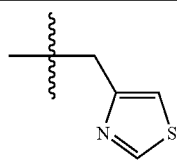 | H | 0 | N—H |
| 214 | CH3 | H | 0 | N—H |
| 215 | 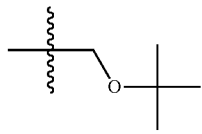 | H | 0 | N—H |
| 216 | 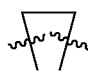 | | 0 | N—H |
| 218 | 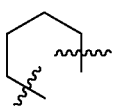 | | 0 | N—H |
| 219 | 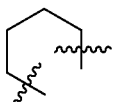 [SMILES: *CCCC*] | | 0 | N—H |
| 220 | | | | |
| 221 | | | | |
| 222 | | | | |
| 223 | | | | |
| 224 | | | | |
| 225 | | | | |
| 226 | | | | |
| 227 | | | | |
| 228 | | | | |
| 229 | | | | |
| 230a | | | | |
| 230b | | | | |
| Compound | R5 | R6 | p | Z2 |
|---|---|---|---|---|
| 1 | 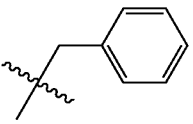 [SMILES: *Cc1ccccc1] | H | 0 | N—H |
| 2 | 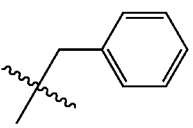 | H | 0 | N—H |
| 3 | 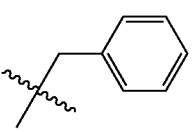 [SMILES: *Cc1ccccc1] | H | 0 | N—H |
| 4 | 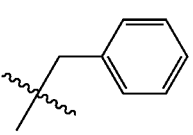 | H | 0 | N—H |
| 5 | 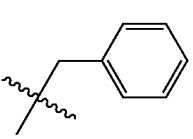 | H | 0 | N—H |

-continued
| | | | | | |
|---|---|---|---|---|---|
| 6 | 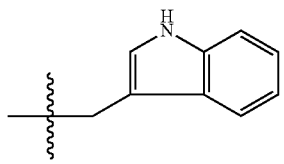 [SMILES: *Cc1c[nH]c2ccccc12] | H | 0 | N—H |
| 7 | 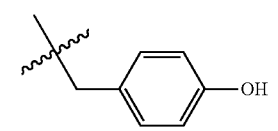 | H | 0 | N—H |
| 8 | H | 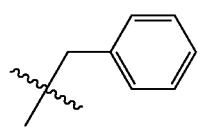 [SMILES: *Cc1ccccc1] | 0 | N—H |
| 9 | H | 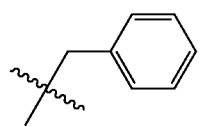 [SMILES: *Cc1ccccc1] | 0 | N—H |
| 10 | 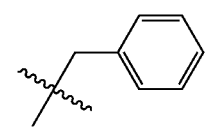 | H | 0 | N—H |
| 11 | 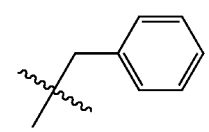 | H | 0 | N—H |
| 12 | H | 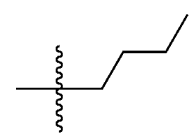 [SMILES: *CCCC] | 0 | N—H |
| 13 | H | 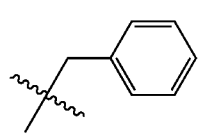 [SMILES: *Cc1ccccc1] | 0 | N—H |
| 14 | H | 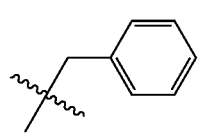 [SMILES: *Cc1ccccc1] | 0 | N—H |
| 15 | 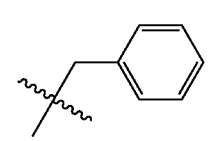 [SMILES: *Cc1ccccc1] | H | 0 | N—H |
| 16 | 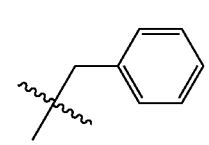 [SMILES: *Cc1ccccc1] | H | 0 | N—H |

| | | | | |
|---|---|---|---|---|
| 17 | 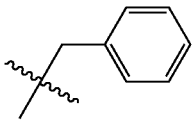 | H | 0 | N—H |
| 18 | H | 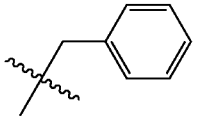 [SMILES: *Cc1ccccc1] | 0 | N—H |
| 19a | H | 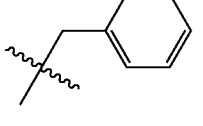 | 0 | N—H |
| 19b | | | | |
| 20 | H | 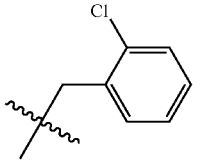 [SMILES: *Cc1ccccc1Cl] | 0 | N—H |
| 21 | H | 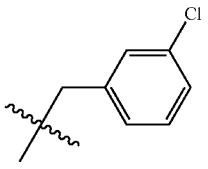 [SMILES: *Cc1cccc(Cl)c1] | 0 | N—H |
| 22 | H | 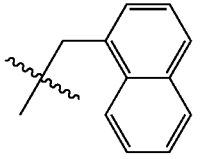 [SMILES: *Cc1cccc2ccccc12] | 0 | N—H |
| 23 | 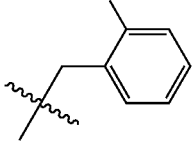 | H | 0 | N—H |
| 24 | 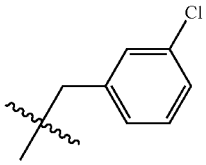 [SMILES: *Cc1cccc(Cl)c1] | H | 0 | N—H |
| 25 | 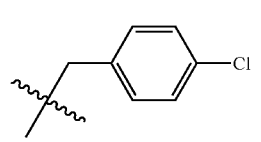 [SMILES: *Cc1ccc(Cl)cc1] | H | 0 | N—H |
| 26 | 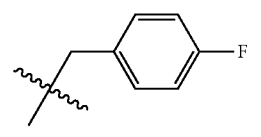 | H | 0 | N—H |

-continued
| | | | | |
|---|---|---|---|---|
| 27 | 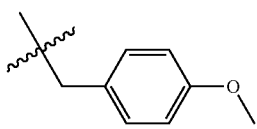 [SMILES: *Cc1ccc(OC)cc1] | H | 0 | N—H |
| 28 | 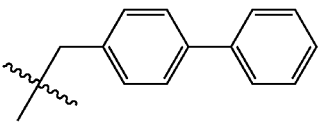 [SMILES: *Cc1ccc(-c2ccccc2)cc1] | H | 0 | N—H |
| 29 | 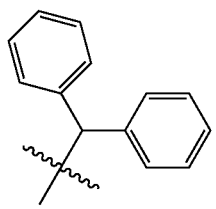 [SMILES: *C(c1ccccc1)c1ccccc1] | H | 0 | N—H |
| 30 | 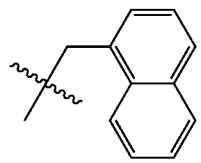 [SMILES: *Cc1cccc2ccccc12] | H | 0 | N—H |
| 31 | 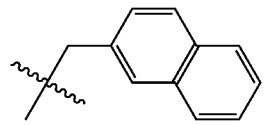 [SMILES: *Cc1ccc2ccccc2c1] | H | 0 | N—H |
| 32 | 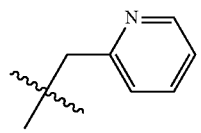 [SMILES: *Cc1ccccn1] | H | 0 | N—H |
| 33 | 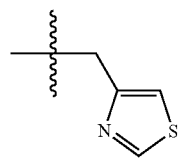 [SMILES: *Cc1cscn1] | H | 0 | N—H |
| 34 | 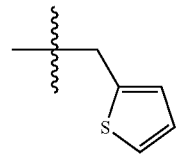 [SMILES: *Cc1cccs1] | H | 0 | N—H |
| 35 | 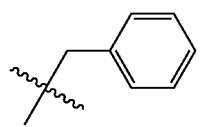 [SMILES: *Cc1ccccc1] | H | 0 | N—H |
| 36 | 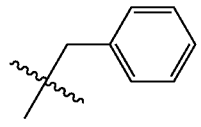 [SMILES: *Cc1ccccc1] | H | 0 | N—H |

-continued
| | | | | |
|---|---|---|---|---|
| 37a | 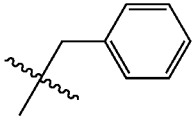 [SMILES: *Cc1ccccc1] | H | 0 | N—H |
| 37b | | | | |
| 38 | 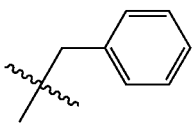 | H | 0 | N—H |
| 39 | 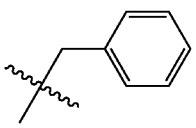 [SMILES: *Cc1ccccc1] | H | 0 | N—H |
| 40 | 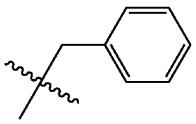 [SMILES: *Cc1ccccc1] | H | 0 | N—H |
| 41 | 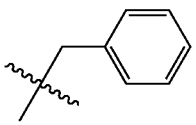 [SMILES: *Cc1ccccc1] | H | 0 | N—H |
| 42 | 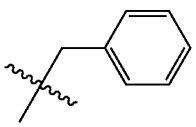 [SMILES: *Cc1ccccc1] | H | 0 | N—H |
| 43 | 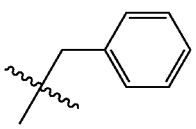 [SMILES: *Cc1ccccc1] | H | 0 | N—H |
| 44 | H | 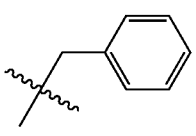 | 0 | N—H |
| 45 | H | 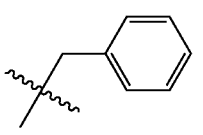 | 0 | N—H |
| 46 | H | 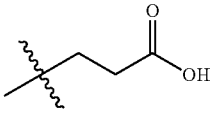 | 0 | N—H |
| 47 | H | 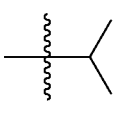 [SMILES: *C(C)C] | 0 | N—H |
| 48 | H | 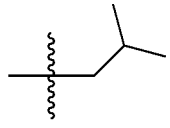 [SMILES: *CC(C)C] | 0 | N—H |
| 49 | $CH_3$ | H | 0 | N—H |

| | | | | |
|---|---|---|---|---|
| 50 | 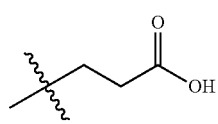 [SMILES: *CCC(=O)O] | H | 0 | N—H |
| 51 | H | H | 0 | N—H |
| 52 | 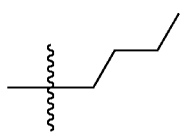 [SMILES: *CCCC] | H | 0 | N—H |
| 53 | 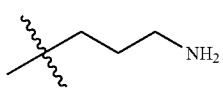 [SMILES: *CCCN] | H | 0 | N—H |
| 54 | 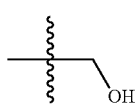 | H | 0 | N—H |
| 55 | 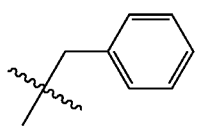 [SMILES: *Cc1ccccc1] | H | 0 | N—H |
| 56 | H | 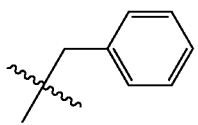 | 0 | N—H |
| 57 | H | 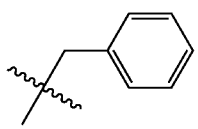 | 0 | N—H |
| 58 | 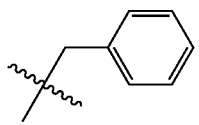 | H | 0 | N—H |
| 59 | 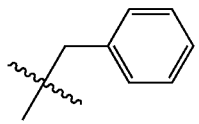 [SMILES: *Cc1ccccc1] | H | 0 | N—H |
| 60 | 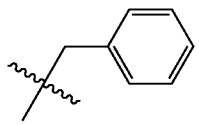 | H | 0 | N—H |
| 61 | 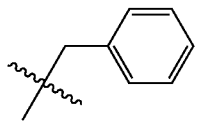 | H | 0 | N—H |
| 62 | 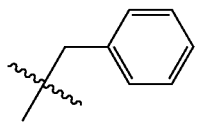 [SMILES: *Cc1ccccc1] | H | 0 | N—H |

-continued
| | | | | |
|---|---|---|---|---|
| 63 | 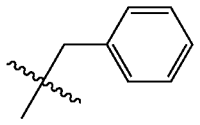 | H | 0 | N—H |
| 64 | 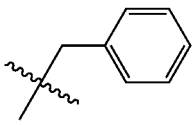 | H | 0 | N—H |
| 65 | 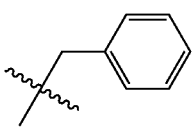 [SMILES: *Cc1ccccc1] | H | 0 | N—H |
| 66 | 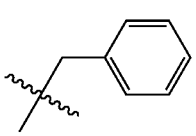 | H | 0 | N—H |
| 67 | 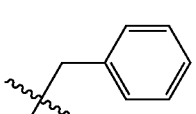 | H | 0 | N—H |
| 68 | 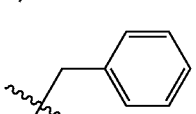 | H | 0 | N—H |
| 69 | 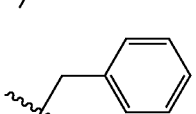 | H | 0 | N—H |
| 70 | 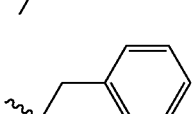 | H | 0 | N—H |
| 71 | 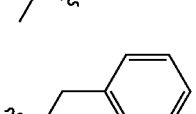 | H | 0 | N—H |
| 72 | 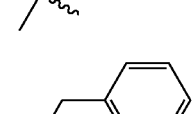 | H | 0 | N—H |
| 73 | 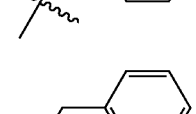 | H | 0 | N—H |
| 74 |  | H | 0 | N—H |

-continued
| | | | | |
|---|---|---|---|---|
| 75 | 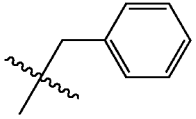 | H | 0 | N—H |
| 76 | 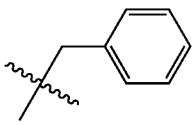 [SMILES: *Cc1ccccc1] | H | 0 | N—H |
| 77 | 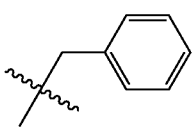 [SMILES: *Cc1ccccc1] | H | 0 | N—H |
| 78 | 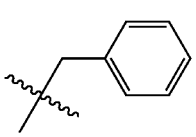 | H | 0 | N—H |
| 79 | 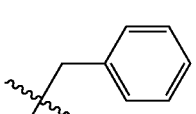 | H | 0 | N—H |
| 80 | 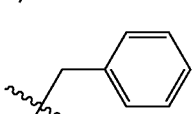 | H | 0 | N—H |
| 81 | 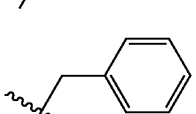 | H | 0 | N—H |
| 82 | 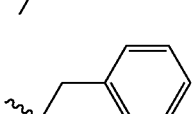 | H | 0 | N—H |
| 83 | 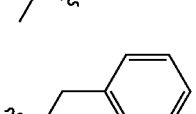 | H | 0 | N—H |
| 84 | 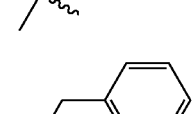 | H | 0 | N—H |
| 85 | 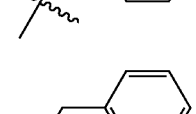 | H | 0 | N—H |
| 86 |  | H | 0 | N—H |

-continued
| 87 | H | CH₃ | 0 | N—H |
| 88 | H | 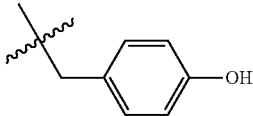 [SMILES: *Cc1ccc(O)cc1] | 0 | N—H |
| 89 | H | 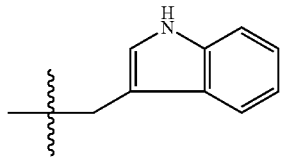 [SMILES: *Cc1c[nH]c2ccccc12] | 0 | N—H |
| 90 | H | 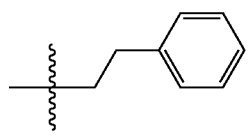 | 0 | N—H |
| 91 | H | 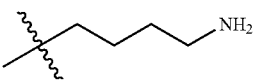 [SMILES: *CCCCN] | 0 | N—H |
| 92 | H | 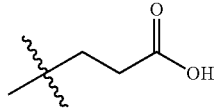 [SMILES: *CCC(=O)O] | 0 | N—H |
| 93 | H | 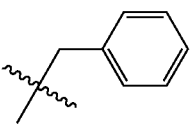 [SMILES: *Cc1ccccc1] | 0 | N—H |
| 94 | H | 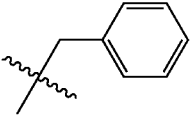 [SMILES: *Cc1ccccc1] | 0 | N—H |
| 95 | H | 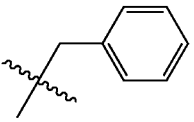 [SMILES: *Cc1ccccc1] | 0 | N—H |
| 96 | H | 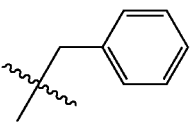 | 0 | N—H |
| 97 | 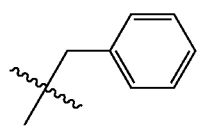 [SMILES: *Cc1ccccc1] | H | 0 | N—H |
| 98 | 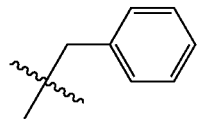 [SMILES: *Cc1ccccc1] | H | 0 | N—H |

-continued
| | | | | |
|---|---|---|---|---|
| 99 | H | 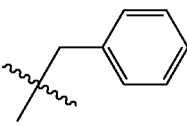 | 0 | N—H |
| 100 | H | 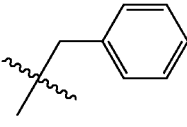 | 0 | N—H |
| 101 | H | 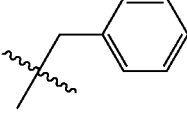 | 0 | N—H |
| 102 | H | 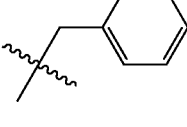 | 0 | N—H |
| 103 | H | 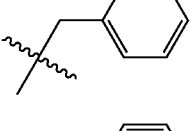 | 0 | N—H |
| 104 | H | 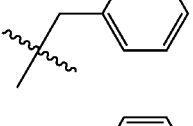 | 0 | N—H |
| 105 | H | 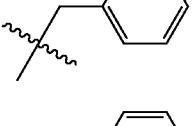 | 0 | N—H |
| 106 | H | 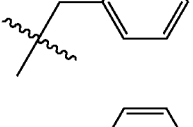 | 0 | N—H |
| 107 | H |  | 0 | N—H |
| 108 | H | 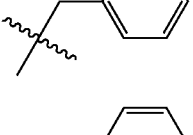 | 0 | N—H |
| 109 | H |  | 0 | N—H |
| 110 | H |  | 0 | N—H |

-continued
| | | | | |
|---|---|---|---|---|
| 111 | H | 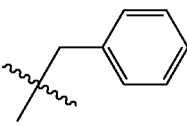 | 0 | N—H |
| 112 | H | 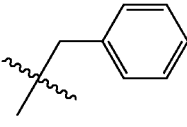 | 0 | N—H |
| 113 | H | 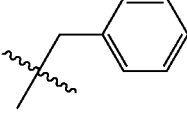 | 0 | N—H |
| 114 | H | 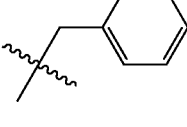 | 0 | N—H |
| 115 | H | 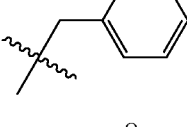 | 0 | N—H |
| 116 | H | 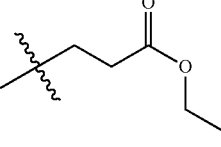 | 0 | N—H |
| 117 | 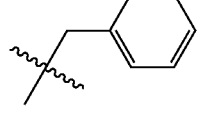 | H | 0 | N—H |
| 118 | 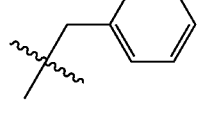 | H | 0 | N—H |
| 119 | 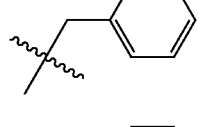 | H | 0 | N—H |
| 120 | 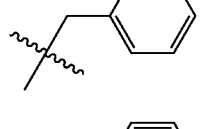 | H | 0 | N—H |
| 121 | 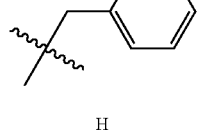 | H | 0 | N—H |
| 122 | H | 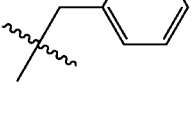 | 0 | N—H |

-continued

| 123 | H | benzyl | 0 | N—H |
| 124 | H | benzyl | 0 | N—H |
| 125 | H | benzyl | 0 | N—H |
| 126 | H | benzyl | 0 | N—H |
| 127 | H | benzyl | 0 | N—H |
| 128 | H | benzyl | 0 | N—H |
| 129 | H | benzyl | 0 | N—H |
| 130 | H | benzyl | 0 | N—H |
| 131 | H | benzyl | 0 | N—H |
| 132 | H | benzyl | 0 | N—H |

Structure 19

| 133 | H | benzyl | 0 | N—H |

-continued
| | | | | |
|---|---|---|---|---|
| 134 | H | 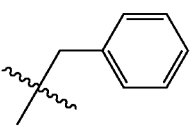 [SMILES: *Cc1ccccc1] | 0 | N—H |
| 135 | H | 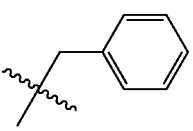 [SMILES: *Cc1ccccc1] | 0 | N—H |
| 136a | H | 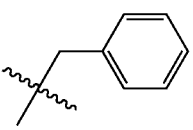 [SMILES: *Cc1ccccc1] | 0 | N—H |
| 136b | | | | |
| 137 | H | 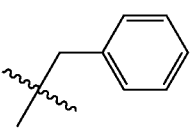 | 0 | N—H |
Structure 19
| | | | | |
|---|---|---|---|---|
| 138 | H | 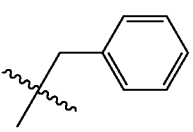 [SMILES: *Cc1ccccc1] | 0 | N—H |
| 139 | H | 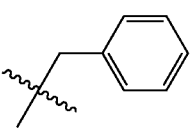 [SMILES: *Cc1ccccc1] | 0 | N—H |
| 140 | H | 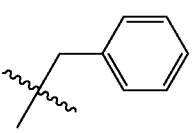 [SMILES: *Cc1ccccc1] | 0 | N—H |
| 141 | H | 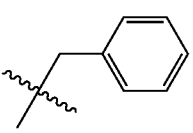 [SMILES: *Cc1ccccc1] | 0 | N—H |
| 142 | H | 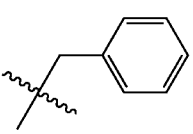 [SMILES: *Cc1ccccc1] | 0 | N—H |
| 143 | H | 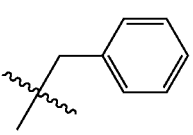 [SMILES: *Cc1ccccc1] | 0 | N—H |
| 144 | 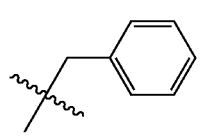 [SMILES: *Cc1ccccc1] | H | 0 | N—H |

-continued
| | | | | | |
|---|---|---|---|---|---|
| 145a | 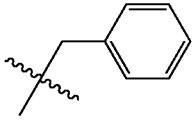 [SMILES: *Cc1ccccc1] | H | | 0 | N—H |
| 145b | | | | | |
| 146a | 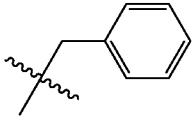 [SMILES: *Cc1ccccc1] | H | | 0 | N—H |
| 146b | | | | | |
| 147 | 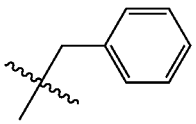 [SMILES: *Cc1ccccc1] | H | | 0 | N—H |
| 148 | 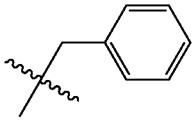 | H | | 0 | N—H |
| 149 | 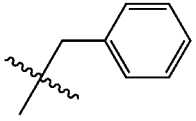 [SMILES: *Cc1ccccc1] | H | | 0 | N—H |
| 150a | 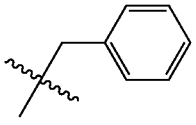 [SMILES: *Cc1ccccc1] | H | | 0 | N—H |
| 150b | | | | | |
| 151 | 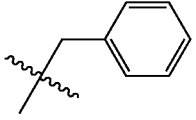 [SMILES: *Cc1ccccc1] | H | | 0 | N—H |
| 152a | 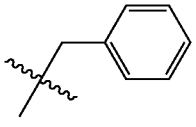 | H | | 0 | N—H |
| 152b | | | | | |
| 153 | | H | 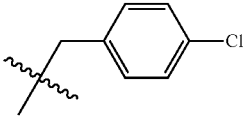 [SMILES: *Cc1ccc(Cl)cc1] | 0 | N—H |
| 154 | | H | 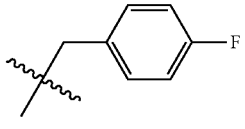 [SMILES: *Cc1ccc(F)cc1] | 0 | N—H |
| 155 | | H | 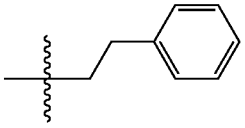 | 0 | N—H |

-continued
| | | | | |
|---|---|---|---|---|
| 156 | H | 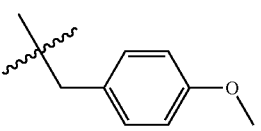 [SMILES: *Cc1ccc(OC)cc1] | 0 | N—H |
| 157 | H | 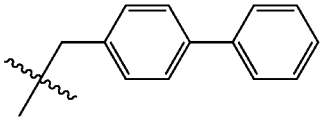 | 0 | N—H |
| 158 | H | 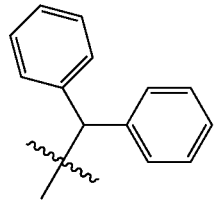 [SMILES: *C(c1ccccc1)c1ccccc1] | 0 | N—H |
| 159 | H | 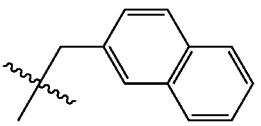 | 0 | N—H |
| 160a | H | 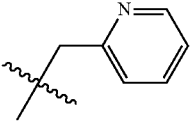 | 0 | N—H |
| 160b | | | | |
| 161a | H | 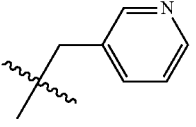 [SMILES: *Cc1cccnc1] | 0 | N—H |
| 161b | | | | |
| 162a | H | 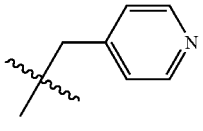 [SMILES: *Cc1ccncc1] | 0 | N—H |
| 162b | | | | |
| 163 | H | 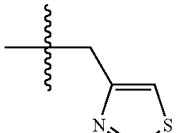 | 0 | N—H |
| 164 | H | 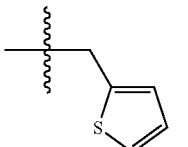 | 0 | N—H |
| 165 | H | 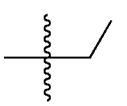 | 0 | N—H |

US 8,349,887 B2
163                                                                       164
-continued
| 166 | H | 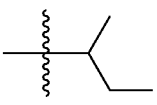 | 0 | N—H |
| 167 | H | 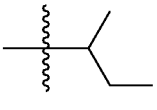 | 0 | N—H |
| 168 | 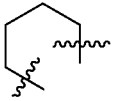 [SMILES: *CCCC*] | H | 0 | N—H |
| 169 | 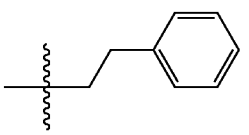 [SMILES: *CCc1ccccc1] | H | 0 | N—H |
| 170 | 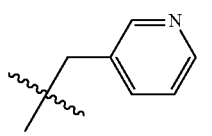 [SMILES: *Cc1cccnc1] | H | 0 | N—H |
| 171 | 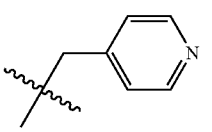 [SMILES: *Cc1ccncc1] | H | 0 | N—H |
| 172 | H | 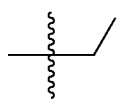 [SMILES: *CC] | | |
| 173 | 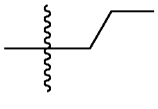 [SMILES: *CCC] | H | 0 | N—H |
| 174 | 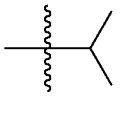 | H | 0 | N—H |
| 175 | 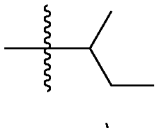 | H | 0 | N—H |
| 176 | 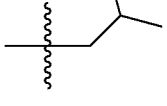 | H | 0 | N—H |
| 177 | 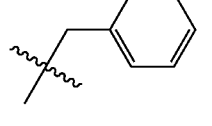 | H | 0 | N—H |
| 178 | 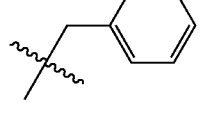 | H | 0 | N—H |

-continued
| 179 | 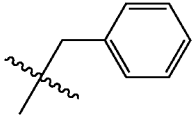 | H | 0 | N—H |
| 180 | 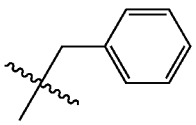 | H | 0 | N—H |
| 181 | 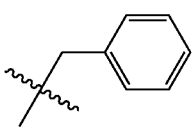 [SMILES: *Cc1ccccc1] | H | 0 | N—H |
| 182a | 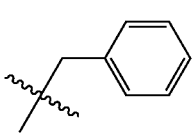 | H | 0 | N—H |
| 182b | | | | |
| 183 | 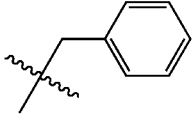 [SMILES: *Cc1ccccc1] | H | 0 | N—H |
| 184 | 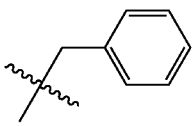 | H | 0 | N—H |
| 184 | | | | |
| 185 | 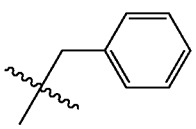 | H | 0 | N—H |
| 186 | 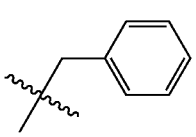 [SMILES: *Cc1ccccc1] | H | 0 | N—H |
| 187 | 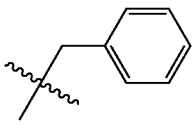 [SMILES: *Cc1ccccc1] | H | 0 | N—H |
| 188 | 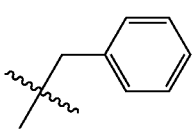 | H | 0 | N—H |
| 189a | 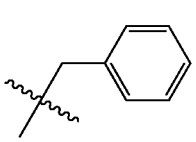 [SMILES: *Cc1ccccc1] | H | 0 | N—H |
| 189b | | | | |

-continued
| | | | | |
|---|---|---|---|---|
| 190 | 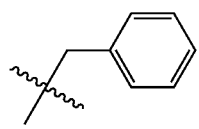 [SMILES: *Cc1ccccc1] | H | 0 | N—H |
| 191 | 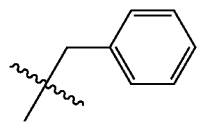 | H | 0 | N—H |
| 192 | 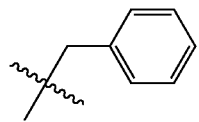 | H | 0 | N—H |
| 193 | 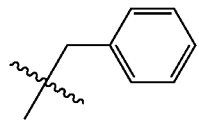 | H | 0 | N—H |
| 194a | 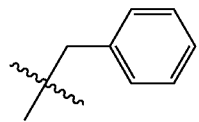 [SMILES: *Cc1ccccc1] | H | 0 | N—H |
| 194b | | | | |
| 195 | 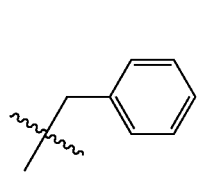 [SMILES: *Cc1ccccc1] | H | 0 | N—H |
| 196 | 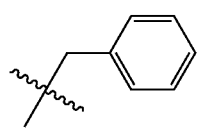 [SMILES: *Cc1ccccc1] | H | 0 | N—H |
| 197 | 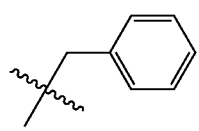 | H | 0 | N—H |
| 199 | H | 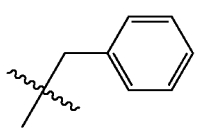 | 0 | N—H |
| 200 | H | 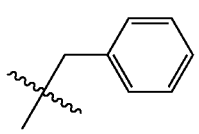 [SMILES: *Cc1ccccc1] | 0 | N—H |
| 201 | 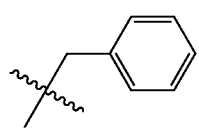 | H | 0 | N—H |

-continued
| | | | | | |
|---|---|---|---|---|---|
| 202 | 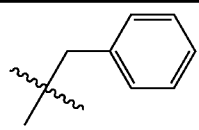 | | H | 0 | N—H |
| 203 | H | 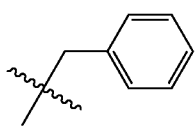 [SMILES: *Cc1ccccc1] | | 0 | N—H |
| 204 | H | 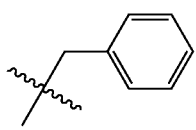 | | 0 | N—H |
| 205 | 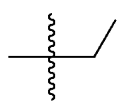 [SMILES: *CC] | | H | 0 | N—H |
| 206 | 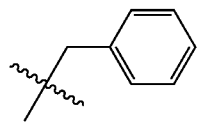 [SMILES: *Cc1ccccc1] | | H | 0 | N—H |
| 207 | H | 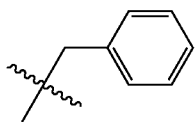 [SMILES: *Cc1ccccc1] | | 0 | N—H |
| 208a | H | 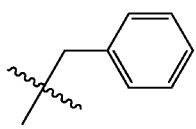 | | 0 | N—H |
| 208b | | | | | |
| 209 | 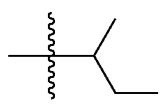 [SMILES: *C(C)CC] | | H | 0 | N—H |
| 210 | H | 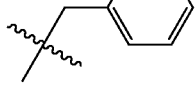 | | 0 | N—H |
| 211 | H | 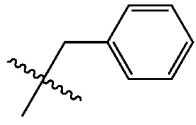 [SMILES: *Cc1ccccc1] | | 0 | N—H |
| 212 | 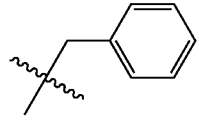 [SMILES: *Cc1ccccc1] | | H | 0 | N—H |
| 213 | 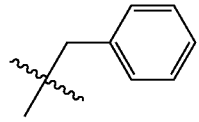 | | H | 0 | N—H |

-continued
| | | | | | |
|---|---|---|---|---|---|
| 214 | 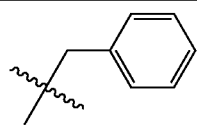 | H | | 0 | N—H |
| 215 | 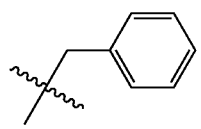 [SMILES: *Cc1ccccc1] | H | | 0 | N—H |
| 216 | | H | 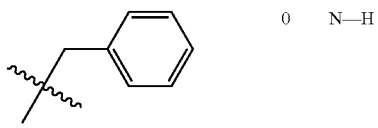 | 0 | N—H |
| 218 | | H | 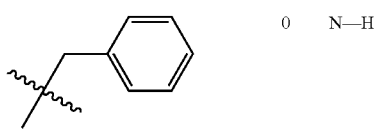 | 0 | N—H |
| 219 | | H | 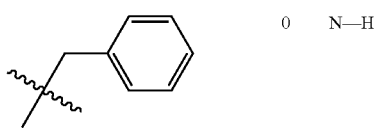 | 0 | N—H |
| 220 | | | | | |
| 221 | | | | | |
| 222 | | | | | |
| 223 | | | | | |
| 224 | | | | | |
| 225 | | | | | |
| 226 | | | | | |
| 227 | | | | | |
| 228 | | | | | |
| 229 | | | | | |
| 230a | | | | | |
| 230b | | | | | |
| Compound | T | $K_i$ (nM) |
|---|---|---|
| 1 | 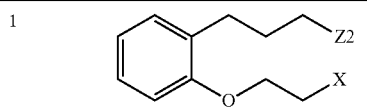 | B |
| 2 | 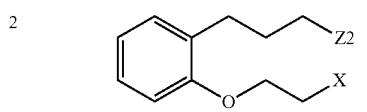 | C |
| 3 | 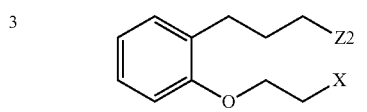 | C |
| 4 | 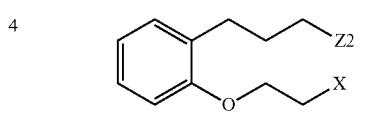 | B |
| 5 | 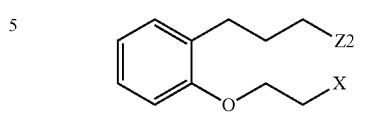 | C |

| | | |
|---|---|---|
| 6 | 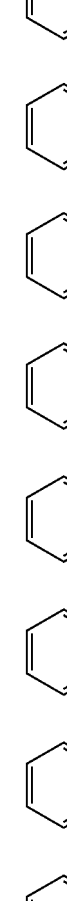 | C |
| 7 | | C |
| 8 | | B |
| 9 | | C |
| 10 | | B |
| 11 | | B |
| 12 | | C |
| 13 | | C |
| 14 | | C |
| 15 | | A |
| 16 | | A |
| 17 | | A |
| 18 | | B |

-continued
| | | |
|---|---|---|
| 19a | 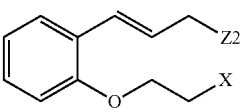 | A |
| 19b | | C |
| 20 | 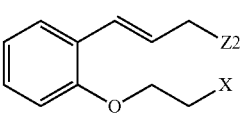 | A |
| 21 | 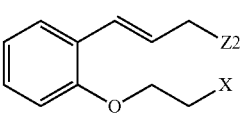 | A |
| 22 | 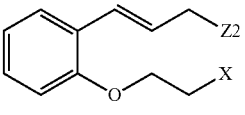 | B |
| 23 | 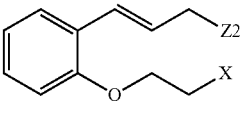 | A |
| 24 | 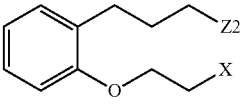 | A |
| 25 | 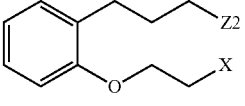 | A |
| 26 | 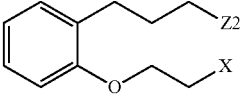 | A |
| 27 | 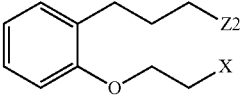 | A |
| 28 | 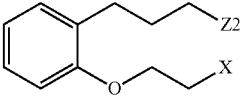 | B |
| 29 | 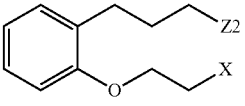 | B |
| 30 | 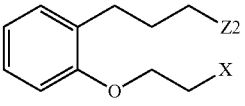 | A |
| 31 | 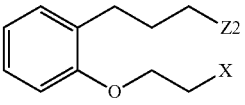 | A |

-continued

| | | |
|---|---|---|
| 32 | [structure: benzene with propyl-Z2 and O-ethyl-X] | B |
| 33 | [structure: benzene with propyl-Z2 and O-ethyl-X] | C |
| 34 | [structure: benzene with propyl-Z2 and O-ethyl-X] | B |
| 35 | [structure: benzene with O-CH(CH3)-CH2-X and propyl-Z2] | B |
| 36 | [structure: benzene with O-CH(CH3)-CH2-X and propyl-Z2] | B |
| 37a | [structure: benzene with CH=CH-Z2 and propyl-X] | B |
| 37b | | B |
| 38 | [structure: benzene with pentyl-Z2 and CH2-X] | B |
| 39 | [structure: benzene with CH=CH-CH2-Z2 and O-ethyl-X] | B |
| 40 | [structure: benzene with CH=CH-CH2-Z2 and O-ethyl-X] | A |
| 41 | [structure: benzene with propyl-Z2 and O-ethyl-X] | B |
| 42 | [structure: benzene with propyl-Z2 and O-ethyl-X] | A |
| 43 | [structure: benzene with propyl-Z2 and O-ethyl-X] | B |

-continued
| | | |
|---|---|---|
| 44 | 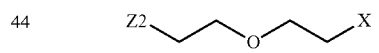 | G |
| 45 | 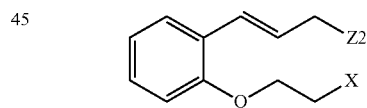 | G |
| 46 | 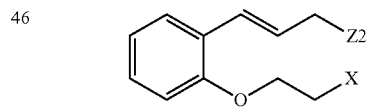 | G |
| 47 | 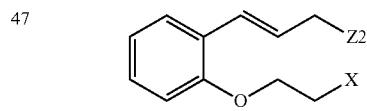 | C |
| 48 | 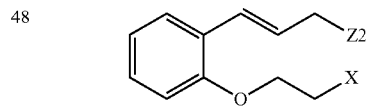 | G |
| 49 | 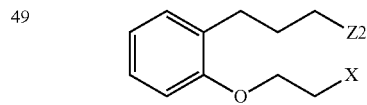 | G |
| 50 | 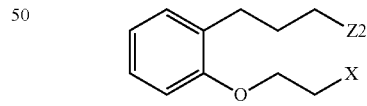 | G |
| 51 | 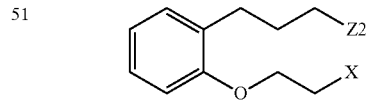 | G |
| 52 | 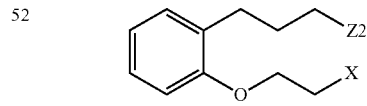 | C |
| 53 | 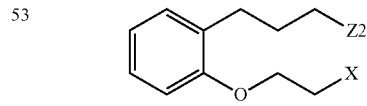 | G |
| 54 | 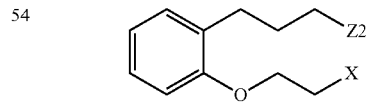 | G |
| 55 | 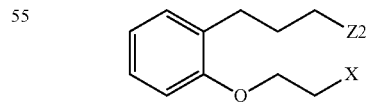 | D |
| 56 | 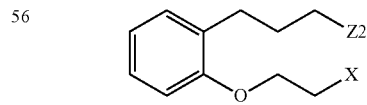 | G |
| 57 | 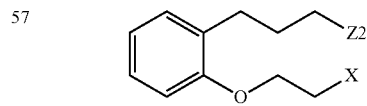 | C |

-continued

| | | |
|---|---|---|
| 58 | 2-(Z2-propyl)phenyl O-CH2-X | G |
| 59 | 2-(Z2-propyl)phenyl O-CH2-X | D |
| 60 | 2-(Z2-propyl)phenyl O-CH2-X | C |
| 61 | 2-(Z2-propyl)phenyl O-CH2-X | C |
| 62 | 2-(Z2-propyl)phenyl O-CH2-X | D |
| 63 | 2-(Z2-propyl)phenyl O-CH2-X | G |
| 64 | 2-(Z2-propyl)phenyl O-CH2-X | G |
| 65 | 2-(Z2-propyl)phenyl O-CH2-X | D |
| 66 | 2-(Z2-propyl)phenyl O-CH2-X | C |
| 67 | 2-(Z2-propyl)phenyl O-CH2-X | C |
| 68 | 2-(Z2-propyl)phenyl O-CH2-X | D |
| 69 | 2-(Z2-propyl)phenyl O-CH2-X | G |
| 70 | 2-(Z2-propyl)phenyl O-CH2-X | G |
| 71 | 2-(Z2-propyl)phenyl O-CH2-X | G |

-continued

| | | |
|---|---|---|
| 72 | 2-(3-Z2-propyl)phenyl 2-X-ethyl ether | D |
| 73 | 2-(3-Z2-propyl)phenyl 2-X-ethyl ether | G |
| 74 | 2-(3-Z2-propyl)phenyl 2-X-ethyl ether | D |
| 75 | 2-(3-Z2-propyl)phenyl 2-X-ethyl ether | C |
| 76 | 2-(3-Z2-propyl)phenyl 2-X-ethyl ether | G |
| 77 | bis(2-Z2-methyl/X-methyl phenyl) sulfide | C |
| 78 | cis-1-X-methyl-3-Z2-methyl cyclopentane | G |
| 79 | 2-(3-Z2-propyl)phenyl 2-X-ethyl ether | C |
| 80 | 2-(3-Z2-propyl)phenyl 2-X-ethyl ether | G |
| 81 | Z2-CH2CH2-O-CH2CH2-X | G |
| 82 | Z2-CH2CH2-C≡C-CH2CH2-X | G |
| 83 | Z2-CH2CH2-CH=CH-CH2CH2-X | G |
| 84 | 1,3-bis(X-methyl/Z2-methyl)benzene | D |
| 85 | 1,3-(X-methyl)(Z2-ethyl)benzene | G |

| | | |
|---|---|---|
| 86 | 2-(CH2-Z2), 4-(CH2-X) thiazole | G |
| 87 | 2-(CH2CH2CH2-Z2), 1-(OCH2CH2-X) benzene | G |
| 88 | 2-(CH2CH2CH2-Z2), 1-(OCH2CH2-X) benzene | D |
| 89 | 2-(CH2CH2CH2-Z2), 1-(OCH2CH2-X) benzene | D |
| 90 | 2-(CH2CH2CH2-Z2), 1-(OCH2CH2-X) benzene | D |
| 91 | 2-(CH2CH2CH2-Z2), 1-(OCH2CH2-X) benzene | G |
| 92 | 2-(CH2CH2CH2-Z2), 1-(OCH2CH2-X) benzene | G |
| 93 | 2-(CH2CH2CH2-Z2), 1-(OCH2CH2-X) benzene | D |
| 94 | 2-(CH2CH2CH2-Z2), 1-(OCH2CH2-X) benzene | D |
| 95 | 2-(CH2CH2CH2-Z2), 1-(OCH2CH2-X) benzene | D |
| 96 | 2-(CH2CH2CH2-Z2), 1-(OCH2CH2-X) benzene | G |
| 97 | 2-(CH2CH2CH2-Z2), 1-(OCH2CH2-X) benzene | C |
| 98 | 2-(CH2CH2CH2-Z2), 1-(OCH2CH2-X) benzene | G |

| | | | |
|---|---|---|---|
| 99 | 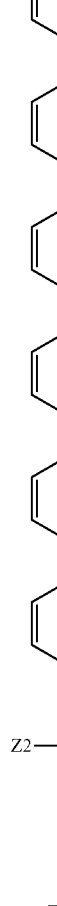 | G | |
| 100 | | C | |
| 101 | | C | |
| 102 | | C | |
| 103 | | G | |
| 104 | | G | |
| 105 | | C | |
| 106 | 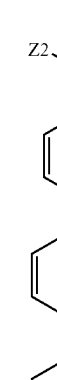 | G | |
| 107 |  | G | |
| 108 |  | D | |
| 109 | 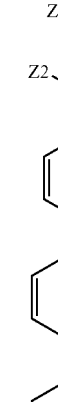 | D | |
| 110 |  | G | |
| 111 |  | C | |

-continued
| | | |
|---|---|---|
| 112 | 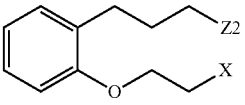 | D |
| 113 | 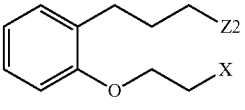 | C |
| 114 | 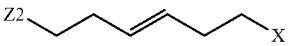 | G |
| 115 | 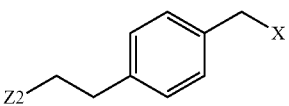 | G |
| 116 | 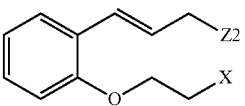 | D |
| 117 | 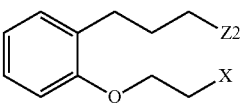 | B |
| 118 | 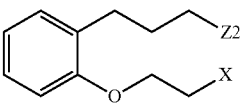 | B |
| 119 | 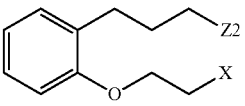 | C |
| 120 | 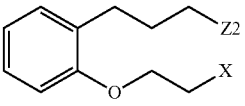 | B |
| 121 | 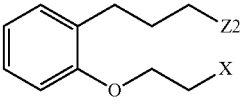 | G |
| 122 | 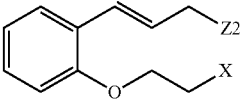 | C |
| 123 | 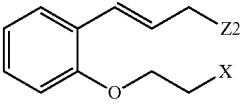 | C |
| 124 | 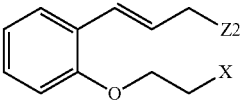 | D |
| 125 | 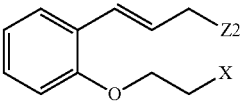 | G |

-continued
| 126 | 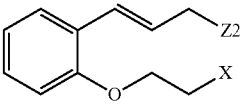 | C |
| 127 | 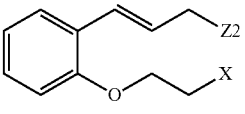 | C |
| 128 | 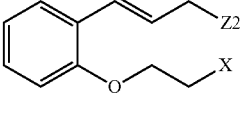 | G |
| 129 | 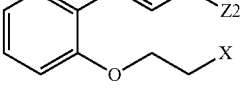 | G |
| 130 | 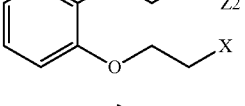 | D |
| 131 | 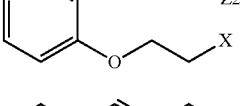 | C |
| 132 | 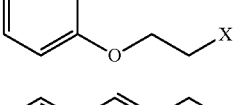 | F |
| 133 | 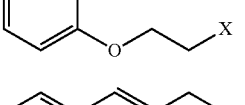 | F |
| 134 | 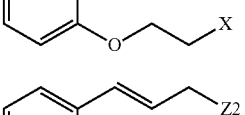 | C |
| 135 | 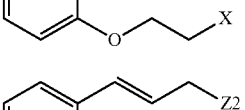 | C |
| 136a | 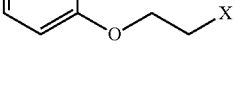 | B |
| 136b | | C |
| 137 | 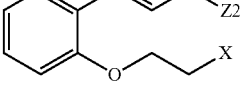 | B |
| 138 | 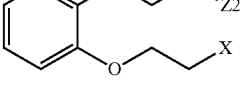 | B |

-continued
| | | |
|---|---|---|
| 139 | 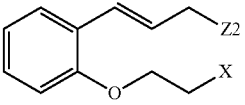 | C |
| 140 | 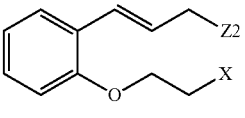 | C |
| 141 | 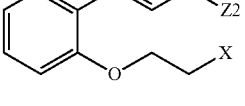 | C |
| 142 | 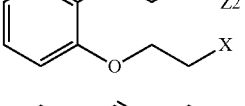 | C |
| 143 | 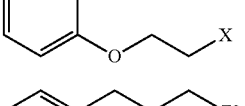 | C |
| 144 | 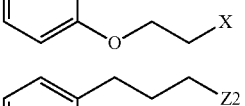 | C |
| 145a | 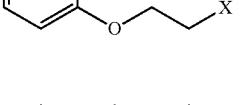 | C |
| 145b | | F |
| 146a | 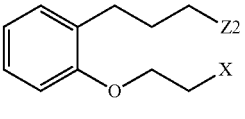 | F |
| 146b | | F |
| 147 | 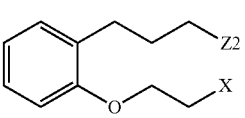 | F |
| 148 | 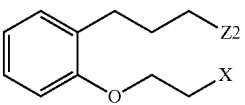 | F |
| 149 | 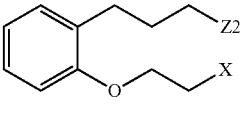 | D |
| 150a | 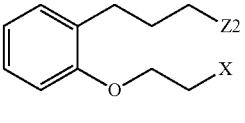 | C |
| 150b | | G |
| 151 | 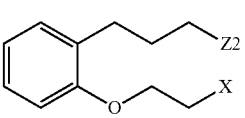 | F |

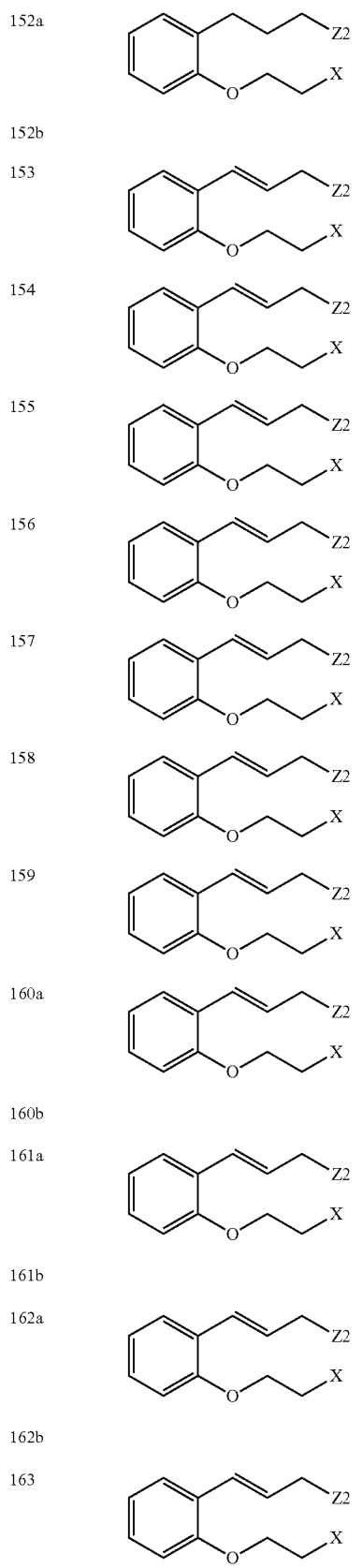

-continued
| | | |
|---|---|---|
| 164 | 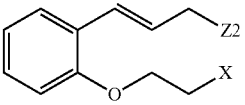 | C |
| 165 | 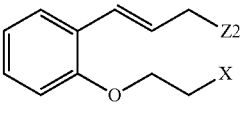 | G |
| 166 | 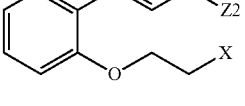 | G |
| 167 | 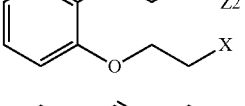 | G |
| 168 | 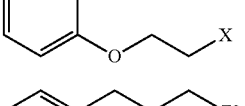 | C |
| 169 | 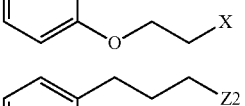 | B |
| 170 | 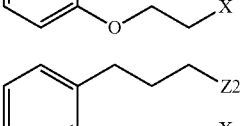 | B |
| 171 | 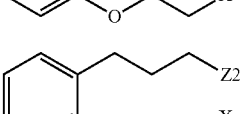 | B |
| 172 | 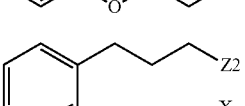 | G |
| 173 | 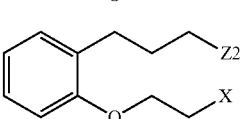 | C |
| 174 | 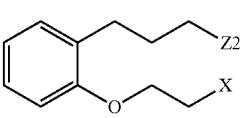 | C |
| 175 | 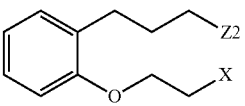 | C |
| 176 | 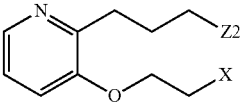 | B |
| 177 | 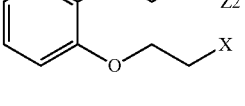 | B |

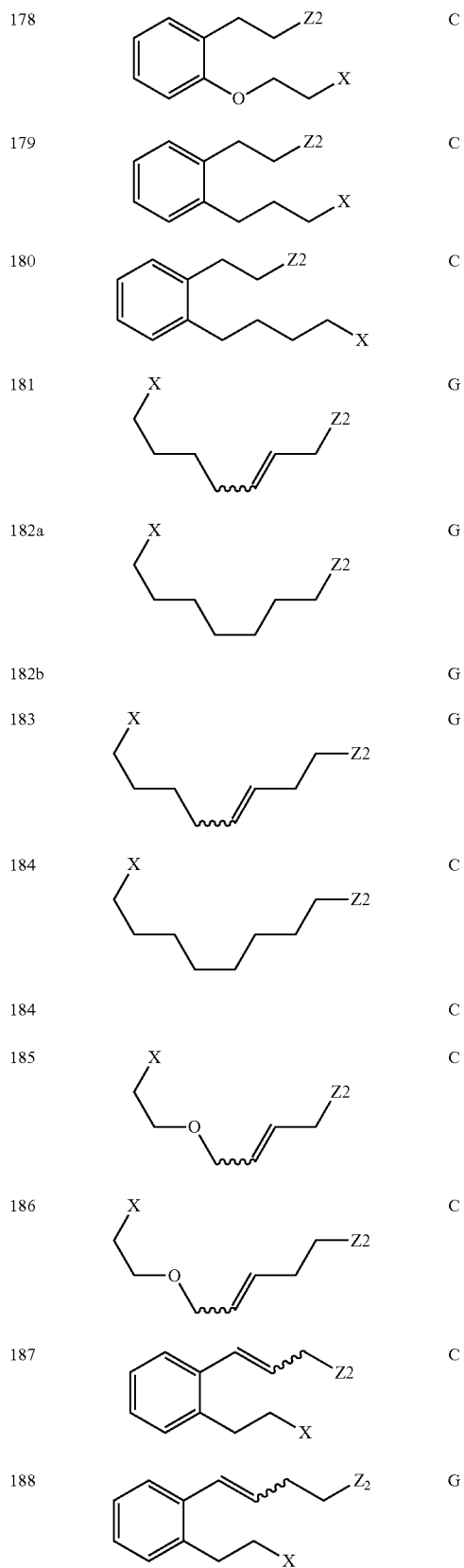

-continued
| | | |
|---|---|---|
| 189a | 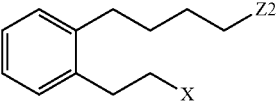 | C |
| 189b | | C |
| 190 | 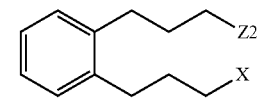 | B |
| 191 | 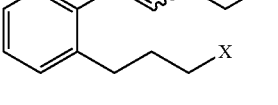 | C |
| 192 | 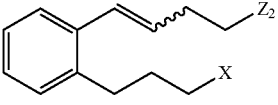 | B |
| 193 | 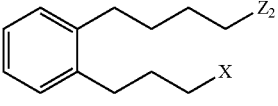 | C |
| 194a | 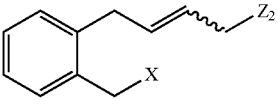 | C |
| 194b | | C |
| 195 | 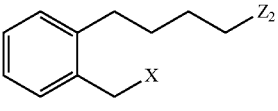 | B |
| 196 | 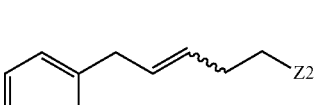 | G |
| 197 | 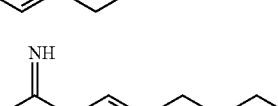 | C |
| 199 | 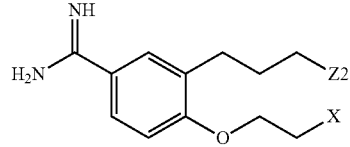 | C |
| 200 | 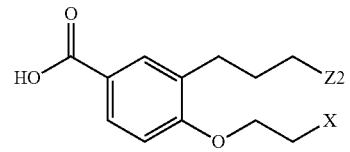 | B |
| 201 | 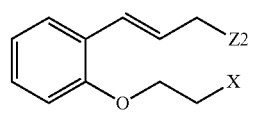 | C |

-continued
| | | |
|---|---|---|
| 202 | 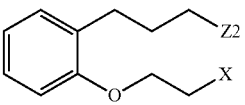 | G |
| 203 | 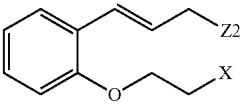 | D |
| 204 | 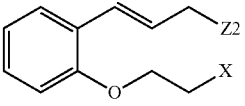 | G |
| 205 | 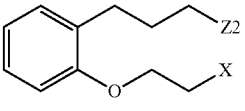 | G |
| 206 | 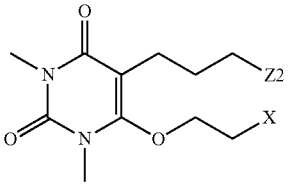 | G |
| 207 | 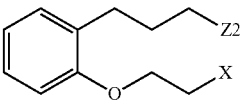 | G |
| 208a | 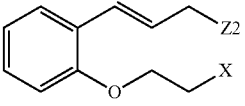 | B |
| 208b | | B |
| 209 | 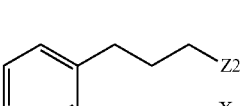 | C |
| 210 | 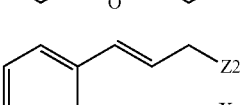 | F |
| 211 | 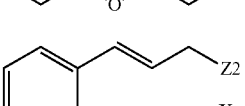 | F |
| 212 | 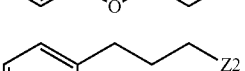 | C |
| 213 | 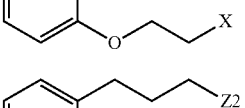 | F |
| 214 | 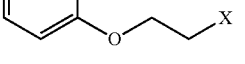 | C |

-continued

| | | | |
|---|---|---|---|
| 215 | [structure: benzene with propyl-Z2 chain and O-CH2CH2-X] | | D |
| 216 | [structure: benzene with propyl-Z2 chain and O-CH2CH2-X] | | D |
| 218 | [structure: benzene with allyl-Z2 (E-alkene) and O-CH2CH2-X] | | B |
| 219 | [structure: benzene with allyl-Z2 (E-alkene) and O-CH2CH2-X] | | C |
| 220 | | | D |
| 221 | | | C |
| 222 | | | D |
| 223 | | | D |
| 224 | | | G |
| 225 | | | C |
| 226 | | | B |
| 227 | | | C |
| 228 | | | G |
| 229 | | | B |
| 230a | | | C |
| 230b | | | D |

Binding activity determined using Method B1, expressed as follows:
A = 0.1-10 nM;
B = 10-100 nM;
C = 0.1-1.0 µM;
D = 1-10 µM;
E > 500 nM (highest concentration tested);
F > 1 µM (highest concentration tested);
G > 10 µM (or no activity at highest concentration tested)

TABLE 3B

Binding Activity at the Human Ghrelin Receptor for Representative Compounds of the Invention

| Compound | $R_2$ | $R_3$ | $R_4$ | $R_7$ | $R_5$ |
|---|---|---|---|---|---|
| 298 | cyclopropyl | CH3 | H | CH3 | 4-fluorobenzyl |
| 299 | cyclopropyl | CH3 | H | CH3 | 4-chlorobenzyl |
| 301 | 4-hydroxybenzyl | cyclopentyl | | H | H |
| 303 | neopentyl | tetrahydropyranyl (O-containing ring) | | H | H |

TABLE 3B-continued

| 305 | sec-butyl-methyl | CH3 | H | CH3 | 1H-imidazol-4-ylmethyl |
|---|---|---|---|---|---|
| 306a | cyclopropyl | CH3 | H | CH3 | 4-fluorobenzyl |
| 306b | | diastereomer | | | |
| 307 | cyclopropyl | CH3 | H | CH3 | 4-fluorobenzyl |
| 308 | cyclopropyl | CH3 | H | CH3 | 4-chlorobenzyl |
| 309 | cyclopropyl | CH3 | H | CH3 | 4-fluorobenzyl |
| 310 | cyclopropyl | CH3 | H | CH3 | thiophen-3-ylmethyl |
| 311 | cyclopropyl | CH3 | H | CH3 | 3-tert-butyl-4-hydroxybenzyl |
| 312 | cyclopropyl | CH3 | H | CH3 | 2-fluorobenzyl |
| 313 | cyclopropyl | CH3 | H | CH3 | 3-fluorobenzyl |
| 314 | cyclopropyl | CH3 | H | CH3 | 2,4-dichlorobenzyl |

TABLE 3B-continued

| # | | | | | |
|---|---|---|---|---|---|
| 315 | cyclopropyl | CH3 | H | CH3 | 3,4-dichlorobenzyl |
| 316 | cyclopropyl | CH3 | H | CH3 | 3,4-difluorobenzyl |
| 317 | cyclopropyl | CH3 | H | CH3 | 3,5-difluorobenzyl |
| 318 | cyclopropyl | CH3 | H | CH3 | pentafluorobenzyl |
| 319 | cyclopropyl | CH3 | H | CH3 | 4-bromobenzyl |
| 320 | cyclopropyl | CH3 | H | CH3 | 4-iodobenzyl |
| 321 | cyclopropyl | CH3 | H | CH3 | 4-cyanobenzyl |
| 322 | cyclopropyl | CH3 | H | CH3 | 4-(trifluoromethyl)benzyl |
| 323 | cyclopropyl | CH3 | H | CH3 | 3,4-dimethoxybenzyl |
| 324 | cyclopropyl | CH3 | H | CH3 | 2-(1H-indol-3-yl)propyl |

TABLE 3B-continued

| | R1 | R2 | R3 | R4 | R5 |
|---|---|---|---|---|---|
| 325 | sec-butyl | cyclohexyl | H | H | |
| 326 | sec-butyl | cyclohexyl | H | H | |
| 327a | sec-butyl | cyclohexyl | H | H | |
| 327b | diastereomer | | | | |
| 328 | sec-butyl | cyclohexyl | H | H | |
| 329 | sec-butyl | cyclohexyl | H | H | |
| 330 | sec-butyl | cyclohexyl | H | H | |
| 331a | sec-butyl | cyclohexyl | H | H | |
| 331b | diastereomer | | | | |
| 332a | sec-butyl | cyclohexyl | H | H | |
| 332b | diastereomer | | | | |
| 333 | sec-butyl | cyclohexyl | H | H | |
| 335 | methoxymethyl-methyl | CH3 | H | CH3 | 4-fluorobenzyl |
| 336 | methoxymethyl | CH3 | H | CH3 | 4-fluorobenzyl |

TABLE 3B-continued

| # | R1 | R2 | R3 | R4 |
|---|---|---|---|---|
| 337 | H2N-CH(CH3)-* | CH3 | H | CH3 | 4-F-benzyl |
| 338 | H2N-CH2-CH(CH3)-* | CH3 | H | CH3 | 4-F-benzyl |
| 339 | H2N-(CH2)3-* | CH3 | H | CH3 | 4-F-benzyl |
| 340 | CH3-S-CH2-CH2-* | CH3 | H | CH3 | 4-F-benzyl |
| 341 | (thiophen-3-yl)methyl | cyclohexyl | H | H |
| 342 | (2-cyanophenyl)methyl | cyclohexyl | H | H |
| 343 | (2-methoxyphenyl)methyl | cyclohexyl | H | H |
| 344 | CH3-O-CH2-* | cyclohexyl | H | H |
| 345a | sec-butyl | tetrahydropyran-4-yl | H | H |
| 345b | diastereomer | | | |
| 346 | cyclopropylmethyl | cyclohexyl | H | H |
| 347 | 3-methylbutan-2-yl | cyclohexyl | H | H |

TABLE 3B-continued

| | | | | | |
|---|---|---|---|---|---|
| 348a | sec-butyl | CH3 | CH3 | H | H |
| 348b | | diastereomer | | | |
| 353a | sec-butyl | CH3 | H | CH3 | 4-F-benzyl |
| 353b | | diastereomer | | | |
| 354 | cyclopropyl-methyl | CH3 | H | CH3 | 4-F-benzyl |
| 355 | cyclopropyl-methyl | CH3 | H | CH3 | 4-F-benzyl |
| 356 | cyclopropyl-methyl | CH3 | H | CH3 | 4-F-benzyl |
| 357 | cyclopropyl-methyl | CH3 | H | CH3 | 4-F-benzyl |
| 358a | sec-butyl | cyclopentyl | | H | H |
| 358b | | diastereomer | | | |
| 359 | sec-butyl | cyclopentyl | | H | H |
| 360 | sec-butyl | cyclopentyl | | H | H |
| 361 | sec-butyl | cyclopentyl | | H | H |
| 362 | sec-butyl | cyclopentyl | | H | H |

TABLE 3B-continued

| | | | | | |
|---|---|---|---|---|---|
| 363 | sec-butyl-like | cyclohexyl-like | H | H | |
| 364 | sec-butyl-like | cyclohexyl-like | H | H | |
| 365 | sec-butyl-like | cyclohexyl-like | H | H | |
| 366 | sec-butyl-like | cyclohexyl-like | H | H | |
| 367 | cyclopropyl | CH3 | H | CH3 | 4-fluorobenzyl |
| 368a | sec-butyl-like | cyclohexyl-like | H | H | |
| 368b | diastereomer | | | | |
| 369 | sec-butyl-like | cyclohexyl-like | H | H | |
| 370 | sec-butyl-like | cyclohexyl-like | H | H | |
| 371 | sec-butyl-like | cyclohexyl-like | H | H | |
| 372 | cyclopropyl | CH3 | H | CH3 | 4-fluorobenzyl |
| 373 | cyclopropyl | CH3 | H | CH3 | 4-fluorobenzyl |
| 374 | cyclopropyl | CH3 | H | CH3 | 4-fluorobenzyl |

TABLE 3B-continued

| | | | | | |
|---|---|---|---|---|---|
| 375 | cyclopropyl | CH3 | H | CH3 | 4-F-benzyl |
| 376 | cyclopropyl | CH3 | H | CH3 | 4-F-benzyl |
| 377 | cyclopropyl | CH3 | H | CH3 | 4-F-benzyl |
| 378 | cyclopropyl | CH3 | H | CH3 | 4-F-benzyl |
| 379 | cyclopropyl | CH3 | H | CH3 | 4-F-benzyl |
| 380 | sec-butyl | cyclopentyl | H | H | |
| 381 | sec-butyl | cyclopentyl | H | H | |
| 382 | sec-butyl | cyclopentyl | H | H | |
| 383 | sec-butyl | cyclopentyl | H | H | |
| 384 | sec-butyl | cyclopentyl | H | H | |
| 385 | sec-butyl | cyclopentyl | H | H | |
| 386 | sec-butyl | cyclopentyl | H | H | |

TABLE 3B-continued

| | | | | | |
|---|---|---|---|---|---|
| 387 | sec-butyl(methyl) | cyclopentyl | H | H | |
| 388 | sec-butyl(methyl) | cyclohexyl | H | H | |
| 389a | 1-methylcyclopropyl | | CH3 | H | CH3 | 4-fluorobenzyl |
| 389b | diastereomer | | | | |
| 390 | sec-butyl(methyl) | cyclohexyl | H | H | |
| 391 | 1-methylcyclopropyl | | CH3 | H | CH3 | 3,4,5-trifluorobenzyl |
| 392 | sec-butyl(methyl) | cyclopentyl | H | H | |
| 393 | sec-butyl(methyl) | cyclohexyl | H | H | |
| 394 | 1-methylcyclopropyl | | CH3 | H | CH3 | 4-fluorobenzyl |
| 395 | sec-butyl(methyl) | piperidinyl (NH) | H | H | |
| 398 | 1-methylcyclopropyl | | CH3 | H | CH3 | 4-fluorobenzyl |
| 399a | sec-butyl(methyl) | cyclohexyl | H | H | |
| 399b | diastereomer | | | | |

TABLE 3B-continued

| | | | | | |
|---|---|---|---|---|---|
| 400 | cyclopropyl | CH3 | H | CH3 | 4-F-benzyl |
| 401 | cyclopropyl | CH3 | H | CH3 | 4-F-benzyl |
| 402a | sec-butyl (branched) | cyclohexyl | H | H | |
| 402b | diastereomer | | | | |

| Compound | R₆ | Tether | Ki (nM) |
|---|---|---|---|
| 298 | H | phenyl with ortho-O-CH(CH₃)-CH₂-X and propyl-(Z2) chain | B |
| 299 | H | phenyl with ortho-O-CH₂CH₂-X and propyl-(Z2) chain | A |
| 301 | 3-Cl-benzyl | phenyl with ortho-O-CH₂CH₂-X and propenyl-(Z2) chain | B |
| 303 | benzyl | phenyl with ortho-O-CH₂CH₂-X and propenyl-(Z2) chain | B |
| 305 | H | phenyl with ortho-O-CH₂CH₂-X and propyl-(Z2) chain | C |
| 306a | H | pyridine with O-CH₂CH₂-X and propyl-(Z2) chain | B |
| 306b | diastereomer | | B |
| 307 | H | X-CH₂CH₂-O-CH=CH-CH₂CH₂-(Z2) | C |
| 308 | H | phenyl with ortho-O-CH₂CH₂-X and propenyl-(Z2) chain | A |
| 309 | H | phenyl with ortho-O-CH₂CH₂-X and propyl-(Z2) chain | A |

| | | | |
|---|---|---|---|
| 310 | H | 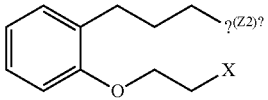 | B |
| 311 | H | 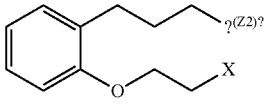 | B |
| 312 | H | 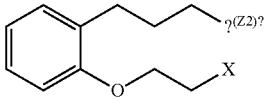 | A |
| 313 | H | 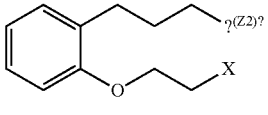 | B |
| 314 | H | 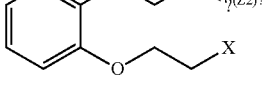 | A |
| 315 | H | 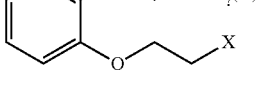 | A |
| 316 | H | 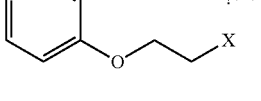 | B |
| 317 | H | 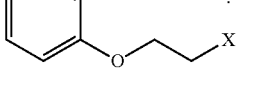 | B |
| 318 | H | 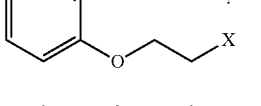 | A |
| 319 | H | 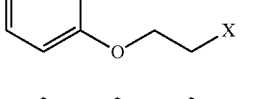 | A |
| 320 | H | 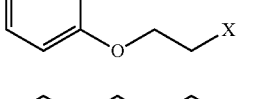 | A |
| 321 | H | 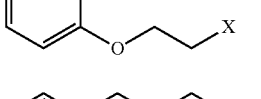 | B |
| 322 | H | 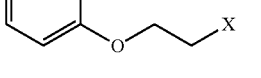 | A |

TABLE 3B-continued

| | | | |
|---|---|---|---|
| 323 | H | (aryl structure) | C |
| 324 | H | (aryl structure) | B |
| 325 | 3-F benzyl | (aryl structure) | B |
| 326 | 3-Br benzyl | (aryl structure) | B |
| 372a | 3,5-diF benzyl | (aryl structure) | B |
| 327b | | diastereomer | C |
| 328 | 3-OMe benzyl | (aryl structure) | B |
| 329 | 3-CN benzyl | (aryl structure) | B |
| 330 | 3,4-diCl benzyl | (aryl structure) | A |
| 331a | 3,4-diF benzyl | (aryl structure) | B |
| 331b | | diastereomer | C |
| 332a | 3-CF₃ benzyl | (aryl structure) | B |
| 332b | | diastereomer | C |

TABLE 3B-continued

| # | R | Group | Class |
|---|---|---|---|
| 333 | (3-thienylmethyl, branched) | 2-(2-X-ethoxy)phenyl-CH=CH-CH2-(Z2) | C |
| 335 | H | 2-(2-X-ethoxy)phenyl-(CH2)3-(Z2) | B |
| 336 | H | 2-(2-X-ethoxy)phenyl-(CH2)3-(Z2) | C |
| 337 | H | 2-(2-X-ethoxy)phenyl-(CH2)3-(Z2) | C |
| 338 | H | 2-(2-X-ethoxy)phenyl-(CH2)3-(Z2) | C |
| 339 | H | 2-(2-X-ethoxy)phenyl-(CH2)3-(Z2) | C |
| 340 | H | 2-(2-X-ethoxy)phenyl-(CH2)3-(Z2) | B |
| 341 | (3-chlorobenzyl, branched) | 2-(2-X-ethoxy)phenyl-CH=CH-CH2-(Z2) | B |
| 342 | (3-chlorobenzyl, branched) | 2-(2-X-ethoxy)phenyl-CH=CH-CH2-(Z2) | C |
| 343 | (3-chlorobenzyl, branched) | 2-(2-X-ethoxy)phenyl-CH=CH-CH2-(Z2) | C |
| 344 | (3-chlorobenzyl, branched) | 2-(2-X-ethoxy)phenyl-CH=CH-CH2-(Z2) | C |
| 345a | (3-chlorobenzyl, branched) | 2-(2-X-ethoxy)phenyl-CH=CH-CH2-(Z2) | C |
| 345b | diastereomer | | B |

TABLE 3B-continued

| # | R1 | R2 | Activity |
|---|----|----|----------|
| 346 | 3-Cl-benzyl | 2-(allyl-(Z2))-phenyl-O-CH2CH2-X | B |
| 347 | benzyloxy-methyl | 2-(allyl-(Z2))-phenyl-O-CH2CH2-X | C |
| 348a | benzyloxy-methyl | 2-(allyl-(Z2))-phenyl-O-CH2CH2-X | C |
| 348b | | diastereomer | C |
| 353a | H | 2-(allyl-(Z2))-6-(propyl-R)-phenyl | B |
| 353b | | diastereomer | B |
| 354 | H | 2-(propargyl-(Z2))-phenyl-O-CH2CH2-X | B |
| 355 | H | 4-F-2-(propyl-(Z2))-phenyl-O-CH2CH2-X | B |
| 356 | H | 4-CF3-2-(propyl-(Z2))-phenyl-O-CH2CH2-X | C |
| 357 | H | 4-(MeSO2NH)-2-(propyl-(Z2))-phenyl-O-CH2CH2-X | C |
| 358a | 3-Cl-benzyl | 2-(allyl-(Z2))-6-(propyl-R)-phenyl | B |
| 358b | | diastereomer | C |
| 359 | 3-Cl-benzyl | 2-(gem-dimethyl-propyl-(Z2))-phenyl-O-CH2CH2-X | C |
| 360 | 3-Cl-benzyl | X-CH2CH2-O-CH2-CH=CH-CH2-(Z2) | C |

TABLE 3B-continued

| # | R1 | R2 | Class |
|---|---|---|---|
| 361 | 3-Cl-benzyl | 2-(but-2-enyl)-phenyl with propyl-R chain, ?(Z2)? | C |
| 362 | 3-Cl-benzyl | 2-pentyl-phenyl-CH2-X, ?(Z2)? | C |
| 363 | 3-Cl-benzyl | X-(CH2)8-?(Z2)? | C |
| 364 | 3-Cl-benzyl | X-(CH2)n-CH=CH-(CH2)n-?(Z2)? | C |
| 365 | 3-Cl-benzyl | R-(CH2)n-?(Z2)? | C |
| 366 | 3-Cl-benzyl | X-(CH2)7-?(Z2)? | C |
| 367 | H | 2-propyl-phenyl-O-CH(CH3)-CH2-X, ?(X2)? | B |
| 368a | 3-Cl-benzyl | 2-propyl-phenyl-O-CH(CH3)-CH2-X, ?(X2)? | B |
| 368b | | diastereomer | B |
| 369 | 3-Cl-benzyl | 2-propyl-phenyl-O-CH2-CH2-X, ?(X2)? | B |
| 370 | 3-Cl-benzyl | X-CH2CH2-O-(CH2)4-?(Z2)? | C |
| 371 | 3-Cl-benzyl | 2-butyl-phenyl-propyl-R, ?(Z2)? | B |
| 372 | H | 4-F-2-(propyl)-phenyl-O-CH2CH2-X, ?(X2)? | A |

TABLE 3B-continued
| | | | |
|---|---|---|---|
| 373 | H | 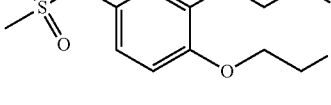 | B |
| 374 | H | 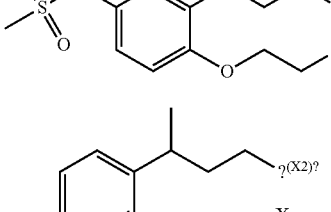 | B |
| 375 | H | 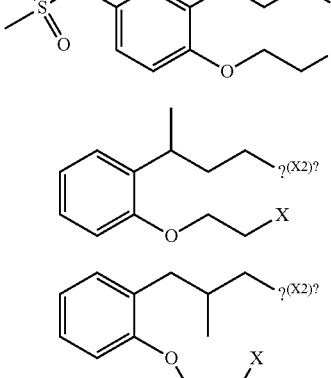 | C |
| 376 | H | 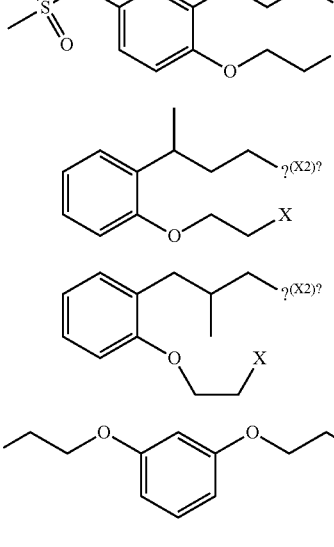 | C |
| 377 | H | 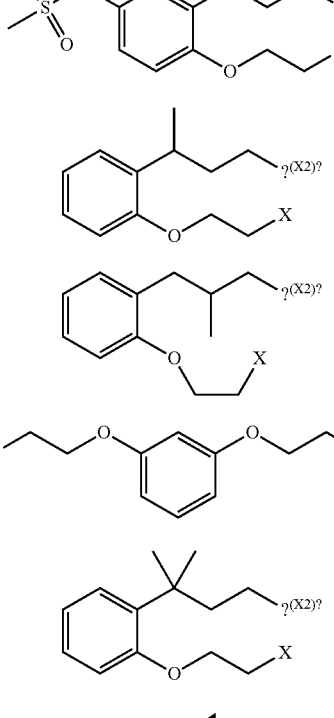 | C |
| 378 | H | 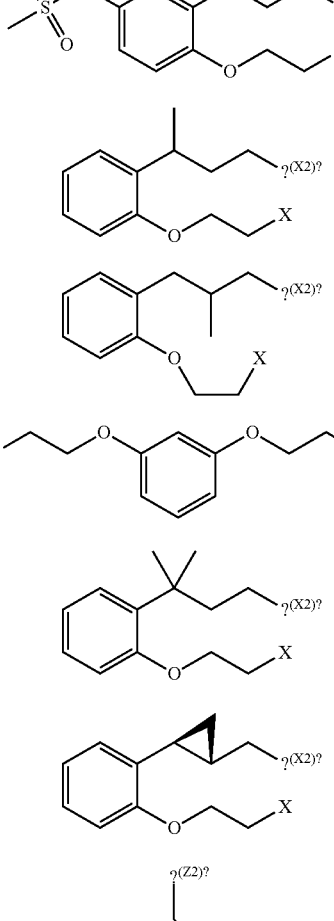 | C |
| 379 | H |  | B |
| 380 |  | 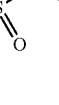 | C |
| 381 | 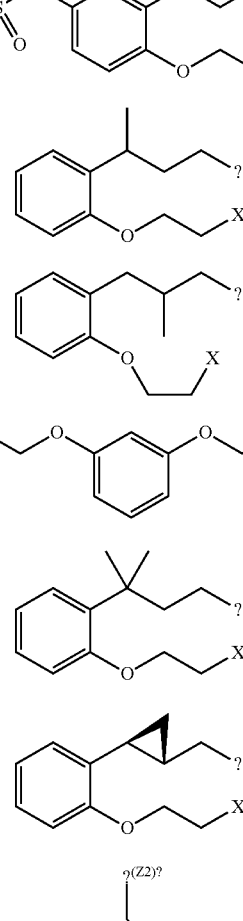 |  | B |
| 382 |  | 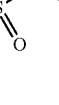 | B |
| 383 | 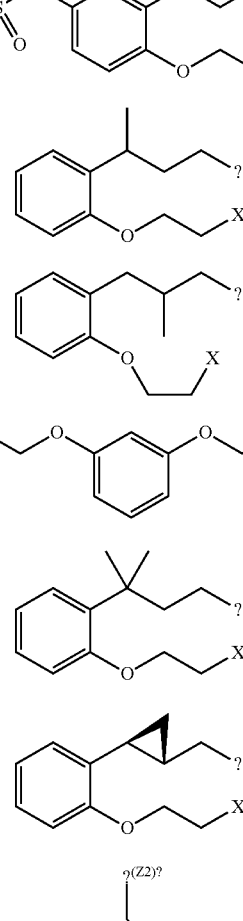 |  | C |

| | | | |
|---|---|---|---|
| 384 | 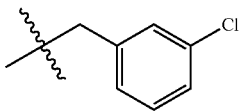 [SMILES: *Cc1cccc(Cl)c1] | 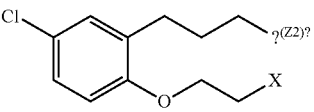 | C |
| 385 | 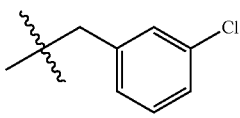 [SMILES: *Cc1cccc(Cl)c1] | 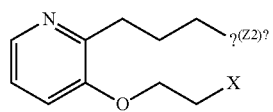 | C |
| 386 | 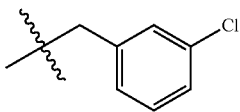 [SMILES: *Cc1cccc(Cl)c1] | 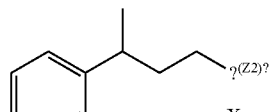 | C |
| 387 | 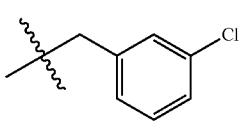 [SMILES: *Cc1cccc(Cl)c1] | 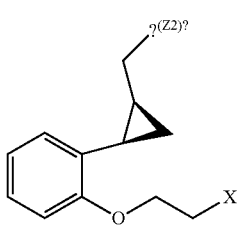 | C |
| 388 | 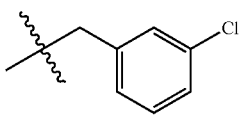 [SMILES: *Cc1cccc(Cl)c1] | 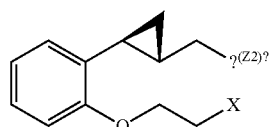 | A |
| 389a | H | 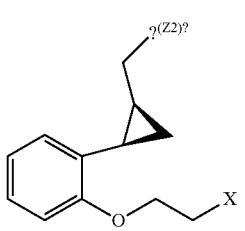 | B |
| 389b | | diastereomer | B |
| 390 | 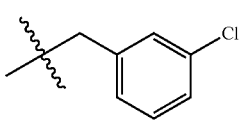 [SMILES: *Cc1cccc(Cl)c1] | 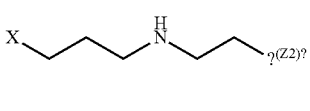 | C |
| 391 | H | 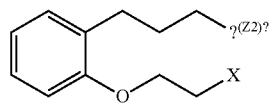 | A |
| 392 | 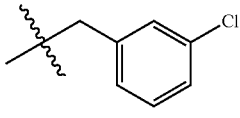 | 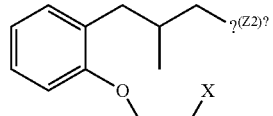 | B |
| 393 | 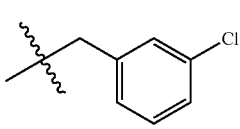 [SMILES: *Cc1cccc(Cl)c1] | 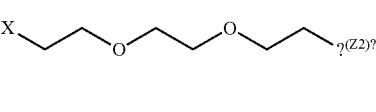 | C |

TABLE 3B-continued
| # | | | |
|---|---|---|---|
| 394 | H | 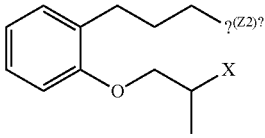 | A |
| 395 | 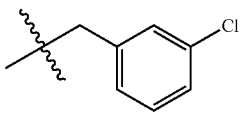 [SMILES: *Cc1cccc(Cl)c1] | 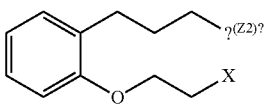 | B |
| 398 | H | 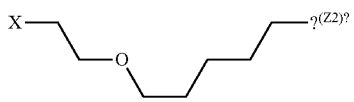 | C |
| 399a | 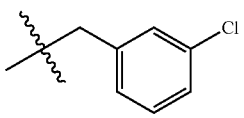 [SMILES: *Cc1cccc(Cl)c1] | 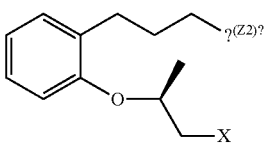 | C |
| 399b | | diastereomer | A |
| 400 | H | 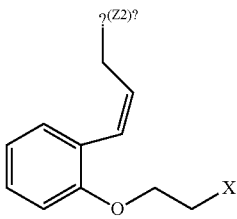 | B |
| 401 | H | 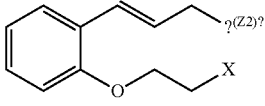 | A |
| 402a | 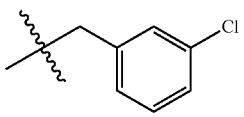 [SMILES: *Cc1cccc(Cl)c1] | 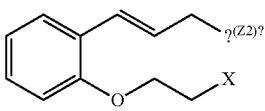 | B |
| 402b | | diastereomer | B |
Binding activity determined using standard method, expressed as follows:
A = 0.1-10 nM;
B = 10-100 nM;
C = 0.1-1.0 μM

TABLE 3C

Binding Activity at the Human Ghrelin Receptor for Representative Compounds of the Invention

| Compound | Structure | Ki (nM) |
|---|---|---|
| 18 | 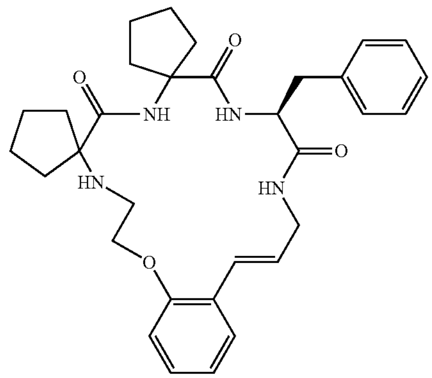 [SMILES: O=C1NC/C=C/c2ccccc2OCCNC2(CCCC2)C(=O)NC2(CCCC2)C(=O)N[C@H]1Cc1ccccc1] | B |
| 334 | 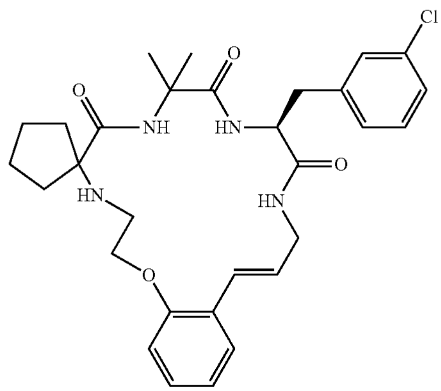 [SMILES: CC1(C)NC(=O)C2(CCCC2)NCCOc2ccccc2/C=C/CNC(=O)[C@H](Cc2cccc(Cl)c2)NC1=O] | B |
| 349 | 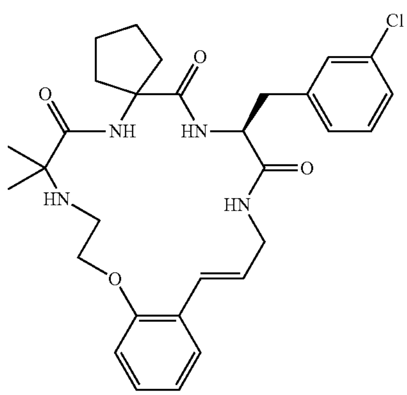 [SMILES: CC1(C)NCCOc2ccccc2/C=C/CNC(=O)[C@H](Cc2cccc(Cl)c2)NC(=O)C2(CCCC2)NC1=O] | B |
| 350 | 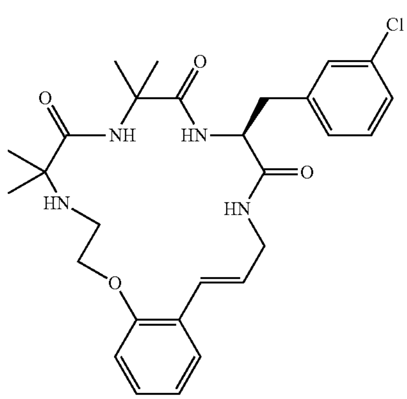 [SMILES: CC1(C)NCCOc2ccccc2/C=C/CNC(=O)[C@H](Cc2cccc(Cl)c2)NC(=O)C(C)(C)NC1=O] | C |

TABLE 3C-continued

Binding Activity at the Human Ghrelin Receptor for Representative Compounds of the Invention

| Compound | Structure | Ki (nM) |
|---|---|---|
| 351 | 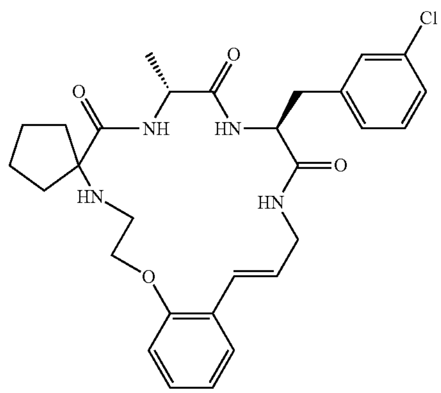 [SMILES: C[C@H]1NC(=O)C2(CCCC2)NCCOc2ccccc2/C=C/CNC(=O)[C@H](Cc2cccc(Cl)c2)NC1=O] | B |
| 352 | 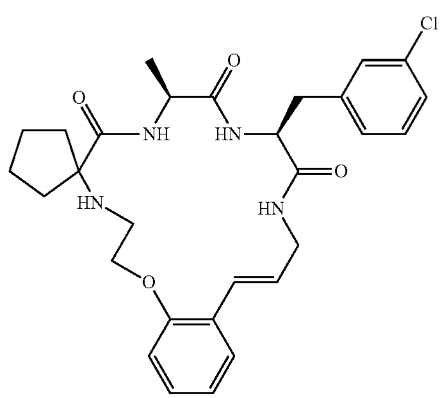 [SMILES: C[C@@H]1NC(=O)C2(CCCC2)NCCOc2ccccc2/C=C/CNC(=O)[C@H](Cc2cccc(Cl)c2)NC1=O] | C |
| 396 | 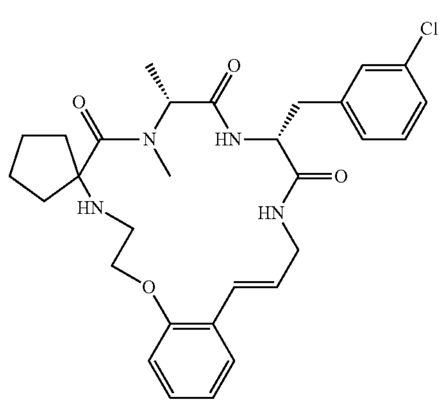 [SMILES: C[C@@H]1C(=O)N[C@H](Cc2cccc(Cl)c2)C(=O)NC/C=C/c2ccccc2OCCNC2(CCCC2)C(=O)N1C] | B |

TABLE 3C-continued

Binding Activity at the Human Ghrelin Receptor for Representative Compounds of the Invention

| Compound | Structure | Ki (nM) |
|---|---|---|
| 397 | 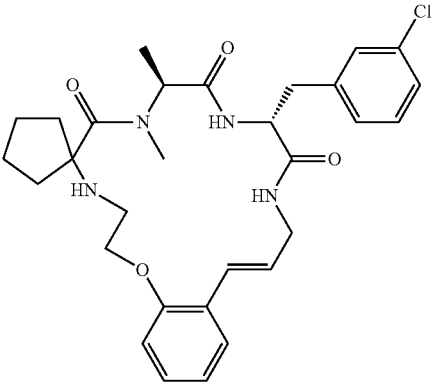 [SMILES: C[C@H]1C(=O)N[C@H](Cc2cccc(Cl)c2)C(=O)NC/C=C/c2ccccc2OCCNC2(CCCC2)C(=O)N1C] | C |

TABLE 3D

Binding Activity at the Human Ghrelin Receptor for Representative Compounds of the Invention

| Compound | R₁ | R₂ | R₃ | R₄ | R₇ | R₅ |
|---|---|---|---|---|---|---|
| 435 | H | cyclopropyl-CH₂- | CH3 | H | CH3 | benzyl |
| 436 | H | cyclopropyl-CH₂- | CH3 | H | CH3 | benzyl |
| 437 | | cyclopentyl | cyclopentyl | | H | H |
| 438 | H | isobutyl | cyclopentyl | | H | H |
| 439 | H | sec-butyl | tetrahydrofuranyl-CH₂- | | H | H |
| 440 | H | sec-butyl | -CH₂-O-CH₂-phenyl | H | CH3 | 4-F-benzyl |
| 441 | H | sec-butyl | cyclohexyl(disubstituted) | | H | H |

TABLE 3D-continued
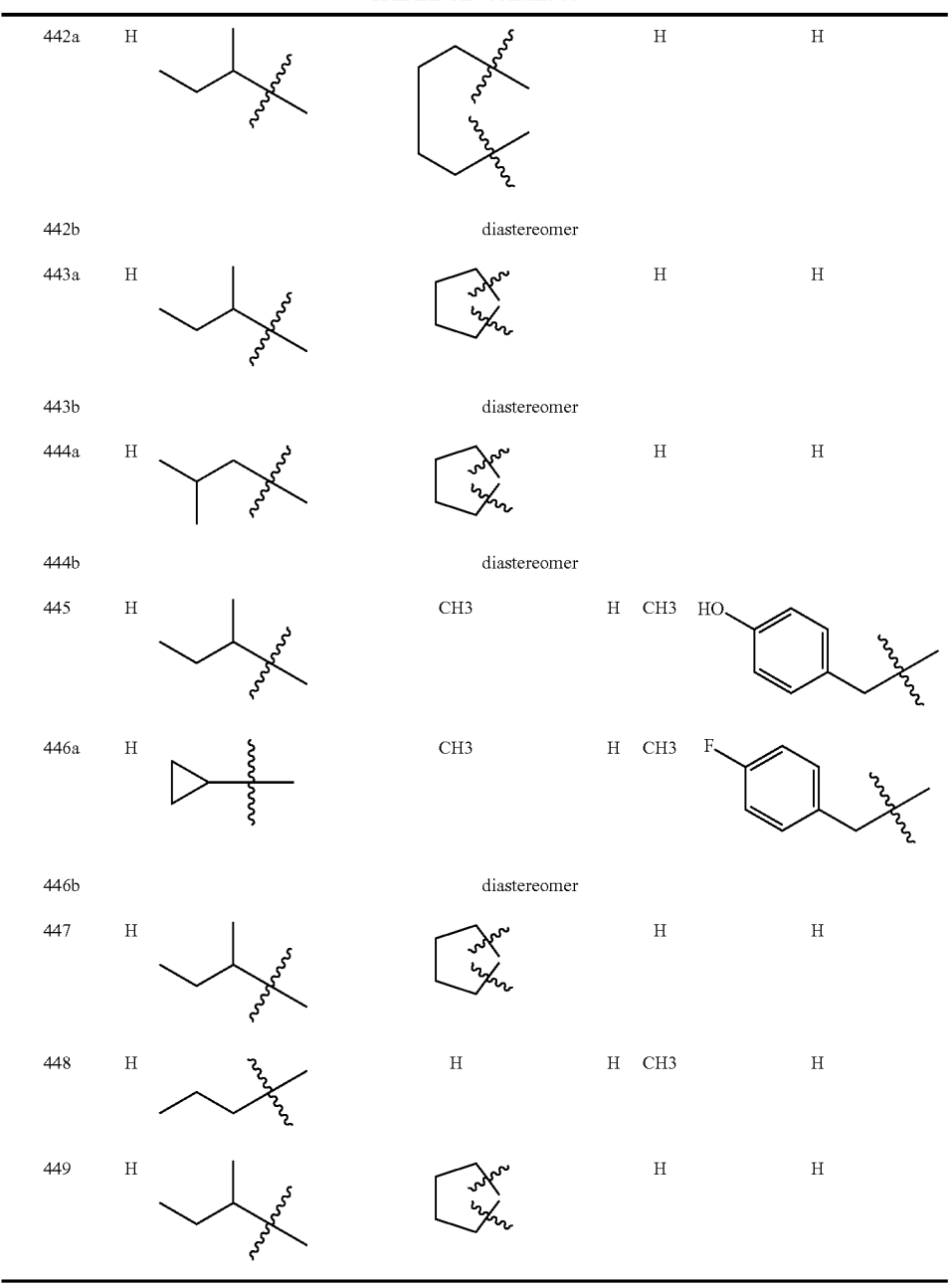
| Compound | R$_6$ | Tether | Ki (nM) |
|---|---|---|---|
| 435 | H | | B |
| 436 | H | | B |

TABLE 3D-continued

| # | R1 | R2 | Class |
|---|---|---|---|
| 437 | 3-Cl-benzyl | 2-(allyl)phenoxyethyl-X | A |
| 438 | 3-Cl-benzyl | 2-(propyl)phenoxy-(S)-propyl-X | D |
| 439 | 3-Cl-benzyl | 2-(allyl)phenoxyethyl-X | D |
| 440 | — | 2-(propyl)phenoxyethyl-X | C |
| 441 | 4-HOOC-benzyl | 2-(allyl)phenoxyethyl-X | D |
| 442a | –C(CH₃)₂CH₂OH | 2-(allyl)phenoxyethyl-X | E |
| 442b | diastereomer | | E |
| 443a | –C(CH₃)₂CH₂OCH₃ | 2-(allyl)phenoxyethyl-X | E |
| 443b | diastereomer | | E |
| 444a | (1H-imidazol-4-yl)-C(CH₃)₂– | 2-(allyl)phenoxyethyl-X | E |
| 444b | diastereomer | | E |

TABLE 3D-continued

| | | | |
|---|---|---|---|
| 445 | H | [structure: phenyl with propyl-(Z2) and O-ethyl-X] | B |
| 446a | H | [structure: X-ethyl-O-ethyl-O-ethyl-(Z2)] | D |
| 446b | | diastereomer | D |
| 447 | [structure: 3-chlorobenzyl] | [structure: R-pentyl-(Z2)] | D |
| 448 | [structure: 1-phenylethyl] | [structure: phenyl with propyl-(Z2) and O-ethyl-X] | D |
| 449 | [structure: 3-chlorobenzyl] | [structure: pyridine with propyl-(Z2) and O-ethyl-X] | D |

For all compounds, designations are based upon formula I, X = $Z_1$ = $Z_2$ = NH, m = n = p = 0
Binding activity determined using standard method, expressed as follows:
A = 0.1-10 nM;
B = 10-100 nM;
C = 0.1-1.0 μM;
D = 1.0-10 μM;
E > 10 μM

TABLE 3E

Binding Activity at the Human Ghrelin Receptor for Representative Compounds of the Invention

| Compound | $K_i$ |
|---|---|
| [structure 220] | D |
| [structure 221] | C |

TABLE 3E-continued
Binding Activity at the Human Ghrelin Receptor
for Representative Compounds of the Invention
| Compound | $K_i$ |
|---|---|
| 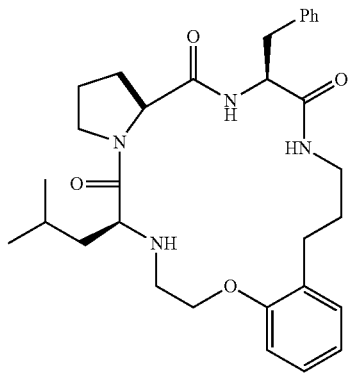 [SMILES: CC(C)C[C@@H]1NCCOc2ccccc2CCCNC(=O)[C@H](Cc2ccccc2)NC(=O)[C@@H]2CCCN2C1=O]<br>222 | D |
| 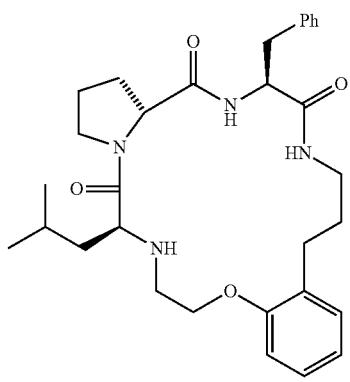 [SMILES: CC(C)C[C@@H]1NCCOc2ccccc2CCCNC(=O)[C@H](Cc2ccccc2)NC(=O)[C@H]2CCCN2C1=O]<br>223 | D |
| 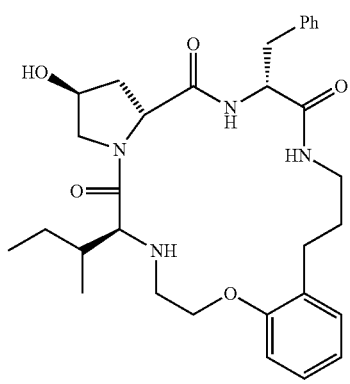 [SMILES: CCC(C)[C@@H]1NCCOc2ccccc2CCCNC(=O)[C@@H](Cc2ccccc2)NC(=O)[C@H]2C[C@H](O)CN2C1=O]<br>224 | G |
| 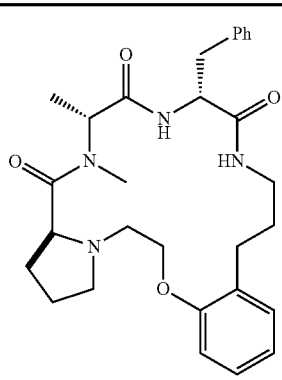<br>225 | C |
| 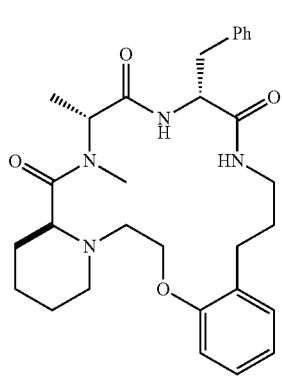 [SMILES: C[C@@H]1C(=O)N[C@H](Cc2ccccc2)C(=O)NCCCc2ccccc2OCCN2CCCC[C@H]2C(=O)N1C]<br>226 | B |
| 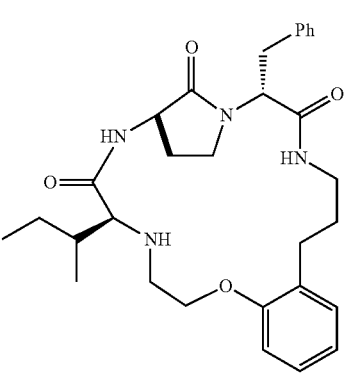 [SMILES: CCC(C)[C@@H]1NCCOc2ccccc2CCCNC(=O)[C@@H](Cc2ccccc2)N2CC[C@@H](NC1=O)C2=O]<br>227 | C |

TABLE 3E-continued

Binding Activity at the Human Ghrelin Receptor
for Representative Compounds of the Invention

| Compound | $K_i$ |
|---|---|
| 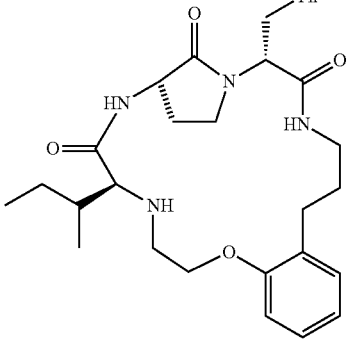<br>228 | G |
| 229 | B |
| 230<br>230 diasteromer | C<br>D |

Binding activity determined using standard method, expressed as follows:
A = 0.1-10 nM;
B = 10-100 nM;
C = 0.1-1.0 µM;
D = 1-10 µM;
E > 500 nM (highest concentration tested);
F > 1 µM (highsest concentration tested);
G > 10 µM (or no activity at highest concentration tested)

B. Aequorin Functional Assay (Ghrelin Receptor)

The functional activity of compounds of the invention found to bind to the GHS-R1a receptor can be determined using the method described below which can also be used as a primary screen for ghrelin receptor activity in a high throughput fashion. (LePoul, E.; et al. Adaptation of aequorin functional assay to high throughput screening. *J. Biomol. Screen.* 2002, 7, 57-65; Bednarek, M. A.; et al. Structure-function studies on the new growth hormone-releasing peptide ghrelin: minimal sequence of ghrelin necessary for activation of growth hormone secretagogue receptor 1a. *J. Med. Chem.* 2000, 43, 4370-4376; Palucki, B. L.; et al. Spiro(indoline-3,4'-piperidine) growth hormone secretagogues as ghrelin mimetics. *Bioorg. Med. Chem. Lett.* 2001, 11, 1955-1957.)

Materials

Membranes were prepared using AequoScreen™ (EURO-SCREEN, Belgium) cell lines expressing the human ghrelin receptor (cell line ES-410-A; receptor accession #60179). This cell line is typically constructed by transfection of the human ghrelin receptor into CHO-K1 cells co-expressing $G_{\alpha 16}$ and the mitochondrially targeted Aequorin (Ref #ES-WT-A5).

1. Ghrelin (reference agonist; Bachem, #H-4864)
2. Assay buffer: DMEM (Dulbecco's Modified Eagles Medium) containing 0.1% BSA (bovine serum albumin; pH 7.0).
3. Coelenterazine (Molecular Probes, Leiden, The Netherlands).

Final test concentrations (N=8) for compounds of the invention:
10, 1, 0.3, 0.1, 0.03, 0.01, 0.003, 0.001 µM.

Compound Handling

Stock solutions of compounds (10 mM in 100% DMSO) were provided frozen on dry ice and stored at −20° C. prior to use. From the stock solution, mother solutions were made at a concentration of 500 µM by 20-fold dilution in 26% DMSO. Assay plates were then prepared by appropriate dilution in DMEM medium containing 0.1% BSA. Under these conditions, the maximal final DMSO concentration in the assay was <0.6%.

Cell Preparation

AequoScreen™ cells were collected from culture plates with $Ca^{2+}$ and $Mg^{2+}$-free phosphate buffered saline (PBS) supplemented with 5 mM EDTA, pelleted for 2 min at 1000× g, re-suspended in DMEM-Ham's F12 containing 0.1% BSA at a density of 5×10⁶ cells/mL, and incubated O/N at rt in the presence of 5 µM coelenterazine. After loading, cells were diluted with assay buffer to a concentration of 5×10⁵ cells/mL.

Assay Protocol

For agonist testing, 50 µL of the cell suspension was mixed with 50 µL of the appropriate concentration of test compound or ghrelin (reference agonist) in 96-well plates (duplicate samples). Ghrelin (reference agonist) was tested at several concentrations concurrently with the test compounds in order to validate the experiment. The emission of light resulting from receptor activation in response to ghrelin or test compounds was recorded using the Hamamatsu FDSS 6000 reader (Hamamatsu Photonics K.K., Japan).

Analysis and Expression of Results

Results were expressed as Relative Light Units (RLU). Concentration response curves were analyzed using GraphPad Prism (GraphPad Software, San Diego, Calif.) by non-linear regression analysis (sigmoidal dose-response) based on the equation $E=E_{max}/(1+EC_{50}/C)n$ where E was the measured RLU value at a given agonist concentration (C), $E_{max}$ was the maximal response, $EC_{50}$ was the concentration producing 50% stimulation and n was the slope index. For agonist testing, results for each concentration of test compound were expressed as percent activation relative to the signal induced by ghrelin at a concentration equal to the $EC_{80}$ (i.e. 3.7 nM). $EC_{50}$, Hill slope and % $E_{max}$ values are reported.

The data show that the representative compounds examined act as agonists at the ghrelin receptor and are devoid of antagonist activity at the concentrations studied. In addition, these compounds were demonstrated to have high selectivity for the ghrelin receptor versus its closest counterpart, the motilin receptor, with which it has 52% sequence homology. (Feighner, S. D.; Tan, C. P.; McKee, K. K.; Palyha, O. C.; Hreniuk, D. L.; Pong, S.-S.; Austin, C. P.; Figueroa, D.; MacNeil, D.; Cascieri, M. A.; Nargund, R.; Bakshi, R.; Abramovitz, M.; Stocco, R.; Kargman, S.; O'Neill, G.; van der Ploeg, L. H. T.; Evans, J.; Patchett, A. A.; Smith, R. G.; Howard, A. D. Receptor for motilin identified in the human gastrointestinal system. *Science* 1999, 284, 2184-2188.) The endogenous peptides themselves have 36% of residues in common and ghrelin was even identified at one point as motilin-related peptide. (Tomasetto, C.; Karam, S. M.; Ribieras, S.; Masson, R.; Lefebvre, O.; Staub, A.; Alexander, G.; Chenard, M. P.; Rio, M. C. Identification and characterization of a novel gastric peptide hormone: the motilin-related peptide. *Gastroenterology* 2000, 119, 395-405.) Ghrelin does not interact appreciably at the motilin receptor, although GHRP-6 does. (Depoortere, I.; Thijs, T.; Thielemans, L.; Robberecht, P.; Peeters, T. L. Interaction of the growth hormone-releasing peptides ghrelin and growth hormone-releasing peptide-6 with the motilin receptor in the rabbit gastric antrum. *J. Pharmacol. Exp. Ther.* 2003, 305, 660-667.) On the other hand, motilin itself as been demonstrated to have some GH-releasing effects. (Samson, W. K.; Lumpkin, M. D.; Nilayer, G.; McCann, S. M. Motilin: a novel growth hormone releasing agent. *Brain Res. Bull.* 1984, 12, 57-62.)

The level of agonist activity and selectivity for representative compounds of the invention are shown below in Table 4. Concentration-response results for exemplary compounds 1-5 are presented in FIG. 5.

TABLE 4

Functional Assay at the Human Ghrelin Receptor and Selectivity Results

| Compound[a] | $K_i$ (nM)* | $EC_{50}$ (nM)** | Selectivity[b] |
|---|---|---|---|
| 1 | B | BB | 142/1 |
| 2 | C | BB | nd |
| 3 | C | BB | nd |
| 4[g] | B[c] | AA | 3012/1 |
| 5 | C | BB | nd |
| 6 | C | AA | 71/1 |
| 7 | C | AA | >100/1 |
| 8[f] | B[d] | AA | 200/1 |
| 9[g] | C[e] | BB | 117/1 |
| 10 | B | AA | 304/1 |
| 11[f] | B | BB | nd |
| 15 | A | nd | >1700/1 |
| 16 | A | nd | >2000/1 |
| 17 | A | AA | 2500/1 |
| 18 | B | AA | 222/1 |
| 19 | C | nd | >1700/1 |
| 20 | A | AA | 1044/1 |
| 21 | A | AA | 1078/1 |
| 23 | A | AA | 30,000/1 |
| 24 | A | nd | 3039/1 |
| 25 | A | AA | 28,000/1 |
| 26 | A | AA | >7700/1 |
| 27[e] | A | AA | >7100/1 |
| 28 | B | AA | nd |
| 30 | A | AA | 13,000/1 |
| 31 | A | AA | 4900/1 |
| 34 | B | nd | >1000/1 |
| 35 | B | AA | nd |
| 36 | B | BB | nd |
| 37a | B | AA | >800/1 |
| 37b | B | BB | nd |
| 38 | B | BB | nd |
| 39[f] | A | BB | 3400/1 |
| 40 | A | AA | >3300/1 |
| 42 | A | nd | 4300/1 |
| 43 | B | nd | 3700/1 |
| 47 | C | AA | nd |
| 97 | B | BB | nd |
| 111 | B | BB | nd |
| 113[g] | B | BB | nd |
| 140 | C | BB | nd |
| 141 | C | AA | nd |
| 153 | B | AA | nd |
| 154 | B | AA | nd |
| 156 | B | AA | nd |
| 168 | C | CC | nd |
| 170 | B | BB | nd |
| 176 | B | AA | 105/1 |
| 177 | B | AA | >100/1 |
| 178 | C | BB | nd |
| 184a | C | BB | 28/1 |
| 184b | C[c] | BB | nd |
| 186 | C | BB | nd |
| 191 | C | BB | nd |
| 192 | B | BB | nd |
| 193 | C | BB | nd |
| 194a | C | BB | nd |
| 194b | C | BB | nd |
| 195 | B | AA | nd |
| 197 | C | CC | 100/1 |
| 214 | C | BB | nd |
| 226 | B | CC | nd |
| 298 | B | AA | 3100/1 |
| 299 | A | AA | nd |
| 306a | B | AA | 714/1 |
| 311 | B | nd | 21/1 |
| 314 | A | AA | >5500/1 |
| 318 | A | AA | nd |
| 322 | A | AA | nd |
| 334 | B | AA | 346/1 |
| 345a | B | AA | >159/1 |
| 346 | B | AA | nd |
| 351 | B | AA | 450/1 |
| 354 | B | AA | nd |
| 358a | B | AA | nd |
| 363 | C | nd | 35/1 |
| 367 | B | AA | nd |
| 368a | A | CC | nd |
| 372 | A | AA | 2500/1 |
| 374 | B | AA | 250/1 |
| 382 | B | BB | 74/1 |
| 388 | A | AA | 400/1 |
| 389a | B | BB | 450/1 |
| 394 | A | BB | 1700/1 |
| 399a | A | CC | 300/1 |
| 445 | B | AA | nd |

[a]All compounds were tested as their TFA salts unless otherwise noted.
[b]Versus the human motilin receptor (nd = not determined)
[c]Average of six (6) experiments
[d]Average of four (4) experiments
[e]Average of two (2) experiments
[f]HCl salt
[g]Formate salt
*Binding activity determined using standard method and expressed as A = 0.1-10 nM; B = 10-100 nM; C = 100-1000 nM
**Functional activity determined using standard method and expressed as AA = 1-100 nM; BB = 100-1000 nM; CC > 1000 nM;
nd = not determined C. Cell Culture Assay for Growth Hormone Release Cell culture assays for determining growth hormone release can be employed as described in Cheng, et al. *Endocrinology* 1989, 124, 2791-2798. In particular, anterior pituitary glands are obtained from male Sprague-Dawley rats and placed in cold culture medium. These pituitaries are sectioned, for example into one-eighth sections, then digested with trypsin. Cells are collected after digestion, pooled, and transferred into 24 well plates (minimum 200,000 cells per well). After a monolayer of cells has formed, generally after at least 4 d in culture, the cells are washed with medium prior to exposure to the test samples and controls. Varying concentrations of the test compounds and of ghrelin as a positive control were added to the medium. The cells are left for 15 min at 37° C., then the medium removed and the cells stored frozen. The amount of GH release was measured utilizing a standard radioimmunoassay as known to those in the art.

D. Pharmacokinetic Analysis of Representative Compounds of the Invention

The pharmacokinetic behavior of compound of the invention can be ascertained by methods well known to those skilled in the art. (Wilkinson, G. R. "Pharmacokinetics: The Dynamics of Drug Absorption, Distribution, and Elimination" in *Goodman & Gilman's The Pharmacological Basis of Therapeutics*, Tenth Edition, Hardman, J. G.; Limbird, L. E., Eds., McGraw Hill, Columbus, Ohio, 2001, Chapter 1.) The following method was used to investigate the pharmacokinetic parameters (elimination half-life, total plasma clearance, etc.) for intravenous, subcutaneous and oral administration of compounds of the present invention.

Collection of Plasma

Rats: male, Sprague-Dawley (~250 g)

Rats/Treatment Group: 6 (2 subsets of 3 rats each, alternate bleeds)

Each sample of test compound was sent in solution in a formulation (such as with cyclodextrin) appropriate for dosing. It will be appreciated by one skilled in the art that appropriate modifications to this protocol can be made as required to adequately test the properties of the compound under analysis.

Typical Dose
1. Intravenous (i.v.): 2 mg/kg
2. Subcutaneous(s.c): 2 mg/kg
3. Oral (p.o.): 8 mg/kg

TABLE 5

Representative Intravenous Blood Sampling Schedule.

| Subset ID | Pre-dose | Time (min.) relative to Dose Administration |||||||||
|---|---|---|---|---|---|---|---|---|---|---|
| | | 1 | 5 | 20 | 60 | 90 | 120 | 180 | 240 | 300 |
| Subset A | ✓ | ✓ | | ✓ | | ✓ | | ✓ | | ✓ | |
| Subset B | | | ✓ | | ✓ | | ✓ | | ✓ | | ✓ |

TABLE 6

Representative Subcutaneous & Oral Blood Sampling Schedule.

| Subset ID | Pre-dose | Time (min.) relative to Dose Administration |||||||||
|---|---|---|---|---|---|---|---|---|---|---|
| | | 5 | 15 | 30 | 60 | 90 | 120 | 180 | 270 | 360 |
| Subset A | ✓ | ✓ | | ✓ | | ✓ | | ✓ | | ✓ | |
| Subset B | | | ✓ | | ✓ | | ✓ | | ✓ | | ✓ |

Plasma Collection
1. Same protocol for all dosing groups
2. For each group, 2 subsets (A and B) of 3 rats/subset At the time intervals indicated above, 0.7 mL of blood were collected from each animal. It is expected that this volume of blood will yield a sample of at least 0.3 mL of plasma. EDTA was used as an anti-coagulant for whole blood collection. Whole blood samples were chilled and immediately processed by centrifugation to obtain plasma.

Plasma samples were stored frozen (−70° C.) until analysis. Analytical detection of parent compound in plasma samples performed by LC-MS after an appropriate preparation protocol: extraction using solid phase extraction (SPE) cartridges (Oasis MCX, Oasis HLB) or liquid-liquid extraction.

HPLC-MS Method
Column: Atlantis dC18 from Waters 2.1×30 mm
Mobile Phases:
A: 95% MeOH, 5% water, 0.1% TFA
B: 95% water, 5% MeOH, 0.1% TFA
Flow: 0.5 mL/min
Gradient (linear):

| Time(min) | A | B |
|---|---|---|
| 0 | 30% | 70% |
| 0.5 | 30% | 70% |
| 2.8 | 100% | 0% |
| 3.8 | 100% | 0% |
| 4.0 | 30% | 70% |
| 5.0 | 30% | 70% |

The analyte was quantitated based upon a standard curve and the method validated with internal standards.

TABLE 7

Pharmacokinetic Parameters for Representative Compounds of the Invention

| Compound | Mode of Administration[a] | Elimination ($t_{1/2}$, min) | Clearance (mL/min/kg) | Bioavailability (oral)[b] |
|---|---|---|---|---|
| 25 | i.v. | 31 | 67 | na |
| 298 | i.v. | 75 | 17 | na |
| 298 | s.c. | 66 | 15 | na |
| 298 | p.o. | 312 | 14 | 29% |

[a] i.v. = intravenous (10 time points over 150 min); s.c. = subcutaneous (10 time points over 360 min), p.o. = oral (10 time points over 240 min)
[b] na = not applicable Results of the time courses for these studies are provided in FIGS. 6A-6D.

E. Gastric Emptying

To examine the effects of compounds of the invention in a model for gastroparesis, compounds were evaluated for possible effects on gastric emptying in fasted rats. For example, compounds 25 and 298 at 100 µg/kg caused a significant increase (≧30%) in gastric emptying relative to the vehicle control group. The relative efficacy (39% increase) of compounds 25 and 298 at 100 µg/kg i.v. was similar to concurrently run positive reference agents GHRP-6 at 20 µg/kg i.v. (40% increase) and metoclopramide at 10 mg/kg i.v. (41% increase). Accordingly, compounds 25 and 298 at a dose of 100 µg/kg demonstrated gastrokinetic activity in rats, with efficiency similar to GHRP-6 at 20 µg/kg and metoclopramide at 10 mg/kg. Further, compound 25 also demonstrated gastric emptying at 30 µg/kg. This is significantly more potent than other compounds interacting at this receptor previously found to enhance GI motility, which were unable to promote gastric emptying at 100 µg/kg (U.S. Pat. No. 6,548,501).

Test Substances and Dosing Pattern

GHRP-6 and test samples were dissolved in vehicle of 9% HPBCD/0.9% NaCl. Immediately following oral administration of methylcellulose (2%) containing phenol red (0.05%)

(2 mL/rat), test substances or vehicle (9% HPBCD/0.9% NaCl) were each administered intravenously (i.v.) at a dosing volume of 5 mL/kg.

Animals

Male Wistar rats were provided by LASCO (A Charles River Licensee Corporation, Taiwan). Space allocation for 6 animals was 45×23×15 cm. Animals were housed in APEC® cages and maintained in a controlled temperature (22° C.-24° C.) and humidity (60%-80%) environment with 12 h light, 12 h dark cycles for at least one week in the laboratory prior to being used. Free access to standard lab chow for rats (Lab Diet, Rodent Diet, PMI Nutrition International, USA) and tap water was granted. All aspects of this work including housing, experimentation and disposal of animals were performed in general accordance with the Guide for the Care and Use of Laboratory Animals (National Academy Press, Washington, D.C., 1996).

Chemicals

Glucose (Sigma, USA), Metoclopramide-HCl (Sigma, USA), Methylcellulose (Sigma, USA), NaOH (Sodium Hydroxide, Wako, Japan), Pyrogen free saline (Altar, Taiwan), Phenol Red-Sodium salt (Sigma, USA) and Trichloroacetic acid (Merck, USA).

Equipment 8-well strip (Costar, USA), 96-well plate (Costar, USA), Animal case (ShinTeh, R. O. C.), Centrifugal separator (Kokusan, H-107, Japan), Glass syringe (1 mL, 2 mL, Mitsuba, Japan), Hypodermic needle (25 G×1", TOP Corporation, Japan), Microtube (Treff, Switzerland), pH-meter (Hanna, USA), Pipetman (P100, Gilson, France), Pipette tips (Costar, USA), Rat oral needle (Natsume, Japan), Spectra Fluor plus (Austria), Stainless scissors (Klappencker, Germany) and Stainless forceps (Klappencker, Germany).

Assay

Test substances were each administered intravenously to a group of 5 O/N-fasted Wistar derived male rats weighing 200±20 g immediately after methylcellulose (2%) containing phenol red (0.05%) was administered orally at 2 mL/animal. The animals were then sacrificed 15 minutes later. The stomach was immediately removed, homogenized in 0.1 N NaOH (5 mL) and centrifuged. Following protein precipitation by 20% trichloroacetic acid (0.5 mL) and re-alkalization of the supernatant with 0.1 N NaOH, total phenol red remaining in the stomach was determined by a colorimetric method at 560 nm. A 30 percent or more ($\geq$30%) increase in gastric emptying, detected as the decrease in phenol red concentration in the stomach relative to the vehicle control group, is considered significant.

Results for two representative compounds of the invention are shown in FIG. 7 and in the Examples below.

F. Gastric Emptying and Intestinal Transit in Rat Model of Postoperative Ileus

This clinically relevant model for POI is adapted from that of Kalff. (Kalff, J. C.; Schraut, W. H.; Simmons, R. L.; Bauer, A. J. Surgical manipulation of the gut elicits an intestinal muscularis inflammatory response resulting in postsurgical ileus. *Ann. Surg.* 1998, 228, 652-663.) Other known models can also be used to study the effect of compounds of the invention. (Trudel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. *Peptides* 2003, 24, 531-534; (b) Trudel, L.; Tomasetto, C.; Rio, M. C.; Bouin, M.; Plourde, V.; Eberling, P.; Poitras, P. Ghrelin/motilin-related peptide is a potent prokinetic to reverse gastric postoperative ileus in rats. *Am. J. Physiol.* 2002, 282, G948-G952.)

Animals
1. Rat, Sprague-Dawley, male, ~300 g.
2. Fasted O/N prior to study.

Induction of Post-Operative Ileus (POI)
1. Isofluorane anaesthesia under sterile conditions.
2. Midline abdominal incision.
3. Intestines and caecum were eviscerated and kept moist with saline.
4. The intestines and caecum were manipulated along its entire length with moist cotton applicators analogous to the 'running of the bowel' in the clinical setting. This procedure was timed to last for 10 min.
5. Intestines were gently replaced into the abdomen and the abdominal wound was stitched closed under sterile conditions.

Dosing
1. Rat was allowed to recover from isofluorane anaesthesia.
2. Test compounds (or vehicle) were administered intravenously via previously implanted jugular catheter.
3. Immediate intragastric gavage of methylcellulose (2%) labeled with radioactive $^{99m}$Tc, t=0.

Experimental
1. At t=15 min, animal was euthanized with $CO_2$.
2. Stomach and 10 cm sections along the small intestine were immediately ligated, cut and placed in tubes for measuring of $^{99m}$Tc in gamma counter.
3. Stomach emptying and small intestinal transit were measured by calculation of the geometric mean.

$$\text{Geometric mean} = \Sigma(\% \text{ total radioactivity} \times \text{number of segment})/100$$

Figure 8:
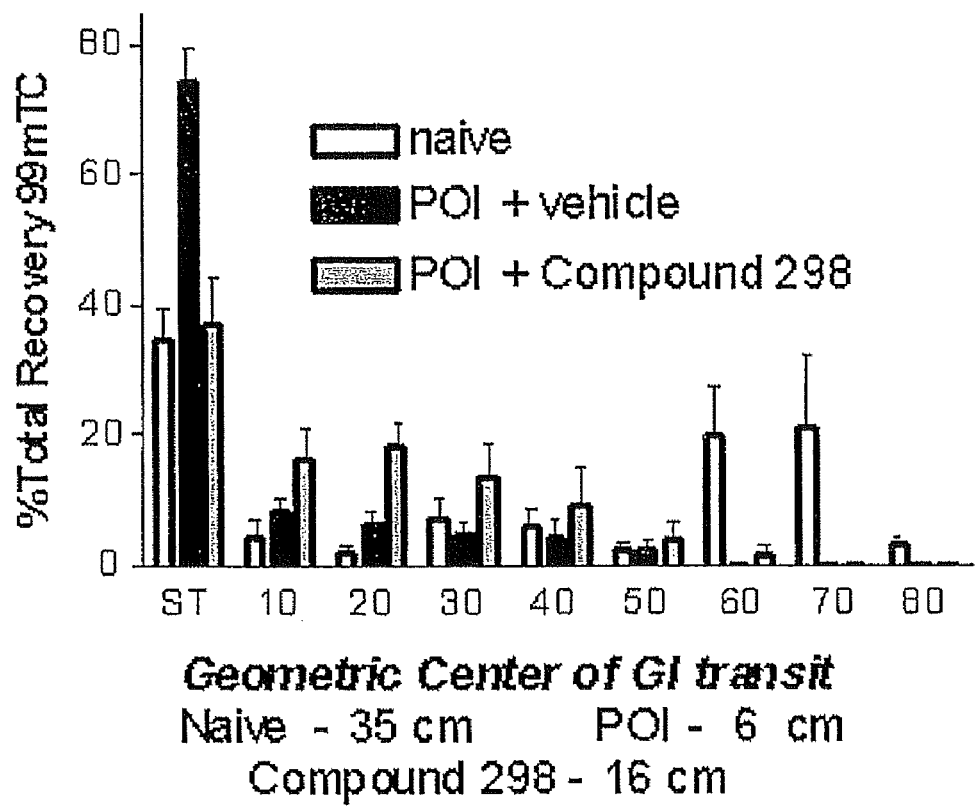
FIG. 8 shows a graph presenting effects on postoperative ileus for an exemplary compound of the present invention.

Results are depicted in the graph in FIG. 8 and indicate that Compound 298 at 100 µg/kg (i.v. n=5) significantly improves postoperative ileus in comparison to POI+vehicle treated rats. Further results are presented in the Examples below.

G. Growth Hormone Response to Test Compounds

The compounds of the invention likewise can be tested in a number of animal models for their effect on GH release. For example, rats (Bowers, C. Y.; Momany, F.; Reynolds, G. A.; Chang, D.; Hong, A.; Chang, K. *Endocrinology* 1980, 106, 663-667), dogs (Hickey, G.; Jacks, T.; Judith, F.; Taylor, J.; Schoen, W. R.; Krupa, D.; Cunningham, P.; Clark, J.; Smith, R. G. *Endocrinology* 1994, 134, 695-701; Jacks, T.; Hickey, G.; Judith, F.; Taylor, J.; Chen, H.; Krupa, D.; Feeney, W.; Schoen, W. R.; Ok, D.; Fisher, M.; Wyvratt, M.; Smith, R. J. *Endocrinology* 1994, 143, 399-406; Hickey, G. J.; Jacks, T. M.; Schleim, K. D.; Frazier, E.; Chen, H. Y.; Krupa, D.; Feeney, W.; Nargund, R. P.; Patchett, A. A.; Smith, R. G. *J. Endocrinol.* 1997, 152, 183-192), and pigs (Chang, C. H.; Rickes, E. L.; Marsilio, F.; McGuire, L.; Cosgrove, S.; Taylor, J.; Chen, H. Y.; Feighner, S.; Clark, J. N.; Devita, R.; Schoen, W. R.; Wyvratt, M.; Fisher, M.; Smith, R. G.; Hickey, G. *Endocrinology* 1995, 136, 1065-1071; Peschke, B.; Hanse, B. S. *Bioorg. Med. Chem. Lett.* 1999, 9, 1295-1298) have all been successfully utilized for the in vivo study of the effects of GHS and would likewise be applicable for investigation of the effect of ghrelin agonists on GH levels. The measurement of ghrelin of GH levels in plasma after appropriate administration of compounds of the invention can be performed using radioimmunoassay via standard methods known to those in the art. (Deghenghi, R.; et al. *Life Sciences* 1994, 54, 1321-1328.) Binding to tissue can be studied using whole body autoradiography after dosing of an animal with test substance containing a radioactive label. (Ahnfelt-Rønne, I.; Nowak, J.; Olsen, U. B. Do growth hormone-releasing peptides act as ghrelin secretagogues? *Endocrine* 2001, 14, 133-135.)

The following method is employed to determine the temporal pattern and magnitude of the growth hormone (GH) response to test compounds, administered either systemically or centrally. Results for compound 298 demonstrating its lack of effect on GH release are presented in FIG. 9. Compound 25 gave similar results. Further results are presented in the Examples below.

Dosing and Sampling Procedures for In Vivo Studies of GH Release

Adult male Sprague Dawley rats (225-300 g) were purchased from Charles River Canada (St. Constant, Canada) and individually housed on a 12-h light, 12-h dark cycle (lights on, time: 0600-1800) in a temperature (22±1° C.)— and humidity-controlled room. Purina rat chow (Ralston Purina Co., St. Louis, Mo.) and tap water were freely available. For these studies, chronic intracerebroventricular (icv) and intracardiac venous cannulas were implanted under sodium pentobarbital (50 mg/kg, ip) anesthesia using known techniques. The placement of the icv cannula was verified by both a positive drinking response to icv carbachol (100 ng/10 µl) injection on the day after surgery and methylene blue dye at the time of sacrifice. After surgery, the rats were placed directly in isolation test chambers with food and water freely available until body weight returned to preoperative levels (usually within 5-7 d). During this time, the rats were handled daily to minimize any stress associated with handling on the day of the experiment. On the test day, food was removed 1.5 h before the start of sampling and was returned at the end. Free moving rats were iv injected with either test sample at various levels (3, 30, 300, 1000 µg/kg) or normal saline at two different time points during a 6-h sampling period. The times 1100 and 1300 were chosen because they reflect typical peak and trough periods of GH secretion, as previously documented. The human ghrelin peptide (5 µg, Phoenix Pharmaceuticals, Inc., Belmont, Calif.) was used as a positive control in the experiments and was diluted in normal saline just before use. To assess the central actions of test compounds on pulsatile GH release, a 10-fold lower dose of the test sample or normal saline was administered icv at the same time points, 1100 and 1300. Blood samples (0.35 mL) were withdrawn every 15 min over the 6-h sampling period (time: 1000-1600) from all animals. To document the rapidity of the GH response to the test compound, an additional blood sample was obtained 5 min after each injection. All blood samples were immediately centrifuged, and plasma was separated and stored at −20° C. for subsequent GH assay. To avoid hemodynamic disturbance, the red blood cells were resuspended in normal saline and returned to the animal after removal of the next blood sample. All animal studies were conducted under procedures approved by an animal care oversight committee.

GH Assay Method

Plasma GH concentrations were measured in duplicate by double antibody RIA using materials supplied by the NIDDK Hormone Distribution Program (Bethesda, Md.). The averaged plasma GH values for 5-6 rats per group are reported in terms of the rat GH reference preparation. The standard curve was linear within the range of interest; the least detectable concentration of plasma GH under the conditions used was approximately 1 ng/mL. All samples with values above the range of interest were reassayed at dilutions ranging from 1:2 to 1:10. The intra- and interassay coefficients of variation were acceptable for duplicate samples of pooled plasma containing a known GH concentration.

4. Pharmaceutical Compositions

The macrocyclic compounds of the present invention or pharmacologically acceptable salts thereof according to the invention may be formulated into pharmaceutical compositions of various dosage forms. To prepare the pharmaceutical compositions of the invention, one or more compounds, including optical isomers, enantiomers, diastereomers, racemates or stereochemical mixtures thereof, or pharmaceutically acceptable salts thereof as the active ingredient is intimately mixed with appropriate carriers and additives according to techniques known to those skilled in the art of pharmaceutical formulations.

A pharmaceutically acceptable salt refers to a salt form of the compounds of the present invention in order to permit their use or formulation as pharmaceuticals and which retains the biological effectiveness of the free acids and bases of the specified compound and that is not biologically or otherwise undesirable. Examples of such salts are described in *Handbook of Pharmaceutical Salts Properties, Selection, and Use*, Wermuth, C. G. and Stahl, P. H. (eds.), Wiley-Verlag Helvetica Acta, Zürich, 2002 [ISBN 3-906390-26-8]. Examples of such salts include alkali metal salts and addition salts of free acids and bases. Examples of pharmaceutically acceptable salts, without limitation, include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates.

If an inventive compound is a base, a desired salt may be prepared by any suitable method known to those skilled in the art, including treatment of the free base with an inorganic acid, such as, without limitation, hydrochloric acid, hydrobromic acid, hydroiodic, carbonic acid, sulfuric acid, nitric acid, phosphoric acid, and the like, or with an organic acid, including, without limitation, formic acid, acetic acid, propionic acid, maleic acid, succinic acid, mandelic acid, fumaric acid, malonic acid, pyruvic acid, oxalic acid, stearic acid, ascorbic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, 2-hydroxyethanesulfonic acid, benzenesulfonic acid, cyclohexyl-aminosulfonic acid or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine, lysine and arginine; ammonia; primary, secondary, and tertiary amines such as ethylenediamine, N,N'-dibenzylethylenediamine, diethanolamine, choline, and procaine, and cyclic amines, such as piperidine, morpholine, and piperazine; as well as inorganic salts derived from sodium, calcium, potassium, magnesium, manganese, iron, copper, zinc, aluminum, and lithium.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

Compositions for injection will include the active ingredient together with suitable carriers including propylene glycol-alcohol-water, isotonic water, sterile water for injection (USP), emulPhor™-alcohol-water, cremophor-EL™ or other suitable carriers known to those skilled in the art. These carriers may be used alone or in combination with other conventional solubilizing agents such as ethanol, propylene glycol, or other agents known to those skilled in the art.

Where the macrocyclic compounds of the present invention are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges and pastilles, wherein the active ingredient is formulated with a carrier such as sugar and acacia, tragacanth or gelatin and glycerin.

Compositions for rectal administration include suppositories containing a conventional suppository base such as cocoa butter.

Compositions suitable for transdermal administration include ointments, gels and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

In some embodiments, the composition is provided in a unit dosage form such as a tablet or capsule.

In further embodiments, the present invention provides kits including one or more containers comprising pharmaceutical dosage units comprising an effective amount of one or more compounds of the present invention.

The present invention further provides prodrugs comprising the compounds described herein. The term "prodrug" is intended to mean a compound that is converted under physiological conditions or by solvolysis or metabolically to a specified compound that is pharmaceutically active. The "prodrug" can be a compound of the present invention that has been chemically derivatized such that, (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that, (i) it retains some, all or none of the bioactivity of its parent drug compound, and (ii) it is metabolized in a subject to yield a biologically active derivative of the compound. Known techniques for derivatizing compounds to provide prodrugs can be employed. Such methods may utilize formation of a hydrolyzable coupling to the compound.

The present invention further provides that the compounds of the present invention may be administered in combination with a therapeutic agent used to prevent and/or treat metabolic and/or endocrine disorders, gastrointestinal disorders, cardiovascular disorders, obesity and obesity-associated disorders, central nervous system disorders, genetic disorders, hyperproliferative disorders and inflammatory disorders. Exemplary agents include analgesics (including opioid analgesics), anesthetics, antifungals, antibiotics, antiinflammatories (including nonsteroidal anti-inflammatory agents), anthelmintics, antiemetics, antihistamines, antihypertensives, antipsychotics, antiarthritics, antitussives, antivirals, cardioactive drugs, cathartics, chemotherapeutic agents (such as DNA-interactive agents, antimetabolites, tubulin-interactive agents, hormonal agents, and agents such as asparaginase or hydroxyurea), corticoids (steroids), antidepressants, depressants, diuretics, hypnotics, minerals, nutritional supplements, parasympathomimetics, hormones (such as corticotrophin releasing hormone, adrenocorticotropin, growth hormone releasing hormone, growth hormone, thyrotropin-releasing hormone and thyroid stimulating hormone), sedatives, sulfonamides, stimulants, sympathomimetics, tranquilizers, vasoconstrictors, vasodilators, vitamins and xanthine derivatives.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

In therapeutic use for treatment of conditions in mammals (i.e. humans or animals) for which a modulator, such as an agonist, of the ghrelin receptor is effective, the compounds of the present invention or an appropriate pharmaceutical composition thereof may be administered in an effective amount. Since the activity of the compounds and the degree of the therapeutic effect vary, the actual dosage administered will be determined based upon generally recognized factors such as age, condition of the subject, route of delivery and body weight of the subject. The dosage can be from about 0.1 to about 100 mg/kg, administered orally 1-4 times per day. In addition, compounds can be administered by injection at approximately 0.01-20 mg/kg per dose, with administration 1-4 times per day. Treatment could continue for weeks, months or longer. Determination of optimal dosages for a particular situation is within the capabilities of those skilled in the art.

5. Methods of Use

The compounds of formula I, II and/or III of the present invention can be used for the prevention and treatment of a range of medical conditions including, but not limited to, metabolic and/or endocrine disorders, gastrointestinal disorders, cardiovascular disorders, obesity and obesity-associated disorders, central nervous system disorders, genetic disorders, hyperproliferative disorders, inflammatory disorders and combinations thereof where the disorder may be the result of multiple underlying maladies. In particular embodiments, the disease or disorder is irritable bowel syndrome (IBS), non-ulcer dyspepsia, Crohn's disease, gastroesophogeal reflux disorders, constipation, ulcerative colitis, pancreatitis, infantile hypertrophic pyloric stenosis, carcinoid syndrome, malabsorption syndrome, diarrhea, diabetes including diabetes mellitus (type II diabetes), obesity, atrophic colitis, gastritis, gastric stasis, gastrointestinal dumping syndrome, postgastroenterectomy syndrome, celiac disease, an eating disorder or obesity. In other embodiments, the disease or disorder is congestive heart failure, ischemic heart disease or chronic heart disease. In still other embodiments, the disease or disorder is osteoporosis and/or frailty, congestive heart failure, accelerating bone fracture repair, metabolic syndrome, attenuating protein catabolic response, cachexia, protein loss, impaired or risk of impaired wound healing, impaired or risk of impaired recovery from burns, impaired or risk of impaired recovery from surgery, impaired or risk of impaired muscle strength, impaired or risk of impaired mobility, alterted or risk of altered skin thickness, impaired or risk of impaired metabolic homeostasis or impaired or risk of impaired renal homeostasis. In other embodiments, the disease or disorder involves facilitating neonatal development, stimulating growth hormone release in humans, maintenance of muscle strength and function in humans, reversal or prevention of frailty in humans, prevention of catabolic side effects of glucocorticoids, treatment of osteoporosis, stimulation and increase in muscle mass and muscle strength, stimulation of the immune system, acceleration of wound healing, acceleration of bone fracture repair, treatment of renal failure or insufficiency resulting in growth retardation, treatment of short stature, treatment of obesity and growth retardation, accelerating the recovery and reducing hospitalization of burn patients, treatment of intrauterine growth retardation, treatment of skeletal dysplasia, treatment of hypercortisolism, treatment of Cushing's syndrome, induction of pulsatile growth hormone release, replacement of growth hormone in stressed patients, treatment of osteochondrodysplasias, treatment of Noonans syndrome, treatment of schizophrenia, treatment of depression, treatment of Alzheimer's disease, treatment of emesis, treatment of memory loss, treatment of reproduction disorders, treatment of delayed wound healing, treatment of psychosocial deprivation, treatment of pulmonary dysfunction, treatment of ventilator dependency; attenuation of protein catabolic response, reducing cachexia and protein loss, treatment of hyperinsulinemia, adjuvant treatment for ovulation induction, stimulation of thymic development, prevention of thymic function decline, treatment of immunosuppressed patients, improvement in muscle mobility, maintenance of skin thickness, metabolic homeostasis, renal homeostasis, stimulation of osteoblasts, stimulation of bone remodeling, stimulation of cartilage growth, stimulation of the immune system in companion animals, treatment of disorders of aging in companion animals, growth promotion in livestock, and/or stimulation of wool growth in sheep.

According to a further aspect of the invention, there is provided a method for the treatment of post-operative ileus, cachexia (wasting syndrome), such as that caused by cancer, AIDS, cardiac disease and renal disease, gastroparesis, such as that resulting from type I or type II diabetes, other gastrointestinal disorders, growth hormone deficiency, bone loss, and other age-related disorders in a human or animal patient suffering therefrom, which method comprises administering to said patient an effective amount of at least one member selected from the compounds disclosed herein having the ability to modulate the ghrelin receptor. Other diseases and disorders treated by the compounds disclosed herein include short bowel syndrome, gastrointestinal dumping syndrome, postgastroenterectomy syndrome, celiac disease, and hyperproliferative disorders such as tumors, cancers, and neoplastic disorders, as well as premalignant and non-neoplastic or non-malignant hyperproliferative disorders. In particular, tumors, cancers, and neoplastic tissue that can be treated by the present invention include, but are not limited to, malignant disorders such as breast cancers, osteosarcomas, angiosarcomas, fibrosarcomas and other sarcomas, leukemias, lymphomas, sinus tumors, ovarian, uretal, bladder, prostate and other genitourinary cancers, colon, esophageal and stomach cancers and other gastrointestinal cancers, lung cancers, myelomas, pancreatic cancers, liver cancers, kidney cancers, endocrine cancers, skin cancers and brain or central and peripheral nervous (CNS) system tumors, malignant or benign, including gliomas and neuroblastomas.

In particular embodiments, the macrocyclic compounds of the present invention can be used to treat post-operative ileus. In other embodiments, the compounds of the present invention can be used to treat gastroparesis. In still other embodiments, the compounds of the present invention can be used to treat diabetic gastroparesis. In another embodiment, the compounds of the present invention can be used to treat opioid-induced bowel dysfunction. In further embodiments, the compounds of the present invention can be used to treat chronic intestinal pseudoobstruction.

The present invention further provides methods of treating a horse or canine for a gastrointestinal disorder comprising administering a therapeutically effective amount of a modulator having the structure of formula I, II and/or III. In some embodiments, the gastrointestinal disorder is ileus or colic.

As used herein, "treatment" is not necessarily meant to imply cure or complete abolition of the disorder or symptoms associated therewith.

The compounds of the present invention can further be utilized for the preparation of a medicament for the treatment of a range of medical conditions including, but not limited to, metabolic and/or endocrine disorders, gastrointestinal disorders, cardiovascular disorders, obesity and obesity-associated disorders, genetic disorders, hyperproliferative disorders and inflammatory disorders.

Further embodiments of the present invention will now be described with reference to the following examples. It should be appreciated that these examples are for the purposes of illustrating embodiments of the present invention, and do not limit the scope of the invention.

EXAMPLE 1

Synthesis of Tethers

A. Standard Procedure for the Synthesis of Tether T9

Step T9-1: To a solution of 2-iodophenol (9-0, 200 g, 0.91 mol, 1.0 eq) in DMF (DriSolv®, 560 mL) is added sodium hydride 60% in mineral oil (3.64 g, 0.091 mol, 0.1 eq) by portions (hydrogen is seen to evolve). The reaction is heated for 1 h at 100° C. under nitrogen, then ethylene carbonate is added and the reaction mixture heated O/N at 100° C. The reaction is monitored by TLC (conditions: 25/75 EtOAc/hex; $R_f$: 0.15, detection: UV, CMA). The reaction mixture is allowed to cool, then the solvent evaporated under reduced pressure. The residual oil is diluted in $Et_2O$ (1.5 L), then washed sequentially with 1 N sodium hydroxide (3×) and brine (2×), dried with $MgSO_4$, filtered and the filtrate evaporated under reduced pressure. The crude product is distilled under vacuum (200 μm Hg) at 110-115° C. to provide 9-1.

Step T9-2: A solution of 9-1 (45.1 g, 0.171 mol, 1.0 eq) and Ddz-propargylamine (9-A, synthesized by standard protection procedures, 59.3 g, 0.214 mol, 1.25 eq) in acetonitrile (DriSolv®, 257 mL) was degassed by passing argon through the solution for 10-15 min. To this was added $Et_3N$ (85.5 mL, stirred O/N with $CaH_2$, then distilled) and the mixture was again purged by bubbling with argon, this time for 5 min. Recrystallized copper (I) iodide (1.14 g, 0.006 mol, 0.035 eq) and trans-dichloro-bis(triphenylphosphine) palladium (II) (Strem Chemicals, 3.6 g, 0.0051 mol, 0.03 eq) are added and the reaction mixture stirred for 4 h under argon at rt. After 5-10 min, the reaction mixture turned black. The reaction was monitored by TLC (conditions: 55/45 EtOAc/hex). When complete, the solvent was removed under reduced pressure until dryness, then the residual oil diluted with 1 L of a 15% DCM in $Et_2O$ solution. The organic phase is washed with citrate buffer pH 4-5 (3×), saturated aqueous sodium bicarbonate (2×), and brine (1×), then dried with $MgSO_4$, filtered and the filtrate evaporated under reduced pressure. The crude product thus obtained is purified by a dry pack column starting with 30% EtOAc/Hex (4-8 L) then increasing by 5% EtOAc increments until 55% EtOAc/Hex to give 9-2 as a brown syrup (yield: 65.8 g, 93.2%).

Step T9-3: To a solution of Ddz-amino-alcohol 9-2 (65.8 g, 0.159 mol, 1.0 eq) in 95% ethanol under nitrogen was added

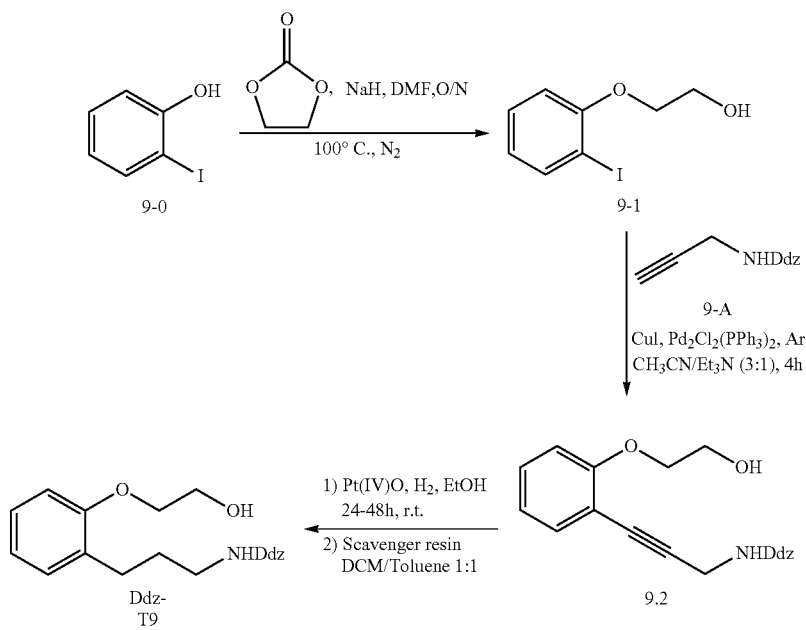

platinum (IV) oxide (3.6 g, 0.016 mol, 0.1 eq) and then hydrogen gas bubbled into the solution for 2 h. The mixture was stirred O/N, maintaining an atmosphere of hydrogen using a balloon. The reaction was monitored by $^1$H NMR until completion. When the reaction is complete, nitrogen was bubbled for 10 min to remove the excess hydrogen. The solvent is evaporated under reduced pressure, then diluted with EtOAc, filtered through a silica gel pad and the silica washed with EtOAc until no further material was eluted as verified by TLC. (55/45 EtOAc/hex) The combined filtrates were concentrated under reduced pressure. The residue is diluted in DCM (500 mL) and 4 eq of scavenger resin was added and the suspension stirred O/N. For this latter step, any of three different resins were used. MP-TMT resin (Argonaut Technologies, Foster City, Calif., 0.73 mmol/g) is preferred, but others, for example, PS-TRIS (4.1 mmol/g) and Si-Triamine (Silicycle, Quebec City, QC, 1.21 mmol/g) can also be employed effectively. The resin was filtered and washed with DCM, the solvent evaporated under reduced pressure, then dried further under vacuum (oil pump) to provide the product. The yield of Ddz-T9 from 9-0 on a 65 g scale was 60.9 g (91%)

$^1$H NMR (CDCl$_3$): δ 7.19-7.01, (m, 2H), 6.92-9.83 (m, 2H), 6.53 (bs, 2H), 6.34 (t, 1H), 5.17 (bt, 1H), 4.08 (m, 2H), 3.98 (m, 2H), 3.79 (s, 6H), 3.01 (bq, 2H), 2.66 (t, 3H), 1.26 (bs, 8H);

$^{13}$C NMR (CDCl$_3$): δ 160.9, 156.8, 155.6, 149.6, 130.4, 127.5, 121.2, 111.7, 103.2, 98.4, 80.0, 69.7, 61.6, 55.5, 40.3, 30.5, 29.3, 27.4 ppm.

Tether T9 can also be synthesized from another tether molecule by reduction as in step T9-3 or with other appropriate hydrogenation catalysts known to those in the art.

B. Standard Procedure for the Synthesis of Tether T33a and T33b (33-2) also occurred in high yield and was followed by Sonagashira reaction with Ddz-propargylamine (33-B). The alkyne in the resulting coupling product, 33-3, was reduced with catalytic hydrogenation. Workup with scavenger resin provided the desired product, Ddz-T33a.

The synthesis of the (S)-enantiomer (Ddz-T33b) was carried out in an identical manner in comparable yield starting from (R)-methyl lactate (33-B)

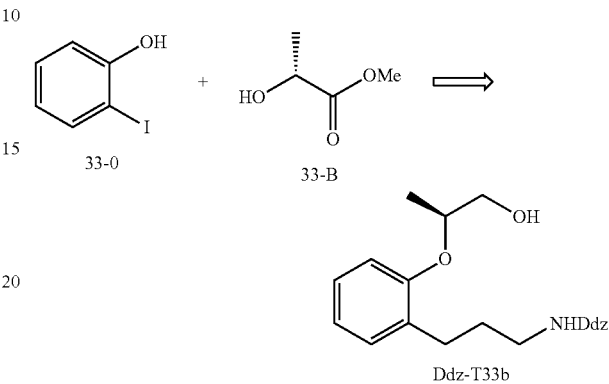

C. Standard Procedure for the Synthesis of Tether Precursor RCM-T$_{A1}$

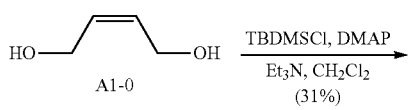

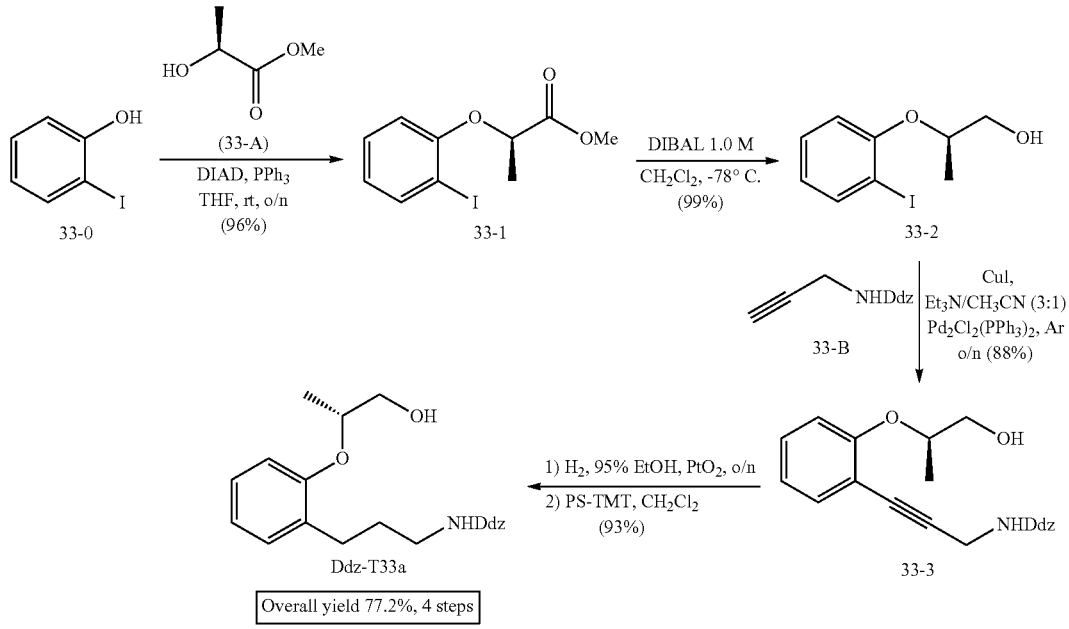

The construction to the (R)-isomer of this tether (T33a) was accomplished from 2-iodophenol (33-0) and (S)-methyl lactate (33-A). Mitsunobu reaction of 33-0 and 33-A proceeded with inversion of configuration in excellent yield to give 33-1. Reduction of the ester to the corresponding alcohol -continued

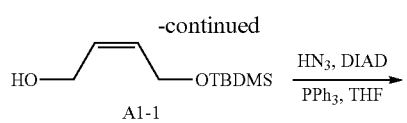

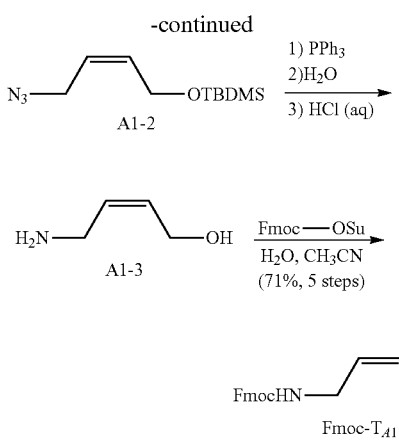

Step A1-1. To a solution of diol A1-0 (50 g, 567 mmol, 1.0 eq) in CH$_2$Cl$_2$ (1.5 L) were added Et$_3$N (34.5 mL, 341 mmol, 0.6 eq) and DMAP (1.73 g, 14.2 mmol, 0.025 eq). TBDMSCl (42.8 g, 284 mmol, 0.5 eq) in CH$_2$Cl$_2$ (100 mL) was added to this mixture at rt over 4 h with a syringe pump. The reaction was monitored by TLC [EtOAc/hexanes (30:70); detection: KMnO$_4$; R$_f$=0.39], which revealed starting material, mono-protected compound and di-protected compound. The mixture was stirred O/N, washed with H$_2$O, saturated NH$_4$Cl (aq) and brine, then dried over MgSO$_4$, filtered and evaporated under reduced pressure. The residue was purified by flash chromatography (EtOAc/hexanes, 30:70) to give the desired mono-protected alcohol A1-1 (yield: 31%).

Step A1-2. To a solution of alcohol A1-1 (26.5 g, 131 mmol, 1.0 eq) in THF (130 mL) at 0° C. was added PPh$_3$ (44.7 g, 170 mmol, 1.3 eq). A freshly prepared and titrated 1.3 M solution of HN$_3$ (149 mL, 157 mmol, 1.5 eq) was added slowly to this mixture, then DIAD (32 mL, 163 mmol, 1.25 eq) also added slowly. This was an exotheric reaction. The resulting mixture was stirred at 0° C. for 1 h with monitoring of the reaction by TLC [EtOAc/hexanes (30:70); detection: KMnO$_4$; R$_f$=0.77]. Compound A1-2 was obtained, but was not isolated and instead used directly for the next step in solution.

Step A1-3. PPh$_3$ (51 g, 196 mmol, 1.5 eq) was added by portion to the solution of A1-2 and the resulting mixture was stirred at 0° C. for 2 h, allowed to warm to rt and maintained there for 3 h, then H$_2$O (24 mL, 1331 mmol, 10 eq) added.

This mixture was heated at 60° C., O/N. The reaction was monitored by TLC [EtOAc/hexanes (1:9); detection: KMnO$_4$; R$_f$=baseline]. After cooling, a solution of 2 N HCl (327 mL, 655 mmol, 5.0 eq) was added and the resulting mixture stirred at rt for 2 h to obtain compound A1-3 in solution, which was used directly in the next step. TLC [DCM/MeOH/30% NH$_4$OH (7:3:1); detection: KMnO$_4$; R$_f$=0.32].

Step A1-4. For the next transformation, THF was evaporated under reduced pressure from the above reaction mixture and the remaining aqueous phase extracted with Et$_2$O (5×150 mL) and CHCl$_3$ (3×150 mL). The organic phases were monitored by TLC and if any A1-3 was observed, the organic phase was then extracted with 2 N HCl. The aqueous phase was neutralized cautiously to pH 8 with 10 N NaOH. CH$_3$CN (400 mL) was added to this aqueous solution and Fmoc-OSu (41.9 g, 124 mmol, 0.95 eq) in CH$_3$CN (400 mL) added slowly over 50 min. The solution was stirred at rt O/N. The reaction progress was monitored by TLC [EtOAc/hexanes (1:1); detection: ninhydrin; R$_f$=0.27]. The aqueous phase was extracted with Et$_2$O, then the combined organic phase dried over MgSO$_4$ and concentrated under reduced pressure. The solid residue obtained was mixed with H$_2$O (120 mL), stirred 30 min, filtered (to remove succinimide byproduct) and dried O/N under vacuum (oil pump). The solid was purified by flash chromatography [gradient: EtOAc/hexanes (50:50) to EtOAc/hexanes (70:30), with the change of eluent once Fmoc-OSu was removed as indicated by TLC] to give compound T$_{A1}$ as a white solid (yield: 71%).

$^1$H NMR (CDCl$_3$, ppm): 7.8 (d, 2H), 7.6 (d, 2H), 7.4 (t, 2H), 7.3 (t, 2H), 5.9-5.7 (1H, m), 5.6-5.5 (1H, m), 5.0 (1H, broad), 4.4 (2H, d), 4.2 (2H, d), 3.9 (2H, broad), 2.1 (1H, broad).

$^{13}$C NMR (CDCl$_3$, ppm): 156.8, 144.1, 141.5, 131.9, 128.3, 127.9, 127.3, 125.2, 120.2, 67.0, 58.0, 47.4, 38.0.

D. Standard Procedure for the Synthesis of Tether Precursor RCM-T$_{A2}$

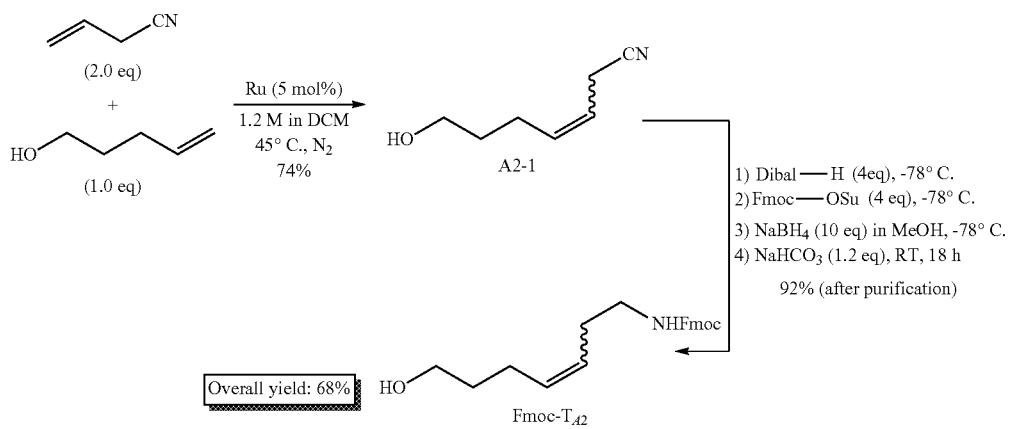

This material was accessed through application of the cross metathesis reaction shown to construct the carbon backbone. The resulting nitrile was reduced to the amine, which was protected in situ with Fmoc or other appropriate protecting group prior to attachment to the resin, which was performed using standard solid phase chemistry procedures known to those in the art. This standard procedure would also be applicable to homologues of T$_{A2}$.

E. Standard Procedure for the Synthesis of Tether Precursor RCM-$T_{B1}$

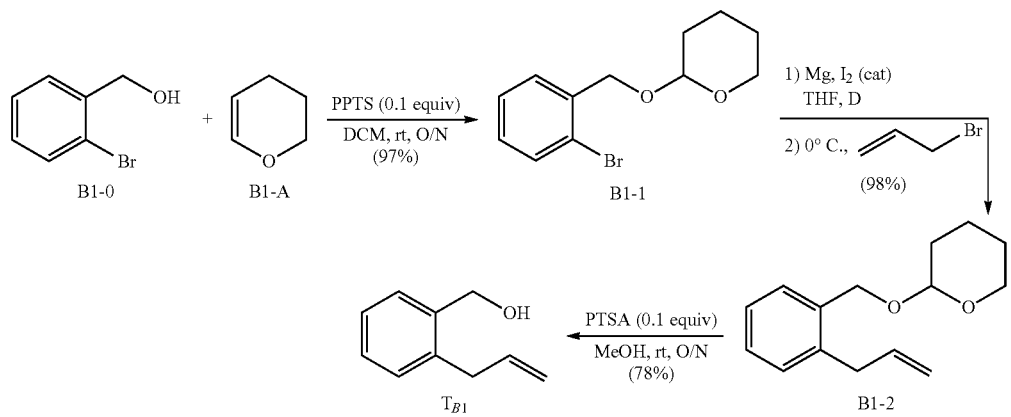

Step B1-1. To 2-bromobenzyl alcohol (B1-0, 30 g, 160 mmol) in DCM (DriSolv®, 530 mL) as an approximately 0.3 M solution, was added dihydropyran (B1-A, 22 mL, 241 mmol). Pyridinium p-toluenesulfonate (PPTS, 4.0 g, 16 mmol) was added and the reaction mixture stirred vigorously at rt O/N. A saturated solution of $Na_2CO_3$ (aq, 200 mL) was then added and the mixture stirred for 30 min. The DCM layer was separated, washed successively with saturated $Na_2CO_3$ (aq, 2×100 mL) and brine (2×50 mL), and dried over anhydrous $MgSO_4$. The solvent was evaporated under reduced pressure and the crude residue was purified by dry-pack silica-gel column [EtOAc/hexanes (1:9); before loading the crude material, the silica was neutralized by flushing with 1% $Et_3N$ in DCM] This afforded B1-1 as a colorless oil (42 g, 97%). TLC [EtOAc/hexanes (1:9); $R_f$=0.56]

Step B1-2. Magnesium turnings (2.21 g, 90 mmol) were added to an approximately 0.8 M solution of B1-1 (from which several portions of toluene were evaporated to remove traces of water, 22.14 g, 81.8 mmol) in anhydrous THF (distilled from sodium benzophenone ketyl, 100 mL) under an atmosphere of nitrogen. The reaction was initiated by adding iodine chips (50 mg, 0.002 equiv). The reaction mixture was heated to reflux for 2 h, during which time most of the Mg turnings disappeared. The reaction was allowed to cool to rt. In a separate flame-dried round-bottomed flask, freshly distilled allyl bromide (6.92 mL, 81.8 mmol) was diluted with anhydrous THF (50 mL) under a nitrogen atmosphere and cooled to 0° C. using an ice-water bath. To this was gradually transferred the now cooled Grignard solution over a period of 20-30 min using a cannula ensuring that the unreacted magnesium turnings remained in the source flask. The contents of the Grignard preparation flask were washed (2×5 mL dry THF) and the washings transferred via cannula to the allyl bromide solution as well. The resulting mixture was stirred O/N under $N_2$ while allowing it to gradually warm to rt. The reaction was quenched by adding saturated $NH_4Cl$ (aq) solution, then diluted with 100 mL $Et_2O$ and the layers separated. The aqueous phase was extracted with $Et_2O$ (3×100 mL) and the combined organic layers dried over $MgSO_4$, then concentrated under reduced pressure to provide B1-2 (18.54 g, 98%). TLC [EtOAc/hexanes (1:9), $R_f$=0.53]. This material was utilized in the next step without further purification.

Step B1-3. 2-(2-Propenyl)benzyl alcohol ($T_{B1}$). The crude THP ether B1-2 (18.54 g, 80 mmol) was dissolved in MeOH (160 mL) and p-toluenesulfonic acid monohydrate (PTSA, 1.52 g, 8 mmol) added. The resulting mixture was stirred at rt O/N, then concentrated under reduced pressure and the residue diluted with $Et_2O$ (100 mL). The organic layer was sequentially washed with 5% $NaHCO_3$ (aq) solution (3×50 mL) and brine (1×50 mL), then dried over $MgSO_4$. The solvent was evaporated under reduced pressure and the residue purified by flash chromatography (EtOAc/hexanes, 1:9), to obtain $T_{B1}$ as a pale-yellow oil (9.2 g, 78%). TLC [EtOAc/hexanes (1:9), detection: UV, PMA; $R_f$=0.24]

F. Standard Procedure for the Synthesis of Tether Precursor RCM-$T_{B2}$

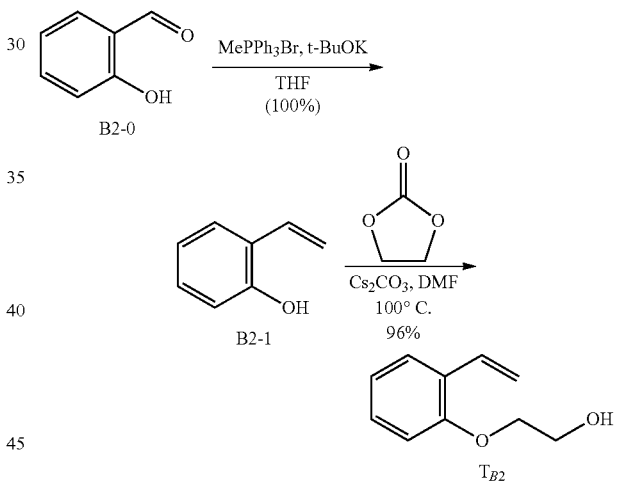

Step B2-1. To a suspension of $MePPh_3Br$ (85.7 g, 240 mmol, 2.2 eq) in THF (500 mL) was added t-BuOK in portions (26.9 g, 240 mmol, 2.2 eq) and the resulting mixture stirred at rt for 2 h during which time it became yellow. The reaction mixture was cooled to −78° C., 2-hydroxybenzaldehyde (B2-0, 11.6 mL, 109 mmol, 1.0 eq) added over 10 min, then it was stirred O/N at rt. The reaction progress was monitored by TLC [EtOAc/hexanes (20:80); detection: UV, CMA; $R_f$=0.25]. A saturated $NH_4Cl$ (aq) solution was added and the resulting aqueous phase extracted with $Et_2O$ (3×). The combined organic phase was dried over $MgSO_4$, filtered and concentrated under reduced pressure. The residue was purified by flash chromatography (EtOAc/hexanes, 30:70) to give B2-1 as a yellow oil. The identity and purity were confirmed by $^1H$ NMR (yield: 100%).

Step B2-2. To a solution of alcohol B2-1 (2.0 g, 16.7 mmol, 1.0 eq) in DMF at 0° C. was added cesium carbonate (1.1 g, 3.34 mmol, 0.2 eq) and the mixture stirred at 0° C. for 15 min. The reaction was warmed to 100° C. and ethylene carbonate added. The resulting mixture was stirred at 100° C., O/N. The reaction was monitored by TLC [EtOAc/hexanes (30:70);

detection: UV, CMA; $R_f$=0.21]. The solution was cooled to rt and H$_2$O added. The resulting aqueous phase was extracted with Et$_2$O (3×). The organic phase was extracted with brine (3×), dried with MgSO$_4$, filtered and concentrated under reduced pressure. A yellow syrup (T$_{B2}$) was obtained (yield: 96%), which was of sufficient purity (as assessed by NMR) for further use without additional purification. Note that this product proved to be unstable in the presence of acid.

$^1$H NMR (CDCl$_3$, ppm): 7.50 (1H, dd, Ph), 7.22 (1H, td, Ph), 7.05 (dd, 1H, PhCH=CH$_2$), 6.98 (1H, t, Ph), 7.90 (1H, d, Ph), 5.75 (1H, dd, PhCH=CHH), 5.30 (1H, dd, PhCH=CHH), 4.15-4.10 (2H, m, PhOCH$_2$CH$_2$OH), 4.05-3.95 (2H, m, PhOCH$_2$CH$_2$OH), 2.05 (1H, s, OH).

G. Standard Procedure for the Synthesis of Tether Precursor RCM-T$_{B3}$

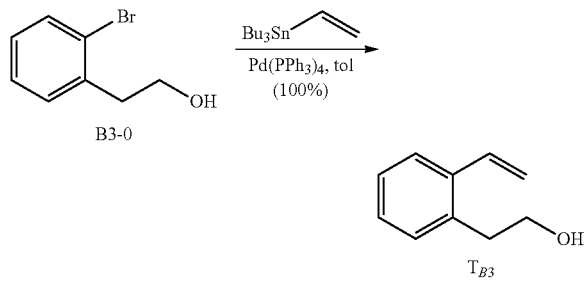

To a solution of 2'-bromophenethylalcohol (B3-0, 2.0 mL, 14.9 mmol, 1.0 eq) in toluene (50 mL) were added tetrakis (triphenylphosphine)palladium(0) [Pd(PPh$_3$)$_4$, 347 mg, 0.30 mmol, 0.02 eq) and vinyltributyltin (6.5 mL, 22.4 mmol, 1.5 eq). The resulting mixture was stirred at reflux for 24 h under N$_2$. Monitoring reaction progress by TLC was difficult since the starting material and product possessed the same R$_f$ [EtOAc/hexanes (30:70)]. The reaction mixture was cooled to rt and saturated KF (aq) solution added at which time a precipitate was formed. The solid was optionally removed by filtration and the aqueous phase extracted with DCM (4×). The combined organic phase was extracted with brine, dried over MgSO$_4$ and concentrated under reduced pressure. The residue was purified by flash chromatography (EtOAc/hexanes, 30:70) to give T$_{B3}$ as a colorless oil. The identity and purity were confirmed by $^1$H NMR (yield: 100%).

$^1$H NMR (CDCl$_3$, ppm): 7.57-7.45 (1H, m, Ph), 7.30-7.15 (3H, m, Ph), 7.05 (dd, 1H, PhCH=CH$_2$), 5.65 (1H, dd, PhCH=CHH), 5.32 (1H, dd, PhCH=CHH), 4.85 (2H, t, PhCH$_2$CH$_2$OH), 2.98 (2H, t, PhCH$_2$CH$_2$OH), 1.50 (1H, s, OH).

H. Standard Procedure for the Synthesis of Tether Precursor RCM-T$_{B4}$

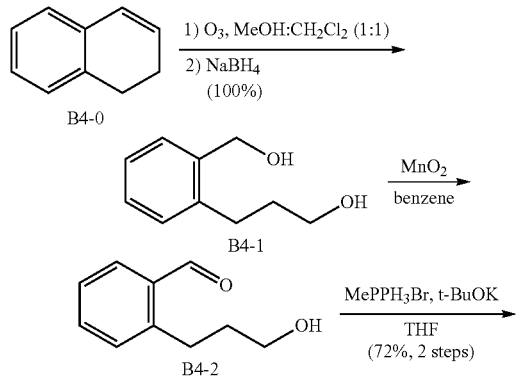

-continued

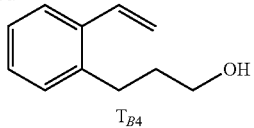

Step B4-1. 1,2-Dihydronaphthalene (B4-0, 5.0 g, 38.4 mmol, 1.0 eq) was dissolved in 200 mL of DCM:MeOH (1:1) and the solution cooled to −78° C. Ozone (O$_3$) was bubbled through the solution until a blue color developed. The reaction was monitored by TLC [EtOAc/hexanes (30:70); detection: UV, CMA; $R_f$=0.25]. Excess O$_3$ was then removed by bubbling N$_2$ through the solution until the blue color had dissipated. Sodium borohydride (2.9 g, 76.8 mmol, 2.0 eq) was added slowly to the mixture, then it was stirred at rt for 1 h. The reaction was monitored by TLC [EtOAc/hexanes (30:70); detection: UV, CMA; $R_f$=0.06]. A saturated NH$_4$Cl (aq) solution was added slowly, then the aqueous phase was extracted with DCM (3×). The combined organic phase was dried over MgSO$_4$, filtered and concentrated under reduced pressure. B4-1 was obtained as a yellow oil (yield: 100%). The identity and purity of the compound was confirmed by NMR analysis and typically was of sufficient purity to be used without further manipulation.

Step B4-2. To a solution of the diol B4-1 (6.38 g, 38.4 mmol, 1.0 eq) in benzene (200 mL) was added MnO$_2$ (85%, 16.7 g, 192 mmol, 5.0 eq) and the resulting mixture stirred 1 h at rt. The reaction was monitored by TLC [EtOAc/hexanes (50:50); detection: UV, CMA; $R_f$=0.24] and more MnO$_2$ (5 eq) added each 1 h period until the reaction was completed, typically this required 2-3 such additions. The MnO$_2$ was filtered through a Celite pad, which was then washed with EtOAc. The combined filtrate and washes were evaporated under reduced pressure to give B4-2. A $^1$H NMR was taken to check the purity of the resulting compound, which typically contained small amounts of impurities. However, this was sufficiently pure for use in the next step, which was preferably performed on the same day as this step since the aldehyde product (B4-2) had limited stability.

Step B4-3. To a suspension of MePPh$_3$Br (30.2 g, 84.5 mmol, 2.2 eq) in THF (200 mL) was added t-BuOK in portions (9.5 g, 84.5 mmol, 2.2 eq) and the resulting mixture stirred at rt for 2 h during which time the solution became yellow. The reaction mixture was cooled to −78° C., B4-2 [6.3 g, 38.4 mmol, 1.0 eq (based on the theoretical yield)] added over 10 min, then the mixture stirred O/N at rt. The reaction was monitored by TLC [EtOAc/hexanes (50:50); detection: UV, CMA; $R_f$=0.33]. A saturated NH$_4$Cl (aq) solution was added and the resulting aqueous phase extracted with EtOAc (3×). The combined organic phase was dried over MgSO$_4$, filtered and concentrated under reduced pressure. The residue was purified by flash chromatography (EtOAc/hexanes, 40:60) to give T$_{B4}$ as a yellow oil. NMR was used to confirm the identity and purity of the product (yield: 73%, 2 steps).

$^1$H NMR (CDCl$_3$, ppm): 7.55-7.45 (1H, m, Ph), 7.25-7.10 (3H, m, Ph), 7.05 (dd, 1H, PhCH=CH$_2$), 5.65 (1H, dd, PhCH=CHH), 5.30 (1H, dd, PhCH=CHH), 3.70 (2H, t, PhCH$_2$CH$_2$CH$_2$OH), 2.80 (2H, t, PhCH$_2$CH$_2$CH$_2$OH), 1.90-1.80 (2H, m, PhCH$_2$CH$_2$CH$_2$OH), 1.45 (1H, s, OH).

I. Standard Procedure for the Synthesis of Tether T45

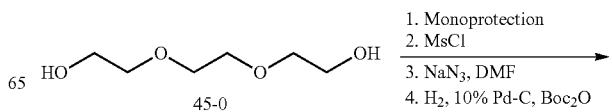

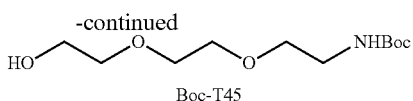
Boc-T45

The protected version of this tether was obtained through standard transformations involving monoprotection of triethyleneglycol (45-0) followed by conversion of the remaining alcohol to a mesylate, displacement with azide and catalytic reduction in the presence of di-t-butyl dicarbonate.

J. Standard Procedure for the Synthesis of Tether T65

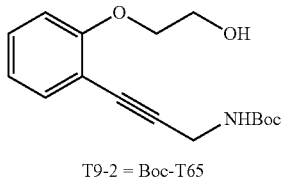 [SMILES: CC(C)(C)OC(=O)NCC#Cc1ccccc1OCCO]

T9-2 = Boc-T65

See the preparation of T9-2 as this tether is actually an intermediate in the synthesis of tether T9.

$^1$H NMR (CDCl$_3$): δ 7.38-7.35 (bd, 1H), 7.30-7.19 (m, 1H), 6.92 (dd, 2H), 4.88 (bs, 1H), 4.16-4.11 (bt, 4H), 3.98-3.95 (t, 2H), 1.46 (s, 9H).

$^{13}$C NMR (CDCl$_3$): δ 156.7, 155.8, 133.6, 130.0, 121.3, 114.8, 113.1, 112.9, 90.2, 70.8, 61.4, 28.6

K. Standard Procedure for the Synthesis of Tether T66

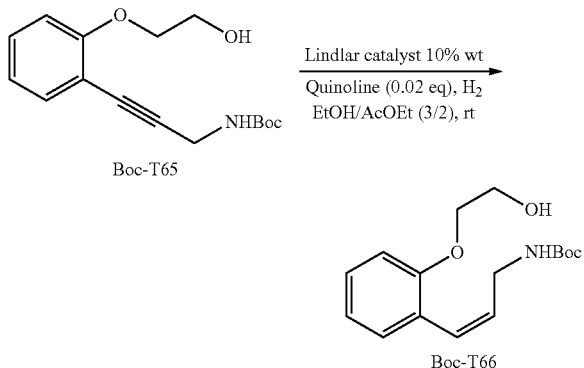

Boc-T66

To a solution of alkyne (Boc-T65, 13.1 g, 45.1 mmol, 1.0 eq) in EtOH/AcOEt (5:1) under N$_2$ is added quinoline (106 μl, 0.9 mmol, 0.02 eq) and the Lindlar catalyst (1.3 g, 10% wt), then hydrogen is bubbled into the mixture. The reaction is monitored (each 30-40 min) by $^1$H NMR until the reaction is complete. Then, the reaction is filtered through a Celite pad and rinsed with AcOEt until there is no more material eluting. The solvent is removed under reduced pressure. The crude product is purified by flash chromatography with 15% AcOEt/Hex to 40% AcOEt/Hex to give Boc-T66 an oil. (Yield: 7.8 g, 59%) TLC (45/55 AcOEt/Hex): R$_f$ 0.15; detection: UV, KMnO$_4$.

$^1$H NMR (CDCl$_3$): δ 7.27-7.21 (td, 1H), 7.15-7.10 (dd, 1H), 7.00.6.85, (m, 2H), 6.62-6.58 (bd, 1H), 5.77-5.70 (dt, 1H), 4.13-4.03 (m, 2H), 3.97-3.95 (m, 2H), 3.9-3.88 (bd, 2H), 1.46, (s, 9H)

L. Standard Procedure for the Synthesis of Tether T67

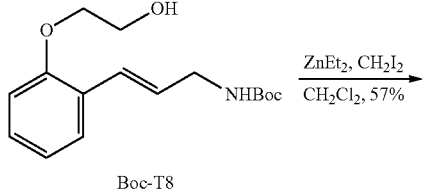

Boc-T8

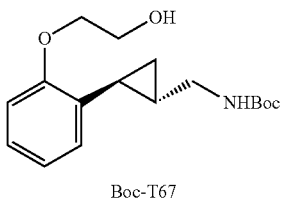

Boc-T67

To a solution of Et$_2$Zn (1 M in hexanes, 153 mL, 153.6 mmol, 3.0 eq) in CH$_2$Cl$_2$ (150 mL) at −20° C. was added CH$_2$I$_2$ (12.4 mL, 153.6 mmol, 3.0 eq) (CAUTION: Pressure can develop.) and the mixture stirred at −20° C. for 15 min. Boc-T8 (15.0 g, 51.2 mmol, 1.0 eq) in CH$_2$Cl$_2$ (100 mL) was then added and the mixture stirred at room temperature O/N. The reaction was monitored by TLC [(60% AcOEt: 40% hexane); detection: UV and CMA; R$_f$=0.39]. The solution was treated with aqueous NH$_4$Cl (saturated) and the aqueous phase was extracted with CH$_2$Cl$_2$. The organic phase was dried over MgSO$_4$ and concentrated under reduced pressure. The residue was purified by flash chromatography (60% AcOEt: 40% hexane) to give Boc-T67 as a yellow oil (yield: 57%).

$^1$H NMR (CDCl$_3$, ppm): 7.18 (1H, t), 7.03 (1H, d), 6.88 (2H, t), 4.23-4.04 (4H, m), 3.73-3.70 (2H, m), 1.48 (1H, broad), 1.28 (9H, s), 1.12-1.06 (1H, m), 1.0-0.93 (1H, m), 0.76 (2H, dt).

M. Standard Procedure for the Synthesis of Tether T68

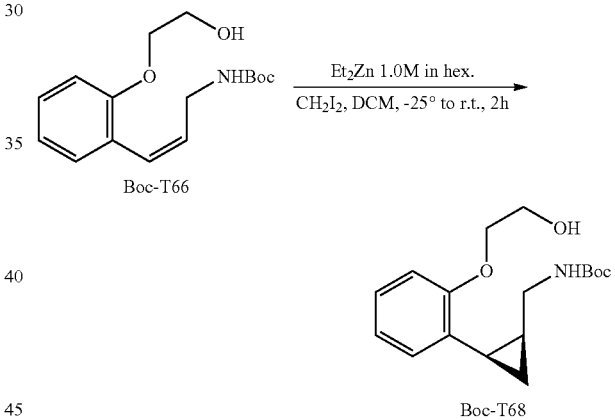

Boc-T68

To a solution of Et$_2$Zn (1 M in hexanes, 49.2 mL, 49.2 mmol, 3.0 eq) in CH$_2$Cl$_2$ (30 mL) at −20° C. was added CH$_2$I$_2$ (3.9 mL, 49.2 mmol, 3.0 eq) and the mixture stirred at −20° C. for 15 min. The alkene (Boc-T66, 4.8 g, 16.4 mmol, 1.0 eq) in CH$_2$Cl$_2$ (50 mL) was then slowly added and the mixture stirred at room temperature for 2 h. The solution was treated with aqueous NH$_4$Cl (saturated) and the aqueous phase extracted with CH$_2$Cl$_2$ (1×) then washed with brine (1×). The organic phase was dried over MgSO$_4$, filtered and the solvent removed under reduced pressure. The crude product is purified by flash chromatography (gradient: 40%, then 50% and finally 60% AcOEt in hexanes) to give Boc-T68 as a yellow oil (yield: 90.7%). TLC (60% AcOEt: 40% hexanes): R$_f$ 0.4; detection: UV, ninhydrin.

$^1$H NMR (CDCl$_3$): δ 7.32-7.20 (td, 2H), 7.10-6.85, (m, 2H), 4.25-4.13 (m, 2H), 4.10-3.99 (m, 2H), 3.41-3.36 (dd, 1H), 2.15-2.02 (m, 1H), 1.38 (s, 9H), 1.04-0.96 (dq, 1H), 0.78-0.73 (q, 1H)

$^{13}$C NMR (CDCl$_3$): δ 158.0, 130.7, 130.4, 127.9, 127.5, 127.1, 121.2, 121.0, 111.6, 111.2, 79.5 69.8, 61.5, 28.7, 17.8, 16.8, 7.2

N. Standard Procedure for the Synthesis of Tether T69
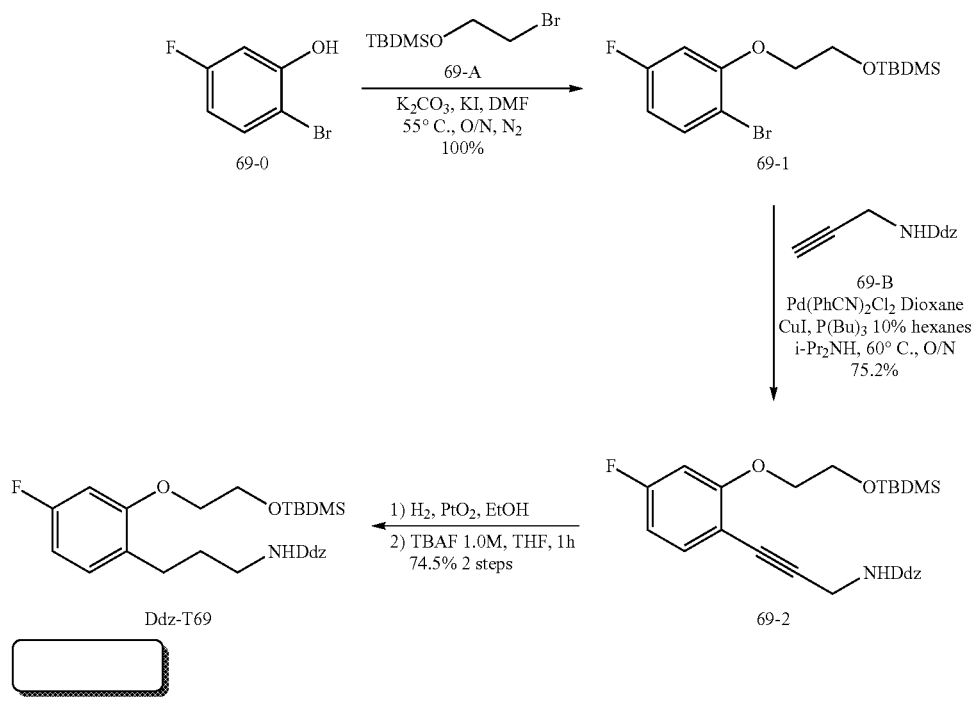
TLC (25/75 AcOEt/Hex): $R_f$: 0.03; detection: UV, ninhydrin
$^1$H NMR (CDCl$_3$): δ 7.06-7.00 (bt, 1H), 6.61-6.52 (m, 4H), 6.35 (m, 1H), 5.12 (bt, 1H), 4.03 (m, 2H), 3.95 (m, 2H), 3.77 (s, 6H), 3.11-3.04 (bq, 2H), 2.60 (bt, 2H), 1.75 (m, 8H)
$^{13}$C NMR (CDCl$_3$): δ 163.9, 160.9, 160.6, 157.6, 157.5, 155.6, 149.5, 130.8, 130.6, 125.9, 107.26, 106.9, 103.2, 98.4, 80.8, 77.5, 69.9, 61.3, 60.9, 60.6, 55.4, 40.3, 30.4, 29.3, 26.9,
LC-MS (Grad_A4) $t_R$: 8.37 min
O. Standard Procedure for the Synthesis of Tether T70
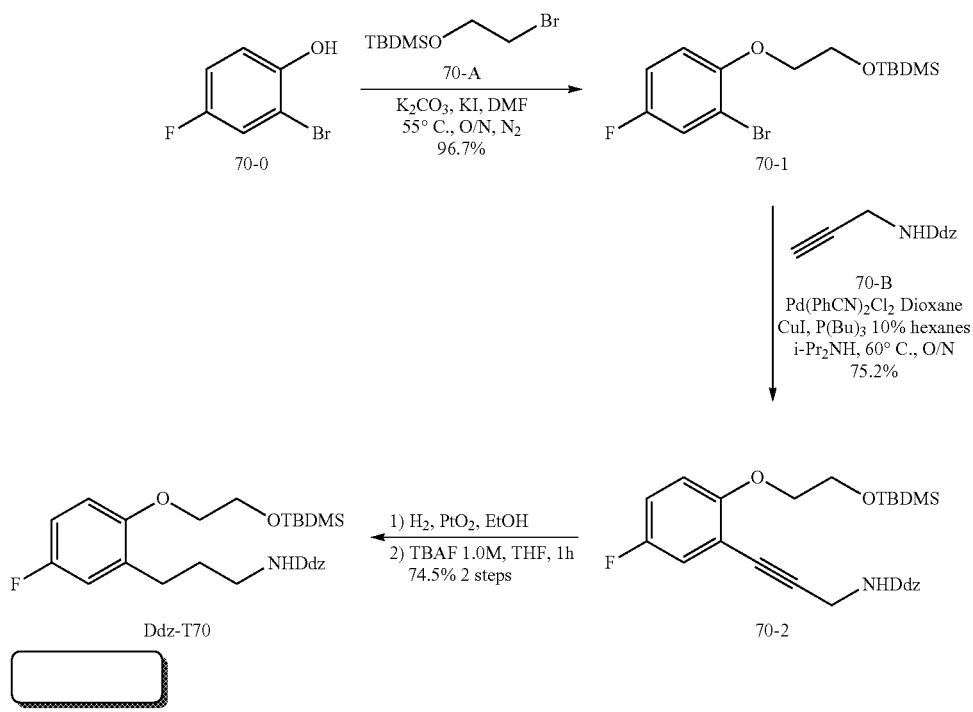

TLC (25/75 AcOEt/Hex): $R_f$: 0.03; detection: UV, ninhydrin
$^1$H NMR (CDCl$_3$): δ 6.84-6.75 (m, 3H), 6.52 (bs, 2H), 6.34 (m, 1H), 5.17 (bt, 1H), 4.01 (m, 2H), 3.93 (m, 2H), 3.77 (s, 6H), 3.10 (bq, 2H), 2.63 (bt, 2H), 1.74 (m, 8H)
$^{13}$C NMR (CDCl$_3$): δ 160.9, 158.9, 155.8, 155.6, 152.9, 152.9, 149.5, 132.4, 132.3, 117.1, 116.8, 112.7, 112.6, 103.2, 98.4, 80.8, 70.4, 61.6, 55.5, 40.2, 30.3, 29.3, 27.4.
LC-MS (Grad_A4) $t_R$: 8.29 min
P. Standard Procedure for the Synthesis of Tether T71
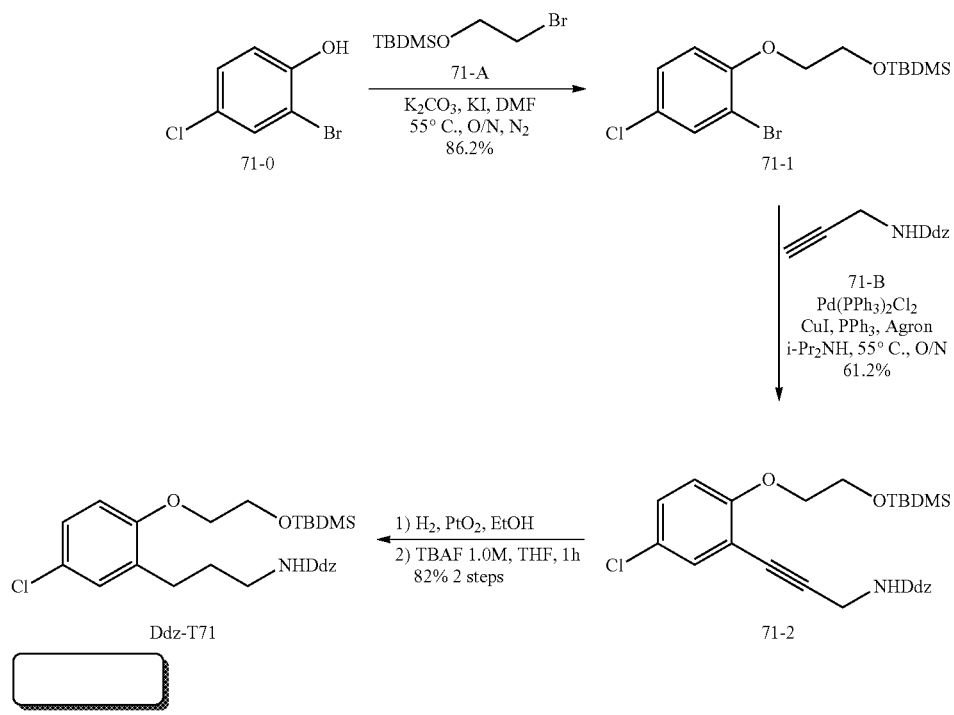
TLC (25/75 AcOEt/Hex): $R_f$: 0.03; detection: UV, ninhydrin
$^1$H NMR (CDCl$_3$): δ 7.12-7.08 (bd, 2H), 6.76-6.73 (d, 1H), 6.52 (m, 2H), 6.33 (bs, 1H), 5.15 (bt, 1H), 4.02 (m, 2H), 3.95 (m, 2H), 3.79 (s, 6H), 3.09 (bq, 2H), 2.61 (bt, 2H), 1.74 (m, 8H)
$^{13}$C NMR (CDCl$_3$): δ 160.8, 155.6, 155.4, 149.5, 132.4, 130.1, 127.0, 126.0, 112.8, 103.2, 98.4, 80.8, 70.0, 61.4, 55.5, 40.3, 30.2, 29.3, 24.5, 27.4
LC-MS (Grad_A4) $t_R$: 9.60 min
Q. Standard Procedure for the Synthesis of Tether T72
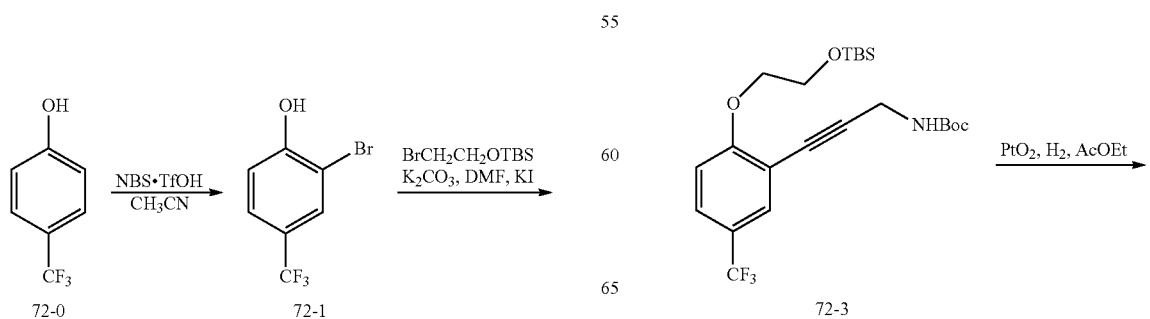

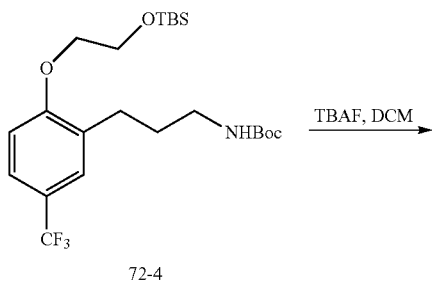
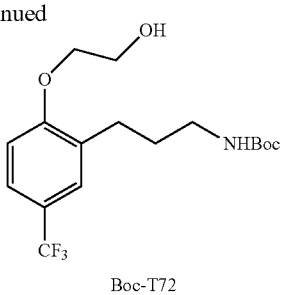
TLC (1/1, Hex/AcOEt): $R_f$: 0.16
$^1$H NMR (ppm): 1.49 (Boc), 1.8 (CH2), 2.7 (CH2), 3.1 (CH2), 4.0 (CH2), 4.1 (CH2), 4.9 (NH), 6.9 (CH aromatic), 7.35 (CH aromatic), 7.4 (CH aromatic)
$^{13}$C NMR (ppm): 29, 30, 40, 61, 70, 110, 124, 128, 132, 160
R. Standard Procedure for the Synthesis of Tether T73
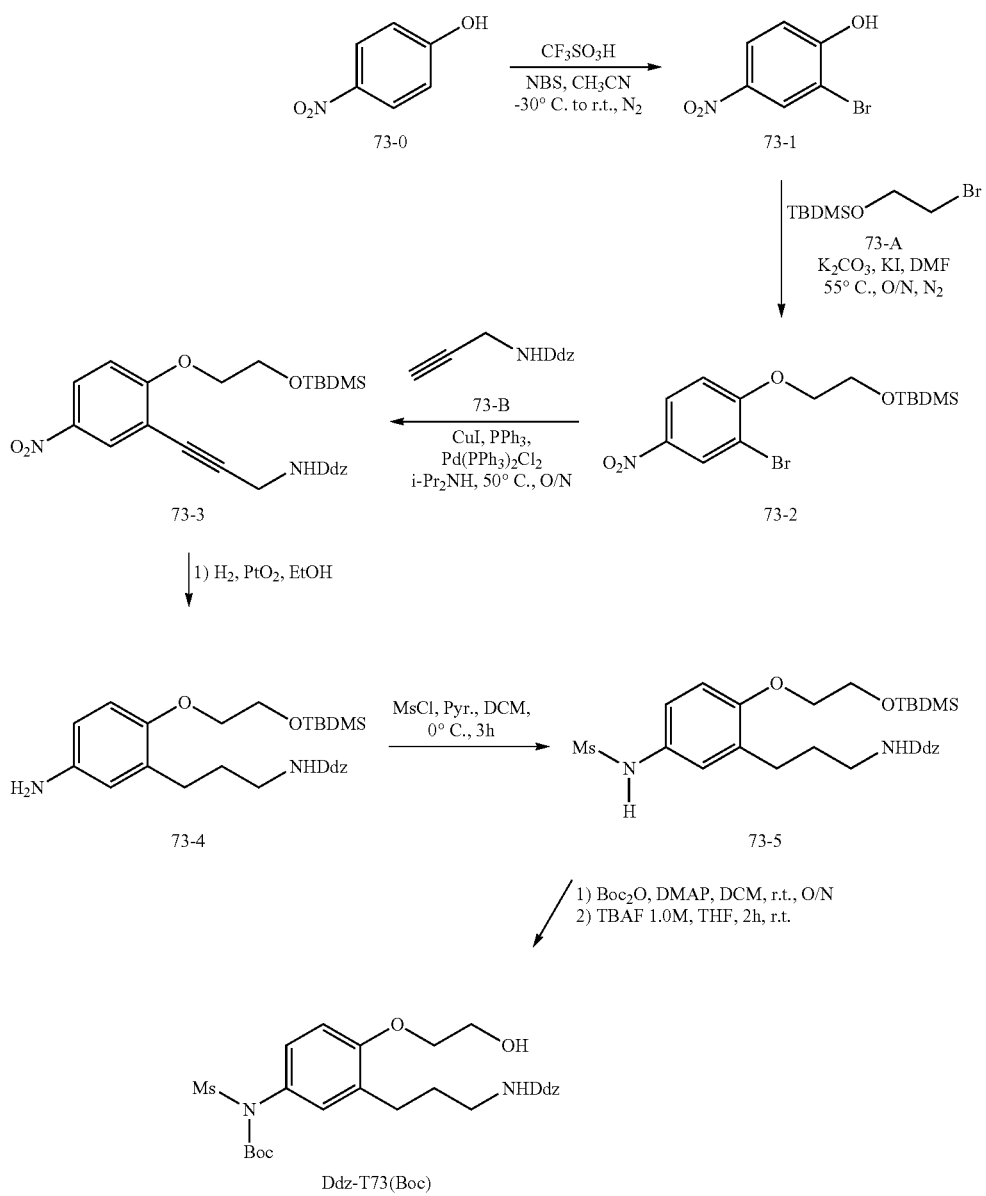

287
TLC (60/40 AcOEt/Hex): $R_f$: 0.11; detection: UV, ninhydrin
$^1$H NMR (CDCl$_3$): δ 7.06-6.99, (m, 2H), 6.84-6.81 (m, 1H), 6.5 (m, 2H), 6.32 (m, 1H), 5.11 (bt, 1H), 4.07 (m, 2H), 3.90 (bt, 2H), 3.79 (s, 6H), 3.39 (s, 3H), 3.09 (bt, 2H), 2.64 (bt, 2H), 1.85-1.74 (m, 8H), 1.46 (bs, 9H)
$^{13}$C NMR (CDCl$_3$): δ 160.8, 157.1, 155.6, 151.9, 149.5, 131.3, 131.0, 128.43, 128.37, 111.6, 103.2, 98.4, 84.8, 80.8, 69.9, 61.4, 60.6, 55.5, 41.8, 40.2, 30.0, 29.3, 28.1, 27.3 ppm.
LC-MS (Grad_A4) $t_R$: 8.26 min.
S. Standard Procedure for the Synthesis of Tether T74
288
TLC (50/50 AcOEt/Hex): $R_f$: 0.09; Detection: UV, CMA
$^1$H NMR (DMSO-d$_6$): δ 7.14 (bd, 1H), 6.76-6.71 (m, 2H), 6.53 (m, 2H), 6.33 (bs, 1H), 5.15 (bt, 1H), 4.08 (m, 2H), 3.95 (m, 2H), 3.79 (s, 6H), 3.41 (s, 3H), 3.01 (bq, 2H), 2.64 (bt, 2H), 1.75 (m, 8H), 1.47 (s, 9H)
$^{13}$C NMR (DMSO-d$_6$): δ 156.1, 152.3, 150.8, 147.0, 144.7, 129.8, 126.9, 125.6, 116.8, 108.4, 98.5, 93.6, 80.3, 76.1, 65.1, 56.7, 50.7, 37.1, 35.6, 25.3, 24.5, 23.4, 22.6
LC-MS (Grad_A4) $t_R$: 8.21 min
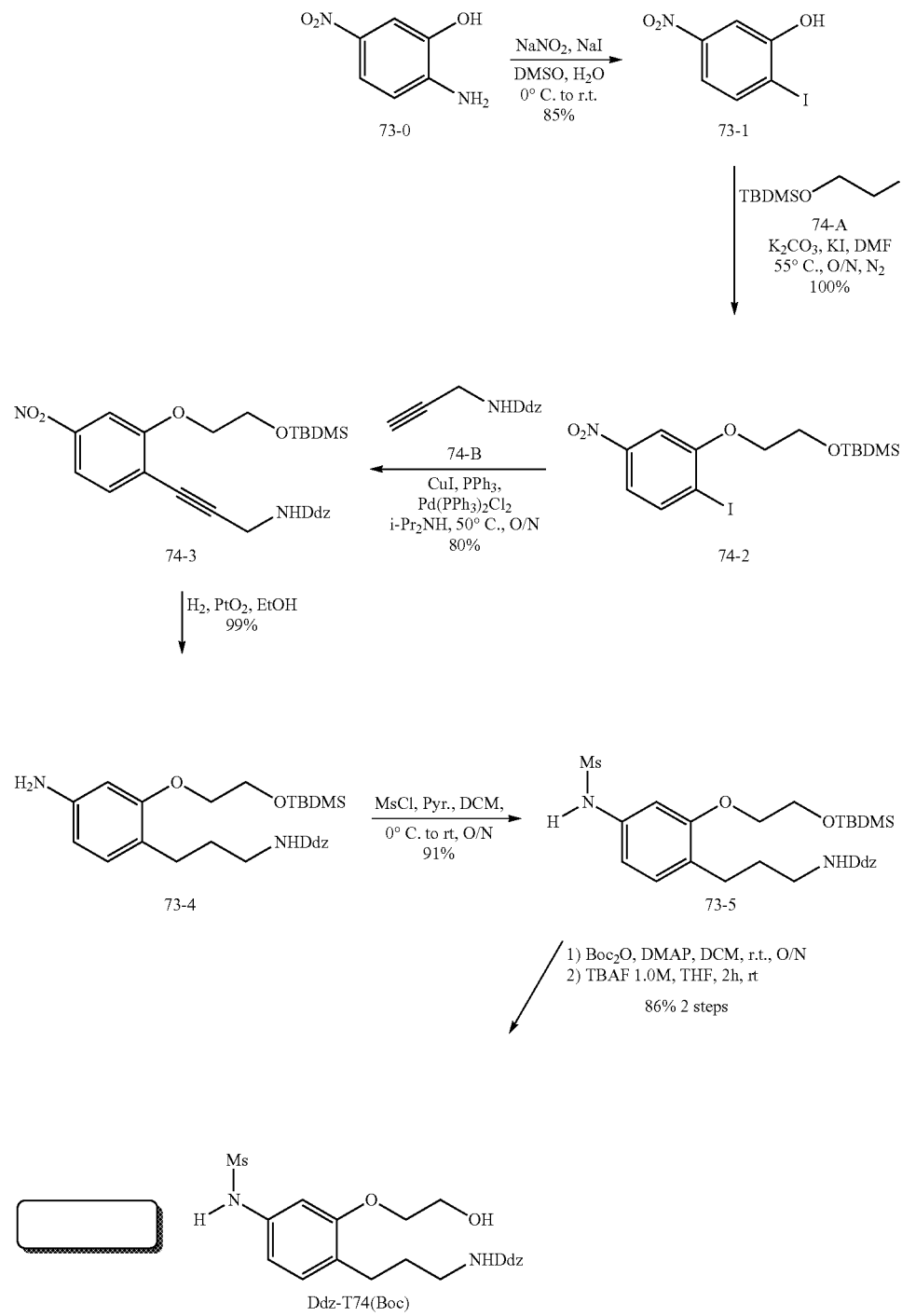

T. Standard Procedure for the Synthesis of Tether T75a and T75b

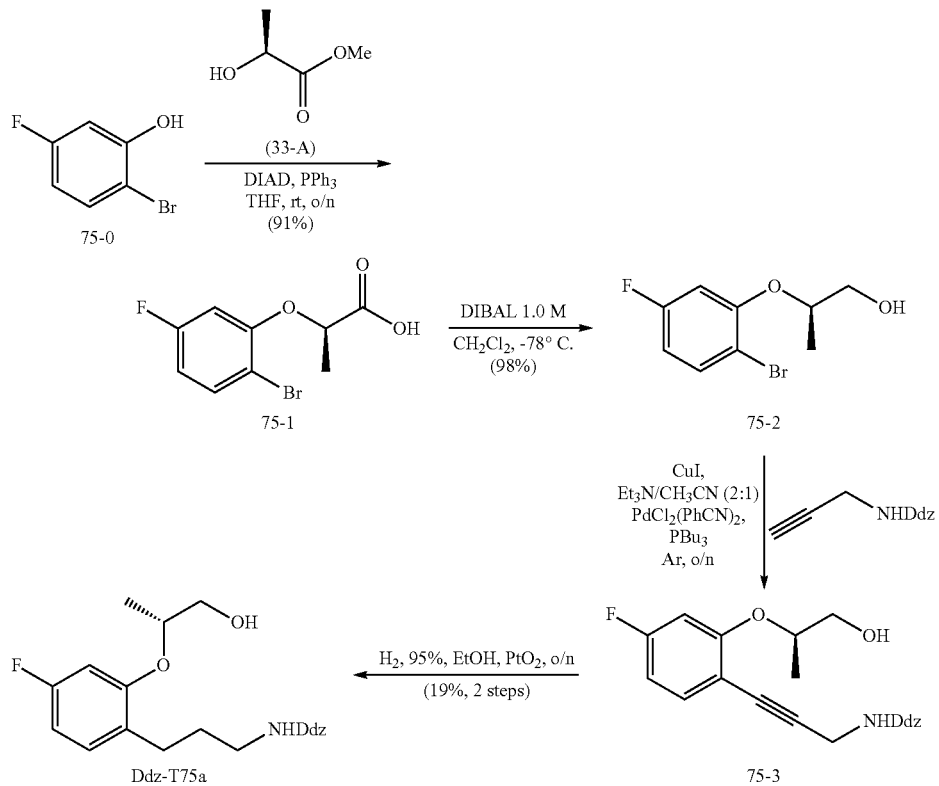

The synthesis of the fluorinated derivative, tether T75, was carried out in an analogous matter to that of the related tether T33 starting from 33-A [(S)-methyl lactate] and appropriately substituted phenol 75-0 to provide 4.1 g of Ddz-T75a as a pale yellow solid. Although the first two steps, Mitsunobu reaction and DIBAL reduction, were high yielding, 91% and 98% respectively, isolation of the final product proved difficult after Sonagashira coupling and hydrogenation, lowering the overall yield to 17%. Again, the corresponding (R)-enantiomer, Ddz-T75b, is accessible by substituting (R)-methyl lactate (33-B) in the above procedure.

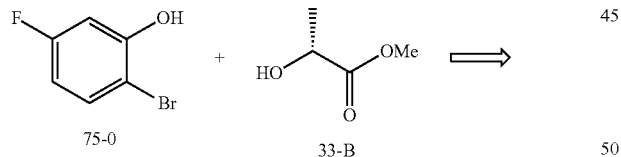

U. Standard Procedure for the Synthesis of Tether T76

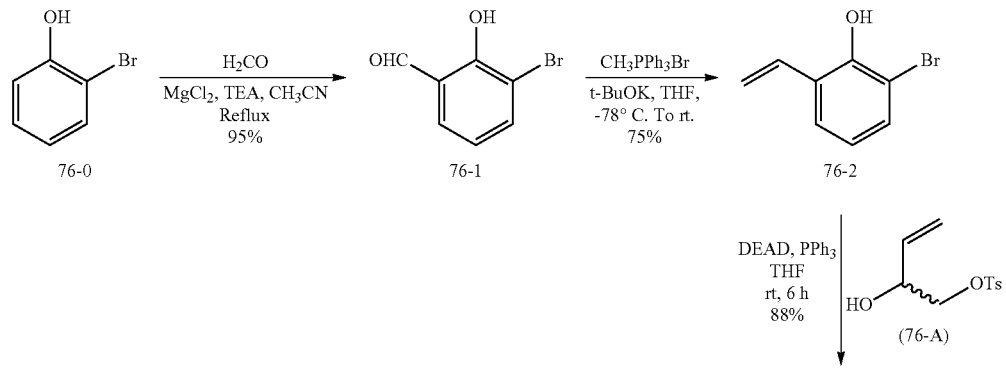

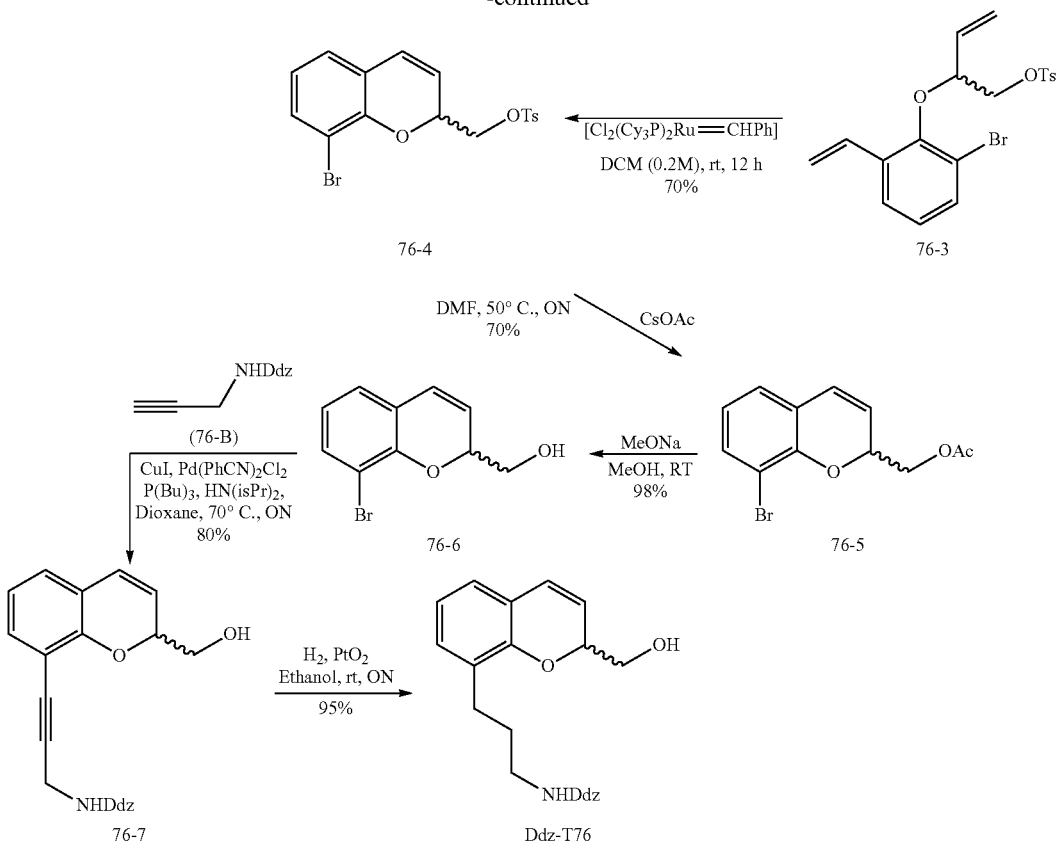

Step T76-1. 3-Bromo-2-hydroxy-benzaldehyde. In a manner analogous to that of the literature (Hofslokken et al. *Acta. Chemica Scand.* 1999, 53, 258), a stirred suspension of 2-bromophenol (76-0, 3.5 g, 20 mmol) and paraformaldehyde (8.1 g, 270 mmol) in 100 mL of dry acetonitrile at room temperature was treated with $MgCl_2$ (2.85 g, 30 mmol) and triethylamine (TEA, 10.45 ml, 75 mmol). The mixture was stirred vigorously at reflux O/N. After this period of time, the mixture was cooled to room temperature, then 30 mL of 5% HCl was added and the product extracted with $Et_2O$ to give 4.0 g (95%) of 76-1.

TLC (hexanes/dichloromethane, 3:1): $R_f$=0.3; detection: CMA and UV

Step T76-2. 2-Bromo-6-vinyl-phenol. To a stirred solution of $CH_3PPh_3Br$ (72 g, 0.033 mol) at room temperature was added, over 5 min, a solution of tBuOK (4.1 g, 0.03 mol) in THF (50 mL). The mixture was cooled to −78° C. and 76-1 (3 g, 0.015 mol) was added dropwise over 15 min. The reaction mixture was allowed to warm to room temperature and stirred for 24 h. After this time, the solvent was removed in vacuo and the residue purified by flash chromatography using hexanes/dichloromethane (3:1) as eluent to afford 76-2 as a colorless oil (2.2 g, 75%).

TLC (hexanes/dichloromethane, 3:1): $R_f$=0.5; detection: CMA and UV

Step T76-3. The tosylate 76-A was synthesized using the literature method (Buono et al. *Eur. J. Org. Chem.* 1999, 1671) and then utilized for 76-3 (Manhas, M. S. *J. Am. Chem. Soc.* 1975, 97, 461-463. Nakano, J. *Heterocycles* 1983, 20, 1975-1978). To a solution of 76-2 (2.5 g, 12 mmol), $Ph_3P$ (4.6 g, 18 mmol) and 76-A (4.3 g, 18 mmol) in 150 mL of THF was slowly added diethylazodicarboxylate (DEAD, 3.5 mL, 18 mmol) at room temperature. The mixture was stirred at room temperature for 6 h until the reaction was complete as indicated by TLC analysis (hexanes/ethyl acetate, 8:2; $R_f$=0.6; detection: CMA and UV). The solvent was removed under high vacuum and the residue was purified by flash chromatography to obtain 76-3 as a pale brown liquid (4.6 g, 88%).

Step T76-4. 76-3 (3.4 g, 8 mmol) was treated with second generation Grubbs catalyst (0.02 mol %) in 50 mL, of DCM (Grubbs, R. *J. Org. Chem.* 1998, 63, 864-866. Gross, *J. Tet. Lett.* 2003, 44, 8563-8565. Hoveyda, A. *J. Am. Chem. Soc.* 1998, 120, 2343-2351). The resulting mixture was stirred at room temperature for 12 h The solvent was then removed under high vacuum and the residue purified by flash column chromatography to obtain 76-4 as a pale brown liquid (2.15 g, 70%). TLC (hexanes/ethyl acetate, 8:2; $R_f$=0.4; detection: CMA and UV).

Step T76-5. To a solution of 76-4 (1.43 g, 0.023 mol) in dry DMF (50 mL) was added cesium acetate (2.09 g, 0.0109 mol) under an argon atmosphere. The solution was stirred at 50° C., O/N. After this time, the solvent was removed under high vacuum and the residue purified by flash chromatography to obtain 76-5 as a pale brown liquid (0.7 g, 70%). TLC (hexanes/ethyl acetate, 8:2; $R_f$=0.6; detection: CMA and UV).

Step T76-6 (8-Bromo-2H-chromen-2-yl)-methanol. To a solution of 76-5 (5.5 g, 0.023 mol) in dry MeOH (150 mL) was added sodium metal in a catalytic amount under an argon atmosphere. The solution was then stirred at room temperature for 60 min. After this time, Amberlite IRA-120 ($H^+$) resin was added to neutralize (pH=7) excess sodium methoxide and the mixture was vigorously stirred for 10 min. The resin was removed by filtration and the filtrate evaporated in vacuo. Pure compound 76-6 was recovered as a colorless oil (4.5 g, 98%).

TLC (hexanes/ethyl acetate, 7:3): $R_f$=0.3; detection: CMA and UV

Step T76-7. 76-6 (4.5 g, 18 mmol) and Ddz-propargyl amine (76-B, 15.16 g, 55.8 mmol) were dissolved in dioxane (150 mL) and diisopropylamine (27 mL). The reaction mixture was degassed by bubbling argon through the solution. PdCl$_2$(PhCN)$_2$ (430 mg, 1.11 mmol, 0.06 eq), CuI (220 mg, 1.11 mmol, 0.06 eq) and tributylphosphine (10% in hexane, 4.4 mL, 2.23 mmol) were added and the mixture was warmed to 70° C. and stirred O/N. The solvent was removed under high vacuum and the residue purified by flash column chromatography to obtain 76-7 as a pale brown liquid (3.2 g, 80%).

TLC (hexanes/ethyl acetate, 1:1): R$_f$=0.3; detection: CMA and UV

Step T76-8. The acetylene 76-7 (4.5 g, 0.2 mol) was dissolved in EtOH (150 mL), then purged with nitrogen for 10 min. PtO$_2$ (10 mol %, 450 mg) was added, and the mixture purged with a balloon full of hydrogen gas. The mixture was then charged into a Parr bomb, flushed with hydrogen (simply fill with hydrogen at 60 psi, then release and refill, repeat this fill-release-refill cycle 3×), and reacted with hydrogen at 60 psi at room temperature O/N. The reaction mixture was filtered through a pad of Celite (use methanol for washing the pad) and the filtrate concentrated to afford a practically pure (clean by $^1$H NMR), but colored sample of Ddz-T76 in quantitative yield. Further purification was achieved by subjecting this material to flash chromatography. TLC (hexanes/ethyl acetate, 1:1; R$_f$=0.3; detection: CMA and UV). Since the product Ddz-T76 has the same R$_f$ as the starting material (76-7), $^1$H NMR is the best way to distinguish them.

$^1$H NMR (CDCl$_3$): δ 1.73 (s, 6H), 1.75-1.95 (m, 4H), 2.60 (m, 2H), 2.70-2.90 (m, 2H), 3.10 (m, 2H), 3.72 (s, 6H), 3.75 (m, 2H), 4.12 (m, 1H), 5.20 (m, 1H), 6.35 (s, 1H), 6.50 (s, 2H), 6.80 (m, 1H), 6.90 (m, 2H).

$^{13}$C NMR (CDCl$_3$): δ 23.93 (CH$_2$), 24.97 (CH$_2$), 27.07 (CH$_2$), 29.35 (CH$_3$), 30.45 (CH$_2$), 40.23 (CH$_2$), 55.47 (CH$_3$), 65.76 (CH$_2$), 80.72 (CH), 98.44 (CH), 103.22 (CH), 120.29 (CH), 121.90 (Cq), 127.76 (CH), 128.14 (CH), 129.42 (Cq), 149.56 (Cq), 152.55 (Cq), 155.56 (Cq), 160.84 (Cq).

LC-MS (Grad_A4): t$_R$: 9.46 min; Mass found: 443.

V. Standard Procedure for the Synthesis of Tether T77

4142-4146; *Bioorg. Med. Chem. Lett.* 2002, 12, 197-200; *J Med Chem.* 1979, 22, 1284-1290.]

Molecular weight calcd. for C$_5$H$_4$BrNO: 173; (M+H)$^+$. found: 174.

Step T77-2. To a solution of 3-bromo-pyridin-2-ol (77-1, 5 g, 0.028 mol), Ph$_3$P (11 g, 0.04 mol) and 2-(tert-butyldimethylsilanyloxy)-ethanol (77-A, 7 g, 0.04 mol) in 50 mL of THF was slowly added diethylazodicarboxylate (8.1 g, 0.04 mol) at room temperature. The progress of the reaction was easily monitored by TLC [hexanes/ethyl acetate (4:1); R$_f$=0.5; detection: CMA]. The mixture was stirred at room temperature for 24 h at which point the reaction was complete by TLC analysis. The solvent was removed under high vacuum and the residue purified by flash chromatography to obtain 77-2 as a pale brown liquid (6.3 g, 68%). [*Tetrahedron Lett.* 1994, 35, 2819-2822; *Tetrahedron Lett.* 1995, 36, 8917-8920; *Synlett*, 1995, 845-846. *Heterocycles* 1990, 31, 819-824.

Molecular weight calcd. for C$_{13}$H$_{22}$BrNO$_2$Si 331; (M+H)$^+$. found: 332.

Step T77-3. The protected alcohol 77-2 (3 g, 9.1 mmol) was dissolved in diisopropylamine (50 mL) and the reaction mixture degassed by bubbling argon through the solution. PdCl$_2$(PPh$_3$)$_2$ (410 mg, 0.61 mmol, 0.06 eq), CuI (74 mg, 0.4 mmol, 0.04 eq) and triphenylphosphine (310 mg, 1.12 mmol) were added, then the mixture was warmed to 70° C. and stirred O/N. The solvent was removed under high vacuum and the residue was purified by flash chromatography to obtain 77-3 as a pale brown liquid (3.36 g, 70%) [*Org. Lett.* 2003, 5, 2441-2444; *J. Chem. Soc. Perkin. Trans* 1 1999, 1505-1510; *J. Org. Chem.* 1993, 58, 2232-2243; *J. Org. Chem.* 1999, 58, 95-99; *Org. Lett.* 2000, 2, 2291-2293; *Org. Lett.* 2002, 4, 2409-2412]

TLC (hexanes/ethyl acetate, 1:3): R$_f$; =0.3; detection: CMA

Molecular weight calcd. for C$_{28}$H$_{40}$N$_2$O$_6$Si: 528; (M+H)$^+$. found: 529.

Step T77-4. The acetylene 77-3 (3 g, 5.67 mmol) was dissolved in EtOH (30 mL) and purged with nitrogen for 10 min. PtO$_2$ (10 mol %, 300 mg) was added and the mixture purged with a balloon full of hydrogen gas. The mixture was

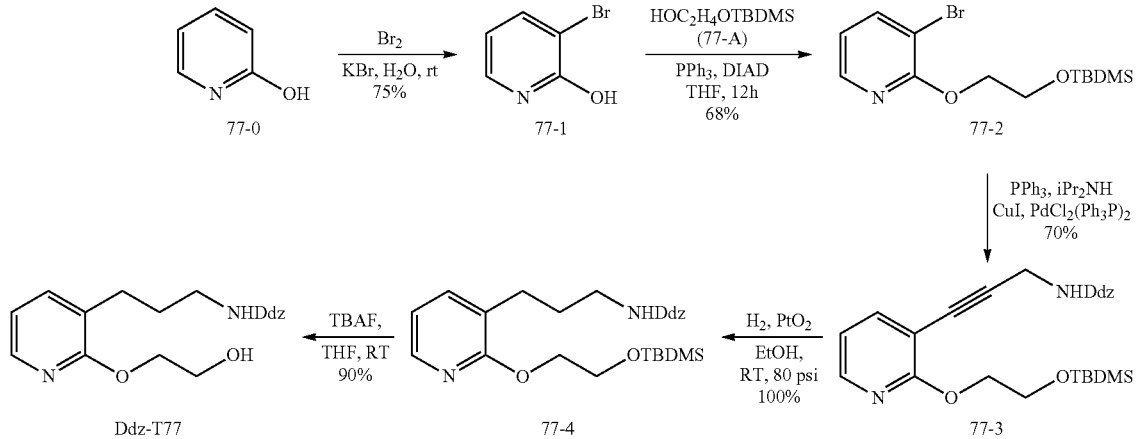

Step T77-1. 3-Bromo-pyridin-2-ol. A stirred suspension of 2-pyridone (77-0, 19 g, 200 mmol) in 200 mL, of 1 M aqueous KBr at room temperature was treated over 15 min with bromine (32 g, 200 mmol; CAUTION: Large quantities of Br$_2$ should be handled carefully!) in 200 mL of 1 M aqueous KBr, then stirred vigorously at room temperature O/N. After 24 h, this solution deposited crystals which were filtered off and then recrystallized from acetonitrile to give 27.2 g (78%) of 3-bromo-pyridin-2-ol. (77-1) [*J. Am. Chem. Soc.* 1982, 104, then charged into a Parr bomb, flushed with hydrogen (fill with hydrogen at 80 psi then release and refill, repeat this fill-release-refill cycle 3×), and maintained with hydrogen at 80 psi at room temperature O/N. The reaction mixture was filtered through a pad of Celite (use methanol for washing the residue on the Celite) and the filtrate plus washings was concentrated under reduced pressure to afford a practically pure (clean $^1$H NMR), but colored sample of 77-4 in a quantitative yield. Further purification was achieved by subjecting this material to flash chromatography. The product 77-4 has the same $R_f$ as the starting material (77-3), hence, $^1$H NMR is the best way to distinguish them.

TLC [(hexanes/ethyl acetate, 1:3); $R_f$=0.3 detection: CMA]

Molecular weight calcd. for $C_{28}H_{44}N_2O_6Si$: 532, (M+H)$^+$. found: 533.

Step T77-5. 77-4 (3 g, 5.6 mmol) was dissolved in anhydrous THF (200 mL). To the clear solution was added TBAF (6.7 mmol, 7 mL) and the mixture stirred for 2 h at room temperature. The solution was then poured into ice water. The aqueous solution was extracted with dichloromethane (3×200 mL). The organic layer was washed sequentially with saturated citrate buffer (1×200 mL), water (200 mL) and brine (200 mL). The washed organic extract was dried over anhydrous sodium sulfate, filtered and evaporated to dryness under reduced pressure to give an oily residue. This syrup was purified by flash chromatography (hexanes/AcOEt, 1:2) to give Ddz-T77 as a syrup (2.10 g, yield 90%). TLC (hexanes/AcOEt, 1:2): $R_f$=0.3; detection: ninhydrin $^1$H NMR (CDCl$_3$): δ 1.73 (s, 6H), 1.75 (m, 2H), 2.65 (m, 2H), 3.15 (m, 2H), 3.75 (s, 6H), 3.90 (m, 2H), 4.50 (m, 2H), 5.01 (sb, 1H), 6.30 (s, 1H), 6.50 (s, 2H), 6.80 (m, 1H), 7.40 (m, 1H), 8.01 (m, 1H).

$^{13}$C NMR (CDCl$_3$): δ 27.23 (CH$_2$), 29.24 (CH$_3$), 29.71 (CH$_2$), 40.17 (CH$_2$), 55.44 (CH$_3$), 62.76 (CH$_2$), 69.11 (CH$_2$), 80.76 (Cq), 98.24 (CH), 103.24 (CH), 117.54 (CH), 124.68 (Cq), 138.82 (CH), 144.17 (CH), 149.45 (Cq), 155.50 (Cq), 160.84 (Cq), 162.03 (Cq). Molecular weight calcd. for $C_{22}H_{30}N_2O_6$: 418; (M+H)$^+$. found: 419.

EXAMPLE 2

Synthesis of Representative Macrocyclic Compounds

The following are provided as representative examples for the macrocyclic compounds of the invention. For solid phase methods, all yields are reported starting from 300-325 mg of PS-aminomethyl resin (loading 2.0 mmol/g) unless otherwise noted. Attachment of the first building block, BB$_3$, varies from 100% to 55% for the more difficult residues, typically sterically crowded structures such as Ile or Val. The remaining couplings for BB$_2$ and BB$_1$ proceed in an average yield of 80-90%. Attachment of the tether using the Mitsunobu reaction yields from 50-90% of the desired linear precursor. The macrocyclization itself proceeds in an average yield of 20-50%. Minimal loss of yield occurs in post-cyclization processing.

All the retention time values presented herein are based on the UV portion of the HPLC data. In the HPLC procedure, ELSD and CLND data (not listed) were also procured to further assess purity of the final products, and for quantification (CLND). All compounds were analyzed using the same HPLC conditions. The details for the HPLC procedure used was as follows: Column: XTerra MS C18 4.6×50 mm, 3.5 μm, from Waters, HPLC: Alliance 2695 from Waters; MS: Platform LC from Micromass/Waters; CLND: 8060 from Antek; PDA: 996 from Waters; Gradient_B4: (i) 0 to 50% MeOH: 0.1% aqueous TFA in 6 min, (ii) 3 min at 50% MeOH: 0.1% aqueous TFA; (iii) 50 to 90% MeOH: 0.1% aqueous TFA in 5 min; (iv) 3 min at 90% MeOH: 0.1% aqueous TFA. Retention time ($t_R$) for the compound is listed.

Modifications were made to the standard methods for compounds 58, 99, 201, 203 and 215.

Compound 1

Yield: 33.4 mg pure macrocycle was obtained (CLND quantification).

$^1$H NMR (300 MHz, DMSO-d$_6$): δ 8.53, 8.41, 8.34 (doublets J=8.7 Hz for all, 1H); 8.13-8.06, 7.82-7.75 (multiplets, 1H); 7.30-7.05 (m, 8H); 6.90-6.77 (m, 2H); 4.58-4.46, 4.40-4.29, 4.27-4.16 (multiplets, 1H); 4.09-3.99, 3.97-3.82 (multiplets, 2H); 3.77-3.44 (m, 2H); 3.37-3.19 (m, 4H); 3.15, 3.08 (2 s, 2H); 2.98-2.86 (m, 5H); 2.52 (s, 3H); 1.94-1.75, 1.60-1.30 (multiplets, 2H); 1.22 (br s, 4H); 0.86-0.75 (m, 3H).

HRMS calc. for $C_{29}H_{40}N_4O_4$; 508.3049. found 508.3040±0.0015.

HPLC $t_R$=8.94 min

Compound 3

Yield: 33.0 mg pure macrocycle was obtained (CLND quantification).

$^1$H NMR (300 MHz, DMSO-d$_6$): δ 8.54 (d, J=9.4 Hz), 8.43-8.36 (m), and 8.12 (br t, J=5.65 Hz) (1H); 7.90 (d, J=6.6 Hz); 7.79-7.72 (m) (1H); 7.30-7.05 (m, 6H); 6.90-6.76 (m, 3H); 4.60-4.50 (m), 4.43 (d, J=18.3 Hz), 4.26-4.16 (m) (1H); 4.13-4.02 (m, 1H); 4.01-3.84 (m, 2H); 3.74-3.41 (m, 2H); 3.17, 3.09 (2 s, 3H); 2.99-2.86 (m, 5H); 2.43-2.18 (m, 1H); 1.97-1.75 (m, 3H); 1.72-1.39 (m, 1H); 0.96 (d, 5.76 Hz, 3H); 0.93-0.77 (m, 2H); 0.68 (d, 5.76 Hz, 3H).

HRMS calc. for $C_{28}H_{38}N_4O_4$; 494.2893. found 494.2888±0.0015.

HPLC $t_R$=8.11 min.

Compound 4

Yield: 15.3 mg pure macrocycle was obtained (CLND quantification).

$^1$H NMR (300 MHz, CD$_3$CN): δ 7.48-7.19 (m, 6H); 7.13-6.98 (m, 3H); 4.71-4.51 (m, 3H); 4.48-4.32 (m, 1H); 4.26-4.01 (m, 1H); 3.79-3.57 (m, 2H); 3.48-3.20 (m, 3H); 3.19-3.06 (m, 5H); 3.01-2.89 (m, 2H); 2.80-2.62 (m, 2H); 2.09-1.96 (m, 3H); 1.94-1.70 (m, 1H); 1.57-1.36 (m, 4H); 1.32-1.26 (m, 1H); 1.08-0.97 (m, 3H).

HRMS calcd for $C_{29}H_{40}N_4O_4$; 508.3049. found 508.3045±0.0015.

HPLC $t_R$=8.37 min

Compound 6

Yield: 28.2 mg macrocycle was obtained (CLND quantification).

$^1$H NMR (300 MHz, DMSO-d$_6$): δ 10.80 (s, 1H); 8.46 (d, J=9.65 Hz), 8.36-8.28 (m), 8.14-8.07 (m), and 8.02 (d, J=9.65 Hz) (1H); 7.73-7.65 (m), 7.59 (d, 8.2 Hz), and 7.51 (d, J=8.2 Hz) (1H); 7.3 (d, J=8.2 Hz, 1H); 7.16-6.91 (m, 5H); 6.89-6.76 (m, 2H); 4.62-4.49 (m) and 4.42-4.24 (m) (1H); 4.15-3.81 (m, 2H); 3.77-3.43 (m, 2H); 3.41-3.19 (m, 6H); 3.22-2.85 (m, 6H); 2.52 (s, 3H); 1.89-1.69 (m, 1H); 1.59-1.02 (m, 4H); 0.88-0.74 (m, 3H).

HRMS calc. for $C_{30}H_{39}N_5O_4$; 533.3002. found 533.2990±0.0016.

HPLC $t_R$=8.22 min.

Compound 8

Yield: 74.9 mg pure macrocycle was obtained (CLND quantification) from 600-650 mg starting resin $^1$H NMR (300 MHz, DMSO-d$_6$): δ 9.47 (br s), 9.07 (s) (1H) and 8.32 (br s) (2H); 7.94 (d, 6.6 Hz, 1H); 7.60-7.42 (m, 2H); 7.38 (d, 9.0 Hz, 1H); 7.28-7.04 (m, 7H); 6.93 (t, 8.1 Hz, 1H); 6.60 (d, J=14.4 Hz) and 6.39-6.27 (m) (1H); 4.51-4.38 (m, 1H); 4.29-4.08 (m, 2H); 3.87-3.63 (m, 2H); 3.40-3.13 (m, 2H); 2:94 (t, J=14.1 Hz, 1H); 2.53-2.50 (m, 1H); 2.32-2.17 (m, 1H); 1.86-1.06 (m, 10H); 0.95-0.79 (m, 6H).

HRMS calc. for $C_{32}H_{42}N_4O_4$; 546.3206. found 546.3198±0.0016.

HPLC $t_R$=9.02 min.

Compound 9

Yield: 33.7 mg pure macrocycle was obtained (CLND quantification).

$^1$H NMR (300 MHz, DMSO-$d_6$): δ 8.48 (s, 1H); 7.92 (d, J=5.3 Hz, 1H); 7.81 (d, J=8.5 Hz, 1H); 7.26-7.08 (m, 7H); 6.88-6.75 (m, 2H); 4.30 (br t, J=10.1 Hz, 1H); 4.0 (t, J=8.6 Hz, 1H); 3.87 (br d, J=8.6 Hz, 1H); 3.70-3.58 (m, 1H); 3.4-3.25 (m, 1H); 3.04-2.85 (m, 3H); 2.73 (d, 7.67 Hz, 1H); 2.53 (s, 3H); 2.35-2.09 (m, 2H); 1.92-1.44 (m, 8H); 1.42-1.18 (m, 2H); 0.85, 0.81 (2 doublets, J=6.76 Hz, 6H).

$^{13}$C NMR (75 MHz, DMSO-$d_6$): δ 176.15; 173.20; 171.27; 157.18; 140.08; 130.72; 130.52; 129.71; 128.64; 127.87; 126.62; 120.88; 111.44; 68.29; 67.10; 66.99; 55.24; 48.42; 41.11; 41.03; 39.36; 36.93; 35.77; 34.65; 32.38; 30.55; 29.96; 23.83; 22.65; 19.87.

HRMS calc. for $C_{31}H_{42}N_4O_4$; 534.3206. found 534.2139±0.0016.

HPLC $t_R$=9.29 min.

Compound 10

Yield: 19.2 mg pure macrocycle was obtained (CLND quantification).

$^1$H NMR (300 MHz, DMSO-$d_6$): δ 8.53, 8.41, 8.38 (doublets, J=8.8, 8.5, 8.5 Hz, 1H); 8.16-8.05, 7.87-7.71 (multiplets, 1H); 7.31-7.04 (m, 7H); 6.91-6.75 (m, 2H); 4.60-4.45, 4.39-4.30, 4.28-4.16 (m, 1H); 4.10-4.00, 3.97-3.83 (m, 2H); 3.73-3.46 (m, 2H); 3.22-3.20 (m 1H), 3.16, 3.09 (2 s, 3H); 2.45-2.39 (m, 1H); 2.99-2.86 (m, 1H); 2.85-2.58 (m, 5H); 2.48-2.22 (m, 1H); 2.07 (s, 1H), 1.95-1.78 (m, 1H), 1.75-1.42 (m, 1H), 1.42-1.17 (m, 4H), 0.88-0.77 (m, 3H).

HRMS calc. for $C_{28}H_{38}N_4O_4$; 494.2893. found 494.2888±0.0015.

HPLC $t_R$=8.27 min

Compound 221

Yield: 50.3 mg macrocycle was obtained (CLND quantification).

$^1$H NMR (300 MHz, DMSO-$d_6$): δ 7.86 (d, J=6.7 Hz) and 7.65-7.58 (m) (1H); 7.28-7.06 (m, 7H); 6.88 (d, 8.06 Hz, 1H); 6.81 (t, J=6.7 Hz, 1H); 4.07-3.91 (m, 3H); 3.77-3.65 (m, 1H); 3.56-3.38 (m, 2H); 3.35-3.25 (m, 3H); 3.25-3.07 (m, 2H); 3.04-2.63 (m, 3H); 2.52 (s, 3H); 2.01-1.71 (m, 4H); 1.66-1.49 (m, 2H); 1.47-1.17 (m, 4H); 0.90-0.78 (m, 3H).

$^{13}$C NMR (75 MHz, DMSO-$d_6$): δ 172.15; 170.81; 170.74; 157.29; 139.62; 130.76; 130.56; 129.56; 128.82; 61.73; 59.29; 56.37; 47.90; 41.11; 41.03; 39.36; 35.81; 35.43; 30.23; 30.03; 29.63; 25.12; 19.15; 14.66.

HRMS calc. for $C_{30}H_{40}N_4O_4$; 520.3049. found 520.3041±0.0016.

HPLC $t_R$=8.30 min

EXAMPLE 3

Alternative Synthetic Strategies

Alternative synthetic strategies amenable to larger scale synthesis of compounds of the present invention are discussed below.

A. Method LSI for Representative Large Scale Synthesis of Compounds of the Invention

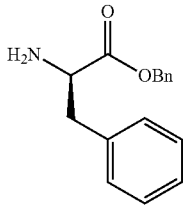
H-(D)Phe-OBn

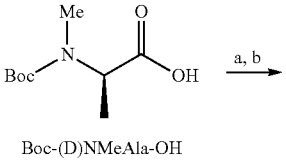
Boc-(D)NMeAla-OH a, b →

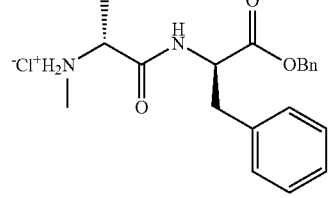
LS1-6 a. EDCl, 6-ClHOBt, DIPEA, THF:DCM;
b. 4M HCl/dioxane (quant. 2 steps)

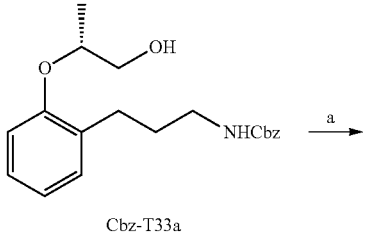
Cbz-T33a a →

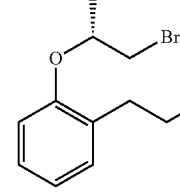
LS1-8 b →

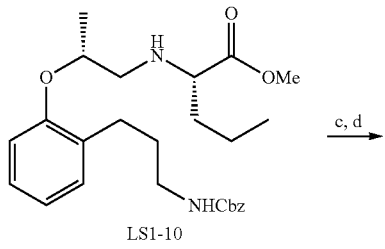
LS1-10 c, d →

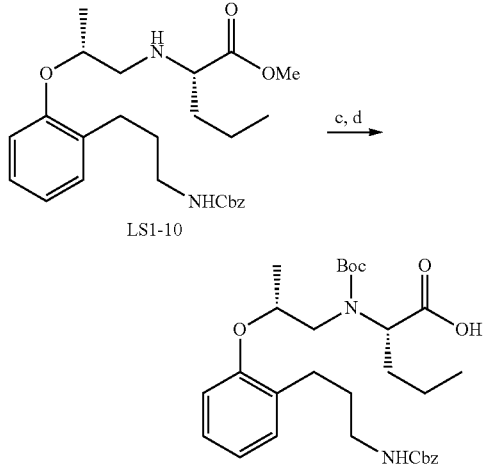
LS1-7 a. NBS, PPh$_3$, DCM (91%); b. H-Nva-OMe, Na$_2$CO$_3$, DMF 110° C. (85%);
c. (Boc)$_2$O, Na$_2$CO$_3$, THF:H$_2$O; d. LiOH, THF: H$_2$O (83% 2 steps)

-continued

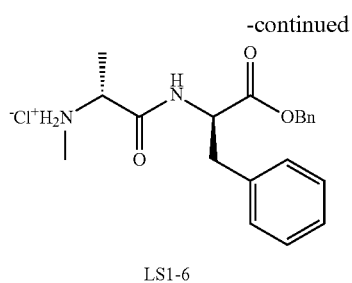

LS1-6

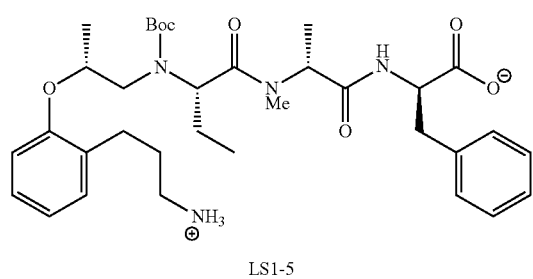

LS1-7 a, b → a. HATU, DIPEA, DCM:THF (73%); b. H$_2$, Pd/C, AcOEt (quant.)

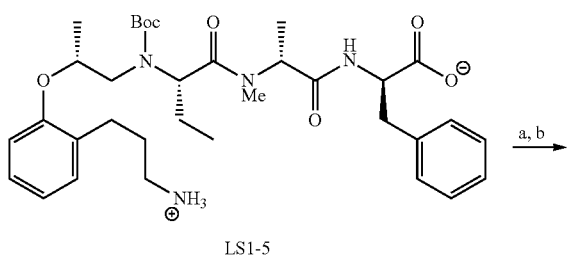

LS1-5 a, b →

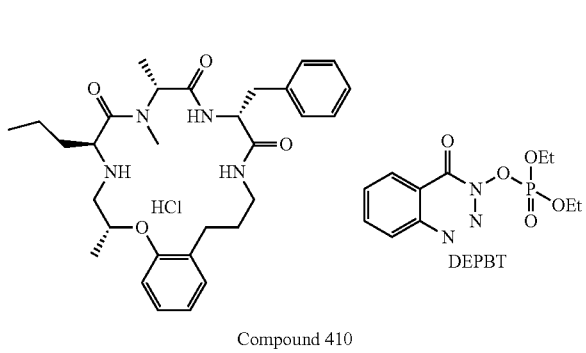

Compound 410 a. DEPBT, DIPEA, THF (67-84%);
b. HCl 4M/dioxane (quant.)

Step LS1-A: Synthesis of LS1-8

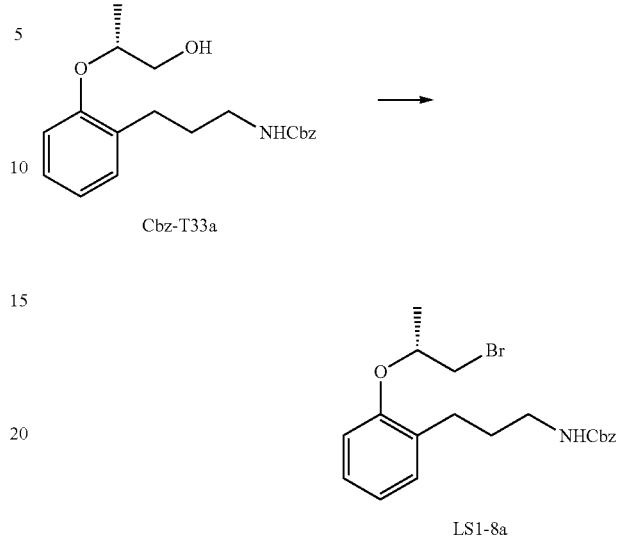

Cbz-T33a

LS1-8a

To alcohol Cbz-T33a (2.4 g, 7.0 mmol, 1.0 eq) in CH$_2$Cl$_2$ (50 mL) were added NBS (1.5 g, 8.4 mmol, 1.2 eq) and PPh$_3$ (2.2 g, 8.4 mmol, 1.2 eq). The mixture was stirred at room temperature O/N and a saturated aqueous NH$_4$Cl solution was added. The aqueous phase was extracted with CH$_2$Cl$_2$ (2×) and the combined organic phases were extracted with a saturated aqueous NH$_4$Cl solution to remove succinimide byproduct. The organic phase was dried over MgSO$_4$ and concentrated under reduced pressure. The residue was purified by flash chromatography (20% AcOEt, 80% hexanes) to give bromide LS1-8a as a yellow oil (2.6 g, 91%).

TLC (30% AcOEt, 70% hexanes): R$_f$=0.56; detection: UV and CMA $^1$H NMR (CDCl$_3$): δ 7.37-7.26 (5H, m, Ph), 7.19-7.13 (2H, m, Ph), 6.90 (1H, t, Ph), 6.83 (1H, d, Ph), 5.10 (2H, s, NHC(O)OCH$_2$Ph), 4.96 (1H, broad, NHCbz), 4.59 (1H, sextuplet, PhOC$\underline{H}$(CH$_3$)CH$_2$Br), 3.58-3.47 (2H, m, CH$_2$Br), 3.19 (2H, q, C$\underline{H_2}$NHCbz), 2.67 (2H, t, PhC$\underline{H_2}$CH$_2$), 1.78 (2H, quint, PhC$\underline{H_2}$CH$_2$), 1.44 (3H, d, CHC$\underline{H_3}$).

LC/MS (Grad_A4): t$_R$=11.15 min

Step LS1-B1: Synthesis of LS1-10

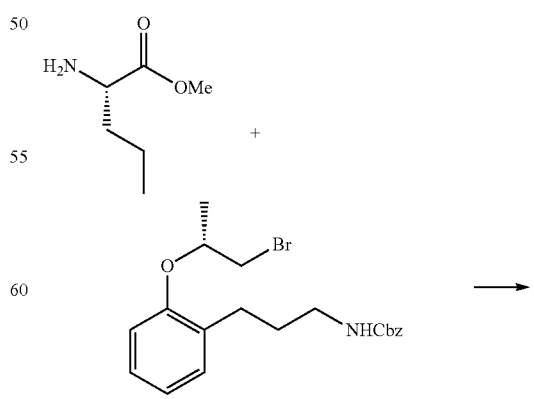

LS1-8a (X = Br)
LS1-8b (X = OTs)

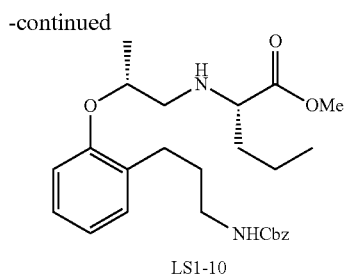

LS1-10

The hydrochloride salt of H-Nva-OMe was dissolved in an aqueous solution of Na$_2$CO$_3$ (1 M) and saturated with NaCl to ensure extraction of all of the free amine. The aqueous solution was extracted with AcOEt (3×). The combined organic phases were extracted with brine, dried over MgSO$_4$, filtered and concentrated under reduced pressure. The free amine, H-Nva-OMe, was recovered in 90% yield. It is important to perform the alkylation with the free amine (H-Nva-OMe) to eliminate chloride formation (OTs to Cl) as a side reaction. In a dried round-bottomed flask, bromide LS1-8a (740 mg, 1.83 mmol, 1.0 eq) and H-Nva-OMe (479 mg, 3.60 mmol, 2.0 eq) were added. Degassed (by stirring under vacuum for 30 min) DMF (3.7 mL), anhydrous Na$_2$CO$_3$ (232 mg, 2.19 mmol, 1.2 eq) and KI (61 mg, 0.37 mmol, 0.2 eq) were added and the mixture stirred at 110° C. O/N. Water was added and the aqueous phase was extracted with Et$_2$O (3×). The combined organic phases were extracted with water (2×), then brine (1×). The organic phase was dried over MgSO$_4$, filtered and concentrated under reduced pressure. The residue was purified by flash chromatography (30% AcOEt: 70% hexanes) to give secondary amine LS1-10 as a yellow oil (709 mg, 85%).

TLC (30% AcOEt, 70% hexanes): R$_f$=0.32; detection: UV and CMA $^1$H NMR (CDCl$_3$): δ 7.35-7.29 (5H, m, Ph), 7.17-7.12 (2H, m, Ph), 6.91-6.84 (2H, m, Ph), 5.51 (1H, broad, CH$_2$N HCHRR'), 5.09 (2H, s, OCH$_2$Ph), 4.67-4.51 (1H, m, PhOC H(CH$_3$)R), 3.65 (3H, s, C(O)OCH$_3$), 3.24-3.10 (3H, m, NHC H(Pr)CO$_2$Me and CH$_2$NHCbz), 2.87-2.41 (4H, m, PhC H$_2$CH$_2$ and NHCH$_2$CH(Me)OPh), 1.86-1.76 (2H, m, PhCH$_2$CH$_2$), 1.70-1.63 (2H, m, CH$_3$CH$_2$CH$_2$), 1.36-1.28 (2H, m, CH$_3$CH$_2$CH$_2$), 1.23 (3H, d, CHCH$_3$), 0.90 (3H, t, C H$_3$CH$_2$CH$_2$).

$^{13}$C NMR (CDCl$_3$): δ 176.44, 156.88, 155.58, 137.14, 131.16, 130.57, 128.68, 128.34, 128.21, 127.33, 120.79, 112.62, 73.16, 66.62, 61.30, 54.21, 51.95, 40.86, 36.02, 30.60, 27.88, 19.20, 17.80, 14.07.

LC/MS (Grad_A4): t$_R$=6.76 min

Step LS1-B2: Alternative Synthesis of LS1-10

To a solution of alcohol Cbz-T33a (8.5 g, 24.7 mmol, 1.0 eq) in CH$_2$Cl$_2$ (125 mL) were added Et$_3$N (10.4 mL, 74.1 mmol, 3.0 eq), TsCl (5.2 g, 27.2 mmol, 1.1 eq) and DMAP (302 mg, 2.47 mmol, 0.1 eq). The mixture was stirred O/N at room temperature and then an aqueous solution of saturated NH$_4$Cl was added. The aqueous phase was extracted with CH$_2$Cl$_2$ (2×) and the combined organic phases were dried over MgSO$_4$, filtered and concentrated under reduced pressure. The residue was purified by flash chromatography (30% AcOEt, 70% hexanes) to give tosylate LS1-8b as an oil (9.4 g, 90%).

TLC (50% AcOEt, 50% hexanes): R$_f$=0.47; detection: UV and CMA $^1$H NMR (CDCl$_3$): δ 7.74 (2H, d, Ph), 7.36-7.26 (7H, in, Ph), 7.14-7.08 (2H, m, Ph), 6.88 (1H, t, Ph), 6.74 (1H, d, Ph), 5.10 (2H, s, NHC(O)OCH$_2$Ph), 4.97 (1H, broad, NHCbz), 4.61-4.55 (1H, m, PhOCH(CH$_3$)CH$_2$OTs), 4.19-4.05 (2H, m, CH$_2$OTs), 3.15 (2H, q, CH$_2$NHCbz), 2.56 (2H, td, PhC H$_2$CH$_2$), 2.42 (3H, s, PhCH$_3$) 1.74 (2H, quint, PhCH$_2$CH$_2$), 1.27 (3H, d, CHCH$_3$)

$^{13}$C NMR (CDCl$_3$): δ 156.67, 155.05, 145.20, 137.04, 133.02, 131.16, 130.65, 130.11, 128.72, 128.28, 128.23, 128.10, 127.39, 121.50, 112.87, 71.99, 71.42, 66.68, 40.79, 30.32, 27.57, 21.87, 16.74.

LC-MS (Grad_A4): t$_R$=11.02 min

Application of the procedure in Step LS1-B1, but substituting the tosylate LS1-8b as alkylating agent gave 73% yield of LS1-10 with 2 eq of H-Nva-OMe.

Step LS1-C1: Synthesis of LS1-7

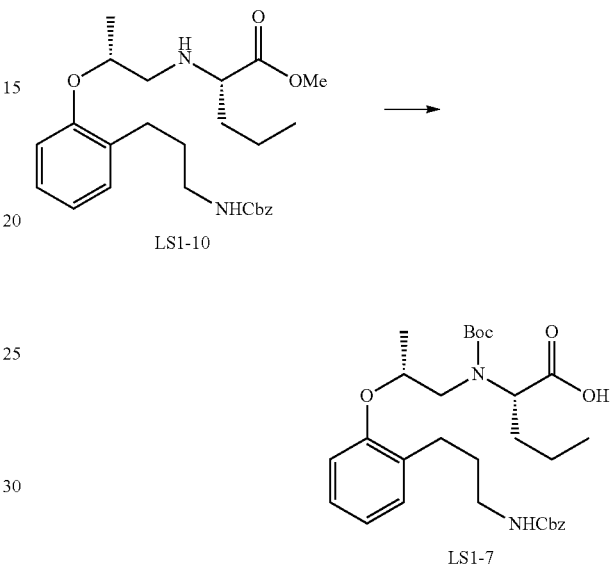

To a solution of amine LS1-10 (697 mg, 1.53 mmol, 1.0 eq) in THF/H$_2$O (1:1, 15 mL) at 0° C. were added Na$_2$CO$_3$ (244 mg, 1.68 mmol, 1.5 eq) and (Boc)$_2$O (366 mg, 1.68 mmol, 1.1 eq), then the mixture stirred at room temperature for 36-48 h. THF was evaporated under reduced pressure and the aqueous phase was extracted with Et$_2$O (3×). The combined organic phases were extracted with brine, dried over MgSO$_4$, filtered and concentrated under reduced pressure. The Boc compound was obtained as a yellow oil and used without further purification for the next reaction.

TLC (30% AcOEt, 70% hexane): R$_f$=0.49; detection: UV and CMA

To a solution of the crude Boc compound in THF/H$_2$O (1:1, 15 mL) was added LiOH (309 mg, 7.35 mmol, 5.0 eq) and the mixture stirred O/N at rt. THF was evaporated under reduced pressure and the remaining aqueous basic phase was then acidified with 1 M HCl to pH 3 (pH paper). The aqueous phase was extracted with AcOEt and the combined organic phases were extracted with water and brine. The organic phase was dried over MgSO$_4$, filtered and concentrated under reduced pressure. Carboxylic acid LS1-7 was obtained as a yellow oil (687 mg, 83%, 2 steps).

TLC (50% AcOEt, 50% hexane): R$_f$=0.32; detection: UV and CMA $^{13}$C NMR (CDCl$_3$): δ 176.11, 156.81, 155.51, 155.18, 136.93, 131.13, 130.37, 128.72, 128.31, 127.44, 121.20, 113.70, 81.36, 73.40, 66.79, 61.99, 40.80, 32.83, 31.56, 30.33, 28.48, 27.48, 20.10, 17.53, 14.11.

LC/MS (Grad_A4): t$_R$=12.50 min

Step LS1-C2: Divergent Synthetic Route (No Amine Protection)

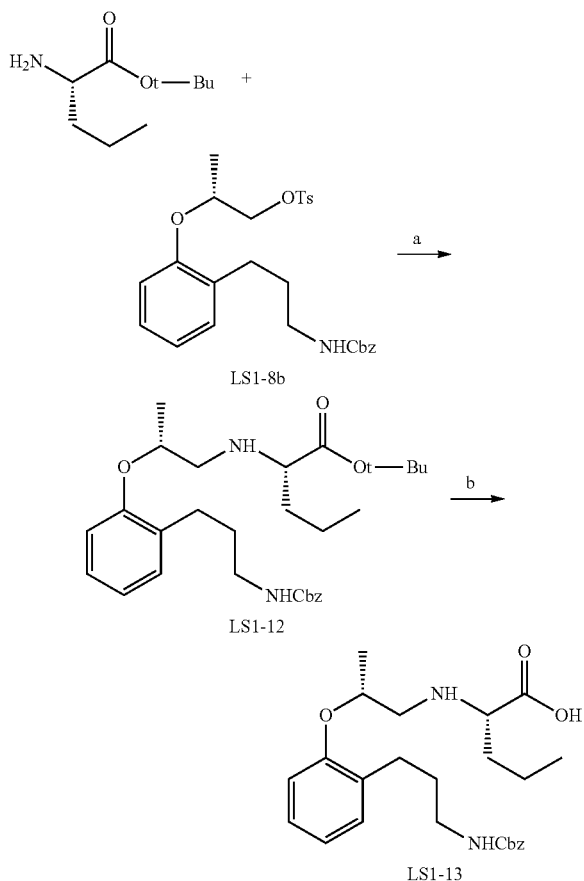

a. Na₂CO₃, DMF 110° C.;
b. HCl 4M/dioxane;

The H-Nva-OtBu.HCl was dissolved in an aqueous solution of Na₂CO₃ (1 M) and saturated with NaCl to ensure extraction of all of the free amine. This aqueous solution was extracted with AcOEt (3×). The combined organic phases were extracted with brine, dried over MgSO₄, filtered and concentrated under reduced pressure. About 90% of the free amine, H-Nva-OtBu, was recovered. It is important to perform the alkylation with the free amine (H-Nva-OtBu) to eliminate chloride side product formation (OTs->Cl).

In a dried round-bottomed flask, tosylate LS1-8b (1.0 g, 2.01 mmol, 1.0 eq) and H-Nva-OtBu (752 mg, 4.02 mmol, 2.0 eq) were added. Degassed (by stirring under vacuum for 30 min) DMF (4 mL) and anhydrous Na₂CO₃ (256 mg, 2.41 mmol, 1.2 eq, note that other bases were less effective) were added and the mixture stirred at 110° C., O/N. Water was added and the aqueous phase extracted with Et₂O (3×). The combined organic phases were extracted with water (2×) and brine (1×). The organic phase was dried over MgSO₄, filtered and concentrated under reduced pressure. The residue was purified by flash chromatography (30% AcOEt: 70% hexanes) to give the amine, LS1-12, as a yellow oil (683 mg, 75%). This crude secondary amine (1.0 eq) was dissolved in 4 M HCl/dioxane (10 eq) and the mixture stirred O/N at room temperature. The solvent was evaporated under reduced pressure and Et₂O added to the residue. A white precipitate was formed upon addition of hexanes to this mixture. The precipitate was filtered and rinsed with cold hexanes to give the desired amino acid, LS1-13, as a white solid.

TLC (50% AcOEt, 50% hexane): R$_f$=0.71; detection: UV and CMA

LS1-13, despite the presence of the free amine, has been used in the remaining part of the synthetic scheme to successfully access the desired macrocycle.

Step LS1-D: Synthesis of Dipeptide LS1-6

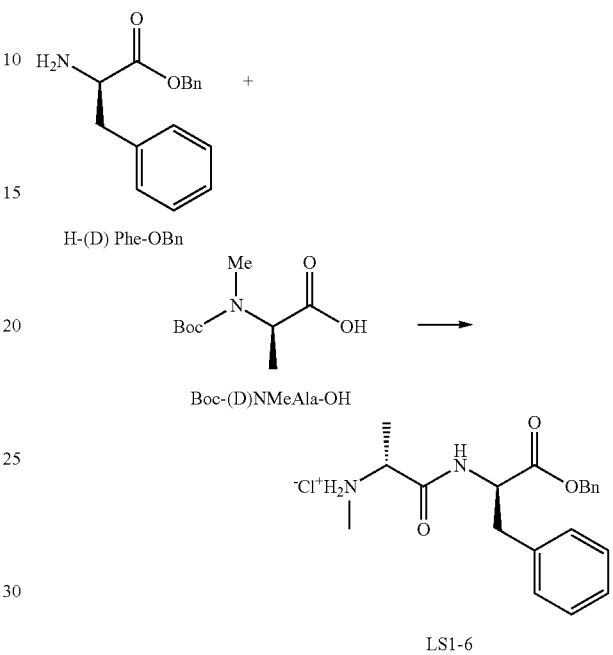

The tosylate salt of H-(D)Phe-OBn was dissolved in an aqueous solution of 1 M Na₂CO₃ and the aqueous solution extracted with AcOEt (3×). The combined organic phases were extracted with brine, dried over MgSO₄, filtered and concentrated under reduced pressure. The free amine H-(D) Phe-OBn was recovered in 90% yield. To a solution of H-(D) Phe-OBn (3.0 g, 11.76 mmol, 1.0 eq) in THF/CH₂Cl₂ 1/1 (60 mL) were added Boc-(D)NMeAla-OH (2.5 g, 12.35 mmol, 1.05 eq), 6-Cl HOBt (2.0 g, 11.76 mmol, 1.0 eq) and DIPEA (10.2 mL, 58.8 mmol, 5.0 eq). The mixture was cooled to 0° C. and EDCI (2.48 g, 12.94 mmol, 1.1 eq) was added. The mixture was stirred 1 h at 0° C. and at room temperature O/N. Solvent was evaporated under reduced pressure and the residue dissolved in AcOEt. The organic phase was washed sequentially with an aqueous 1 M solution of citrate buffer (pH 3.5, 2×), an aqueous solution of saturated NaHCO₃ (2×) and brine (1×). The organic phase was dried over MgSO₄, filtered and concentrated under reduced pressure. The dipeptide was obtained as a yellow oil and used as obtained for the next step (5.3 g, 100%). The dipeptide was dissolved in a solution of HCl/dioxane (4 M, 30 mL, 10 eq), 50 mL, of dioxane were then added to facilitate the agitation and the mixture stirred for 1 h at room temperature; a heterogeneous solution was obtained. The mixture was concentrated under reduced pressure and dried further on mechanical vacuum pump. The dipeptide hydrochloride salt LS1-6 was obtained as pale yellow solid (4.4 g, 100%).

¹H NMR (DMSO-d₆): δ 9.40-8.70 (3H, d and 2 broads, C(O)NH and CH₃NH₂⁺Cl⁻), 7.39-7.17 (10H, m, Ph), 5.11 (2H, s, C(O)OCH₂Ph), 4.69-4.61 (1H, m, CHCH₃), 3.69 (1H, dd, CHCH₂Ph), 3.31 (3H, s, CH₃NH₂⁺Cl⁻), 3.17-3.11 and 2.97-2.90 (CHCH₂Ph), 1.28 (3H, d, CHCH₃)

¹³C NMR (DMSO-d₆): δ 171.33, 169.18, 137.63, 136.31, 129.92, 129.11, 128.95, 128.83, 128.63, 127.30, 67.00, 56.57, 54.38, 36.98, 31.11, 16.47.

LC/MS (Grad_A4): t$_R$=6.17 min

Step LS1-E: Synthesis of Amino Acid LS1-5

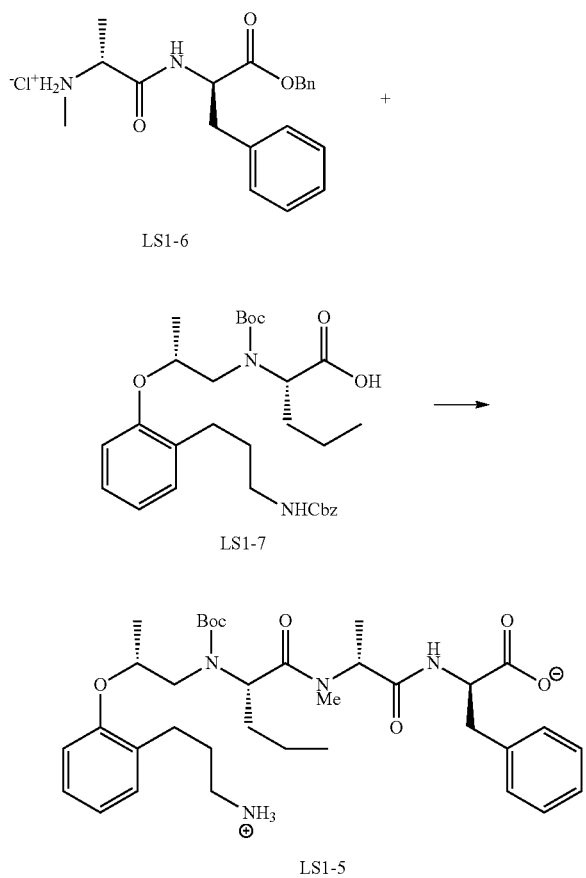

Step LS1-F: Macrocyclization and Final Deprotection

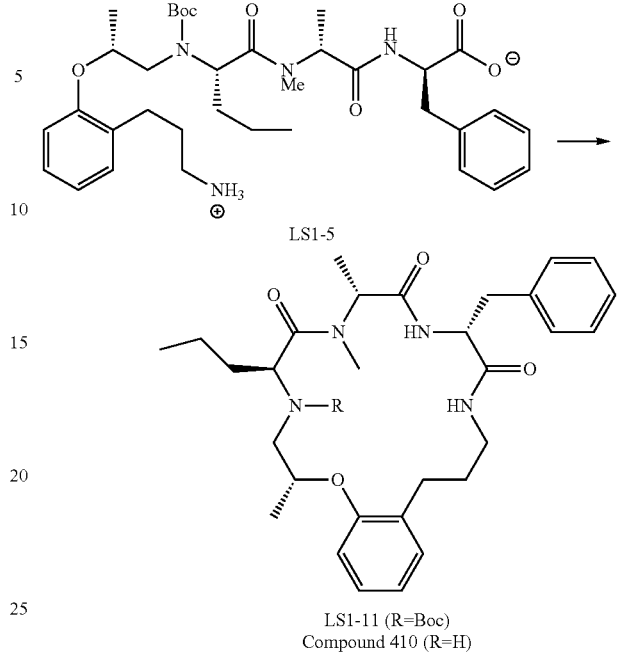

To a solution of acid LS1-7 (1.45 g, 2.67 mmol, 1.05 eq) in THF/CH$_2$Cl$_2$ (1/1, 13 mL) at 0° C. were added hydrochloride salt LS1-6 (958 mg, 2.55 mmol, 1.0 eq), DIPEA (2.2 mL, 12.8 mmol, 5.0 eq) and HATU (1.07 g, 2.81 mmol, 1.1 eq). The mixture was stirred at room temperature O/N. Solvent was evaporated and the residue was dissolved in AcOEt. The organic phase was washed sequentially with an aqueous solution of 1 M citrate buffer (pH=3.5, 2×), aqueous solution of saturated NaHCO$_3$ (2×), then with brine (1×). The organic phase was dried over MgSO$_4$, filtered and concentrated under reduced pressure. The residue was purified by flash chromatography (gradient: 20% AcOEt, 80% hexanes to 30% AcOEt, 70% hexanes) to give the desired fully protected tripeptide as a pale yellow gummy foam (1.6 g, 73%).

TLC (50% AcOEt, 50% hexanes): R$_f$=0.78; detection: UV and CMA

LC/MS (Grad_A4): t$_R$=15.15 min

To a solution of the protected, alkylated tripeptide (1.5 g, 1.75 mmol, 1.0 eq) in AcOEt (231n L) was added 10% Pd/C (20% by weight, 315 mg) and then hydrogen was bubbled through the solution. The mixture was stirred O/N under a hydrogen atmosphere. Nitrogen was bubbled through the reaction, then the mixture filtered on a Celite pad and rinsed with AcOEt. The combined filtrate was evaporated under reduced pressure to give LS1-5 as a white solid (1.1 g, quantitative).

TLC (50% AcOEt, 50% hexanes): R$_f$=0.52; detection: UV and CMA

LCMS (Grad_A4): t$_R$=8.23 min

To a solution of cyclization precursor LS1-5 (50 mg, 0.08 mmol, 1.0 eq) in THF (3.2 mL, for a concentration of 25 mM) was added DIPEA (68 µL, 0.39 mmol, 5.0 eq) and DEPBT (28 mg, 0.094 mmol, 1.2 eq) and the mixture stirred at room temperature O/N. Solvent was evaporated under reduced pressure and the residue purified by flash chromatography (1% MeOH, 99% CH$_2$Cl$_2$) to give Boc-protected macrocycle LS1-11 as a white solid (40 mg, 0.064 mmol, 80%). On a 1 g scale of precursor LS1-5 at a reaction concentration of 25 mM, the yield was 73%.

TLC (5:95 MeOH:DCM): R$_f$=0.43; detection: UV and CMA $^1$H NMR (DMSO-d$_6$ 60° C.): δ 7.62 (1H, d, NH), 7.47 (1H, broad, NH), 7.27-7.08 (7H, m, Ph), 6.85-6.79 (2H, m, Ph), 4.78 (1H, broad), 4.51-4.38 (1H, m), 4.11-4.02 (2H, m), 3.62-3.56 (1H, m), 3.32-3.04 (5H, m), 2.92 (3H, s, N—CH$_3$), 2.72-2.46 (2H, m), 1.90-1.59 (4H, m), 1.46 (9H, s, C(CH$_3$)$_3$), 1.28-1.06 (8H, m), 0.65 (3H, t, CH$_2$CH$_3$).

$^{13}$C NMR (DMSO-d$_6$): δ 172.03, 171.07, 155.83, 155.60, 139.69, 131.82, 130.82, 129.69, 128.73, 127.73, 126.75, 121.06, 113.40, 80.66, 74.75, 57.22, 56.66, 50.49, 35.88, 33.72, 32.71, 30.41, 28.68, 19.35, 18.44, 14.95, 14.19.

LC-MS (Grad_A4): t$_R$=12.82 min

Macrocycle LS1-11 (565 mg, 0.91 mmol, 1.0 eq) was dissolved in a solution of 4 M HCl/dioxane (4.6 mL, 20 eq) and the mixture stirred 2 h at room temperature. The mixture was concentrated under reduced pressure and placed under vacuum (oil pump) to give final macrocycle Compound 410 as a white solid (508 mg, 100%).

Chiral HPLC indicated no racemization when compared to its (L)-antipode at position AA$_3$.

$^1$H NMR (DMSO-d$_6$, 60° C.): δ 9.38 (1H, broad), 8.28 (1H, d), 8.13 (1H, broad), 7.81 (1H, t), 7.28-7.13 (7H, m, Ph), 6.93-6.87 (2H, m, Ph), 4.84-4.77 (1H, m), 4.54-4.40 (3H, m), 3.35-3.07 (6H, m), 2.94 (3H, s, N—CH$_3$), 2.90-2.81 and 2.64-2.47 (2H, m), 1.85-1.64 (4H, m), 1.38-1.21 (5H, m), 1.10 (3H, d, CH$_3$), 0.88 (3H, t, CH$_2$CH$_3$).

$^{13}$C NMR (CDCl$_3$): δ 171.92, 171.46, 170.44, 155.11, 139.07, 131.68, 130.47, 129.87, 128.67, 127.54, 126.90, 121.50, 112.94, 69.83, 67.03, 58.14, 56.33, 55.61, 55.29, 53.88, 50.48, 37.29, 32.29, 31.08, 29.70, 28.58, 18.15, 17.89, 15.20, 14.55.

LC-MS (Grad_A4): t$_R$=6.23 min
LC chiral (Grad35A-05): t$_R$=26.49 min
LC chiral (Grad40A-05): t$_R$=26.54 min

B. Method LS2 for Representative Large Scale Synthesis of Compounds of the Invention
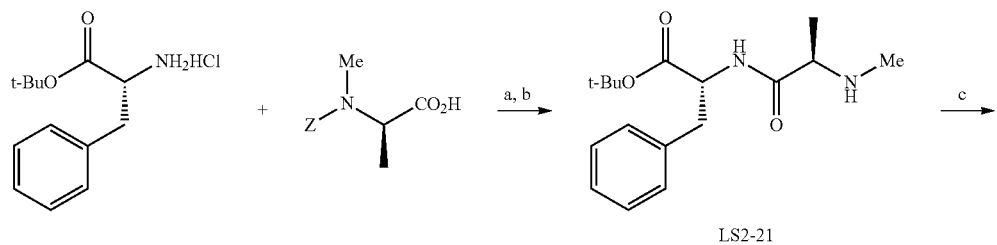
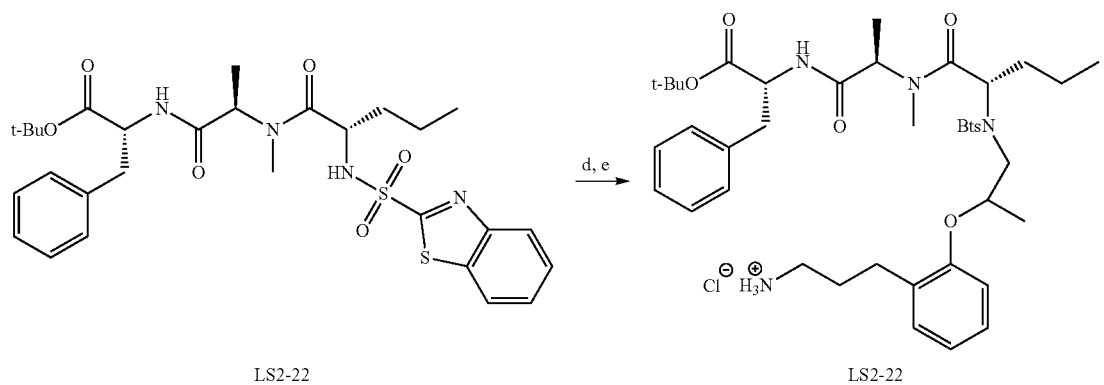
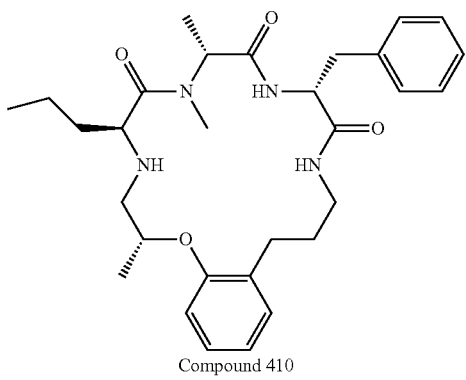
Compound 410
a. EDCl, 6ClHOBt, DIPEA, DMF (quant.);
b. H₂, Pd/C, EtOAc (quant.);
c. Bts-Nva-OH, HATU, DIPEA, DCM (80%);
d. bromide 1-8a, K₂CO₃, KI, DMF 80° C. (70%);
e. TFA:DCM:Et₃SiH (48:50:2);
f. DEPBT, DIPEA, THF (65-90% 2 steps);
g. HSCH₂CO₂H, K₂CO₃, DMF (80-90%)
Step LS2-A: Synthesis of Dipeptide LS2-21
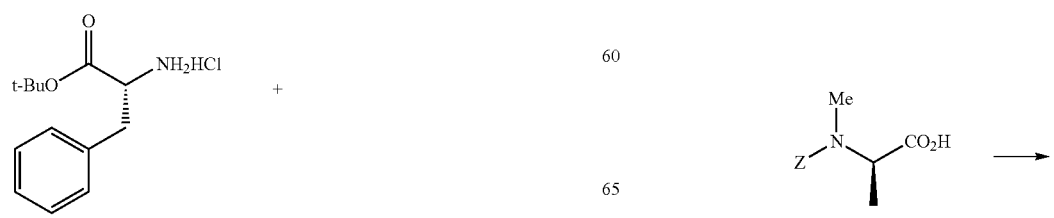
-continued

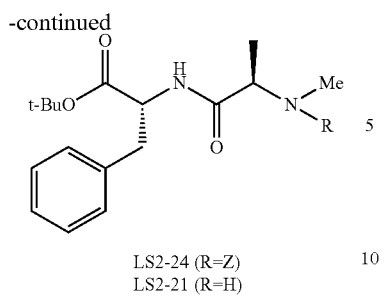

LS2-24 (R=Z)
LS2-21 (R=H)

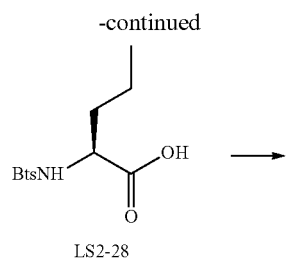

LS2-28

A stirred suspension of H-(D)Phe-OtBu.HCl (5 g, 0.02 mol, 1 eq) and Z-(D)NMeAla-OH (4.98 g, 0.021 mol, 1.05 eq) in 130 mL, of anhydrous THF-DCM (1:1) at room temperature was treated with DIPEA (17.50 mL, 0.1 mol, 5 eq) and 6-Cl-HOBt (3.40 g, 0.02 mol, 1 eq). The mixture was stirred vigorously at room temperature for several minutes, cooled with an ice bath, then EDCI (4.20 g, 0.022 mol, 1.1 eq) was added and the mixture stirred for 1 h. After this period of time, the ice bath was removed and the reaction was stirred at room temperature O/N. The solvent was removed under reduced pressure and the residue dissolved in 100 mL of AcOEt and washed with citrate buffer solution (1 N, 2×100 mL), saturated NaHCO₃ solution (2×100 mL) and brine. The organic layer was dried over anhydrous sodium sulfate, filtered and evaporated to dryness under reduced pressure to give 9.25 g (100%) of a colorless oil, LS2-24. TLC (hexanes/ethyl acetate, 1:1): $R_f$=0.3; detection: CMA and UV $^1$H NMR (CDCl₃): δ 1.25 (m, 2H), 1.40 (s, 9H), 2.66 (s, 3H), 2.85 (dd, 1H), 3.15 (dd, 1H), 4.70 (q, 2H), 5.15 (s, 2H), 6.50 (sb, 1H), 7.15 (m, 2H), 7.20 (m, 3H), 7.35 (m, 5H).

$^{13}$C NMR (CDCl₃): δ 28.18, 38.23, 53.61, 53.61, 67.87, 127.12, 128.40, 128.19, 128.40, 128.61, 128.8, 129.53, 170.01.

LC/MS (Grad_A4); $t_R$=9.73 min; Mass found: 440

Dipeptide LS2-24 (6.9 g, 0.015 mol) was dissolved in AcOEt (100 mL), then purged with nitrogen for 10 min 10% Pd—C (690 mg) was added and the mixture purged with a balloon full of hydrogen gas. The mixture was then hydrogenated under atmospheric pressure using a H₂ balloon. After 12 h, the reaction mixture was filtered through a short pad of Celite, and the filter cake washed with AcOEt. The combined filtrate and washings were concentrated under reduced pressure to afford practically pure (clean NMR), colorless, solid compound LS2-21 (4.30 g, 90%) which was used directly in the next step without further purification.

TLC (100% AcOEt): $R_f$=0.1; detection: CMA and UV.

$^1$H NMR (CDCl₃): δ 1.20 (t, J=7.03 Hz, 3H) (s, 9H), 2.40 (s, /H), 3.01-3.20 (m, 3H), 4.80 (q, 1H), 7.20 (m, 5H), 7.60 (m, 1H).

$^{13}$C NMR (CDCl₃): δ 19.64, 28.18, 35.12, 38.46, 53.06, 60.42, 82.29, 127.05, 128.50, 129.71, 136.61, 170.85, 174.28.

LC-MS (Grad_A4): $t_R$=5.86 min; Mass found: 306

Step LS2-B: Synthesis of Tripeptide LS2-22

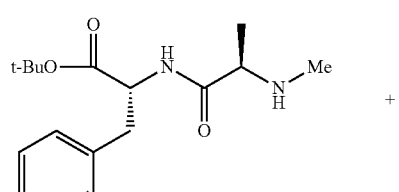

LS2-21

+

A stirred suspension of dipeptide LS2-21 (2 g, 6.50 mmol, 1 eq) and Bts-Nva-OH (LS2-28, 2.15 g, 6.85 mmol, 1.05 eq) in 32 mL of anhydrous DCM at 0° C. was treated with DIPEA (4.50 mL, 0.026 mol, 4 eq) and HATU (2.72 g, 7.18 mmol, 1.1 eq). The mixture was stirred vigorously at 0° C. for 1 h. After this period of time, the ice bath was removed and the reaction stirred at room temperature O/N. The solvent was removed in vacuo and the residue dissolved in 30 mL, of AcOEt. The organic phase was sequentially washed with 1 N citrate buffer solution (2×30 mL), saturated NaHCO₃ solution (2×30 mL) and brine (1×30 mL). The organic layer was then dried over anhydrous sodium sulfate, filtered and evaporated to dryness under reduced pressure. The residue was purified by flash chromatography [ethyl acetate/hexanes (1/1)] to afford LS2-22 as a colorless solid (3.13 g, 80%).

TLC (hexanes/ethyl acetate, 3:2): $R_f$=0.3; detection: CMA and UV $^1$H NMR (CDCl₃): δ 0.95 (m, 3H), 1.20 (d, 2H), 1.40 (s, 9H), 1.42-1.70 (m, 4H), 2.60 (m, 2H), 2.90 (s, 3H), 4.40 (m, 1H), 4.80 (m, 1H), 4.92 (m, 1H), 6.10 (m, 1H), 6.30 (M, 1H), 6.40 (m, 1H), 6.90 (m, 2H), 7.20 (m, 3H), 7.40-7.60 (m, 2H), 7.90 (m, 1H), 8.10 (m, 1H).

$^{13}$C NMR (CDCl₃): δ 23.42, 26.32, 33.12, 48.63, 49.10, 49.85, 77.56, 117.63, 120.67, 122.35, 122.93, 123.11, 123.80, 124.13, 124.68, 124.75, 131.45, 147.67, 165.16, 165.68, 167.66.

LC-MS (Grad_A4): $t_R$=11.48 min; Mass found: 602.

Step LS2-C: Synthesis of LS2-23

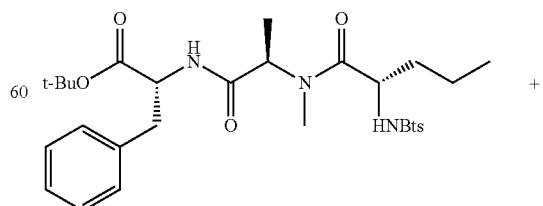

LS2-22

+

Step LS2-D: Synthesis of LS2-26 (Macrolactamization)

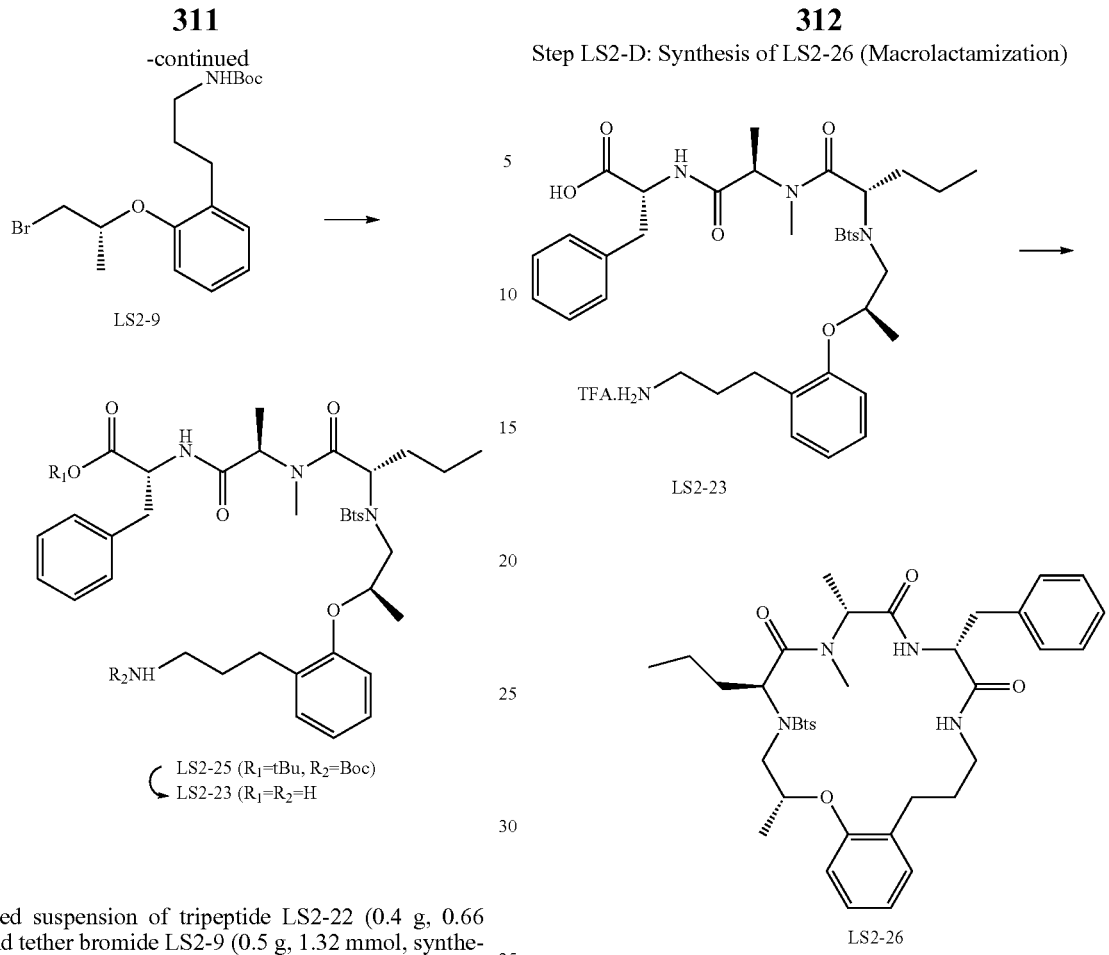

A stirred suspension of tripeptide LS2-22 (0.4 g, 0.66 mmol) and tether bromide LS2-9 (0.5 g, 1.32 mmol, synthesized as in Step LS1-A for the corresponding Cbz derivative) in 1.33 mL of anhydrous DMF at room temperature was treated with KI (0.12 g, 0.66 mmol) and $K_2CO_3$ (0.185 g, 1.32 mmol). The mixture was stirred vigorously at 80° C. for 24 h. After this period of time, this mixture was cooled to room temperature, then 20 mL of water was added and the product extracted with $Et_2O$ (3×30 mL). The combined organic layer was washed with brine (2×30 mL), dried over magnesium sulfate and concentrated under vacuum. The residue was purified by flash chromatography [hexanes/ethyl acetate (1:2)] to afford LS2-25 as a white solid (70%).

TLC (hexanes/ethyl acetate, 2:1): $R_f$=0.4; detection: CMA and UV $^1$H NMR (DMSO-$d_6$): δ 0.5 (m, 1H), 0.70 (m, 1H), 1.01-1.40 (m,) 1.60 (m, 3H), 1.80 (m, 1H), 2.55 (m,), 2.95 (m, 4H), 3.1 (m, 2), 3.30 (m, 2H), 3.60 (m, 1H), 3.90 (m, 1H), 4.30 (m, 1H), 4.80 (m,), 6.80 (m, 3H), 7.05 (m, 6H), 7.60 (2H), 7.95 (m, 1H), 8.20 (m, 1H), 8.25 (m, 1H), 8.90 (s, 2H).

$^{13}$C NMR (CDCl$_3$): δ 13.84, 15.36, 17.40, 17.70, 19.40, 22.17, 27.52, 28.14, 28.67, 30.29, 31.27, 33.27, 38.01, 40.35, 51.02, 53.08, 54.35, 56.72, 70.25, 73.13, 81.10, 113.49, 120.94, 122.28, 125.44, 127.01, 127.19, 127.19, 127.68, 127.68, 127.79, 128.64, 129.57, 130.06, 136.2, 137.10, 165.10, 170.10, 171.10.

LC-MS (Grad_A4): $t_R$=15.10 min; Mass found: 892

100 mg of alkylated tripeptide LS2-25 (100 mg, 0.11 mmol) was treated with 2 mL of 50% TFA, 3% triethylsilane (TES) in DCM, then the mixture stirred for 1 h at room temperature. After this period of time, all solvents were removed under reduced pressure. The crude compound LS2-23 was dried using vacuum pump for 1 h and used directly in the next step without further purification.

LC/MS (Grad_A4): $t_R$=8.55 min; Mass found: 737

To a stirred suspension of alkylated-tripeptide 23 (0.12 mmol) and DIPEA (0.100 mL, 0.56 mmol) in 11.22 mL of anhydrous THF at room temperature was added DEPBT (41 mg, 0.14 mmol). The mixture was stirred vigorously at room temperature O/N. The reaction was then concentrated to dryness under reduced pressure and the residue dissolved in 10 mL of AcOEt. The organic solution was sequentially washed with citrate buffer solution (1 N, 2×30 mL), saturated $NaHCO_3$ (2×30 mL) and brine (1×30 mL). The organic layer was dried over anhydrous sodium sulfate, filtered and evaporated to dryness under reduced pressure. The residue was purified by flash chromatography using [ethyl acetate/hexanes (3:1)] to afford LS2-26 (Bts-410) as a white solid (80 mg, 98%).

TLC (ethyl acetate/hexanes, 3:1): $R_f$=0.3; detection: CMA and UV $^1$H NMR (CDCl$_3$): δ 0.64 (m, 3H), 0.87 (m, 1H), 1.02 (m, 2H), 1.20 (m, 6H), 1.40 (m, 3H), 1.60 (m, 4H), 1.80 (m, 1H0, 2.01 (m, 1H), 2.40 (m, 1H), 2.80 (m, 1H), 3.15 (s, 3H), 3.20 (m, 2H), 3.45 (m, 1H), 3.60-3.80 (m, 2H), 4.40-4.60 (dd, 2H), 4.70 (m, 2H), 5.01 (m, 1H), 5.90 (m, 1H), 6.80 (m, 2H), 6.90 (m, 1H), 7.15-7.25 (m, 7H), 7.60 (m, 2H), 8.01 (m, 1H), 8.10 (m, 1H).

$^{13}$C NMR (CDCl$_3$): δ 13.28, 13.55, 18.75, 18.98, 28.89, 29.92, 29.92, 33.19, 36.81, 36.98, 39.55, 51.94, 53.83, 55.25, 59.51, 74.64, 111.66, 120.64, 122.51, 125.15, 127.10, 127.37, 127.84, 128.07, 128.86, 129.47, 130.51, 136.55, 137.30, 152.58, 155.86, 165.33, 169.75, 170.09, 171.66.

LC/MS (Grad_A4): $t_R$=13.17 min; Mass found: 719.

LC Chiral (column ODRH, Grad 55A-05): $t_R$=42.059.

Step LS2-E: Synthesis of Compound 410

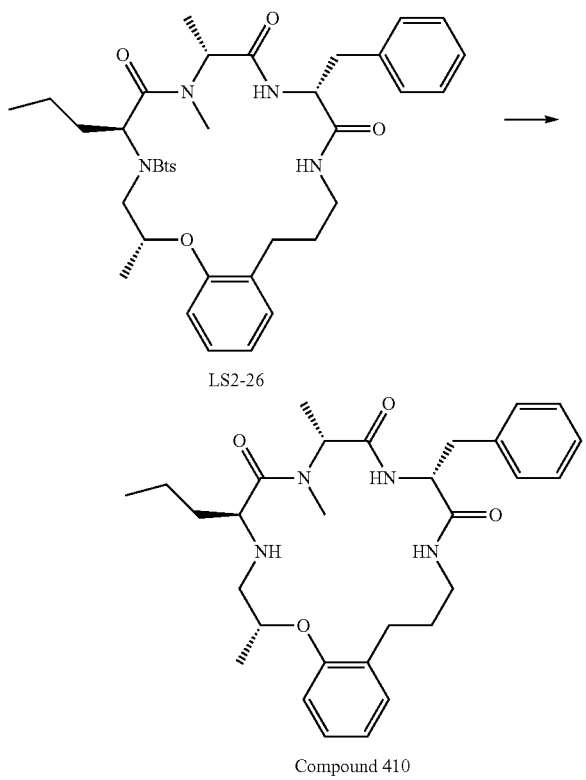

To a stirred suspension of macrocycle LS2-26 (40 mg, 0.003 mmol) in 0.110 mL of DMF was added 23 mg of $K_2CO_3$ and 10 μl of mercaptopropanoic acid at room temperature, then the reaction left O/N. The reaction was concentrated to dryness under reduced pressure and the crude residue dissolved in 10 mL of AcOEt. The organic solution was washed with a saturated solution of $NaHCO_3$ (2×30 mL), then brine (1×30 mL). The organic layer was dried over anhydrous sodium sulfate, filtered and evaporated to dryness under reduced pressure. Compound 410 was thus isolated in 90% yield.

TLC (100% AcOEt): $R_f$=0.2; detection: CMA and UV $^1$H NMR (DMSO-d$_6$): δ 0.79 (m, 3H), 1.20 (m, 9H), 1.30 (M, 1H), 1.60 (m, 1H), 1.90 (m, 1H), 2.10 (s$_b$, 1H), 2.35 (ddd, J=4.98, 4.95, 4.69 Hz, 1H), 2.56 (s$_b$, 1H), 2.63 (m, 1H), 2.80 (ddd, J=4.99, 4.69, 4.40 Hz, 1H), 3.01-3.15 (m, 5H), 3.25 (dd, J=4.69, 4.11 Hz, 1H), 3.30 (s, 2H), 3.55 (sb, 1H), 3.95 (q, J=7.33, 7.04 Hz, 1H), 4.50 (sb, 1H), 6.80 (m, 1H), 6.90 (m, 1H), 7.10-7.30 (m, 7H), 7.70 (m, 2H).

$^{13}$C NMR (DMSO-d$_6$): δ 14.60, 14.84, 18.46, 18.85, 29.80, 29.96, 34.03, 35.84, 36.31, 40.68, 54.79, 55.67, 57.77, 58.11, 73.42, 112.26, 120.58, 126.84, 127.81, 128.80, 129.73, 131.10, 140.10, 158.10, 172.10, 172.40, 176.10.

LC/MS (Grad_A4): $t_R$=6.19 min; Mass found: 522.

EXAMPLE 4

Synthesis and Biological Results for Representative Compound 298

A. Solution Synthesis of Compound 298

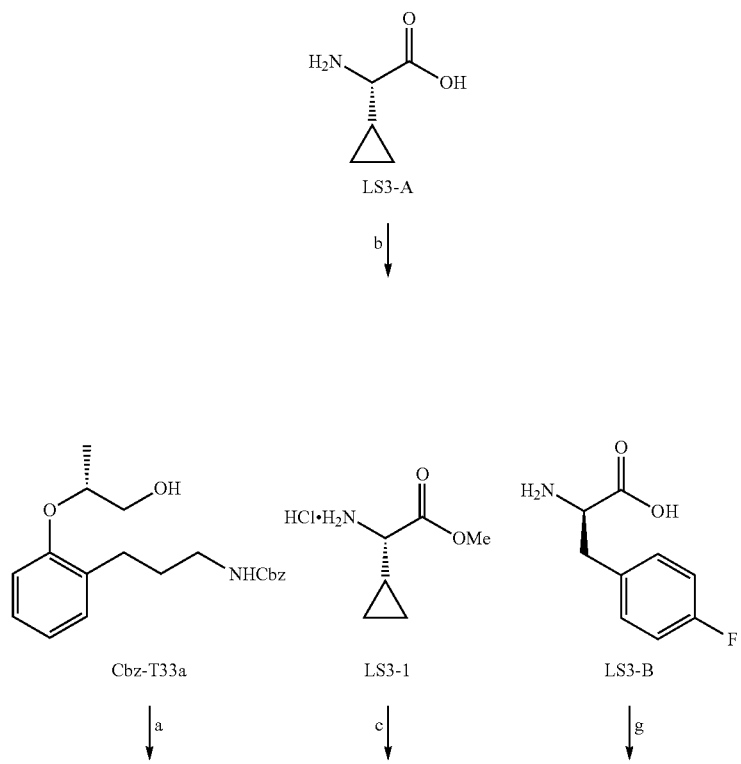

-continued
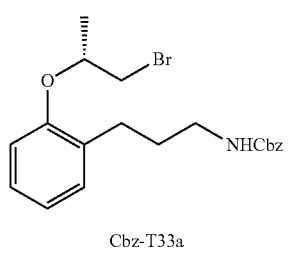 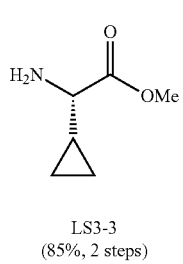 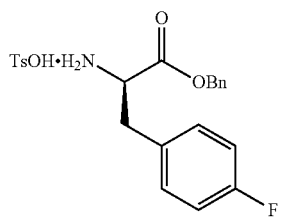
Cbz-T33a     LS3-3 (85%, 2 steps)     LS3-7 (93%)
 ↓ d           ↓ h
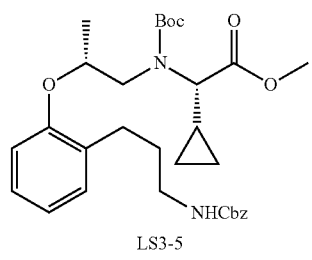 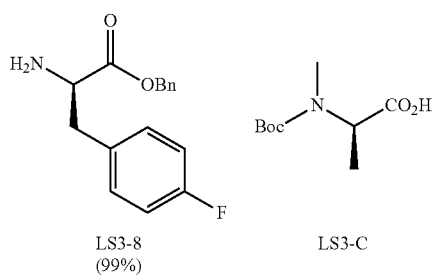
LS3-5     LS3-8 (99%)     LS3-C
↓ e           ↓ i
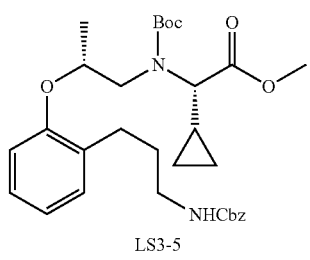 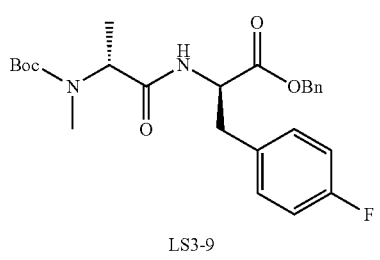
LS3-5     LS3-9
↓ f           ↓ j
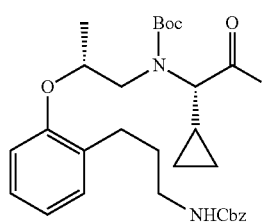 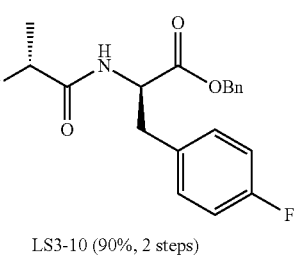
LS3-6 (93%, 2 steps)     LS3-10 (90%, 2 steps) (65%, recrystallized)
↓ k -continued

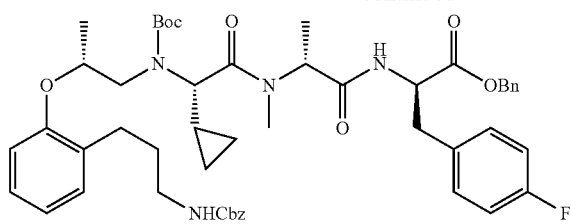
LS3-11 (90%)

↓ m

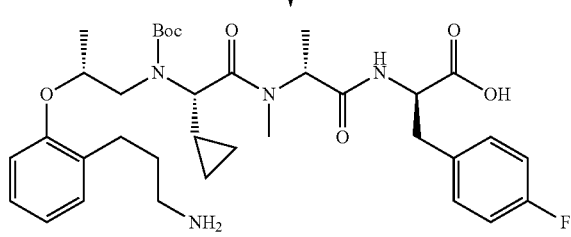
LS3-12 (quant.)

↓ n

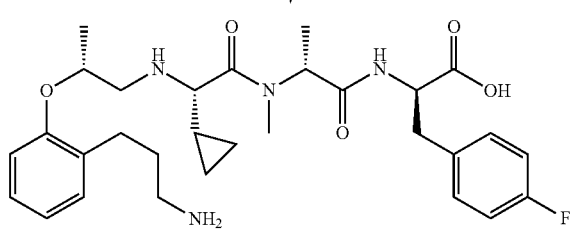
LS3-13

→ p

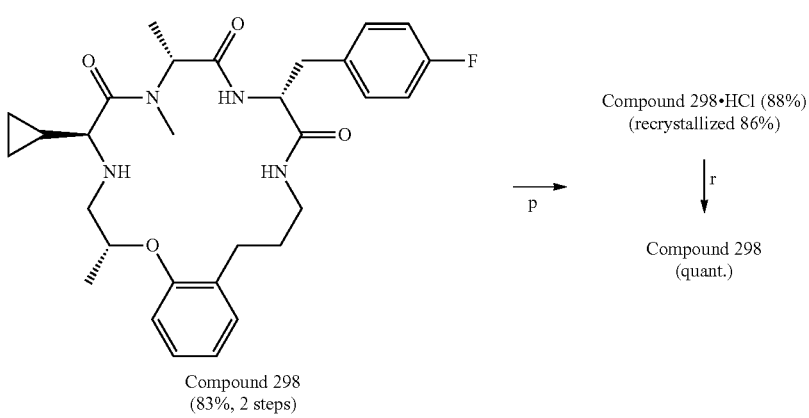
Compound 298
(83%, 2 steps)

→ p

Compound 298•HCl (88%)
(recrystallized 86%)

↓ r

Compound 298
(quant.)

a. NBS, PPh$_3$, DCM;
b. AcCl, MeOH;
c. Na$_2$CO$_3$, AcOEt:DCM;
d. Na$_2$CO$_3$, KI, DMF 100° C.;
e. (Boc)$_2$O, Na$_2$CO$_3$, THF:H$_2$O;
f. LiOH, THF:H$_2$O;
g. TsOH, C$_6$H$_6$;
h. Na$_2$CO$_3$, H$_2$O, AcOEt;
i. 6ClHOBt, EDCl, DIPEA, THF:DCM;
j. HCl, dioxane;
k. HATU, DIPEA, THF:DCM;
m. H$_2$, Pd/C, AcOEt;
n. HCl/dioxane;
p. DEPBT, DIPEA, THF
q. HCl, EtOH;
r. Na$_2$CO$_3$, EtOAc Step LS3-1. Synthesis of cyclopropylglycine methyl ester hydrochloride salt. To a suspension of H-Cpg-OH (LS3-A, 20.0 g, 174 mmol, 1.0 eq) in anhydrous MeOH (350 mL) at 0° C. was slowly added freshly distilled (from PCl$_5$) acetyl chloride (185 mL, 2.6 mol, 15 eq) over 45 min. The mixture was allowed to warm to room temperature and stirred 16-18 h. The reaction was monitored by TLC [MeOH/NH$_4$OH/AcOEt (10: 2:88); detection: ninhydrin; R$_f$=0.50]. The mixture was then concentrated under vacuum, azeotroped with toluene (3×) and dried under high vacuum 16-18 h to give LS3-1 as a pale yellow solid (30.0 g, >100% crude yield).

$^1$H NMR (CD$_3$OD): δ 4.88 (3H, s, NH$_3^+$), 3.85 (3H, s, CH$_3$O), 3.36-3.33 (1H, d, NH$_3^+$CHCH$_3$O), 1.19-1.10 (1H, m, CH(CH$_2$)$_2$), 0.83-0.53 (4H, in, CH(CH$_2$)$_2$).

Step LS3-2. Synthesis of tether bromide. To alcohol Cbz-T33a (21.5 g, 62.6 mmol, 1.0 eq) in anhydrous CH$_2$Cl$_2$ (250 mL) were added NBS (12.8 g, 72.0 mmol, 1.15 eq, larger amounts of NBS lead to dibrominated side product) and PPh$_3$ (18.9 g, 72.0 mmol, 1.15 eq). The round bottom flask was protected from light with foil and the mixture stirred at room temperature 16-18 h with monitoring by TLC [AcOEt/Hexanes (3:7); detection: UV and CMA; R$_f$=0.42]. A saturated aqueous NH$_4$Cl solution (200 mL) was added and the aqueous phase extracted with CH$_2$Cl$_2$ (2×150 mL). The combined organic phases were washed with a saturated aqueous NH$_4$Cl solution (2×200 mL), dried over MgSO$_4$, filtered and concentrated under reduced pressure. The residue was purified by flash chromatography (AcOEt:hexanes, gradient, 5:95 to 15:85) to give bromide LS3-2 as a slightly yellow oil (22.2 g, 88.4%).

$^1$H NMR (CDCl$_3$): δ 7.37-7.26 (5H, in, Ph), 7.19-7.13 (2H, m, Ph), 6.92-6.88 (1H, t, Ph), 6.84-6.81 (1H, d, Ph), 5.10 (2H, s, NHC(O)OCH$_2$Ph), 4.96 (1H, broad, NHCbz), 4.62-4.56 (1H, sextuplet, PhOCH(CH$_3$)CH$_2$Br), 3.58-3.45 (2H, m, CH$_2$Br), 3.22-3.16 (2H, q, CH$_2$NHCbz), 2.69-2.64 (2H, t, PhCH$_2$CH$_2$), 1.83-1.78 (2H, quint, PhCH$_2$CH$_2$), 1.45 (3H, d, CHCH$_3$).

$^{13}$C NMR (CDCl$_3$): δ 156.66, 155.08, 136.99, 131.28, 130.77, 128.75, 128.32, 128.28, 127.49, 121.56, 113.03, 73.12, 66.76, 40.69, 36.12, 30.45, 27.48, 19.00.

LC/MS (Grad_A4): t$_R$=11.04 min

Step LS3-3. The hydrochloride salt LS3-1 was dissolved in an aqueous solution of Na$_2$CO$_3$ (1 M, 275 mL, 0.272 mol, 1.5 eq). The basic aqueous phase was saturated with NaCl and extracted with AcOEt/CH$_2$Cl$_2$ (2:1) (5×100 mL). TLC [MeOH/NH$_4$OH/AcOEt (10:2:88); detection: ninhydrin; R$_f$=0.50]. The combined organic phases were dried over MgSO$_4$, filtered and concentrated under low vacuum at room temperature to give free amino-ester LS3-3 as a yellow oil (19.1 g, 85%, 2 steps). LS3-3 is volatile and should not be left on a mechanical vacuum pump for extended periods of time. To minimize diketopiperazine formation, Step LS3-4 should occur immediately after isolation of LS3-3.

$^1$H NMR (CDCl$_3$): δ 3.70 (3H, s, CH$_3$O), 2.88-2.85 (1H, d, NH$_2$CHCH$_3$O), 1.54 (1H, s, NH$_2$), 1.04-0.97 (1H, m, CH(CH$_2$)$_2$), 0.56-0.27 (4H, m, CH(CH$_2$)$_2$).

Step LS3-4. In a dried round-bottom flask, bromide LS3-2 (47.2 g, 117 mmol, 1.0 eq) and freshly prepared LS3-3 (19.1 g, 148 mmol, 1.2 eq) were added. Degassed anhydrous DMF (117 mL), anhydrous Na$_2$CO$_3$ (14.8 g, 140 mmol, 1.2 eq) and KI (19.4 g, 117 mmol, 1.0 eq) were added and the mixture was stirred at 100° C. under a nitrogen atmosphere for 16-18 h. Reaction progress was monitored by LC-MS and/or TLC. The mixture was cooled down to room temperature and water (200 mL) added and the aqueous phase extracted with MTBE (3×100 mL). The combined organic phases were washed sequentially with water (2×100 mL) and brine (1×100 mL), dried over MgSO$_4$, filtered and concentrated under reduced pressure. The residue was purified by flash chromatography [hexanes/AcOEt/DCM, gradient (85:10:5) to (50:45:5)] to give LS3-4 as an orange oil (43.1 g, 81%).

TLC [hexanes/AcOEt (1:1)]: R$_f$=0.35; detection: UV and CMA $^1$H NMR (CDCl$_3$): δ 7.31-7.22 (5H, m, Ph), 7.07-7.03 (2H, m, Ph), 6.80-6.74 (2H, m, Ph), 5.48 (1H, broad, CH$_2$N HCHRR'), 5.00 (2H, s, OCH$_2$Ph), 4.49-4.43 (1H, m, PhOCH(CH$_3$)R), 3.56 (3H, s, C(O)OCH$_3$), 3.18-3.11 (3H, m, NHCH(Pr)CO$_2$Me and CH$_2$NHCbz), 2.75-2.50 (4H, m, PhCH$_2$CH$_2$ and NHCH$_2$CH(Me)OPh), 1.76-1.68 (2H, m, PhCH$_2$CH$_2$), 1.19-1.14 (3H, d, PhOCH(CH$_3$)R), 0.88-0.80 (1H, m, CH(CH$_2$)$_2$), 0.46-0.13 (4H, m, CH(CH$_2$)$_2$).

LC/MS (Grad_A4): t$_R$=6.63 min

Step LS3-5. To a solution of secondary amine LS3-4 (43.0 g, 94.7 mmol, 1.0 eq) in THF/H$_2$O (1:1, 475 mL) at 0° C. were added Na$_2$CO$_3$ (15.1 g, 113.7 mmol, 1.5 eq) and (Boc)$_2$O (24.8 g, 142.1 mmol, 1.2 eq). The mixture was allowed to warm to room temperature and stirred 24 h. Reaction was monitored by LC/MS and/or TLC. THF was evaporated under vacuum and the residual aqueous phase was extracted with MTBE (3×100 mL). The combined organic phases were washed with brine (1×100 mL), dried over MgSO$_4$, filtered and evaporated under vacuum to give the crude LS3-5 as an orange oil (59.1 g, >100% crude yield).

TLC [hexanes/AcOEt (1:1)]: R$_f$=0.57; detection: UV and CMA

LC/MS (Grad_A4): 12.98 min.

Step LS3-6. To a solution of LS3-5 (52.5 g, 94.7 mmol, 1.0 eq.) in THF/H$_2$O (1:1, 475 mL) at room temperature was added LiOH monohydrate (19.9 g, 474 mmol, 5.0 eq.). The mixture was stirred 16-18 h at room temperature. The reaction was monitored by LC/MS (Grad_A4): t$_R$=12.21 min. TLC [Hexanes/AcOEt (1:1); detection: UV and CMA; R$_f$=baseline]. The reaction mixture was acidified with citrate buffer (1 M, pH 3.5) and THF was then evaporated under vacuum. The residual aqueous phase was extracted with AcOEt (3×150 mL), then the combined organic phases washed with brine (1×100 mL), dried over MgSO$_4$, filtered and concentrated under reduced pressure to give carboxylic acid LS3-6 as a white gummy solid (47.3 g, 93% for 2 steps).

LC/MS (Grad_A4): t$_R$=12.16 min

Step LS3-7. To a suspension of H-(D)Phe(4F)-OH (LS3-B, 55.6 g, 0.30 mol, 1.0 eq) in benzene (1.2 L) was added p-TSA (69.4 g, 0.37 mol, 1.2 eq) and benzyl alcohol (157 mL, 1.52 mol, 5.0 eq). The mixture was stirred at reflux 16-18 h in a Dean-Stark apparatus during which a homogeneous solution was obtained. The mixture was cooled down to room temperature and a white precipitate formed. The precipitate was diluted with Et$_2$O (500 mL), filtered and triturated with Et$_2$O (3×500 mL). The solid was dried under vacuum to give LS3-7 as a white solid (126 g, 93.1%). Substitution of toluene for benzene resulted in reduced reaction time, 2-3 h.

$^1$H NMR (DMSO-d$_6$): δ 8.40 (3H, bs, NH$_3$Cl), 7.47-7.36 (2H, d, Ph), 7.37-7.06 (11H, m, Ph), 5.15 (2H, s, OCH$_2$Ph), 4.37 (1H, bt, CHCH$_2$Ph), 3.09-3.05 (2H, m, CHCH$_2$Ph), 2.27 (3H, s, CH$_3$Ph).

$^{13}$C NMR (DMSO-d$_6$): δ 169.52 163.83, 160.62, 140.01, 138.56, 135.48, 132.16, 132.04, 131.33, 131.28, 129.09, 129.05, 128.84, 128.72, 127.09, 126.20, 116.18, 115.89, 67.83, 53.88, 35.83, 21.47.

LC/MS (Grad_A4): t$_R$=6.12 min

Melting point (uncorrected): 165-167° C.

Step LS3-8. The tosylate salt LS3-7 (122 g) was taken up in an aqueous solution of Na$_2$CO$_3$ (1 M, 500 mL). The resulting basic aqueous solution was extracted with AcOEt (4×500 mL) and the combined organic phases were washed with brine (1×250 mL), dried over MgSO$_4$, filtered and concentrated under reduced pressure to give the amino-ester LS3-8 as a white solid (74.4 g, 99%).

$^1$H NMR (CDCl$_3$): δ 7.38-7.28 (5H, m, OCH$_2$Ph), 7.10-7.06 (2H, m, Ph(4F)), 6.96-6.90 (2H, m, Ph(4F)), 5.13 (2H, d, OCH$_2$Ph), 3.76-3.71 (1H, t, CHCH$_2$Ph), (2H, dq, CHCH$_2$Ph), 1.53 (2H, s, NH$_2$)

Step LS3-9. To a solution of LS3-8 (74.4 g, 0.27 mol, 1.0 eq) in anhydrous THF/CH$_2$Cl$_2$ (1:1, 1120 mL) were added Boc-(D)NMeAla-OH (LS3-C, 57.1 g, 0.28 mol, 1.03 eq), 6-Cl-HOBt (46.2 g, 0.27 mol, 1.0 eq) and DIPEA (238 mL, 1.37 mol, 5.0 eq). The mixture was cooled to 0° C. and EDCI (57.6 g, 0.3 mol, 1.1 eq) was added. The mixture was stirred 1 h at 4° C., allowed to warm to room temperature and stirred 18 h. The solvent was evaporated in vacuo and the residue dissolved in AcOEt (1000 mL). The organic phase was washed sequentially with an aqueous solution of citrate buffer (1 M, pH 3.5, 2×500 mL), H$_2$O (1×500 mL), an aqueous solution of saturated NaHCO$_3$ (CAUTION: CO$_2$ is evolved, 2×500 mL) and brine (1×500 mL). The organic phase was dried over MgSO$_4$ (180 g), filtered and concentrated under reduced pressure to give crude dipeptide LS3-9 as a yellow oil. (127 g, >100% crude yield).

Step LS3-10. The oil LS3-9 was dissolved in 150 mL of dioxane, then a solution of 4 M HCl in dioxane (1360 mL, 20 eq) added and the mixture stirred for 1 h at room temperature. Reaction was monitored by TLC [AcOEt/Hexanes (3:2)]; R$_f$=baseline; detection: UV and ninhydrin]. The mixture was concentrated under reduced pressure and the resulting residue co-evaporated with Et$_2$O (2×500 mL), then dried under vacuum. The crude LS3-10 was obtained as a slightly yellow solid (96 g, 89.7%). This was dissolved in hot 95% EtOH (200 mL), then MTBE (900 mL) added. The mixture was cooled down to room temperature, then put in a freezer (−20° C.) for 18 h. The resulting crystals were collected by filtration and washed with MTBE (2×200 mL), then dried under vacuum to give crystalline dipeptide hydrochloride LS3-10 (62 g, 64.5% recovery).

$^1$H NMR (DMSO-d$_6$): δ 9.31-9.28 (1H, d, C(O)NH), 7.38-7.26 (7H, m, Ph), 7.09-7.04 (2H, m, Ph), 5.10 (2H, s, C(O)OC H$_2$Ph), 4.65-4.57 (1H, m, CHCH$_3$), 3.76-3.69 (1H, d, C HCH$_2$Ph), 3.15-3.08 and 2.99-2.91 (CHCH$_2$Ph), 2.221 (3H, s, CH$_3$NH$_2^+$Cl$^-$), 1.31-1.28 (3H, d, CHCH$_3$).

$^{13}$C NMR (DMSO-d$_6$): δ 171.33, 169.18, 137.63, 136.31, 129.92, 129.11, 128.95, 128.83, 128.63, 127.30, 67.00, 56.57, 54.38, 36.98, 31.11, 16.47.

LC/MS (Grad_A4): t$_R$=6.26 min
LC Chiral (Iso100B_05): t$_R$=29.6 min, 97% UV
Melting point (uncorrected): 140-142° C.

Step LS3-11. To a solution of carboxylic acid LS3-6 (47.3 g, 87.6 mmol, 1.0 eq) and dipeptide hydrochloride salt LS3-10 (36.2 g, 91.9 mmol, 1.05 eq) in anhydrous THF/CH$_2$Cl$_2$ (1:1) (438 mL) at 0° C. were added DIPEA (92 mL, 526 mmol, 6.0 eq) and HATU (34.9 g, 91.9 mmol, 1.05 eq). The mixture was allowed to warm to room temperature and stirred 16-18 h. Reaction was monitored by TLC [AcOEt/Hex (1:1); R$_f$=0.48; detection: UV and CMA] The mixture was concentrated under reduced pressure and the residue dissolved in AcOEt (250 mL). The organic phase was washed sequentially with an aqueous solution of citrate buffer (1 M, pH 3.5, 3×150 mL), H$_2$O (1×150 mL), an aqueous solution of saturated NaHCO$_3$ (2×150 mL) and brine (1×150 mL). The organic phase was dried over MgSO$_4$, filtered and concentrated under reduced pressure. The residue was purified by flash chromatography [AcOEt:hexanes, gradient (10:90) to (50:50)] to give LS3-11 as a white gummy solid (70.0 g, 90%).

LC/MS (Grad_A4): t$_R$=15.06 min

Step LS3-12. To a suspension of 10% Pd/C (13.8 g, 20% by weight) in AcOEt (150 mL) was added a solution of alkylated tripeptide LS3-11 (69.0 g, 78.4 mmol, 1.0 eq) in AcOEt (375 mL), then hydrogen was bubbled through the solution for 16-18 h. The reaction was monitored by TLC [AcOEt/hexanes (1:1); R$_f$=0.22; detection: UV and CMA]. The mixture was purged by nitrogen bubbling, filtered through a Celite pad and rinsed with AcOEt (3×). The combined filtrate and washings were evaporated under reduced pressure to give LS3-12 as a white solid (51.4 g, 100%).

LC/MS (Grad_A4): t$_R$=8.05 min

Step LS3-13. To LS3-12 (51.4 g, 78.4 mmol, 1.0 eq) was added a solution of 3.0 M HCl in dioxane/H$_2$O (75:25, 525 mL, 1.57 mol, 20 eq) and the mixture stirred at room temperature 1.5 h. The solvent was evaporated under vacuum, then the residue was azeotroped with toluene (3×) and dried under vacuum to give crude LS3-13 as an off-white solid (58.0 g, >100% yield).

LC/MS (Grad_A4): t$_R$=5.38 min

Step LS3-14. To a solution of macrocyclic precursor LS3-13 (78.4 mmol based on LS3-12, 1.0 eq) in anhydrous THF (1.57 L, 50 mM) were added DIPEA (68.0 mL, 392 mmol, 7.0 eq) and DEPBT (25.8 g, 86.2 mmol, 1.1 eq). The mixture was stirred at room temperature 16-18 h. The reaction was monitored by TLC [MeOH/AcOEt (1:9); R$_f$=0.38; detection: UV and CMA]. At the end of the reaction, significant quantities of DIPEA salts were in suspension in the solution. Prior to evaporation, these salts were filtered and washed with THF to avoid excessive bumping of the solution during evaporation. The solvent was evaporated under vacuum and the residue taken up in an aqueous solution of Na$_2$CO$_3$ (1 M, 500 mL) and AcOEt (250 mL). The separated basic aqueous phase was extracted with AcOEt (2×250 mL). The combined organic phases were washed with brine (2×250 mL), dried over MgSO$_4$, filtered and evaporated under reduced pressure. The crude material so obtained was purified by flash chromatography [AcOEt:MeOH, gradient (100:0) to (90:10)] to give macrocycle compound 298 as a pale yellow solid (35.0 g, 83%, 2 steps).

LC/MS (Grad_A4): t$_R$=6.19 min

Step LS3-15. To crude compound 298 (18.5 g, 34.4 mmol, 1.0 eq) in anhydrous EtOH (100 mL) was slowly added 1.25 M HCl in EtOH (41.2 mL, 51.5 mmol, 1.5 eq). The mixture was stirred 5 min, cooled down to 0° C. and filtered while still cold. The white precipitate was washed with cold anhydrous EtOH (3×75 mL) and dried under vacuum to give compound 298 hydrochloride as an amorphous white solid (15.3 g, 88% recovery, corrected).

Purification of Compound 298. Amorphous compound 298 hydrochloride (14.2 g, 24.7 mmol) was dissolved in a hot mixture of EtOH/H$_2$O (9:1, 215 mL). The solution was cooled down to room temperature and then placed in a freezer (−20° C.) for 16-18 h. The crystals were collected by filtration and washed with cold anhydrous EtOH (3×75 mL) to give compound 298 hydrochloride as a crystalline white solid (12.4 g, 86% recovery).

Crystalline compound 298 hydrochloride (11.4 g, 19.9 mmol) was taken up in 1 M Na$_2$CO$_3$/AcOEt (1:1, 200 mL) and stirred until complete dissolution of the solid. The separated basic aqueous phase was extracted with AcOEt (2×50 mL). The combined organic phases were washed with brine (1×50 mL), dried over MgSO$_4$, filtered and evaporated under vacuum. The oily residue was dissolved in a minimum amount of AcOEt, then hexanes was added until a white precipitate formed. The mixture was evaporated and dried under vacuum to give compound 298 as a white amorphous solid (11.1 g, 100% recovery).

LC/MS (Grad_A4): 6.18 min; Purity (UV/ELSD/CLND): 100/100/100.

This reaction sequence has been repeated in comparable yields starting from 1 kg Cbz-T33a, 518 g LS3-A and 1 kg LS3-B to yield over 400 g of the desired macrocyclic product compound 298 and/or the corresponding HCl salt form. Similar procedures can be applied for other compounds of the invention.

As an alternative, the t-butyl ester of Cpg (LS3-14), produced under standard conditions, can be utilized as was described in Step LS3-4 to provide alkylated Cpg LS3-15 by reaction with Cbz-T33a. This species, without protection of the secondary amine on LS3-16 (produced by standard acid deprotection of the t-butyl ester of LS3-15), then undergoes chemoselective coupling with dipeptide LS3-10 to prepare LS3-17. Straightforward simultaneous hydrogenolysis of both Cbz and benzyl protecting groups then leads to intermediate LS3-13 in a more efficient approach that avoids two steps.

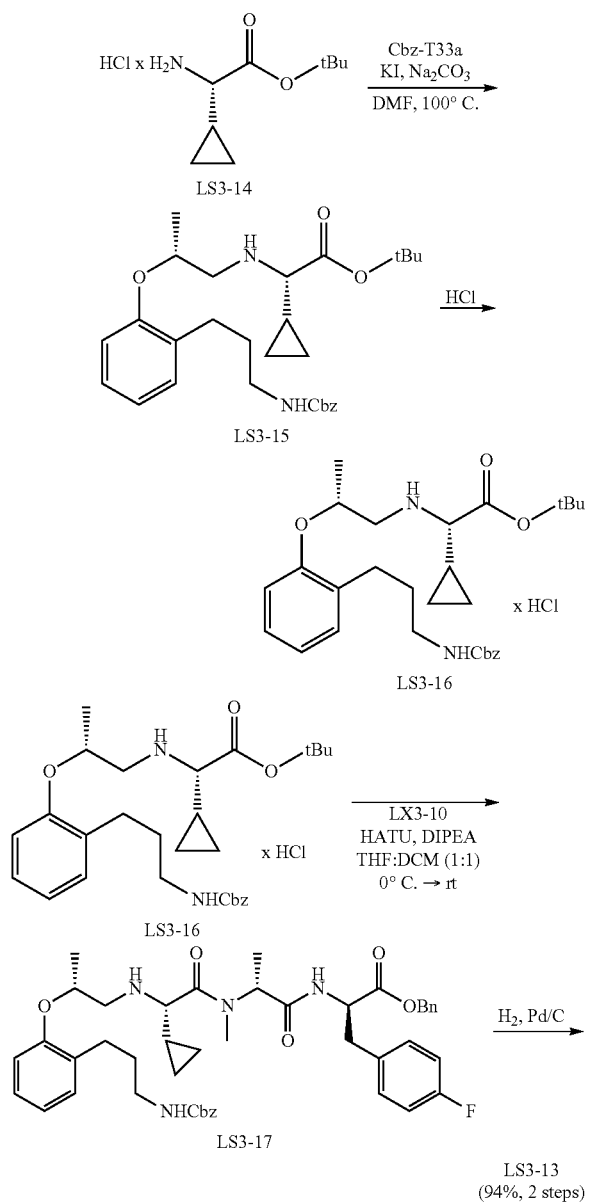

Step LS3-17. To the hydrochloride salt of carboxylic acid LS3-16 (2.1 g, 4.41 mmol, 1.0 eq) and LS3-10 (1.7 g, 4.59 mmol, 1.05 eq) in anhydrous THF/CH$_2$Cl$_2$ (1:1, 22 mL) at 0° C. were added DIPEA (5.3 mL, 30.6 mmol, 7.0 eq) and HATU (1.7 g, 4.59 mmol, 1.05 eq). The mixture was allowed to warm to room temperature and stirred 16-18 h. The reaction was monitored by LC-MS. The mixture was concentrated under reduced pressure and the residue dissolved in AcOEt (150 mL). The organic phase was washed sequentially with an aqueous solution of citrate buffer (1 M, pH 3.5, 3×25 mL), H$_2$O (1×25 mL), an aqueous solution of saturated NaHCO$_3$ (2×25 mL) and brine (1×25 mL). The organic phase was dried over MgSO$_4$, filtered and concentrated under vacuum to give LS3-17 as a white solid (3.5 g, >100% crude yield).

LC/MS (Grad_A4): $t_R$=12.09 min.

Step LS3-18. To a suspension of 10% Pd/C (596 mg, 20% by weight) in 95% EtOH (10 mL) was added a solution of alkylated tripeptide LS3-17 (3.0 g, 3.82 mmol, 1.0 eq) in AcOEt (15 mL) and hydrogen bubbled through the solution for 2 h. The mixture was then stirred under a hydrogen atmosphere for 16-18 h. The reaction was monitored by TLC [100% AcOEt; R$_f$=Baseline; detection: UV and CMA]. The mixture was purged by nitrogen bubbling, filtered through a Celite pad and rinsed with 95% EtOH (3×20 mL). The combined filtrate and rinses were evaporated under reduced pressure to give LS3-13 as a white solid (2.0 g, 94%).

LC/MS (Grad_A4): $t_R$=5.40 min.

B. Biological Results

1. Radioligand Binding Assay on Ghrelin Receptor (Human Clone, hGHS-R1a)

Objective
1. To demonstrate that compound 298 has a direct, high affinity interaction with hGHS-R1a.

Key Aspects of Method
1. Binding performed on membranes prepared from HEK293 expressing the transfected, cloned human ghrelin receptor (hGHS-R1a).
2. [$^{125}$I]Ghrelin was used as the radioligand for displacement ($K_d$=0.01 nM, test concentration=0.007 nM).
3. Ghrelin (unlabeled, 1 µM) was used to determine non-specific binding.
4. Compound 298 tested in duplicate samples over an 11-point concentration curve.

Results

Figure 10:
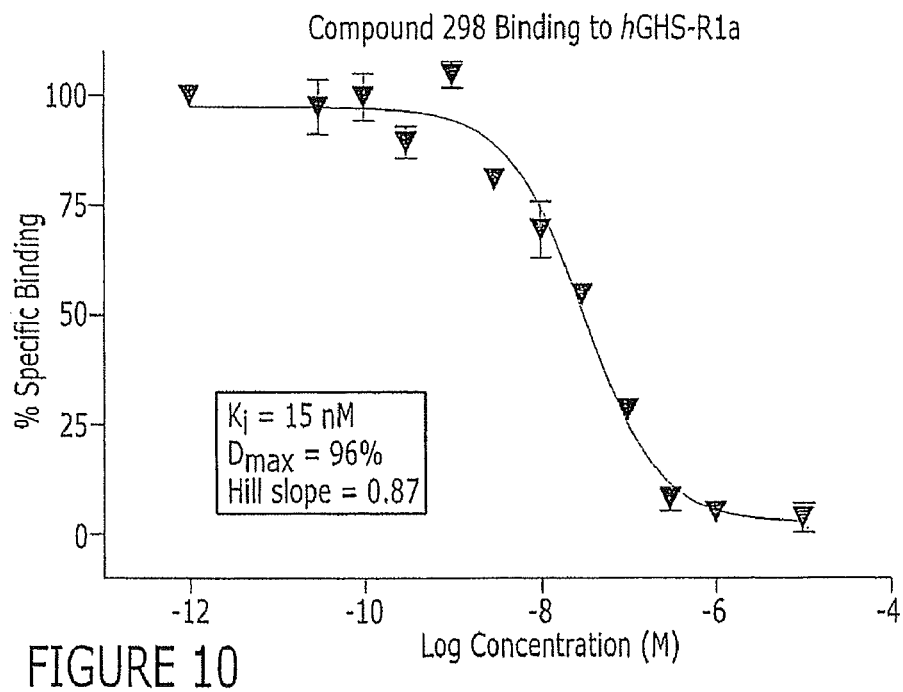
FIG. 10 shows a competitive binding curve for binding of an exemplary compound of the present invention to the hGHS-R1a receptor.

Compound 298 binding to hGHS-R1a has been run multiple times. A representative binding inhibition curve as shown in FIG. 10 demonstrates that compound 298 binds competitively, reversibly, and with high affinity to hGHS-R1a.

2. Cell-Based, Functional Assays on Ghrelin Receptor (Human Clone, hGHS-R1a) Objectives
1. To demonstrate that compound 298 is a full agonist at hGHS-R1a.
2. To measure the potency of compound 298 agonist activity at hGHS-R1a.

Key Aspects of Method
1. Assay performed on CHO-K1 cells expressing the transfected, cloned human ghrelin receptor (hGHS-R1a) and G$_{\alpha 16}$.
2. Suspended cells incubated O/N with coelenterazine.
3. Stimulation of hGHS-R1a activates G$_{\alpha 16}$, causing intercellular Ca2+ release which ultimately leads to the oxidation of coelenterazine and the emission of a quantitative luminescent signal.
4. Ghrelin was used as the positive control.
5. Compound 298 tested in duplicate samples over an 8-point concentration curve.

Results

Figure 11:
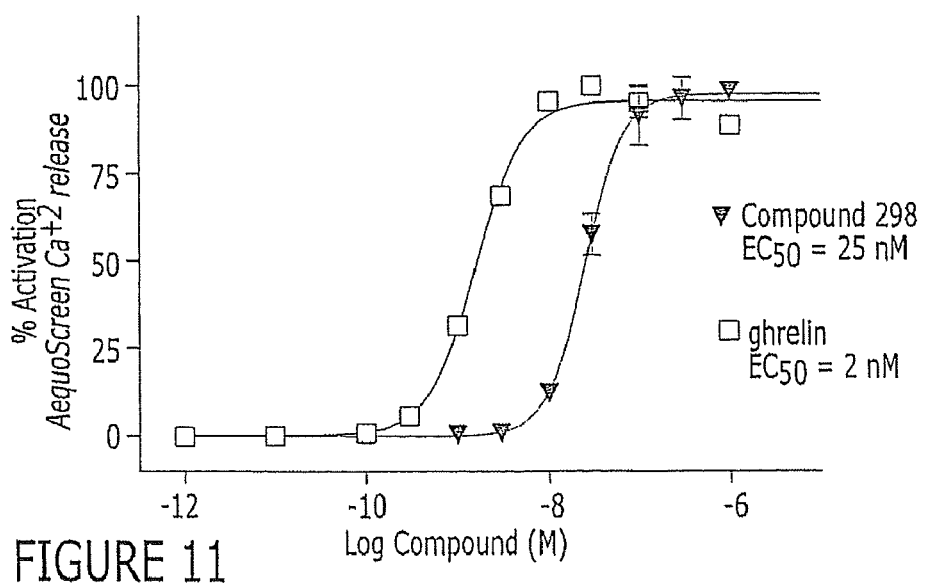
FIG. 11 shows an activation curve demonstrating the agonism of an exemplary compound of the present invention.

Compound 298 activates hGHS-R1a with an EC$_{50}$=25 nM as shown in FIG. 11. Compound 298 is a full agonist based on its similar, maximal efficacy to the ghrelin peptide (positive control).

3. Compound 298 (i.v.) Effect on Growth Hormone (GH) Release in Conscious, Freely-Moving Rats.

Ghrelin (and analogues thereof) is known to potently stimulate GH release from the pituitary in various species including rat following intravenous dosing.

Objectives
1. To determine whether compound 298 stimulates GH release in rat.
2. To determine whether compound 298 modulates ghrelin-induced GH release in rat.

Method
1. Model adapted from Tannenbaum et al. (2003), Endocrinology 144:967-974.
2. Rats implanted with chronic, intravenous (i.v.) cannulae.

3. Rats allowed to move freely even while dosing drug or sampling blood to minimize stress-induced changes in GH release.
4. Compound 298 administered at GH peak and trough levels to measure:
   a. Stimulatory effect, if any, on GH release; and
   b. Whether any stimulatory effect is sustained with repeated dosing.
5. Blood samples are drawn at defined, 15-minute intervals throughout the test day and growth hormone (GH) measured directly by radioimmunoassay.
6. Compound 298 tested at 3, 30, 300, 1000 µg/kg (i.v., N=5-6/rats per group).
7. Ghrelin (positive control) tested at 5 µg (i.v.).

Results

Figure 9:
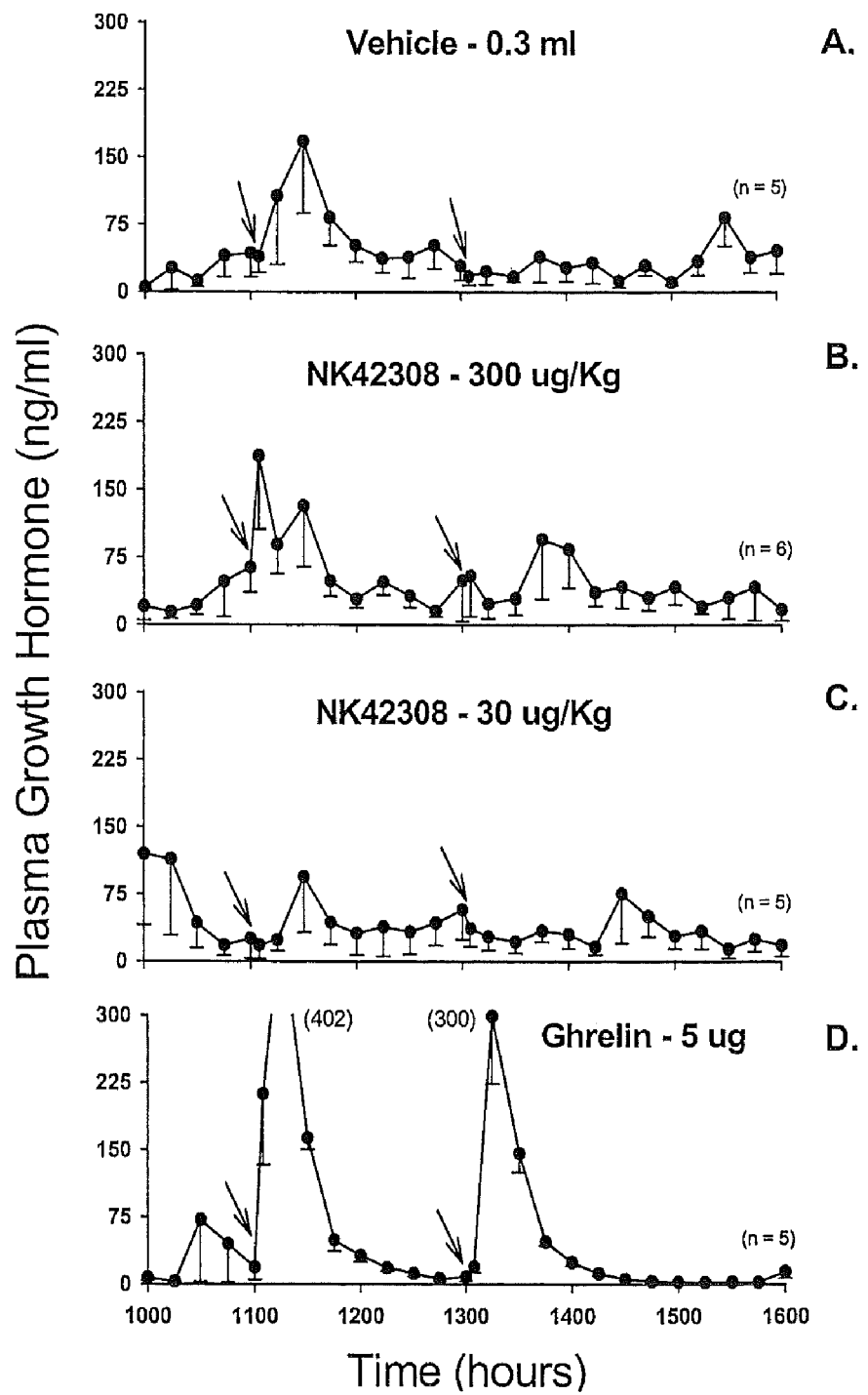
FIG. 9 (panels A through D) shows graphs depicting the effect on pulsatile growth hormone release for an exemplary compound of the present invention.
Figure 12:
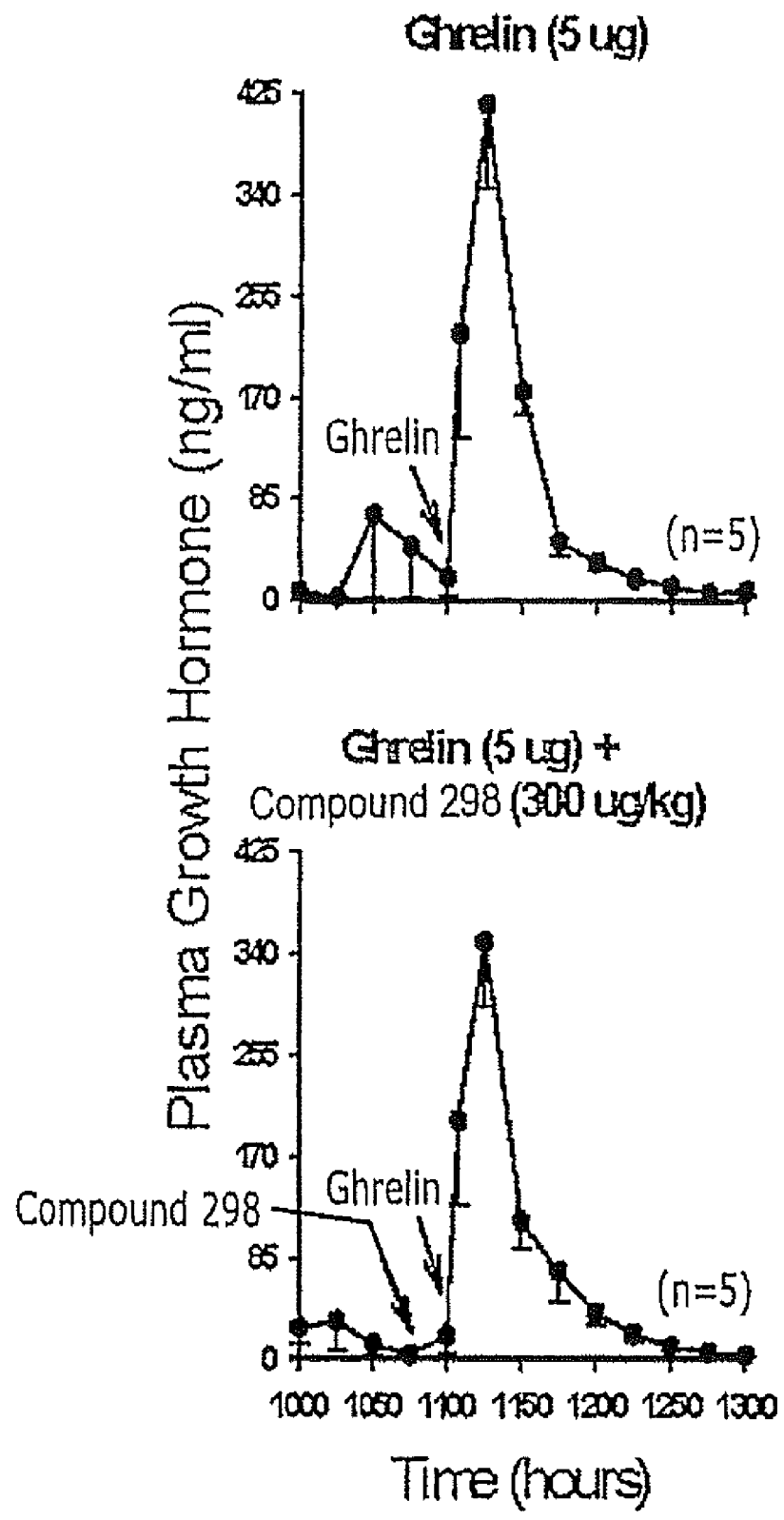
FIG. 12 shows a graph depicting the lack of effect on ghrelin-induced growth hormone release for an exemplary compound of the present invention.

Compound 298 at doses up to 1000 µg/kg causes no significant difference in pulsatile GH release in comparison to vehicle controls (see FIG. 9 for effects of 30 µg/kg and 300 µg/kg doses). Ghrelin at a dose of 5 µg causes a significant increase in GH release when dosed at both peak and trough levels (positive control). Compound 298 dosed 10 min. prior to ghrelin neither inhibits nor augments ghrelin-induced GH release (FIG. 12). As a secondary indicator of GH release, the effects of compound 298 on the levels of IGF-1 were also examined at the 1000 µg/kg dose. No appreciable changes in IGF-1 levels from control upon treatment with compound 298 were observed.

4. Compound 298 Effect on hGHS-R1a Receptor Desensitization

G-protein coupled receptors can undergo receptor desensitization upon agonist stimulation, where the degree of receptor desensitization is partly characteristic of the agonist. Lesser receptor desensitization is desirable because this correlates with lesser development of tolerance with chronic use of drug. This factor, among others, has been implicated in the poor clinical performance of GHS.

Objective
1. To determine the extent to which Compound 298 causes desensitization of the ghrelin receptor (human clone, hGHS-R1a).

Method
1. Studies by FLIPR (Fluorometric Imaging Plate Reader, Molecular Devices).
2. Assay performed on HEK293 cells expressing hGHS-R1a.
3. Compound 298 agonist potency was measured using duplicate samples over a 12-point concentration curve; $EC_{50}$ for compound 298 established.
4. In a separate experiment, cells expressing hGHS-R1a are exposed to a range of concentrations of compound 298 (1, 10, 100, 1000 nM) for 3 minutes. Compound 298 washed out, then cells treated with a concentration of ghrelin ($EC_{100}$) that elicits maximal stimulation at non-desensitized receptors.
5. A $DC_{50}$ value is calculated. The $DC_{50}$ value is defined as the pre-treatment concentration of compound 298 that desensitizes the ghrelin ($EC_{100}$) response by 50%.

Results

Figure 13A:
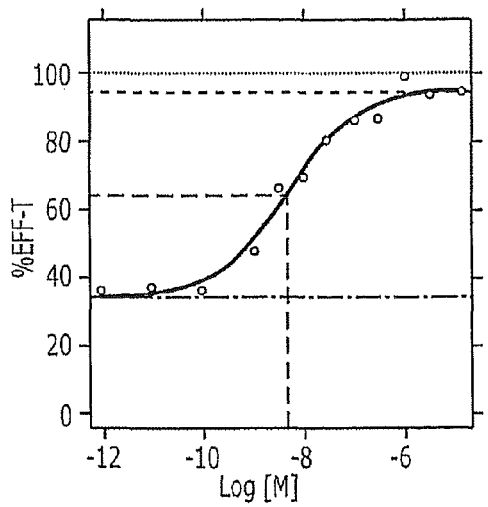
FIG. 13 shows graphs depicting receptor desensitization associated with binding of exemplary compounds of the present invention to the hGHS-R1a receptor.
Figure 13B:
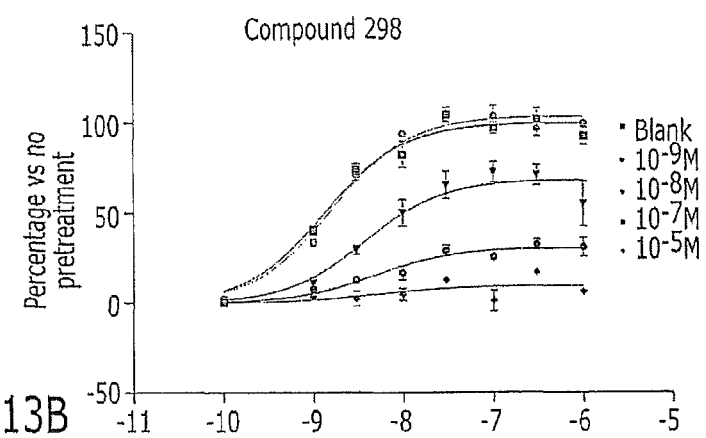
Figure 13C:
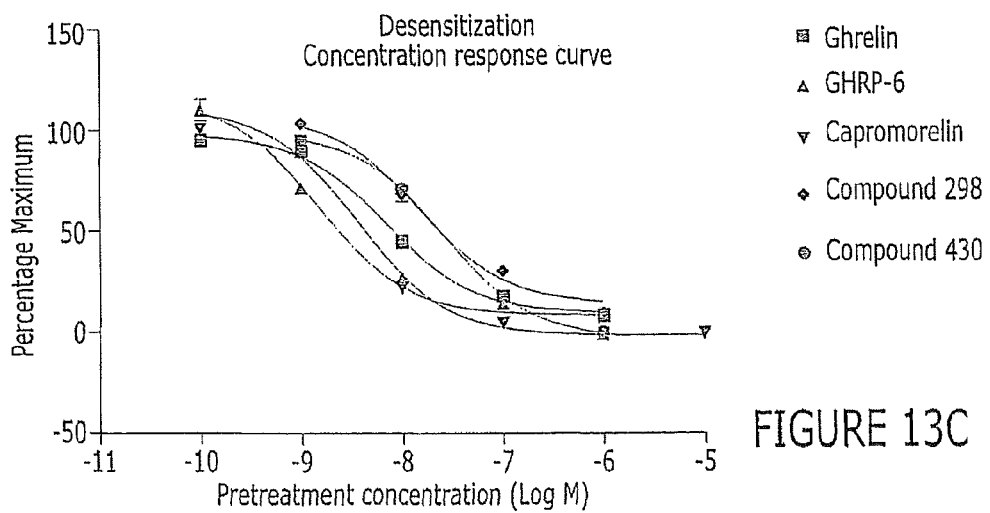

Compound 298 is a full agonist ($EC_{50}$=5 nM; FIG. 13A). Increasing pre-treatment concentrations of compound 298 desensitize the maximal response to $EC_{100}$ ghrelin ($DC_{50}$=32 nM; FIG. 13B). The $DC_{50}$ value is >6-fold less potent than the $EC_{50}$ value, thus compound 298 stimulates the receptor more potently than it desensitizes the receptor. Compound 298 desensitizes the receptor ~10-fold less potently than other ghrelin agonists (i.e. ghrelin peptide and the GHS capromorelin [Pfizer]; FIG. 13C).

Compound 298 has a favorable desensitization profile since it (1) stimulates the receptor 6-fold more potently that it desensitizes the receptor and (2) elicits desensitization at a 10-fold lower potency than the endogenous ligand (i.e. ghrelin) and alternate, small-molecule ghrelin agonists. Accordingly, compound 298 may elicit less tolerance than alternate ghrelin agonists with chronic dosing.

5. Compound 298 Effect on Gastric Emptying of a Solid Meal in Naïve Rat Objectives
1. To ascertain data for compound 298 as a prokinetic agent with potent effects on gastric emptying, a model for gastroparesis.

Methods
1. Overnight-fasted rats (male, Wistar, ~200 g, N=5/group) were given a meal of methylcellulose (2%) by intragastric gavage. The meal was labeled with phenol red (0.05%).
2. Test articles (i.e. vehicle, compound 298, metoclopramide, etc.) were administered by intravenous injection immediately after meal.
3. Animals were sacrificed 15 minutes later; the stomach was immediately removed and homogenized in 0.1 N NaOH and centrifuged.
4. Total phenol red remaining in the stomach was quantified by a colorimetric method at 560 nm
5. A >30% increase in gastric emptying, detected based on the phenol red concentration in comparison to the control group, is considered significant.

Results

Figure 14A:
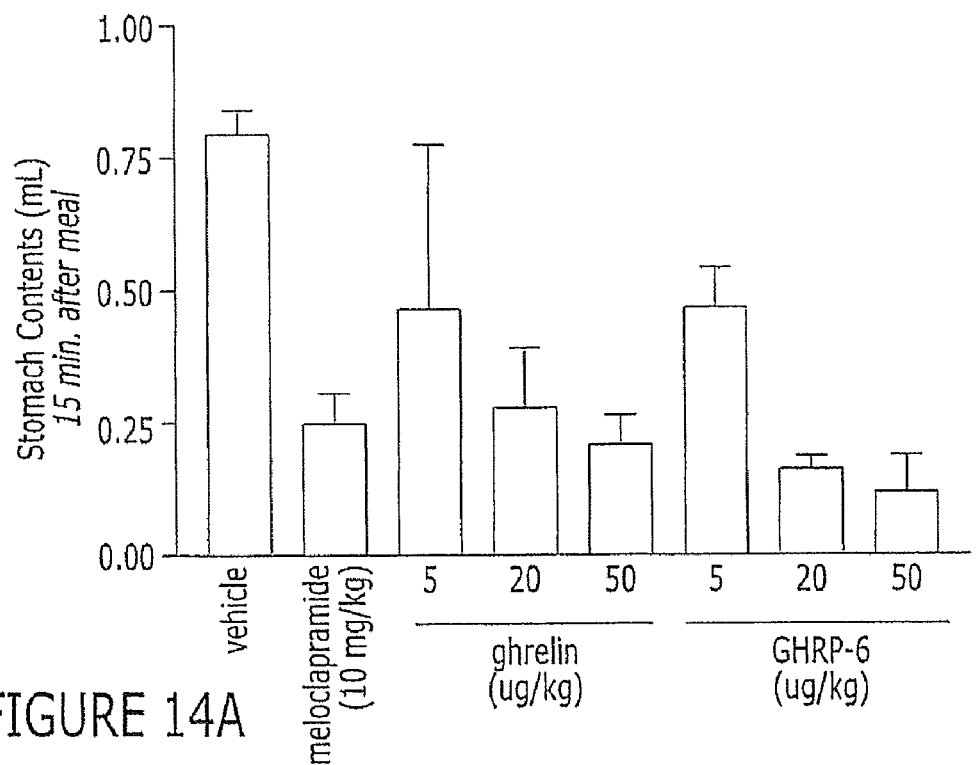
FIG. 14 (panels A and B) shows graphs presenting effects on gastric emptying for an exemplary compound of the present invention.
Figure 14B:
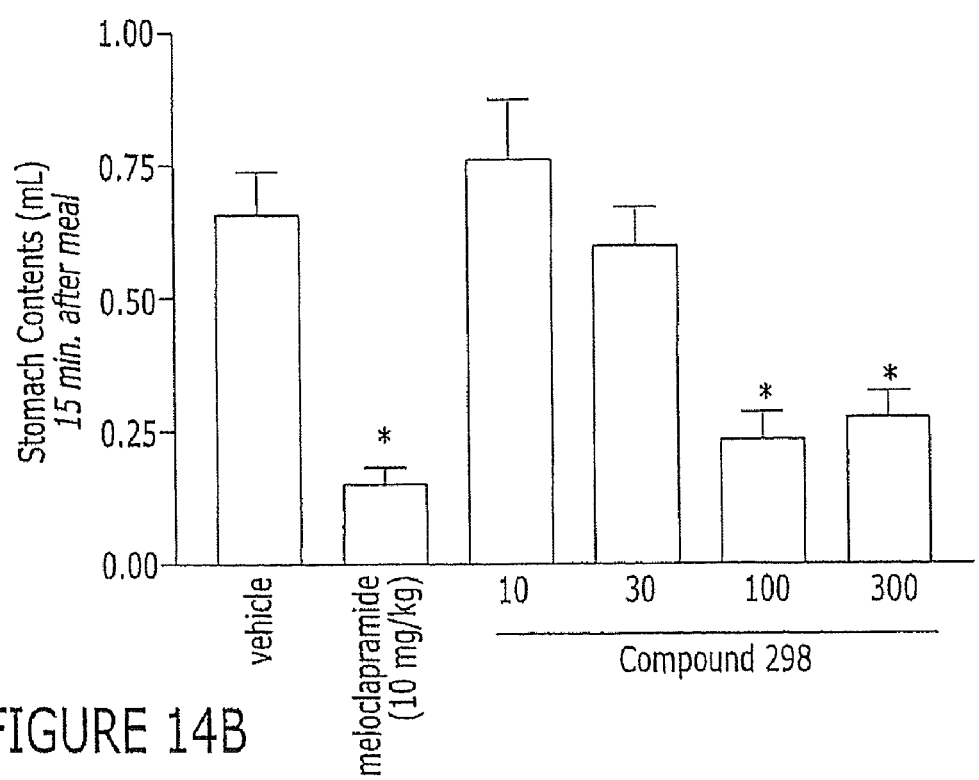

Metoclopramide (marketed gastroparesis product), ghrelin and GHRP-6 (reference peptide agonists at hGHS-R1a) all demonstrated significant gastric emptying (FIG. 14A). Compound 298 caused significant gastric emptying in a dose-dependent manner with ~100-fold superior potency to metoclopramide (FIG. 14B). Compound 298 potently stimulated gastric emptying of a solid meal in naïve rats with a 100-fold superior potency to metoclopramide, a currently used drug with prokinetic activity.

6. Effect of Compound 298 in the Treatment of Post-Operative Ileus in Rat Objective To measure the therapeutic utility of compound 298 in a rat model of post-operative ileus (POI).

Methods
1. Model adapted from Kälff et al. (1998), Ann Surg 228: 652-63.
2. Rats (male, Sprague-Dawley, 250-300 g) were implanted with jugular vein catheters to accommodate dosing of test articles.
3. Rats were fasted O/N, anesthetized with isofluorane and subjected to abdominal surgery.
4. Following an abdominal incision, the small intestine caecum and large intestine were eviscerated for a period of 15 min and kept moist with saline.
5. A "running of the bowel" was performed, a clinically-relevant manipulation of the intestines characterized by first pinching the upper small intestine and continuing this manipulation down through the large intestine.
6. Rats are allowed a 15 min recovery beginning after the disappearance of any effects of the isofluorane anesthesia.
7. Rats are dosed with vehicle or compound 298 (30, 100, or 300 µg/kg, i.v., N=6/gp) followed by intragastric gavage of $^{99m}Tc$ methylcellulose (2%) meal.
8. After 15 min, the rats were euthanized and the stomach and consecutive 10 cm segments of the intestine were isolated. Radioactivity ($^{99m}Tc$) in each tissue isolate was measured as a means of measuring the transit of the meal.

Results

Figure 15:
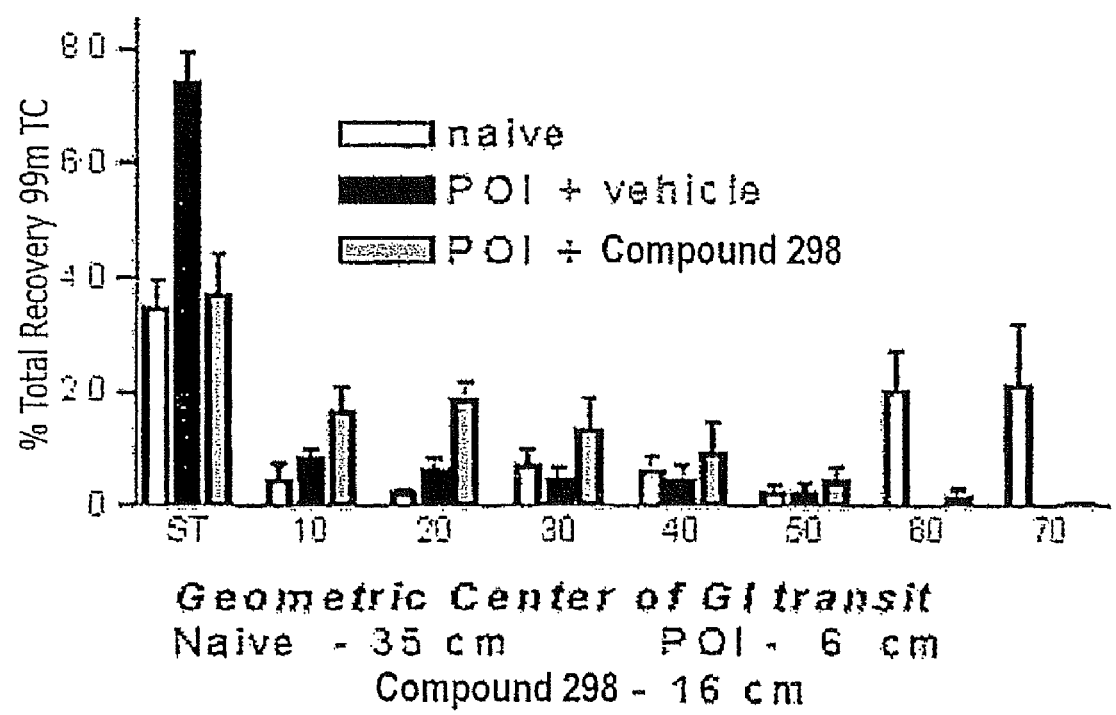
FIG. 15 shows a graph presenting effects on postoperative ileus for an exemplary compound of the present invention.

In FIG. 15, the distribution of the bars indicates the distribution of the meal in the stomach ('ST') and consecutive 10 cm segments of the small intestine at 15 min post-oral gavage. Abdominal surgery coupled with a running of the bowel caused a significant ileus in rats as determined by comparison of the naïve (i.e. unoperated) and POI treatment groups. Compound 298 significantly increased gastric emptying and intestinal transit at test concentrations of 100 and 300 µg/kg (i.v.).

The data corresponding to the 100 µg/kg dose is presented in FIG. 15. At 100 µg/kg (i.v.), compound 298 significantly promoted GI transit by 2.7× as measured by the geometric center of the meal in comparison to the POI+vehicle treatment group. Compound 298 significantly improved gastric emptying and intestinal transit in rats with post-operative ileus. Compound 298 can effectively treat an existing, post-surgical ileus; thus, prophylactic use prior to surgery is not required as is the case for opioid antagonists in clinical development.

7. The Effect of Compounds of the Invention on Gastric Emptying and Gastrointestinal Transit in a Model of Opioid-Delayed Gastric Emptying Opioid analgesics, such as morphine, are well known to delay gastrointestinal transit which is an important side-effect for this class of drugs. The clinical term for this syndrome is opioid bowel dysfunction (OBD). Importantly, patients recovering from abdominal surgery experience post-operative ileus that is further exacerbated by concomitant opioid therapy for post-surgical pain.

Objective
1. To determine whether compounds of the invention may have therapeutic utility in the treatment of OBD.

Methods
1. Rats (male, Sprague-Dawley, 250-300 g) are implanted with jugular vein catheters to accommodate dosing of test articles.
2. Overnight-fasted rats are administered morphine (3 mg/kg s.c.).
3. After 30 min, rats are to be dosed with vehicle or compound 298 (300 or 1000 µg/kg, i.v., n=4-to-6/gp) followed by intragastric gavage of $^{99m}$Tc methylcellulose (2%) meal.
4. After 15 min, the rats are euthanized and the stomach and consecutive 10 cm segments of the intestine are isolated. Radioactivity ($^{99m}$Tc) in each tissue isolate is measured as a means of measuring the transit of the meal.

Figure 16A:
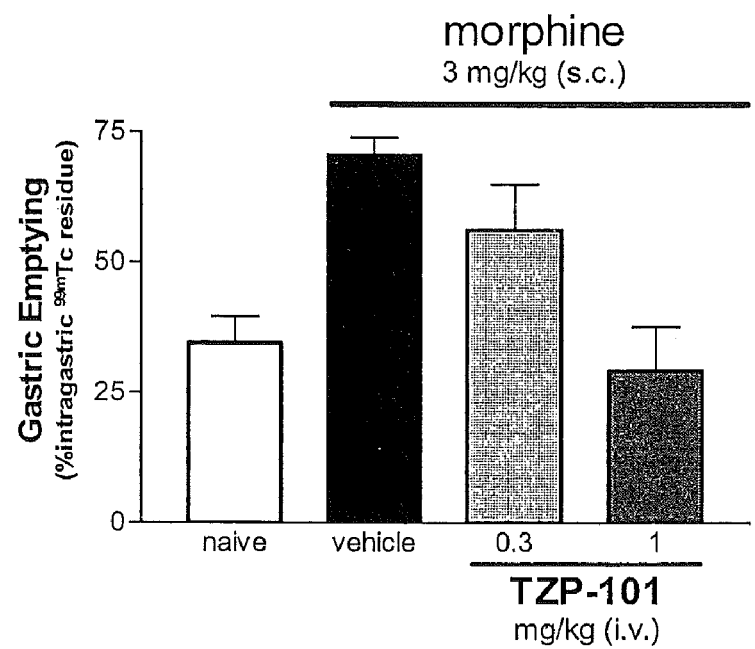
FIG. 16 shows graphs depicting reversal of morphine-delayed gastric emptying (panel A) and morphine-delayed gastrointestinal transit (panel B) for an exemplary compound of the present invention.
Figure 16B:
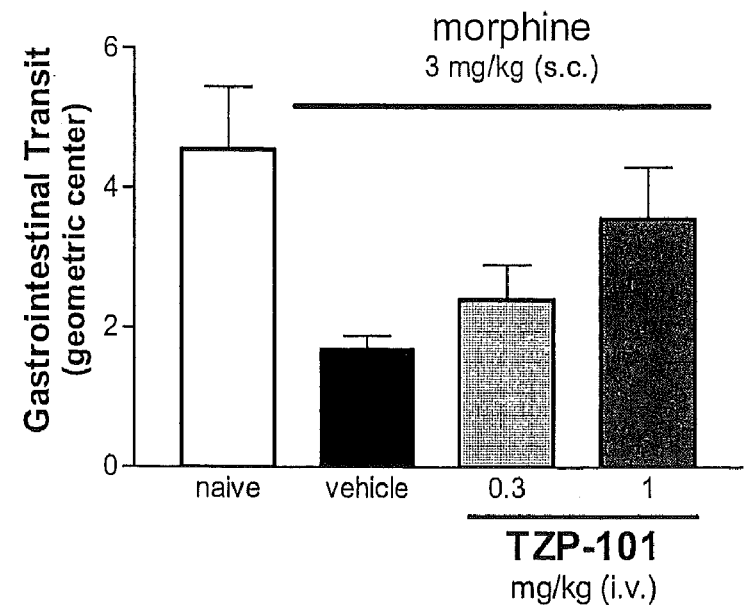

Results
Morphine (3 mg/kg, s.c.) significantly delayed gastric emptying and intestinal transit in rats (FIG. 16A). Opioid-delayed gastrointestinal transit was effectively reversed in a dose-dependent manner by treatment with compound 298 (i.v.) (FIG. 16B).

8. Metabolic Stability in Human Plasma

Drugs are susceptible to enzymatic degradation in plasma through the action of various proteinases and esterases. Thus, plasma stability is often performed as a metabolic screen in the early phases of drug discovery. The aim of this study was to measure the metabolic stability of compounds of the invention in human plasma.

Experimental Method
The stability of compound 298 in human plasma at 37° C. has been measured at 2 and 24 h. Two forms of compound 298 have been studied: free amine and corresponding HCl salt. Also, the stability of compound 298 has been established in plasma alone and in plasma buffered with phosphate-buffered saline (PBS) where the ratio of plasma to phosphate buffer (pH 7.0) is 20:1. Assays were both performed and analyzed in triplicate samples. Compound 298 was extracted from plasma matrix using an SPE technique (Oasis MCX cartridge). Sample analysis is done using LC-MS in APCI$^+$ mode. The level of compound 298 in plasma samples is compared to the level of compound 298 in a spiked sample stored at −60° C. from the same pool of plasma. Results are presented as a percent recovery of compound 298.

TABLE 8

Percent Recovery of Compound 298 Following Incubation in Human Plasma (37° C.).

| | Triplicates | | | | | | | |
|---|---|---|---|---|---|---|---|---|
| | Free amine | | Free Amine + PBS | | HCl Salt | | HCl Salt + PBS | |
| | 2 Hours (%) | 24 Hours (%) | 2 Hours (%) | 24 Hours (%) | 2 Hours (%) | 24 Hours (%) | 2 Hours (%) | 24 Hours (%) |
| Assay #1 | 101.0 | 105.5 | 98.3 | 97.9 | 100.2 | 96.6 | 102.9 | 97.8 |
| Assay #2 | 100.3 | 95.6 | 100.4 | 100.8 | 99.1 | 104.3 | 97.4 | 101.9 |
| Assay #3 | 101.3 | 100.9 | 98.3 | 101.9 | 101.6 | 102.3 | 99.4 | 98.5 |
| Mean | 100.9 | 100.7 | 99.0 | 100.2 | 100.3 | 101.1 | 99.9 | 99.4 |
| Standard Deviation | 0.5 | 4.9 | 1.2 | 2.1 | 1.3 | 4.0 | 2.7 | 2.2 |
| RSD | 0.5 | 4.9 | 1.3 | 2.1 | 1.3 | 4.0 | 2.7 | 2.2 |

As shown in Table 8, compound 298 is stable in human plasma at 37° C. for at least 24 hours independent of compound form (i.e. free amine or salt) or whether or not the plasma samples are pH buffered with PBS.

9. Compound 298 Interaction Profile at Nine Human Cytochrome P450 Enzyme Subtypes Compound 298 (0.0457 to 100 µM) has minimal inhibitory activity at all cyp450 enzymes tested, except cyp3A4, and has moderate inhibitory activity at cyp3A4. The inhibitory activity observed for compound 298 at cyp3A4 was not anticipated to be physiologically relevant based on the low doses of compound 298 required for therapeutic activity. Also, there was no indication that compound 298 would undergo a drug-drug interaction with opioid analgesics that may be co-administered to POI patients.

10. Compound 298 Profile in hERG Channel Inhibition

Compound 298 (1, 10 µM) had no significant effect on hERG channel function in comparison to vehicle (0.1% DMSO) controls. E-4031 (positive control) completely inhibited hERG channel currents at 500 nM.

EXAMPLE 5

Gastroparesis Animal Model

High caloric meals are well known to impede gastric emptying. This observation has recently been exploited by Megens, A. A.; et al. (unpublished) to develop a rat model for delayed gastric emptying as experienced in gastroparesis.

Materials
1. Wistar rats, male, 200-250 g
2. Chocolate test meal: 2 mL Clinutren ISO® (1.0 kcal/mL, Nestle SA, Vevey Switzerland)

Method

The test meal is given to the subjects by oral gavage at time=0. After 60 min, the subjects are sacrificed, the stomachs excised and the contents weighed. Untreated animals experienced a significant delay in gastric emptying as denoted by the higher residual stomach content.

Test compounds were administered intravenously as aqueous solutions, or solutions in normal saline, at time=0 at three dose levels (0.08 mg/kg; 0.30-0.31 mg/kg, 1.25 mg/kg). When necessary, for example compounds 21, 299 and 415, 10% cyclodextrin (CD) was added to solubilize the material. Test compounds examined utilizing subcutaneous injection are administered at time=−30 min. Four to five (4-5) rats were tested per group, except in the case of the cyclodextrin control in which ten (10) rats comprised the group.

Figure 17A:
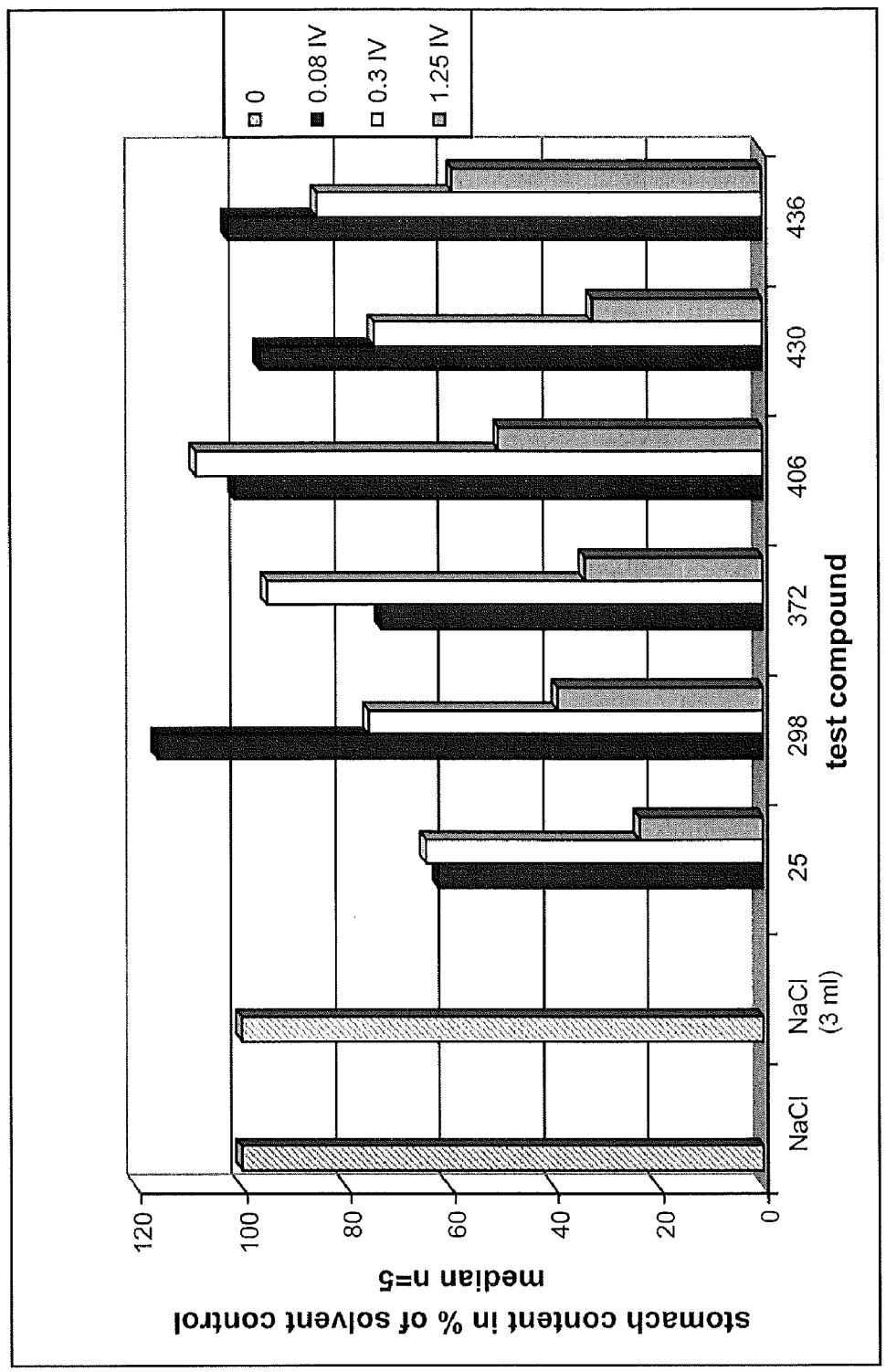
FIG. 17 (panels A and B) shows graphs depicting effects on gastroparesis for exemplary compounds of the present invention.
Figure 17B:
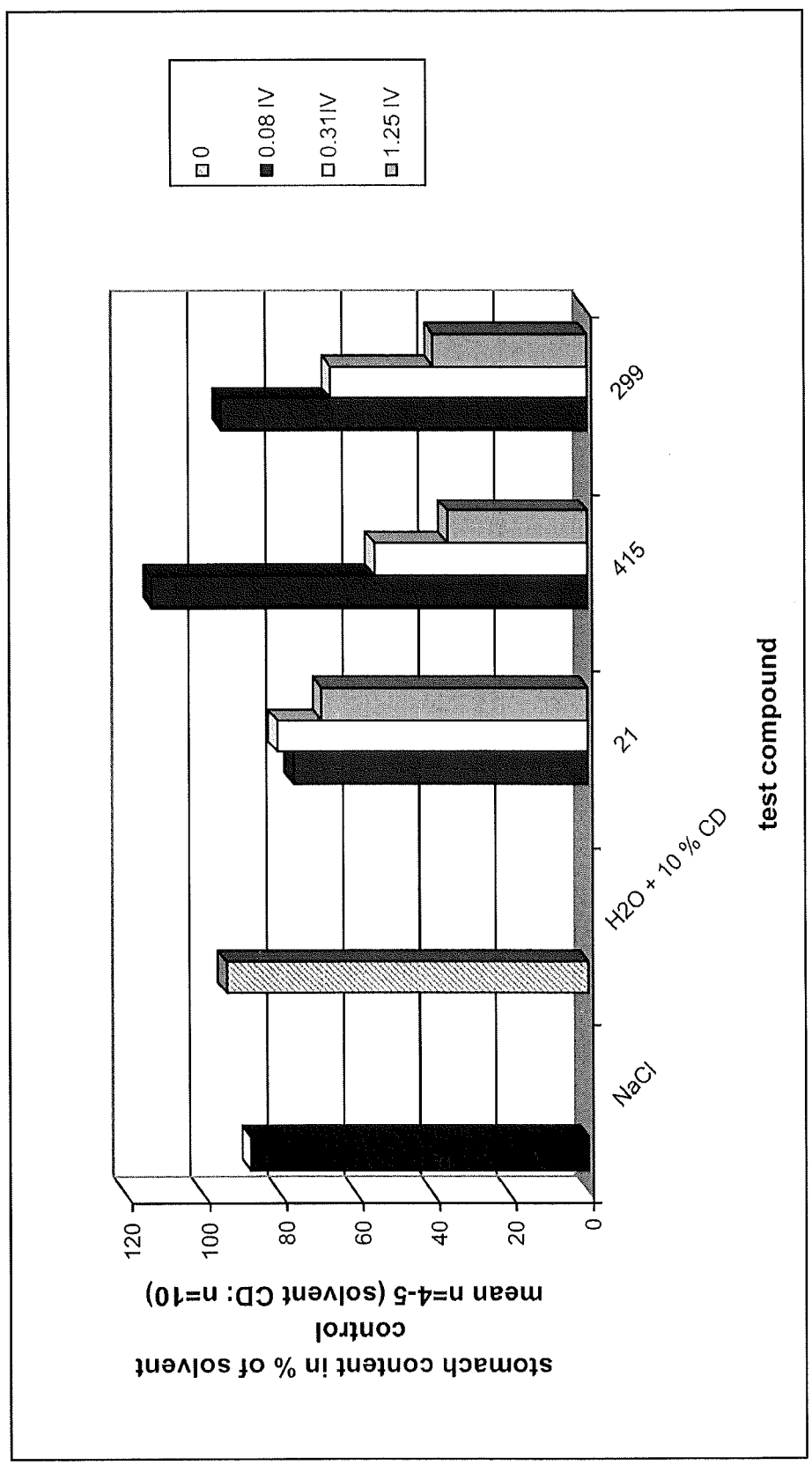

Results are reported as percentage relative to the stomach weight for injection only of solvent as a control as shown in FIGS. 17A and 17B and illustrate the gastric emptying capability of the compounds of the present invention. These results are applicable for the utility of these compounds for the prevention and/or treatment of gastroparesis and/or post-operative ileus.

The foregoing is illustrative of the present invention, and is not to be construed as limiting thereof. The invention is defined by the following claims, with equivalents of the claims to be included therein.

The invention claimed is:

1. A method of treating cachexia comprising administering to a subject in need thereof an effective amount of a compound selected from the group consisting of the following:

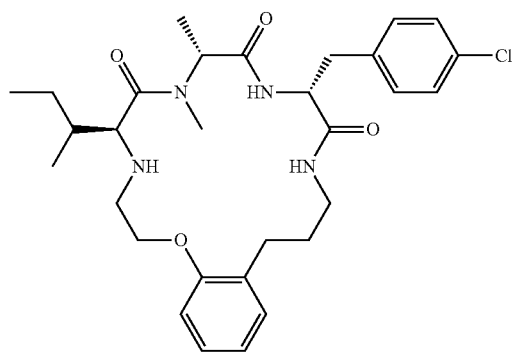

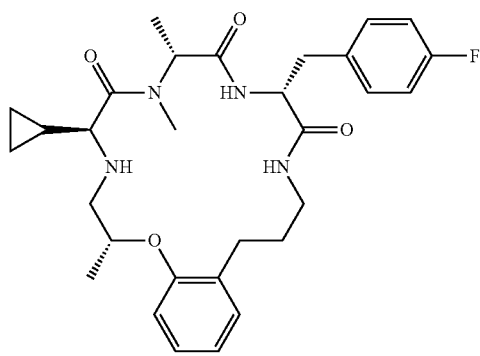

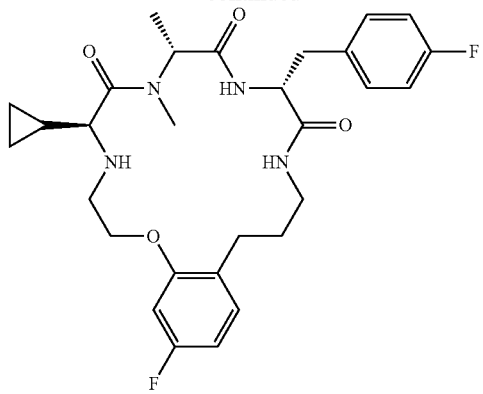

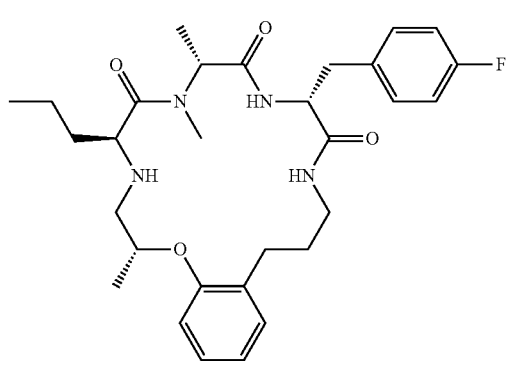

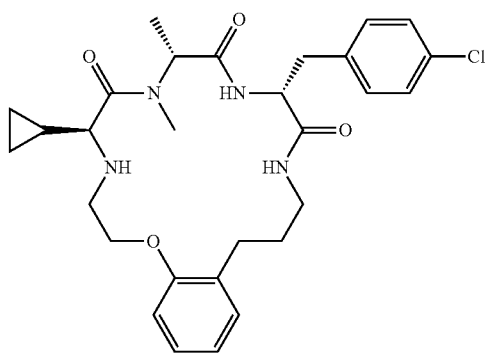

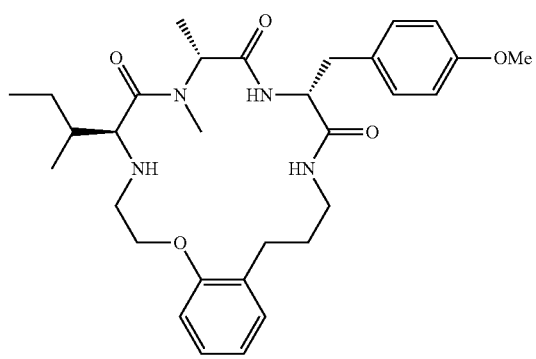

331
-continued
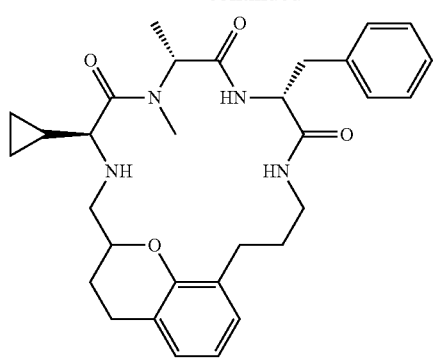
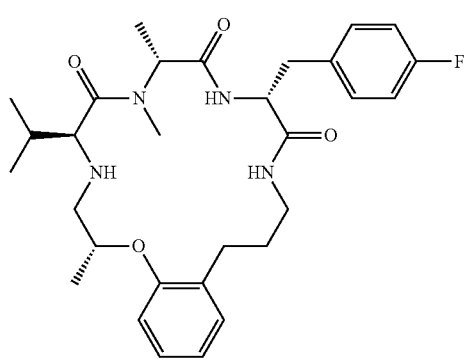
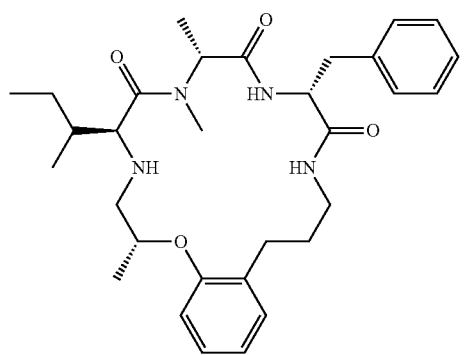
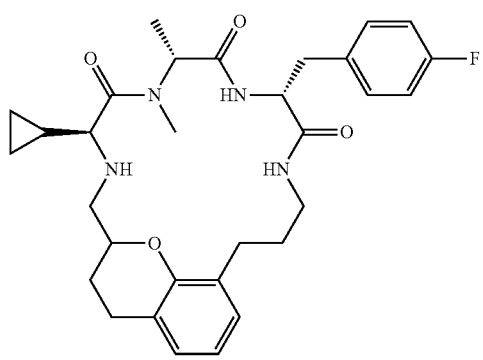
332
-continued
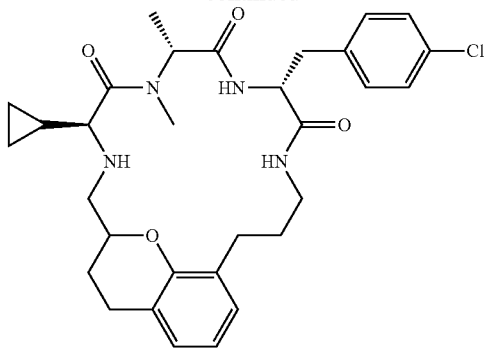
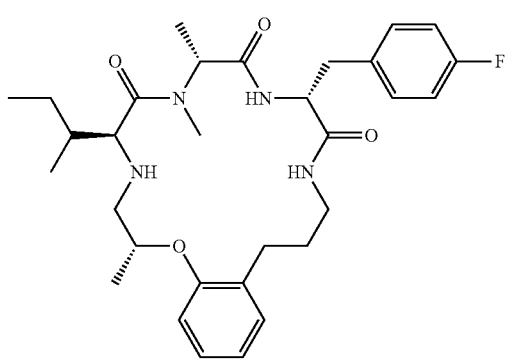
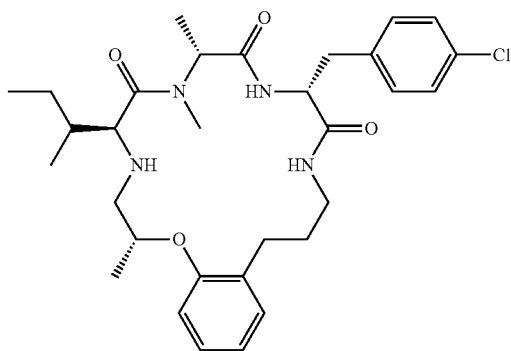
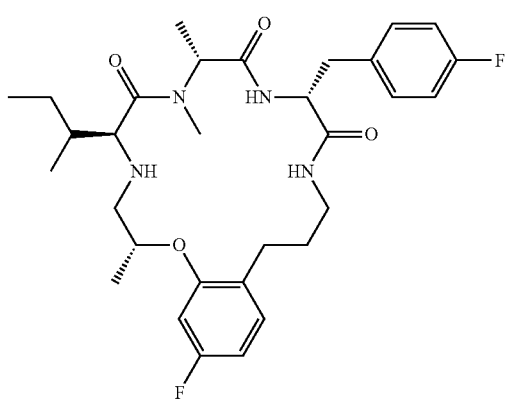

333
-continued
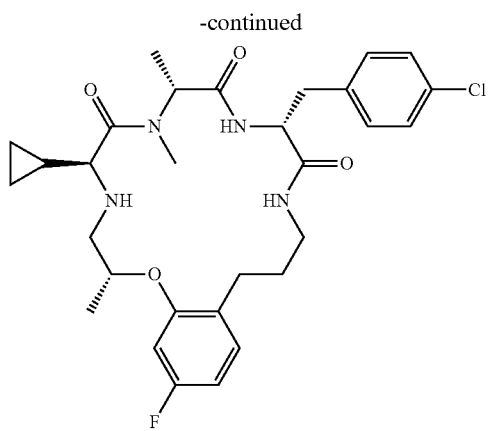
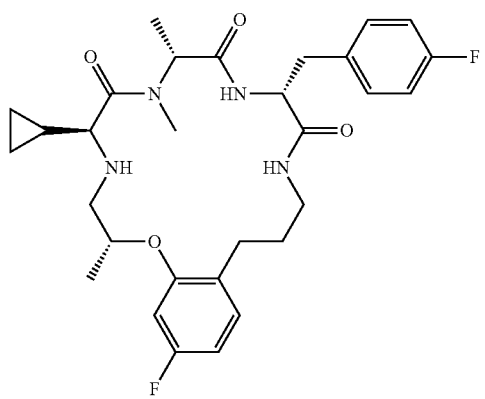
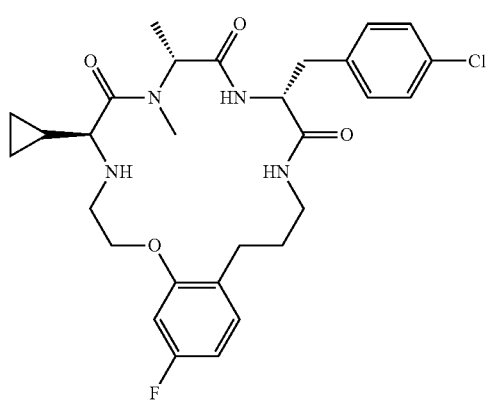
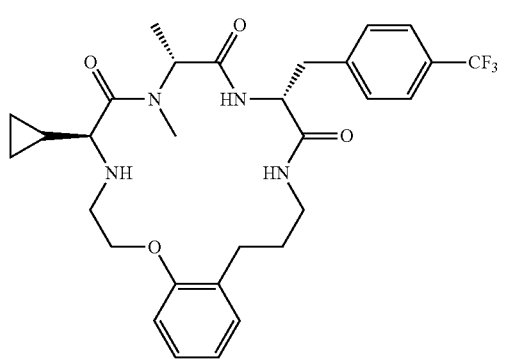
334
-continued
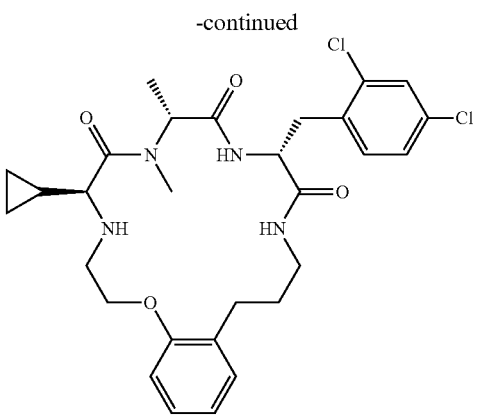
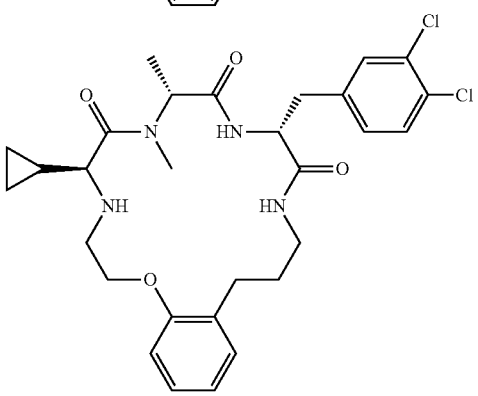
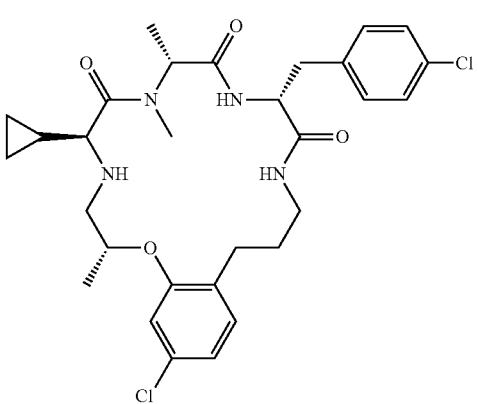
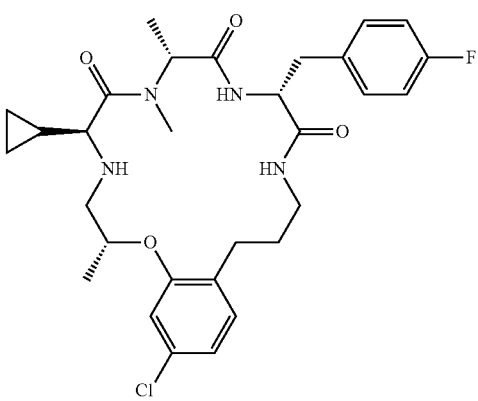

335

-continued

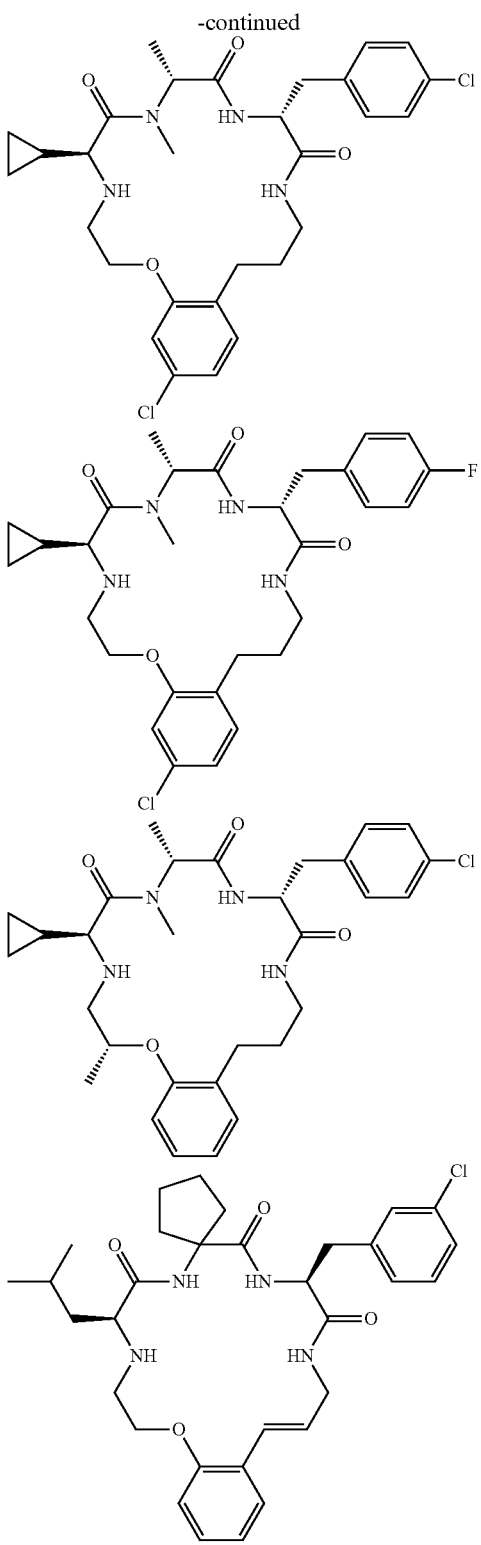

336

-continued

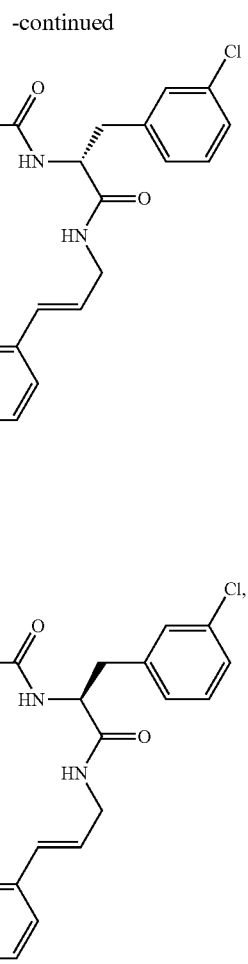

or pharmaceutically acceptable salts thereof.

2. The method of claim 1, wherein the compound is administered orally.

3. The method of claim 1, wherein the compound is administered parenterally.

4. The method of claim 1, wherein the compound is administered intravenously.

5. The method of claim 1, wherein the compound is administered subcutaneously.

6. The method of claim 1, wherein the cachexia is induced by cancer, cardiac disease, acquired immunodeficiency syndrome (AIDS) or renal disease.

* * * * *

UNITED STATES PATENT AND TRADEMARK OFFICE
CERTIFICATE OF CORRECTION

PATENT NO. : 8,349,887 B2
APPLICATION NO. : 13/173929
DATED : January 8, 2013
INVENTOR(S) : Fraser et al.

It is certified that error appears in the above-identified patent and that said Letters Patent is hereby corrected as shown below:

In the Specification:

Column 23, Line 39: Please correct "$-NR_{pp}SO_2NR_{qq}N_{rr}$" to read -- $-NR_{pp}SO_2NR_{qq}R_{rr}$ --

Column 28, 6$^{th}$, 7$^{th}$, 8$^{th}$ compounds: Please correct

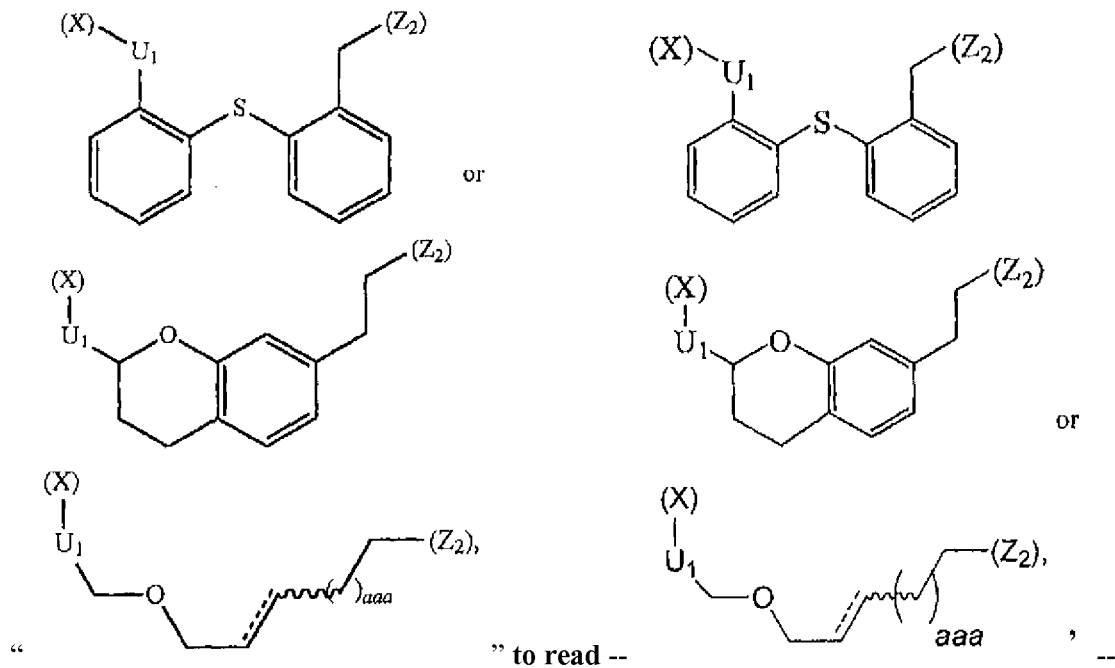

Column 78, formula, Lines 65-67: Please correct
"$D_{max}$=1–test concentration with maximal displace-
ment–non-specific binding×100 total binding–non-
specific binding"
to read
--$D_{max}$ = 1 - test concentration with maximal displacement – non-specific binding X 100

Signed and Sealed this
Eleventh Day of November, 2014

Michelle K. Lee
*Deputy Director of the United States Patent and Trademark Office*

CERTIFICATE OF CORRECTION (continued)
U.S. Pat. No. 8,349,887 B2 total binding – non-specific binding--

Column 80, Table: Please add --Table 3A-- to the top of this table so that it looks like the following:

TABLE 3A

Binding Activity at the Human Ghrelin Receptor for Compounds of the Invention

Col. 80, Table 3A, Compounds 2-3, Header $R_2$: Please correct

| Compound | X | $R_1$ | $R_2$ |
|---|---|---|---|
| 2 | N-H | H | 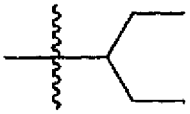 |
| 3 | N-H | H | 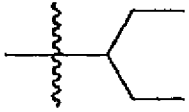 |

" "

to read

| Compound | X | $R_1$ | $R_2$ |
|---|---|---|---|
| 2 | N-H | H | 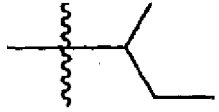 |
| 3 | N-H | H | 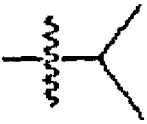 |

-- --

CERTIFICATE OF CORRECTION (continued)
U.S. Pat. No. 8,349,887 B2

Column 81, Table 3A, Compounds 14-16, Header $R_2$: Please correct figures in $R_2$ (column headers included for clarity)

| Compound | X | $R_1$ | $R_2$ |
|---|---|---|---|
| 14 | N-H | H | (isopropyl group) |
| 15 | N-H | H | (isopropyl group) |
| 16 | N-H | H | (isopropyl group) |

" to read

| Compound | X | $R_1$ | $R_2$ |
|---|---|---|---|
| 14 | N-H | H | (isopropyl group) |
| 15 | N-H | H | (isopropyl group) |
| 16 | N-H | H | (isopropyl group) |

--

Column 87, Table 3A, Compound 58, Header X: Please correct (column headers included for clarity)

| Compound | X | $R_1$ | $R_2$ |
|---|---|---|---|
| 58 | N—Ae | | |

" to read

| Compound | X | $R_1$ | $R_2$ |
|---|---|---|---|
| 58 | N–Ac | | |

--

Column 88, Table 3A, Compound 59, Header R₇: Please correct (column headers included for clarity)
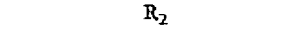
" to read
--  --
Column 107, Table 3A, Compound 184, Header Compound: Please correct (column headers included for clarity)
" to read
--  --
Column 115, Table 3A, Compound 41, Header R3: Please correct (column headers included for clarity)
" to read

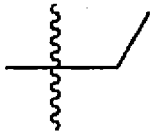
Column 125, Table 3A, Compound 141, Header $R_3$-$R_4$: Please correct figure bond (column headers included for clarity)
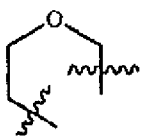
to read
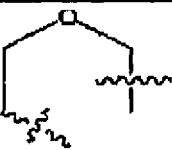
Column 125, Table 3A, Compound 144, Header $R_3$ and $R_4$: Please correct (column headers included for clarity)
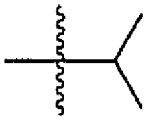
to read
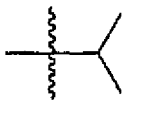

Columns 131-132, Table 3A, Compounds 184, Headers Compound, $R_3$, $R_4$, n, and $Z_1$: Please correct (column headers included for clarity)

| Compound | $R_3$ | $R_4$ | n | $Z_1$ |
|---|---|---|---|---|
| 184 | $CH_3$ | H | 0 | N–H |
| 184 | $CH_3$ | H | 0 | N–H | to read

| Compound | $R_3$ | $R_4$ | n | $Z_1$ |
|---|---|---|---|---|
| 184a | $CH_3$ | H | 0 | N–H |
| 184b | | | | |

Columns 131-132, Compounds 197-200, Headers $R_3$, $R_4$, n, and $Z_1$: Please correct (column headers included for clarity)

| Compound | $R_3$ | $R_4$ | n | $Z_1$ |
|---|---|---|---|---|
| 197 | | | | |
| 199 | [cyclohexyl structure] | | 0 | N–H |
| 200 | $CH_3$ | H | 0 | N–H | to read

| Compound | $R_3$ | $R_4$ | n | $Z_1$ |
|---|---|---|---|---|
| 197 | $CH_3$ | H | 0 | N–H |
| 199 | [cyclopentyl structure] | | 0 | N–H |
| 200 | [cyclohexyl structure] | | 0 | N–H |

Column 164, Table 3A, Compound 168, Headers $R_5$ and $R_6$: Please correct (column headers included for clarity)

| Compound | $R_5$ | $R_6$ | p | $Z_2$ |
|---|---|---|---|---|
| 168 | [cyclohexyl structure] | H | 0 | N–H |

CERTIFICATE OF CORRECTION (continued)
U.S. Pat. No. 8,349,887 B2 to read

| Compound | R$_5$ | R$_6$ | p | Z$_2$ |
|---|---|---|---|---|
| 168 | | (cyclohexyl structure) | 0 | N–H |
| -- | | | | -- |

Column 164, Table 3A, Compound 172, Headers p and Z$_2$: Please correct (column headers included for clarity)

| Compound | R$_5$ | R$_6$ | p | Z$_2$ |
|---|---|---|---|---|
| " 172 | H | (structure) | | " | to read

| Compound | R$_5$ | R$_6$ | p | Z$_2$ |
|---|---|---|---|---|
| 172 | H | (structure) | 0 | N–H |
| -- | | | | -- |

Column 165-166, Table 3A, Compounds 184, Header Compound: Please correct (column headers included for clarity)

| Compound | R$_5$ | R$_6$ | p | Z$_2$ |
|---|---|---|---|---|
| 184 | (benzyl structure) | H | 0 | N—H |
| " 184 | | | | " | to read

| Compound | R$_5$ | R$_6$ | p | Z$_2$ |
|---|---|---|---|---|
| 184a | (benzyl structure) | H | 0 | N—H |
| 184b | | | | |
| -- | | | | -- |

Column 183-184, Table 3A, Compound 78, Header T: Please correct (column headers included for clarity)

| Compound | T | $K_1$ (nM) |
|---|---|---|
| 78 | [structure: X—cyclopentane—Z2] | G |

" to read

| Compound | T | $K_1$ (nM) |
|---|---|---|
| 78 | [structure: X—tetrahydrofuran (O)—Z2] | G |

--  --

Column 187-188, Table 3A, Compound 109, Header T: Please correct (column headers included for clarity)

| Compound | T | $K_1$ (nM) |
|---|---|---|
| 109 | [structure: benzene with propyl-Z2 and O-ethyl-X substituents] | D |

" to read

| Compound | T | $K_1$ (nM) |
|---|---|---|
| 109 | [structure: pyridine with propyl-Z2 and O-ethyl-X substituents] | D |

--  --

Columns 195-196, Table 3A, Compound 152a, Header $K_1$(nM): Please correct (column headers included for clarity)

| Compound | T | $K_1$ (nM) |
|---|---|---|
| 152a | [structure: benzene with propyl-Z2 and O-ethyl-X substituents] | |

" to read

| Compound | T | $K_1$ (nM) |
|---|---|---|
| 152a | 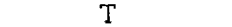 | C |
Columns 195-196, Table 3A, Compound 161a, Header $K_1$(nM): Please correct (column headers included for clarity)
| Compound | T | $K_1$ (nM) |
|---|---|---|
| 161a | | G |
"  " to read
| Compound | T | $K_1$ (nM) |
|---|---|---|
| 161a | | F |
Columns 199-200, Table 3A, Compounds 184, Header Compound: Please correct (column headers included for clarity)
| Compound | T | $K_1$ (nM) |
|---|---|---|
| 184 | 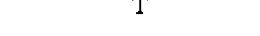 | C |
| 184 | | C |
"  " to read

| Compound | T | $K_1$ (nM) |
|---|---|---|
| 184a | [structure: X—(CH2 chain)—Z2] | C |
| -- 184b | | C -- |

Column 199-200, Table 3A, Compound 188, Header $K_1$(nM): Please correct (column headers included for clarity)

| Compound | T | $K_1$ (nM) |
|---|---|---|
| " 188 | [structure: phenyl with Z1 and X substituents] | G " | to read

| Compound | T | $K_1$ (nM) |
|---|---|---|
| -- 188 | [structure: phenyl with Z1 and X substituents] | F -- |

Column 203-204, Table 3A, Compound 206, Header T: Please correct the figure (column headers included for clarity)

| Compound | T | $K_1$ (nM) |
|---|---|---|
| " 206 | [structure: pyrimidinedione with Z2 and X substituents] | G " | to read

| Compound | T | $K_1$ (nM) |
|---|---|---|
| 206 | 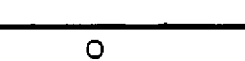 | G |

Columns 207-208, Table 3B, Compound 306b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| " 306b | | | diastereomer | | " | to read

| Compound | $R_2$ | $R_3$ | $R_4$ | $R_7$ | $R_5$ |
|---|---|---|---|---|---|
| 306b | | | | | diastereomer |

Columns 211-212, Table 3B, Compound 327b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 327b " | | | diastereomer | | " | to read

| Compound | $R_2$ | $R_3$ | $R_4$ | $R_7$ | $R_5$ |
|---|---|---|---|---|---|
| 327b | | | | | diastereomer |

Compound 331b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| " 331b | | | -diastereomer | | " | to read

| Compound | $R_2$ | $R_3$ | $R_4$ | $R_7$ | $R_5$ |
|----------|-------|-------|-------|-------|-------|
| 331b     |       |       |       |       | diastereomer |

--                                                                                                                    --

Columns 211-212, Table 3B, Compound 332b, Headers $R_4$, $R_7$ and $R_5$: Please correct (column headers included for clarity)

| Compound | $R_2$ | $R_3$ | $R_4$ $R_7$ | $R_5$ |
|----------|-------|-------|-------------|-------|
| 332b     |       |       | diastereomer |      |

" "

to read

| Compound | $R_2$ | $R_3$ | $R_4$ | $R_7$ | $R_5$ |
|----------|-------|-------|-------|-------|-------|
| 332b     |       |       |       |       | diastereomer |

--                                                                                                                    --

Column 213-214, Table 3B, Compound 345b, Headers $R_4$, $R_7$ and $R_5$: Please correct (column headers included for clarity)

| Compound | $R_2$ | $R_3$ | $R_4$ $R_7$ | $R_5$ |
|----------|-------|-------|-------------|-------|
| 345b     |       |       | diastereomer |      |

" "

to read

| Compound | $R_2$ | $R_3$ | $R_4$ | $R_7$ | $R_5$ |
|----------|-------|-------|-------|-------|-------|
| 345b     |       |       |       |       | diastereomer |

--                                                                                                                    --

Column 215-216, Table 3B, Compound 348b, Headers $R_4$, $R_7$ and $R_5$: Please correct (column headers included for clarity)

| Compound | $R_2$ | $R_3$ | $R_4$ $R_7$ | $R_5$ |
|----------|-------|-------|-------------|-------|
| 348b     |       |       | diastereomer |      |

" "

to read

| Compound | $R_2$ | $R_3$ | $R_4$ | $R_7$ | $R_5$ |
|----------|-------|-------|-------|-------|-------|
| 348b     |       |       |       |       | diastereomer |

--                                                                                                                    --

Compound 353b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 353b | | | | diastereomer | |
| " | | | | | " | to read

| Compound | $R_2$ | $R_3$ | $R_4$ | $R_7$ | $R_5$ |
|---|---|---|---|---|---|
| 353b | | | | | diastereomer |
| -- | | | | | -- |

Compound 358b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 358b | | | | diastereomer | |
| " | | | | | " | to read

| Compound | $R_2$ | $R_3$ | $R_4$ | $R_7$ | $R_5$ |
|---|---|---|---|---|---|
| 358b | | | | | diastereomer |
| -- | | | | | -- |

Column 217-218, Table 3B, Compound 368b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 368b | | | | diastereomer | |
| " | | | | | " | to read

| Compound | $R_2$ | $R_3$ | $R_4$ | $R_7$ | $R_5$ |
|---|---|---|---|---|---|
| 368b | | | | | diastereomer |
| -- | | | | | -- |

Column 221-222, Table 3B, Compound 389b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 389b | | | | diastereomer | |
| " | | | | | " | to read

| Compound | $R_2$ | $R_3$ | $R_4$ | $R_7$ | $R_5$ |
|---|---|---|---|---|---|
| 389b | | | | | diastereomer |
| -- | | | | | -- |

Compound 399b, Headers $R_4$, $R_7$ and $R_5$: Please correct (column headers included for clarity)

| Compound | $R_2$ | $R_3$ | $R_4$ | $R_7$ | $R_5$ |
|---|---|---|---|---|---|
| 399b | | | | diastereomer | |

"  "

to read

| Compound | $R_2$ | $R_3$ | $R_4$ | $R_7$ | $R_5$ |
|---|---|---|---|---|---|
| 399b | | | | | diastereomer |

--  --

Column 223-224, Table 3B, Compound 402b, Headers $R_4$ and $R_5$: Please correct (column headers included for clarity)

| Compound | $R_2$ | $R_3$ | $R_4$ | $R_7$ | $R_5$ |
|---|---|---|---|---|---|
| 402b | | | | diastereomer | |

"  "

to read

| Compound | $R_2$ | $R_3$ | $R_4$ | $R_7$ | $R_5$ |
|---|---|---|---|---|---|
| 402b | | | | | diastereomer |

--  --

Column 223-224, Table 3B, Compound 306b, Header Tether: Please correct (column headers included for clarity)

| Compound | $R_6$ | Tether | Ki (nM) |
|---|---|---|---|
| 306b | | diastereomer | B |

"  "

to read

| Compound | $R_6$ | Tether | Ki (nM) |
|---|---|---|---|
| 306b | | | B |

--  --

Column 227, Table 3B, Compound 372a, Header Compound: Please correct (column headers included for clarity)

| Compound | R$_6$ | Tether | Ki (nM) |
|---|---|---|---|
| 372a | 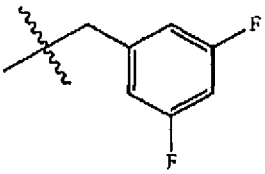 | 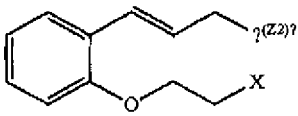 | B |

" to read "

| Compound | R$_6$ | Tether | Ki (nM) |
|---|---|---|---|
| 327a | 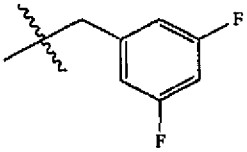 | 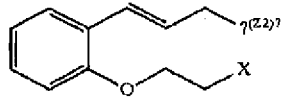 | B |

--  --

Compound 327b, Header Tether: Please correct (column headers included for clarity)

| Compound | R$_6$ | Tether | Ki (nM) |
|---|---|---|---|
| 327b | | diastereomer | C |

" to read "

| Compound | R$_6$ | Tether | Ki (nM) |
|---|---|---|---|
| 327b | | | C |

--  --

Columns 227-228, Table 3B, Compound 331b, Header Tether: Please correct (column headers included for clarity)

| Compound | R$_6$ | Tether | Ki (nM) |
|---|---|---|---|
| 331b | | diastereomer | C |

" to read "

| Compound | R$_6$ | Tether | Ki (nM) |
|---|---|---|---|
| 331b | | | C |

--  --

Compound 332b, Header Tether: Please correct (column headers included for clarity)

| Compound | $R_6$ | Tether | Ki (nM) |
|---|---|---|---|
| 332b | | diastereomer | C |

" to read "

| Compound | $R_6$ | Tether | Ki (nM) |
|---|---|---|---|
| 332b | | | C |

--  --

Columns 229-230, Table 3B, Compound 345b, Header Tether: Please correct (column headers included for clarity)

| Compound | $R_6$ | Tether | Ki (nM) |
|---|---|---|---|
| 345b | | diastereomer | B |

" to read "

| Compound | $R_6$ | Tether | Ki (nM) |
|---|---|---|---|
| 345b | | | B |

--  --

Column 231-232, Table 3B, Compound 348b, Header Tether: Please correct (column headers included for clarity)

| Compound | $R_6$ | Tether | Ki (nM) |
|---|---|---|---|
| 348b | | diastereomer | C |

" to read "

| Compound | $R_6$ | Tether | Ki (nM) |
|---|---|---|---|
| 348b | | | C |

--  --

Column 231-232, Table 3B, Compound 353b, Header Tether: Please correct (column headers included for clarity)

| Compound | $R_6$ | Tether | Ki (nM) |
|---|---|---|---|
| 353b | | diastereomer | B |

" to read

| Compound | $R_6$ | Tether | Ki (nM) |
|---|---|---|---|
| 353b | | | B |

--   --

Compound 358b, Header Tether: Please correct (column headers included for clarity)

| Compound | $R_6$ | Tether | Ki (nM) |
|---|---|---|---|
| 358b | | diastereomer | C |

" to read "

| Compound | $R_6$ | Tether | Ki (nM) |
|---|---|---|---|
| 358b | | | C |

--   --

Columns 233-234, Table 3B, Compound 368b, Header Tether: Please correct (column headers included for clarity)

| Compound | $R_6$ | Tether | Ki (nM) |
|---|---|---|---|
| 368b | | diastereomer | B |

" to read "

| Compound | $R_6$ | Tether | Ki (nM) |
|---|---|---|---|
| 368b | | | B |

--   --

Columns 237-238, Table 3B, Compound 389b, Header Tether: Please correct (column headers included for clarity)

| Compound | $R_6$ | Tether | Ki (nM) |
|---|---|---|---|
| 389b | | diastereomer | B |

" to read "

| Compound | $R_6$ | Tether | Ki (nM) |
|---|---|---|---|
| 389b | | | B |

--   --

Columns 239-240, Table 3B, Compound 399b, Header Tether: Please correct (column headers included for clarity)

CERTIFICATE OF CORRECTION (continued)
U.S. Pat. No. 8,349,887 B2

| Compound | $R_6$ | Tether | $K_i$ (nM) |
|---|---|---|---|
| 399b | | diastereomer | A |

"

to read

| Compound | $R_6$ | Tether | $K_i$ (nM) |
|---|---|---|---|
| 399b | | | A |

"

Compound 402b, Header Tether: Please correct (column headers included for clarity)

| Compound | $R_6$ | Tether | $K_i$ (nM) |
|---|---|---|---|
| 402b | | diastereomer | B |

"

to read

| Compound | $R_6$ | Tether | $K_i$ (nM) |
|---|---|---|---|
| 402b | | | B |

"

Columns 245-246, Table 3D, Compounds 437-441, Headers $R_3$ - $R_4$: Please correct (column headers included for clarity)

| Compound | $R_1$ | $R_2$ | $R_3$ | $R_4$ | $R_7$ | $R_5$ |
|---|---|---|---|---|---|---|
| 437 | | [cyclopentyl] | [cyclopentyl] | H | | H |
| 438 | H | [isopropyl] | [cyclohexyl] | H | | H |
| 439 | H | [sec-butyl] | [tetrahydropyranyl] | H | | H |
| 440 | H | [sec-butyl] | [CH₂-O-benzyl] | H | CH₃ | [4-fluorobenzyl] |
| 441 | H | [sec-butyl] | [cyclopentyl] | H | | H |

"

to read

| Compound | R₁ | R₂ | R₃ | R₄ | R₇ | R₅ |
|---|---|---|---|---|---|---|
| 437 | | (cyclopentyl) | | (cyclopentyl) | H | H |
| 438 | H | (isobutyl) | | (cyclopentyl) | H | H |
| 439 | H | (sec-butyl) | | (tetrahydrofuranyl) | H | H |
| 440 | H | (sec-butyl) | (benzyloxymethyl) | H | CH₃ | (4-fluorobenzyl) |
| 441 | H | (sec-butyl) | | (cyclopentyl) | H | H |

Column 247, Table 3D, Compounds 442a-449, Headers R₃, R₄, R₇: Please correct (column headers included for clarity)

| Compound | $R_1$ | $R_2$ | $R_3$ | $R_4$ | $R_7$ | $R_5$ |
|---|---|---|---|---|---|---|
| 442a | H | sec-butyl | cyclopentyl | | H | H |
| 442b | | | diastereomer | | | |
| 443a | H | sec-butyl | cyclopentyl | | H | H |
| 443b | | | diastereomer | | | |
| 444a | H | isobutyl | cyclopentyl | | H | H |
| 444b | | | diastereomer | | | |
| 445 | H | sec-butyl | CH3 | H | CH3 | 4-hydroxybenzyl |
| 446a | H | cyclopropylmethyl | CH3 | H | CH3 | 4-fluorobenzyl |
| 446b | | | diastereomer | | | |
| 447 | H | sec-butyl | cyclopentyl | | H | H |
| 448 | H | n-butyl | H | H | CH3 | H |
| 449 | H | sec-butyl | cyclopentyl | | H | H |

" "

to read

| Compound | R₁ | R₂ | R₃ | R₄ | R₇ | R₅ |
|---|---|---|---|---|---|---|
| 442a | H | *(sec-butyl group)* | | *(cyclopentyl)* | H | H |
| 442b | | | | | diastereomer | |
| 443a | H | *(sec-butyl group)* | | *(cyclopentyl)* | H | H |
| 443b | | | | | diastereomer | |
| 444a | H | *(isobutyl group)* | | *(cyclopentyl)* | H | H |
| 444b | | | | | diastereomer | |
| 445 | H | *(sec-butyl group)* | CH₃ | H | CH₃ | *(4-hydroxybenzyl)* |
| 446a | H | *(cyclopropyl group)* | CH₃ | H | CH₃ | *(4-fluorobenzyl)* |
| 446b | | | | | diastereomer | |
| 447 | H | *(sec-butyl group)* | | *(cyclopentyl)* | H | H |
| 448 | H | *(butyl group)* | H | H | CH₃ | H |
| 449 | H | *(sec-butyl group)* | | *(cyclopentyl)* | H | H |

CERTIFICATE OF CORRECTION (continued)
U.S. Pat. No. 8,349,887 B2

Column 249-252, Table 3D, Compounds 442b, 443b, 444b and 446b, Headers $R_6$ and Tether: Please correct (column headers included for clarity)

| Compound | $R_6$ | Tether | Ki (nM) |
|---|---|---|---|
| 442b | | diastereomer | E |
| 443a | [structure: CH2-O-CH3] | [structure: styryl-phenyl-O-CH2CH2-X] | E |
| 443b | | diastereomer | E |
| 444a | [structure: imidazole-CH2-] | [structure: styryl-phenyl-O-CH2CH2-X] | E |
| 444b | | diastereomer | E |
| 445 | H | [structure: propyl-phenyl-O-CH2CH2-X] | B |
| 446a | H | [structure: X-CH2CH2-O-CH2CH2-O-CH2CH2-] | D |
| 446b | | diastereomer | D |

" "

to read

CERTIFICATE OF CORRECTION (continued)

U.S. Pat. No. 8,349,887 B2

| Compound | R₆ | Tether | Ki (nM) |
|---|---|---|---|
| 442b | | | E |
| 443a | (CH₃OCH₂C(CH₃)−) | styryl-phenyl-OCH₂CH₂X | E |
| 443b | | | E |
| 444a | (imidazolyl-CH₂C(CH₃)−) | styryl-phenyl-OCH₂CH₂X | E |
| 444b | | | E |
| 445 | H | (CH₂)₃-phenyl-OCH₂CH₂X | B |
| 446a | H | X-CH₂CH₂-O-CH₂CH₂-O-CH₂CH₂- | D |
| 446b | | | D |

Column 270, Tether T9: Please correct

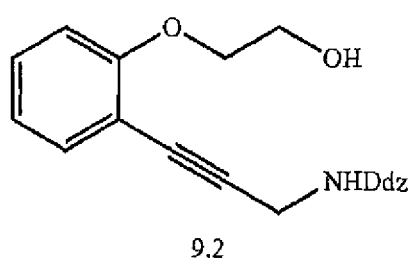

9.2

" to read --

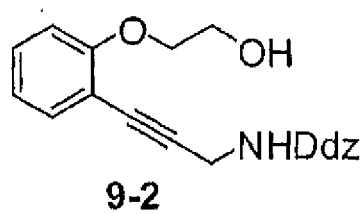

9-2

--

CERTIFICATE OF CORRECTION (continued)
U.S. Pat. No. 8,349,887 B2

Column 281, Tether T69, Ddz-T69: Please correct

Ddz-T69

Ddz-T69

4 steps
Overall yield: 56%

" " to read -- --

Tether T69, Ddz-T70: Please correct

Ddz-T70

Ddz-T70

4 steps
Overall yield: 54%

" " to read -- --

Column 283, Tether T71, DdzT71: Please correct

Ddz-T71

Ddz-T71

4 steps
Overall yield: 43%

" " to read -- --

Column 284, Tether T71, 71-B: Please correct

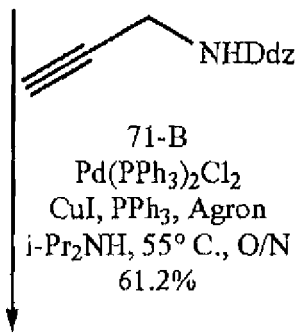

71-B
Pd(PPh$_3$)$_2$Cl$_2$
CuI, PPh$_3$, Agron
i-Pr$_2$NH, 55° C., O/N
61.2%

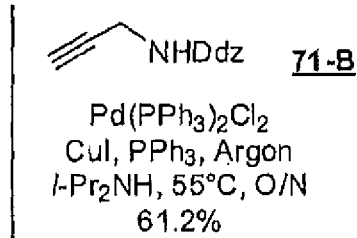

71-B
Pd(PPh$_3$)$_2$Cl$_2$
CuI, PPh$_3$, Argon
i-Pr$_2$NH, 55°C, O/N
61.2%

" " to read -- --

Tether T72, 72-2: Please correct
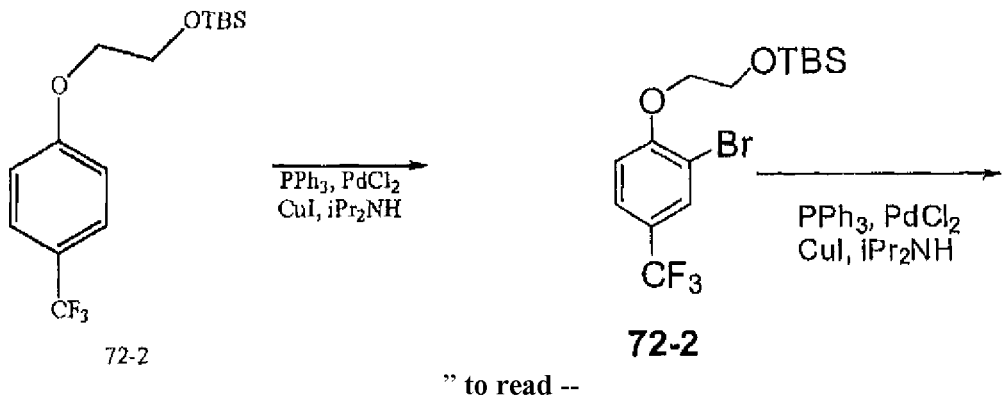
" to read --
Columns 287-288, Tether T74, identifiers: Please correct
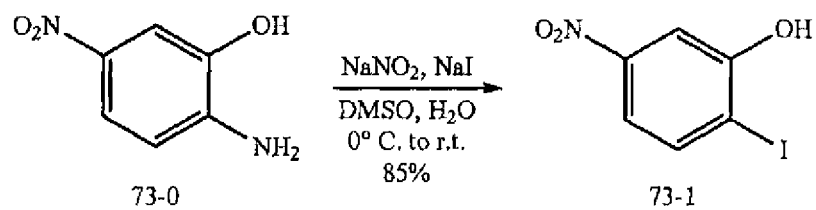
" to read
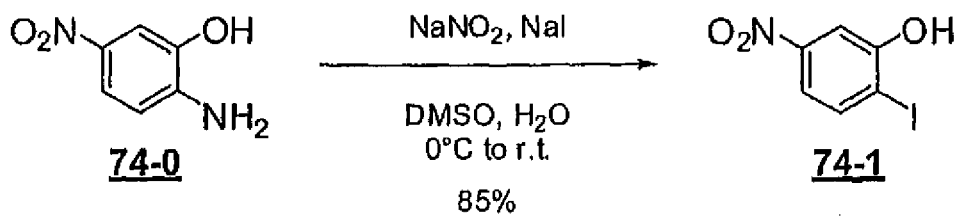
and
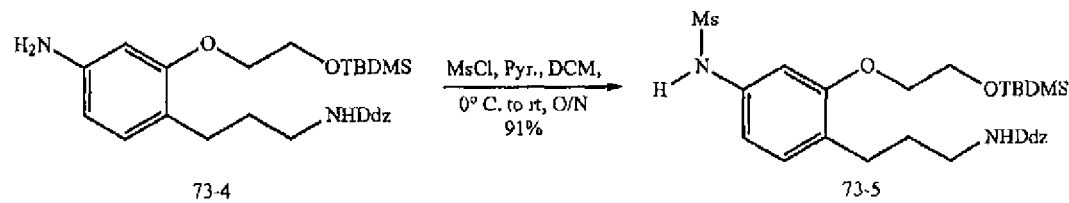
" to read
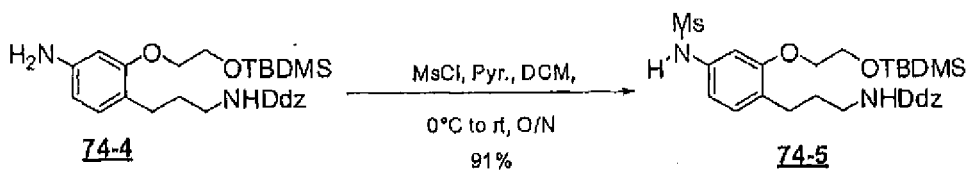

Column 287, Tether T74, Ddz-T74(Boc): Please correct
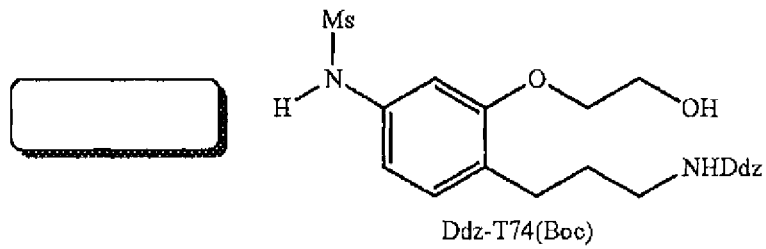
Ddz-T74(Boc)
" " to read
Ddz-T74(Boc)
-- --
Column 289, Tether T75a and T75b, 75-1: Please correct
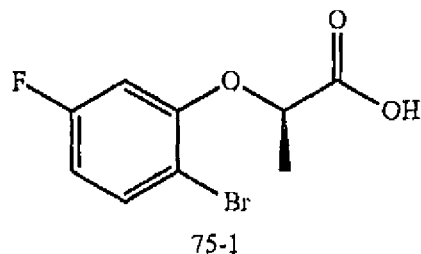
75-1
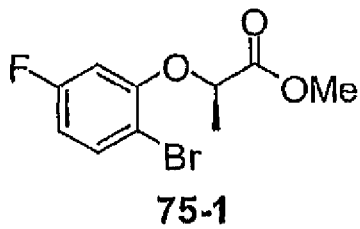
75-1
" " to read -- --
Column 299, LS1-5, Lines 25-35: Please correct
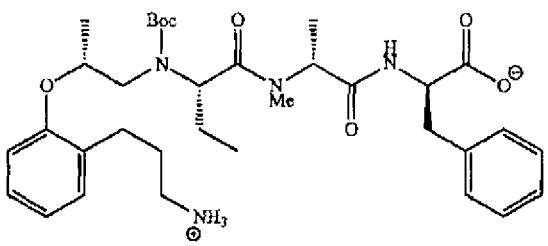
LS1-5
" " to read

CERTIFICATE OF CORRECTION (continued)
U.S. Pat. No. 8,349,887 B2

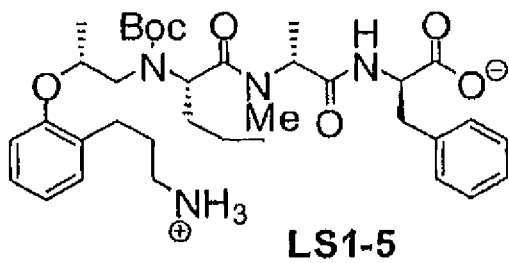

LS1-5

Column 299, LS1-5, Lines 37-47: Please correct

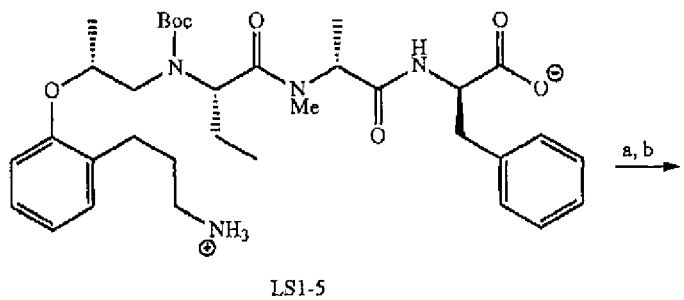

" LS1-5 "

to read

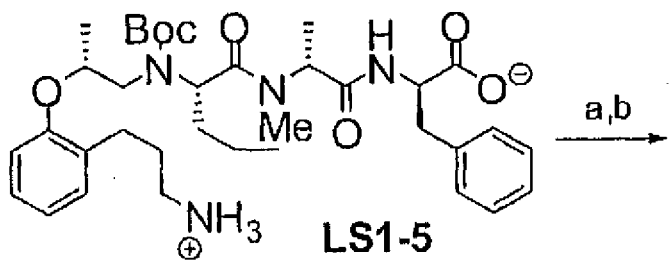

LS1-5

Column 303, LS1-13, Lines 28-38: Please correct

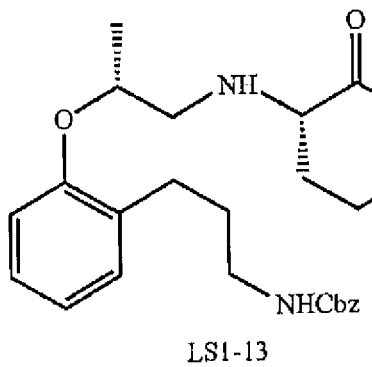

LS1-13

" to read --

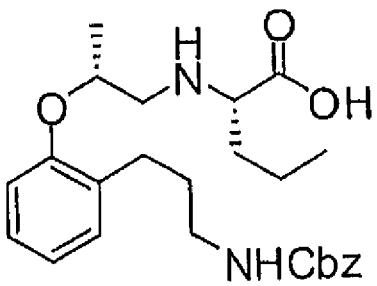

LS1-13

Column 308, LS2-22: Please correct
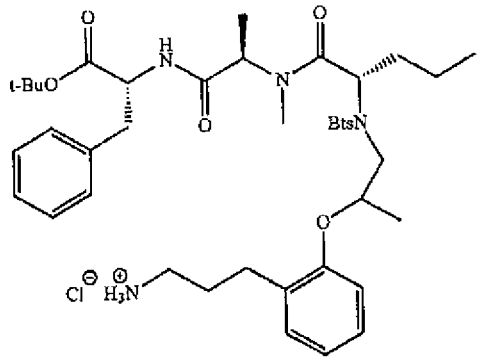
LS2-22
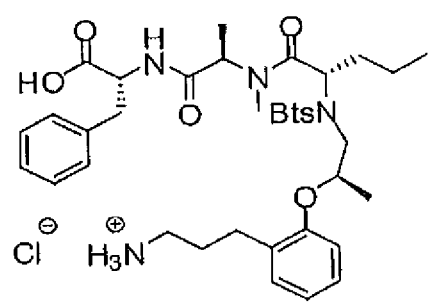
LS2-23
" to read --     --
Column 315, Synthesis of Compound 298: Please correct
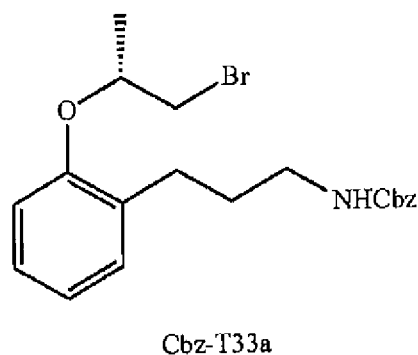
Cbz-T33a
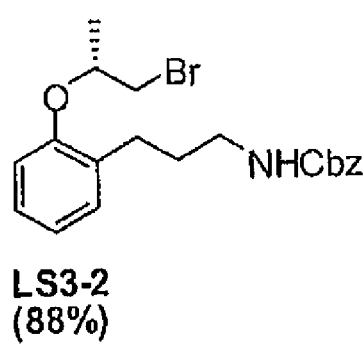
LS3-2 (88%)
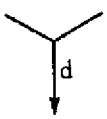
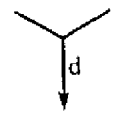
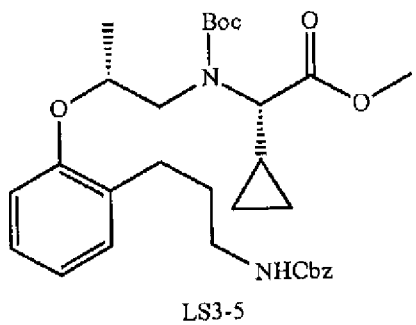
LS3-5
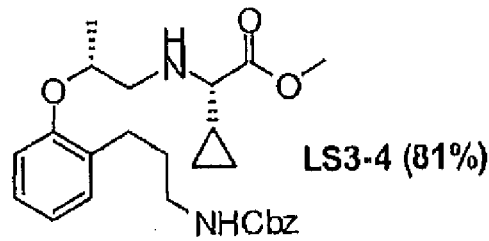
LS3-4 (81%)
" to read --     --

Columns 315-316, LS3-6 and LS3-10: Please correct
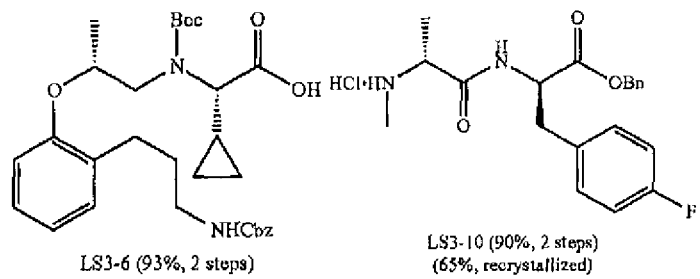
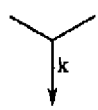
" to read "
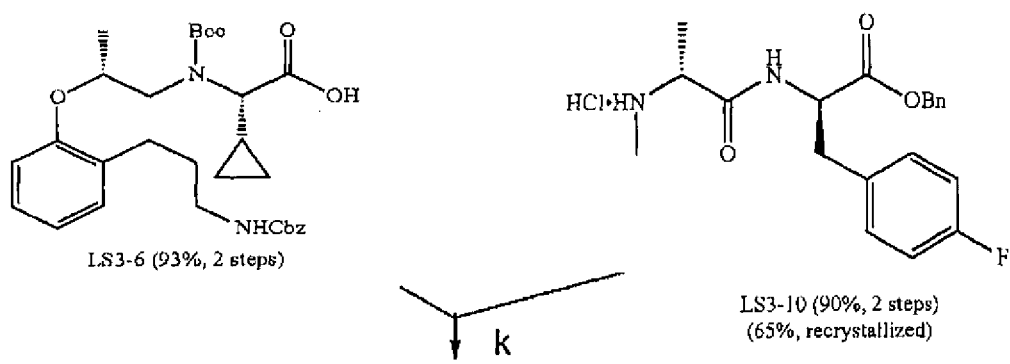
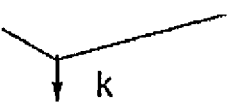
-- --
Column 317, Compound 298
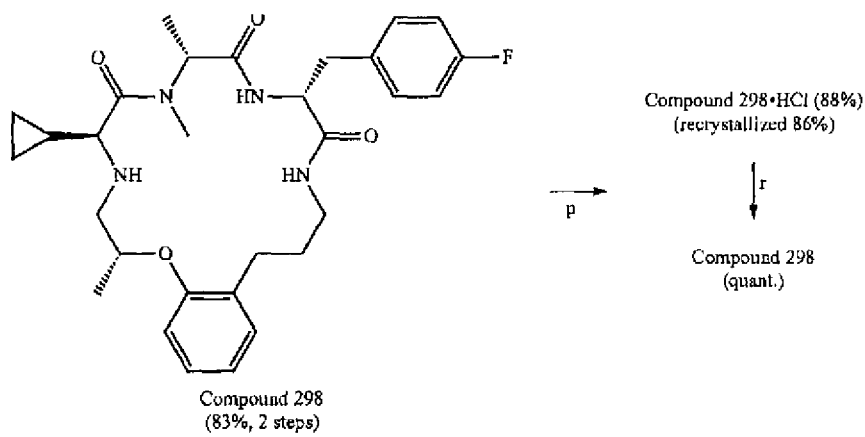
" to read "

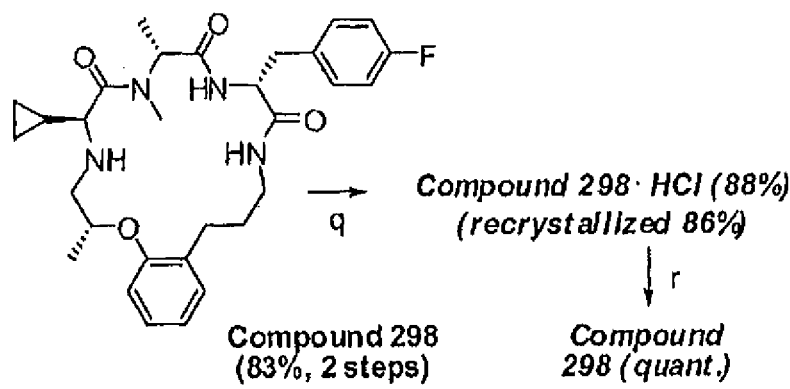
Column 323, LS3-16, Lines 22-31: Please correct
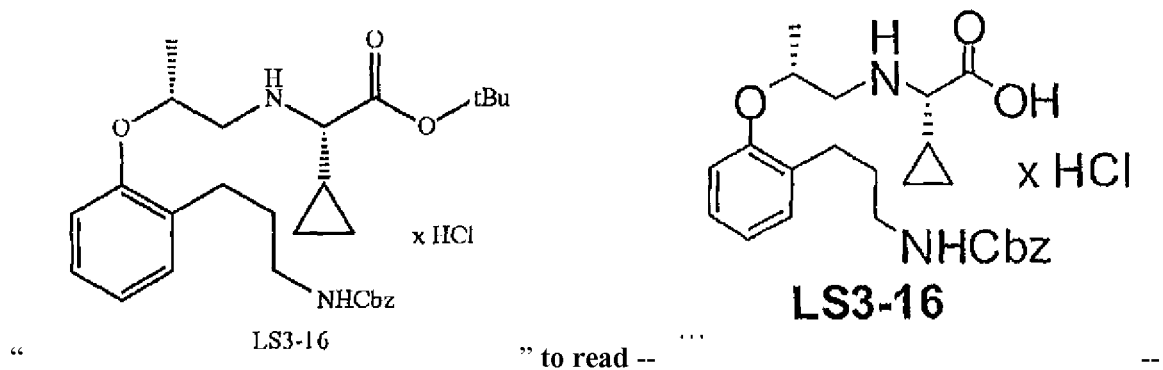
" to read --
Column 323, LS3-16, Lines 32-40: Please correct
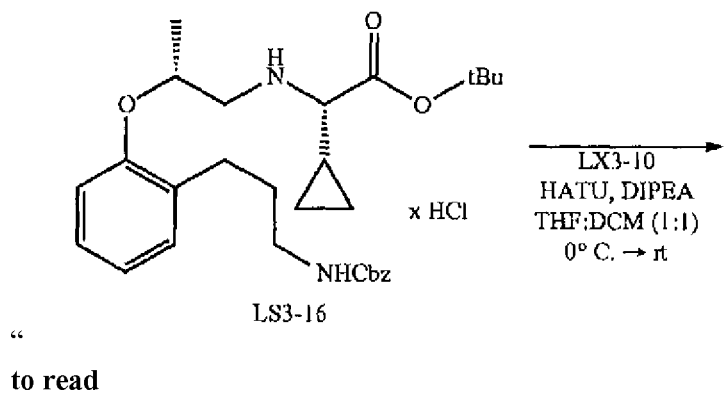
to read

CERTIFICATE OF CORRECTION (continued)
U.S. Pat. No. 8,349,887 B2

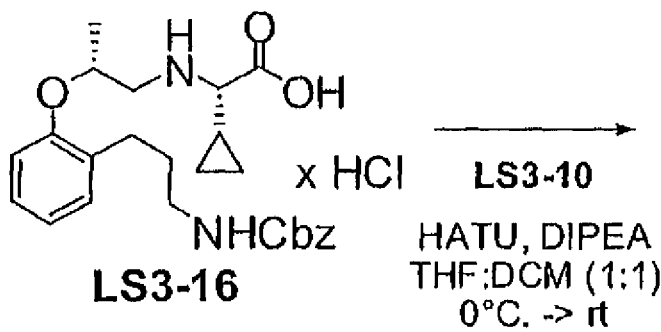

Column 328, Table 8, Headers: Please correct

"
Percent Recovery of Compound 298 Following Incubation in Human Plasma (37° C.).

| | Triplicates | | | | | | |
|---|---|---|---|---|---|---|---|
| Free amine | | Free Amine + PBS | | HCl Salt | | HCl Salt + PBS | |
| 2 Hours (%) | 24 Hours (%) | 2 Hours (%) | 24 Hours (%) | 2 Hours (%) | 24 Hours (%) | 2 Hours (%) | 24 Hours (%) |

"
to read

Percent Recovery of Compound 298 Following Incubation in Human Plasma (37° C.).

| Triplicates | Free amine | | Free Amine + PBS | | HCl Salt | | HCl Salt + PBS | |
|---|---|---|---|---|---|---|---|---|
| | 2 Hours (%) | 24 Hours (%) | 2 Hours (%) | 24 Hours (%) | 2 Hours (%) | 24 Hours (%) | 2 Hours (%) | 24 Hours (%) |

In the Claims:

Column 329, Line 29: Please correct "The invention claimed is:"
to read -- What is claimed is: --